(12) United States Patent
Rendler et al.

(10) Patent No.: US 9,024,019 B2
(45) Date of Patent: May 5, 2015

(54) INSECTICIDAL TRIAZINONE DERIVATIVES

(71) Applicant: Syngenta Participations AG, Basel (CH)

(72) Inventors: Sebastian Rendler, Stein (CH); Jurgen Harry Schaetzer, Stein (CH); Shuji Hachisu, Berkshire (GB); Peter Maienfisch, Stein (CH); Thomas Pitterna, Stein (CH); Olivier Jacob, Stein (CH); Jerome Yves Cassayre, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/359,593

(22) PCT Filed: Nov. 20, 2012

(86) PCT No.: PCT/EP2012/073032
§ 371 (c)(1),
(2) Date: May 21, 2014

(87) PCT Pub. No.: WO2013/079350
PCT Pub. Date: Jun. 6, 2013

(65) Prior Publication Data
US 2014/0329819 A1 Nov. 6, 2014

(30) Foreign Application Priority Data
Nov. 29, 2011 (EP) .................................... 11191056

(51) Int. Cl.
| C07D 401/12 | (2006.01) |
| C07D 401/14 | (2006.01) |
| C07D 403/12 | (2006.01) |
| C07D 403/14 | (2006.01) |
| C07D 405/14 | (2006.01) |
| C07D 413/14 | (2006.01) |
| A01N 43/707 | (2006.01) |
| A01N 43/80 | (2006.01) |
| A01N 43/88 | (2006.01) |

(52) U.S. Cl.
CPC .............. *A01N 43/80* (2013.01); *C07D 403/12* (2013.01); *C07D 401/14* (2013.01); *C07D 405/14* (2013.01); *C07D 413/14* (2013.01); *A01N 43/707* (2013.01); *C07D 401/12* (2013.01); *C07D 403/14* (2013.01); *A01N 43/88* (2013.01)

(58) Field of Classification Search
USPC ........................................... 544/182; 514/242
See application file for complete search history.

(56) References Cited

U.S. PATENT DOCUMENTS

| 5,179,094 A | | 1/1993 | Kristiansen et al. |
| 6,034,083 A | * | 3/2000 | Szczepanski et al. ........ 514/242 |

FOREIGN PATENT DOCUMENTS

| DE | 4011740 A1 | 10/1990 |
| DE | 4213233 A1 | 10/1992 |
| EP | 0314315 A2 | 5/1989 |
| EP | 0391849 A2 | 10/1990 |

OTHER PUBLICATIONS

International Search Report for International Application No. PCT/EP2012/073092.

* cited by examiner

*Primary Examiner* — Venkataraman Balasubramanian
(74) *Attorney, Agent, or Firm* — Brian D. McAlhaney

(57) ABSTRACT

Compounds of the formula (I) or (I'), wherein the substituents are as defined in claim 1, are useful as pesticides.

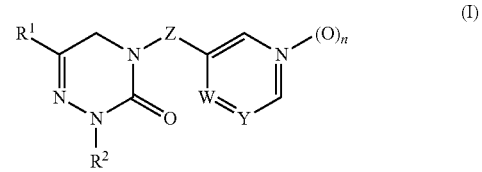

(I)

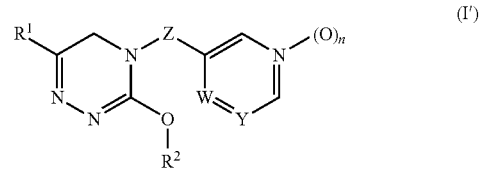

(I')

19 Claims, No Drawings

INSECTICIDAL TRIAZINONE DERIVATIVES

This application is a 371 filing of International Application No. PCT/EP2012/073032, filed Nov. 20, 2012, which claims priority benefit to EP Patent No. 11191056.8 filed Nov. 29, 2011, the contents of all of which are incorporated herein by reference.

The present invention relates to new N-amino-1,2,4-triazinones, to processes for preparing them, to pesticidal, in particular insecticidal, acaricidal, molluscicidal and nematicidal compositions comprising them and to methods of using them to combat and control pests such as insect, acarine, mollusc and nematode pests.

It has now surprisingly been found that certain new substituted N-amino-1,2,4-triazinone derivatives have good insecticidal properties.

The present invention therefore provides compounds of the formula I or I':

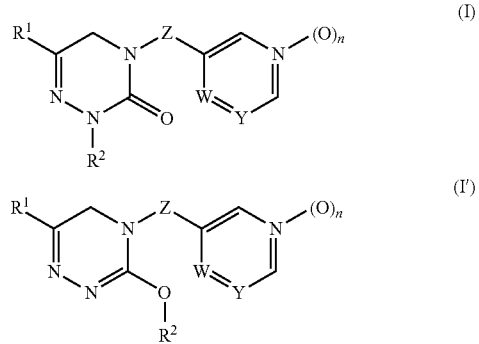

wherein, $R^2$ is hydrogen, formyl, $C_1$-$C_6$alkyl, $C_1$-$C_3$haloalkyl, $C_1$-$C_3$alkoxy, $C_1$-$C_3$haloalkoxy, $C_1$-$C_6$alkoxy$C_1$-$C_3$alkyl, $C_1$-$C_6$alkoxy$C_1$-$C_3$alkoxy$C_1$-$C_3$alkyl, $C_2$-$C_6$alkynyl, $C_1$-$C_4$cyanoalkyl, $C_2$-$C_6$alkenyl, phenyl$C_1$-$C_4$alkyl, $C_1$-$C_6$alkylcarbonyl, $C_1$-$C_6$haloalkylcarbonyl, $C_1$-$C_6$alkoxycarbonyl, $C_1$-$C_4$alkoxycarbonyl$C_1$-$C_4$alkyl, phenyl$C_1$-$C_6$alkylcarbonyl, phenyl$C_1$-$C_6$alkoxycarbonyl, heteroarylcarbonyl, phenylcarbonyl, $C_1$-$C_6$alkylsulfonyl, phenylsulfonyl, $C_3$-$C_6$cycloalkylcarbonyl (wherein a ring methylene group may optionally be replaced by O or S), $C_3$-$C_6$cycloalkoxycarbonyl (wherein a ring methylene group may optionally be replaced by O or S), $C_3$-$C_6$cycloalkyl$C_1$-$C_4$alkylcarbonyl (wherein a ring or chain methylene group may optionally be replaced by O or S), $C_1$-$C_6$alkoxy$C_1$-$C_6$alkoxycarbonyl, Y is N or C—$R^3$, wherein $R^3$ is hydrogen, hydroxy, $C_1$-$C_4$alkoxy, $C_2$-$C_6$alkenyl, $C_2$-$C_6$alkynyl, $C_3$-$C_6$cycloalkyl (wherein a ring methylene group may optionally be replaced by O or S), $C_3$-$C_6$cycloalkyl$C_1$-$C_4$alkyl (wherein a ring or chain methylene group may optionally be replaced by O or S), halogen, cyano, or nitro, $C_1$-$C_3$haloalkylthio, $C_1$-$C_3$haloalkylsulfenyl, $C_1$-$C_3$haloalkylsulfonyl, or $C_1$-$C_3$haloalkoxy, W is C—H or N;

n is 0 or 1;

Z is —N=CH— or —NR$^4$—CH$_2$— wherein R$^4$ is hydrogen, formyl, $C_1$-$C_6$alkyl, $C_1$-$C_6$alkylcarbonyl, $C_1$-$C_6$haloalkylcarbonyl, $C_1$-$C_6$alkoxycarbonyl, $C_2$-$C_6$alkenyloxycarbonyl, $C_2$-$C_6$alkynyl, $C_2$-$C_6$alkenyl, or phenyl$C_1$-$C_6$alkyloxycarbonyl;

$R^1$ is either $Q^1$, $Q^2$, or $Q^3$

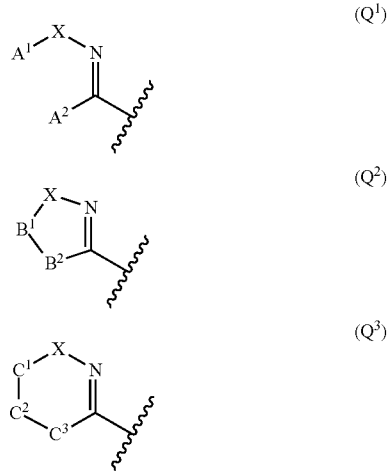

Wherein,

X is O, S, or NR$^5$ wherein R$^5$ is hydrogen, $C_1$-$C_6$alkyl, $C_1$-$C_6$haloalkyl, $A^1$ is hydrogen, $C_1$-$C_6$alkyl, $C_1$-$C_3$haloalkyl, $C_2$-$C_6$alkynyl, $C_1$-$C_4$cyanoalkyl, $C_2$-$C_6$alkenyl, phenyl$C_1$-$C_4$alkyl, heteroaryl$C_1$-$C_4$alkyl, phenyl, heteroaryl, $C_1$-$C_6$alkylcarbonyl, $C_1$-$C_6$haloalkylcarbonyl, $C_1$-$C_6$alkoxycarbonyl, phenyl$C_1$-$C_5$alkylcarbonyl, phenylcarbonyl, $C_1$-$C_6$alkylsulfonyl, phenylsulfonyl, $C_3$-$C_6$cycloalkyl (wherein a ring methylene group may optionally be replaced by O or S), $C_3$-$C_6$cycloalkyl$C_1$-$C_4$alkyl (wherein a ring or chain methylene group may optionally be replaced by O or S), $C_3$-$C_6$cycloalkylcarbonyl (wherein a ring methylene group may optionally be replaced by O or S), or $C_3$-$C_6$cycloalkyl$C_1$-$C_4$alkylcarbonyl (wherein a ring or chain methylene group may optionally be replaced by O or S);

$A^2$ is hydrogen, $C_1$-$C_6$alkyl, $C_1$-$C_3$haloalkyl, $C_2$-$C_6$alkynyl, $C_1$-$C_4$cyanoalkyl, $C_2$-$C_6$alkenyl, phenyl$C_1$-$C_4$alkyl, heteroaryl$C_1$-$C_4$alkyl, phenyl, heteroaryl, $C_3$-$C_6$cycloalkyl (wherein a ring methylene group may optionally be replaced by O or S), $C_3$-$C_6$cycloalkyl$C_1$-$C_4$alkyl (wherein a ring or chain methylene group may optionally be replaced by O or S), $C_1$-$C_6$alkylamino, $C_1$-$C_6$dialkylamino, $C_1$-$C_6$alkyloxy, hydroxy, amino;

$B^1$ is CR$^6$R$^7$, or C(O), S(O)$_m$, wherein m is 1 or 2

$B^2$ is CR$^8$R$^9$, O, NR$^{19}$ wherein R$^{19}$ is hydrogen, $C_1$-$C_6$alkyl, or $C_1$-$C_6$haloalkyl;

$C^1$ is CR$^{11}$R$^{12}$, C(O);

$C^2$ is CR$^{13}$R$^{14}$;

$C^3$ is CR$^{15}$R$^{16}$, O, NR$^{17}$; wherein R$^{17}$ is hydrogen, $C_1$-$C_6$alkyl, or $C_1$-$C_6$haloalkyl, wherein R$^6$, R$^7$, R$^8$, R$^9$, R$^{11}$, R$^{12}$, R$^{13}$, R$^{14}$ R$^{15}$, and R$^{16}$ are each independently of the other hydrogen, $C_1$-$C_6$alkyl, $C_1$-$C_3$haloalkyl, phenyl, heteroaryl, $C_3$-$C_6$cycloalkyl (wherein a ring methylene group may optionally be replaced by O or S), $C_3$-$C_6$cycloalkyl($C_1$-$C_4$)alkyl (wherein a ring or chain methylene group may optionally be replaced by O or S), or wherein R$^6$, R$^7$, R$^8$, R$^9$, R$^{11}$, R$^{12}$, R$^{13}$, R$^{14}$ R$^{15}$, and R$^{16}$ form a 3-6-membered carbocycle (wherein a ring methylene group may optionally be replaced by O or S), wherein the phenyl and the heteroaryl groups above may independently of each other optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, or a tautomer thereof in each case in a free form or in salt form.

In the compounds of the formula (I) or (I'), each alkyl moiety either alone or as part of a larger group is a straight or branched chain and is, for example, methyl, ethyl, n-propyl, n-butyl, iso-propyl, sec-butyl, iso-butyl, tert-butyl, n-pentyl, iso-pentyl and n-hexyl.

Alkoxy groups have a preferred chain length of from 1 to 6, in particular 1 to 4 carbon atoms. Alkoxy is, for example, methoxy, ethoxy, propoxy, i-propoxy, n-butoxy, isobutoxy, sec-butoxy or tert-butoxy. Such groups can be part of a larger group such as alkoxyalkyl and alkoxyalkoxyalkyl. Alkoxyalkyl is, for example, methoxymethyl, methoxyethyl, ethoxymethyl, ethoxyethyl, n-propoxymethyl, n-propoxyethyl or isopropoxymethyl. In alkylthioalkyl groups, oxygen is replaced by sulphur.

Halogen is generally fluorine, chlorine, bromine or iodine. Preferred halogens are fluorine and chlorine.

Haloalkyl groups preferably have a chain length of from 1 to 6, in particular 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Compounds of formula (I) or (I') which have at least one basic centre can form, for example, acid addition salts, for example with strong inorganic acids such as mineral acids, for example perchloric acid, sulphuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula (I) or (I') which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In a preferred group of compounds of formula (I) or (I'):
$R^2$ is preferably hydrogen, $C_1$-$C_6$alkylcarbonyl, $C_1$-$C_6$alkoxycarbonyl, formyl, phenyl$C_1$-$C_6$alkylcarbonyl, phenyl$C_1$-$C_6$alkoxycarbonyl, phenylcarbonyl, $C_3$-$C_6$cycloalkylcarbonyl, $C_1$-$C_6$alkoxy$C_1$-$C_6$alkoxycarbonyl, particularly preferred hydrogen, $C_1$-$C_6$alkylcarbonyl, $C_1$-$C_6$alkoxycarbonyl or formyl, and most preferably hydrogen, wherein the phenyl groups above may independently of each other optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro.

Y is preferably C—H, C—F, N, C—CF$_3$, C—CH$_3$, C-cyclo-Pr or C—CN, and most preferably C—H, C—F, N, C—CF$_3$ or C—CN and even more preferably Y is C—F, C—H or N.
W is preferably C—H.
n is preferably 0.
Z is preferably —N=CH— or —NH—CH$_2$—, and most preferably —N=CH—.
When $R^1$ is $Q^1$,
X is preferably O, N—CH$_3$ or N—H, and most preferably O,
$A^1$ is preferably hydrogen, $C_1$-$C_6$alkyl, $C_1$-$C_3$haloalkyl, $C_2$-$C_6$alkynyl, $C_2$-$C_6$alkenyl, phenyl$C_1$-$C_4$alkyl, heteroaryl$C_1$-$C_4$alkyl, $C_3$-$C_6$cycloalkyl (wherein a ring methylene group may optionally be replaced by O or S), or $C_3$-$C_6$cycloalkyl$C_1$-$C_4$alkyl (wherein a ring or chain methylene group may optionally be replaced by O or S), and most preferably hydrogen, $C_1$-$C_6$alkyl, $C_1$-$C_3$haloalkyl. In a preferred embodiment $A^1$ is $C_1$-$C_6$alkyl or $C_1$-$C_3$haloalkyl,
$A^2$ is preferably hydrogen, $C_1$-$C_6$alkyl, $C_1$-$C_3$haloalkyl, phenyl, heteroaryl or $C_3$-$C_6$cycloalkyl, and most preferably hydrogen, $C_1$-$C_6$alkyl, $C_1$-$C_3$haloalkyl or cyclopropyl. In a preferred embodiment, $A^2$ is hydrogen or $C_1$-$C_4$alkyl, wherein the phenyl and the heteroaryl groups above may independently of each other optionally be substituted by $C_1$-$C_3$alkyl, $C_1$-$C_3$haloalkyl, $C_1$-$C_3$alkoxy, $C_1$-$C_3$haloalkoxy, $C_3$alkylthio, $C_1$-$C_3$alkylsulfinyl, $C_1$-$C_3$alkylsulfonyl, halogen, cyano, or by nitro.
When $R^1$ is $Q^2$,
X is preferably O, N—CH$_3$ or N—H, and most preferably 0,
$B^1$ is preferably CH$_2$, CH(CH$_3$), CH(CF$_3$), C(CF$_3$)(CH$_3$), C(CH$_3$)$_2$, C(CF$_3$)$_2$, C(CH$_2$)$_2$, S(O)$_2$, C(Aryl)H or C(Aryl)(CH$_3$), and most preferably C(CH$_3$)$_2$, C(CF$_3$)$_2$ or CH(CH$_3$) and in a particularly preferred embodiment $B^1$ is C(CH$_3$)$_2$, C(CF$_3$)$_2$.
$B^2$ is preferably O, NH, N(CH$_3$) or CH$_2$ and most preferably O or CH$_2$, and in a particularly preferred embodiment CH$_2$.
When $R^1$ is $Q^3$
X is preferably O, N—CH$_3$ or N—H, and most preferably O,
$C^1$ is preferably CH$_2$, C(O), CH(CH$_3$), C(CH$_3$)$_2$ or C(CH$_2$)$_2$, and most preferably C(O) or CH$_2$ and in a particularly preferred embodiment CH$_2$
$C^2$ is preferably CH$_2$, CH(CH$_3$), C(CH$_3$)$_2$ or C(CH$_2$)$_2$, and most preferably CH$_2$, or C(CH$_3$)$_2$ and in a particularly preferred embodiment CH$_2$.
$C^3$ is preferably CH$_2$, NH, N(CH$_3$), or O, and most preferably CH$_2$ or O and in a particularly preferred embodiment O.
Of particular interest are those compounds of the formula (I) or (I'), wherein
$R^2$ is preferably H, C(O)Me
Y is preferably CH, CF or N
Z is preferably N=CH or NH—CH$_2$, and
$R^1$ is $Q^1$ with X is O, $A^1$ is H, CH$_3$ or ethyl, $A^2$ is H or CH$_3$, or
$R^1$ is $Q^2$ with X is O, $B^1$ is CMe$_2$, or C(CF$_3$)$_2$, $B^2$ is CH$_2$, or
$R^1$ is $Q_3$ with X is O $C^1$ is CH$_2$ or CO, $C^2$ is CH$_2$, and $C^3$ is O, CH$_2$ or NH.
In a particularly preferred group of compounds of the formula (I) or (I'),
$R^2$ is H, C(O)CH$_3$, C(O)Ot-Bu, C(O)OCH$_2$Ph, C(O)OEt, C(O)O(CH$_2$)$_2$OCH$_3$, C(O)iso-Butyl, C(O)iso-Propyl, or C(O)cyclo-Pr, and preferably H,
Y is C—H, C—F, C—Cl, C—Br, C—CH$_3$, C—CF$_3$, C-cyclo-Pr, C—C≡N, C—CH=CH$_2$, or N and preferably C—H, C—F, or N,
W is CH or N,
n is 0 or 1, and preferably 0,
Z is N=CH or NH—CH$_2$,
$R^1$ is $Q^1$ with X is O, N-Me or NH and preferably O, $A^1$ is H, CH$_3$, ethyl, CH$_2$CF$_3$, tert-Butyl, 3,5-Cl$_2$C$_6$H$_3$, CH$_2$-

2,6-Cl$_2$C$_6$H$_3$, and preferably H, CH$_3$, ethyl, A$^2$ is H, CH$_3$, ethyl, CF$_3$, t-C$_4$H$_9$, 3,5-Cl$_2$C$_6$H$_3$, preferably H or CH$_3$ Most preferably,
R$^2$ is H, C(O)CH$_3$, C(O)Ot-Bu, C(O)OCH$_2$Ph, C(O)OEt, C(O)O(CH$_2$)$_2$OCH$_3$, C(O)iso-Butyl, C(O)iso-Propyl, or C(O)cyclo-Pr, and preferably H, Y is C—H, C—F, C—Cl, C—Br, C—CH$_3$, C—CF$_3$, C-cyclo-Pr, C—C≡N, C—CH═CH$_2$, or N and preferably C—H, C—F, or N, W is CH or N, n is 0 or 1, and preferably 0, Z is N═CH or NH—CH$_2$, R$^1$ is Q$^1$ with X is O, A$^1$ is H, CH$_3$, ethyl, CH$_2$CF$_3$, tert-Butyl, 3,5-Cl$_2$C$_6$H$_3$, CH$_2$-2,6-Cl$_2$C$_6$H$_3$, and preferably H, CH$_3$, ethyl, and A$^2$ is H.

In a particularly preferred group of compounds of the formula (I) or (I'),
R$^2$ is H, C(O)CH$_3$, C(O)Ot-Bu, C(O)OCH$_2$Ph, C(O)OEt, C(O)O(CH$_2$)$_2$OCH$_3$, C(O)iso-Butyl, C(O)iso-Propyl, or C(O)cyclo-Pr, and preferably H, Y is C—H, C—F, C—Cl, C—Br, C—CH$_3$, C—CF$_3$, C-cyclo-Pr, C—C≡N, C—CH═CH$_2$, or N and preferably C—H, C—F, or N, W is CH or N, n is 0 or 1, and preferably 0, Z is N═CH or NH—CH$_2$, R$^1$ is Q$^2$ with X is O, N-Me or NH and preferably O, B$^1$ is CMe$_2$, CHMe, C(CF$_3$)Me, C(CF$_3$)$_2$, CH(CF$_3$), CH(3,5-Cl$_2$C$_6$H$_3$), CH(2,6-Cl$_2$C$_6$H$_3$), C(CF$_3$)(3,5-Cl$_2$C$_6$H$_3$), C(CH$_2$)$_2$ and preferably CMe$_2$, or C(CF$_3$)$_2$, B$^2$ is CH$_2$, O or NH, and preferably CH$_2$.

Most preferably,
R$^2$ is H, C(O)CH$_3$, C(O)Ot-Bu, C(O)OCH$_2$Ph, C(O)OEt, C(O)O(CH$_2$)$_2$OCH$_3$, C(O)iso-Butyl, C(O)iso-Propyl, or C(O)cyclo-Pr, and preferably H, Y is C—H, C—F, C—Cl, C—Br, C—CH$_3$, C—CF$_3$, C-cyclo-Pr, C—C≡N, C—CH═CH$_2$, or N and preferably C—H, C—F, or N, W is CH or N, n is 0 or 1, and preferably 0, Z is N═CH or NH—CH$_2$, R$^1$ is Q$^2$ with X is O, B$^1$ is CMe$_2$, CHMe, C(CF$_3$)Me, C(CF$_3$)$_2$, CH(CF$_3$), CH(3,5-Cl$_2$C$_6$H$_3$), CH(2,6-Cl$_2$C$_6$H$_3$), C(CF$_3$)(3,5-Cl$_2$C$_6$H$_3$), C(CH$_2$)$_2$, and preferably CMe$_2$, or C(CF$_3$)$_2$, B$^2$ is CH$_2$.

In a particularly preferred group of compounds of the formula (I) or (I'),
R$^2$ is H, C(O)CH$_3$, C(O)Ot-Bu, C(O)OCH$_2$Ph, C(O)OEt, C(O)O(CH$_2$)$_2$OCH$_3$, C(O)iso-Butyl, C(O)iso-Propyl, or C(O)cyclo-Pr, and preferably H, Y is C—H, C—F, C—Cl, C—Br, C—CH$_3$, C—CF$_3$, C-cyclo-Pr, C—C≡N, C—CH═CH$_2$, or N and preferably C—H, C—F, or N, W is CH or N, n is 0 or 1, and preferably 0, Z is N═CH or NH—CH$_2$, R$^1$ is Q$^3$ with X is O, N-Me or NH and preferably O, C$^1$ is CH$_2$ or CO, C$^2$ is CH$_2$, and C$^3$ is O, CH$_2$ or NH.

The compounds of the invention may be prepared by a variety of methods. For example, the compounds of formula (I) or (I'), wherein the substituents have the meanings assigned to them above, may be prepared by means of processes known per se, e.g. by treating compounds of the general formula (II), wherein R$^2$ can either be hydrogen (IIa) or any substituent as defined as above (IIb and II'b), and wherein R$^2$ be either attached to oxygen (II'b) or nitrogen (IIb), with aldehydes of the general formula (III) or nitriles of the general formula (IV) applying procedures known in the art, described for example in U.S. Pat. No. 5,384,403 (Scheme 1). The obtained compounds of the general formula (Ia) may be converted into compounds of the general formula (Ic) or (I' c) applying procedures known in the art, described for example in U.S. Pat. No. 8,034,931. Compounds of the general formula (Ia) may also be converted into compounds of the general formula (Ib) applying procedures known in the art, described for example in U.S. Pat. No. 5,384,403. Compounds of the general formula (Ic) or (I' c) may be converted into compounds of the general formula (Id) or (I' d) applying procedures known in the art, described for example in U.S. Pat. No. 8,034,931. Compounds of the general formula (Ib) may be further converted into compounds of the general formula (Id) or (I' d) applying procedures known in the art, described for example in EP735035.

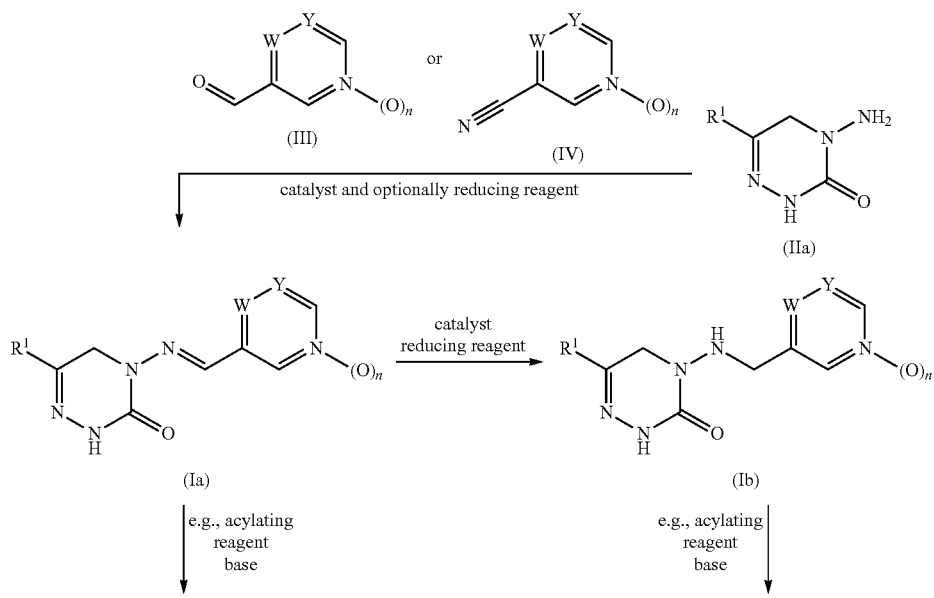

Scheme 1.

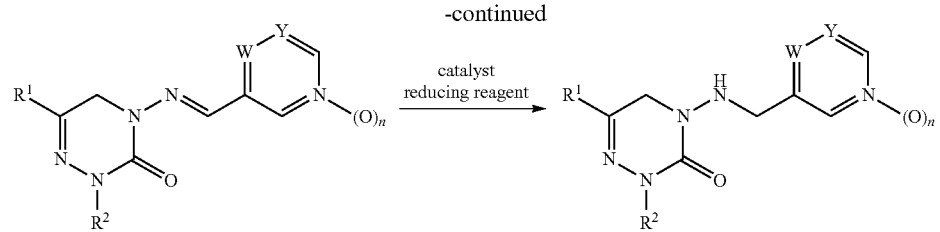

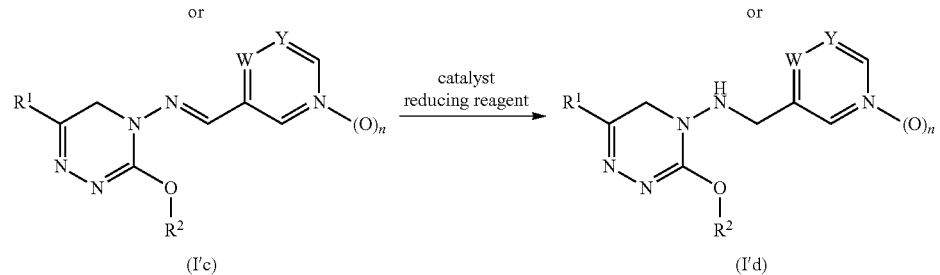

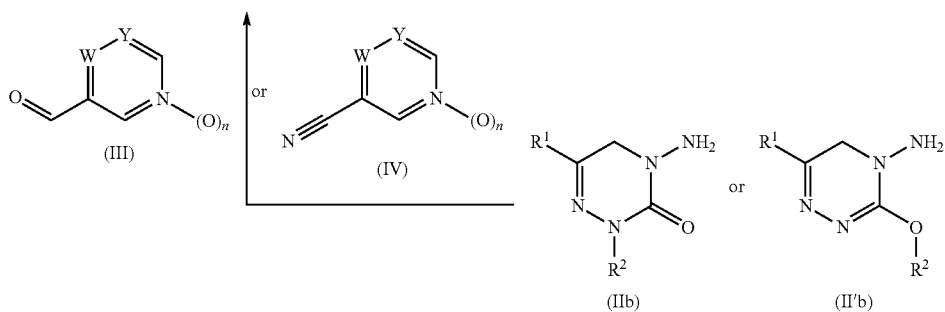

Aldehydes of the general formula (III) and nitriles of the general formula (IV) are known compounds or may be prepared by methods known to persons skilled in the art.

Triazinones of the general formula (II) can be either (IIa) wherein $R^2$ is hydrogen or (IIb), wherein $R^2$ can be any substituent as defined as above. Compounds of the general formula (IIa) may be prepared from compounds of the general formula (V) and (VI) applying procedures known in the art, described for example in U.S. Pat. No. 534,842 and U.S. Pat. No. 5,648,487 (Scheme 2). Compounds of the general formula (IIb) may be prepared from compounds of the general formula (V) and (VI) applying procedures known in the art, described for example in WO2008121670. Oxadiazolones of the general formula (V), preferably with $R^a$ being $C_1$-$C_6$-fluoroalkyl, e.g. trifluoromethyl or $C_1$-$C_6$alkyl, e.g. methyl, are known in the literature or may be prepared by methods known to persons skilled in the art. Halomethylketones (Hal=Halogen, preferably chloro or bromo) of the general formula (VI) are either known in the literature or may be prepared by methods known to persons skilled in the art.

Scheme 2.

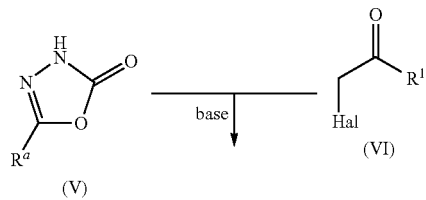

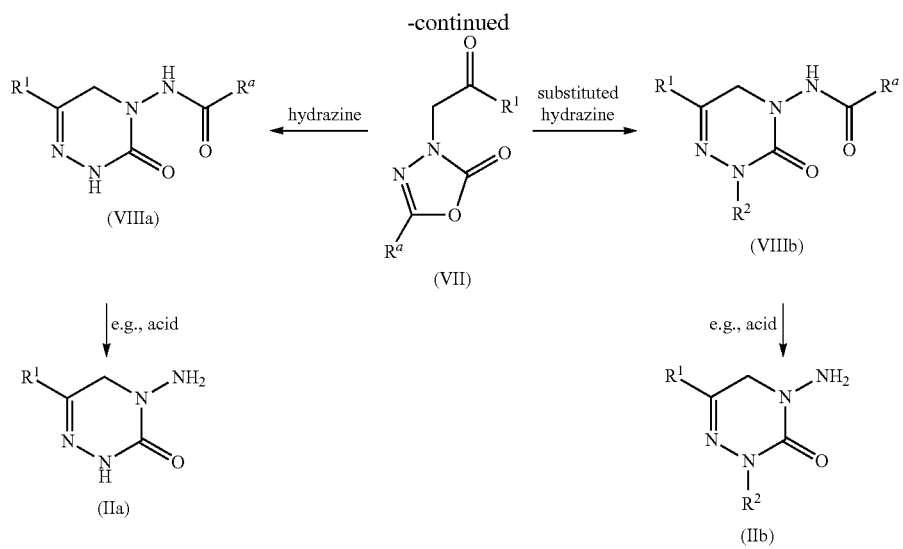

Alternatively, triazinones of the general formula (IIc) (wherein $A^2$=H) and (IId) (wherein $A^2$ is defined as above) wherein $R^1$ is $Q^1$ may be prepared by various methods from the intermediate of the general formula (IX) as shown in Scheme 3.

Compounds of formula (IIc) wherein X and $A^1$ are defined as above may be prepared from compounds of formula (XIIIa) (wherein $PG^1$, $PG^2$ and $PG^3$ stand independently of each other for hydrogen or a nitrogen protecting group ("PG") selected from those described in the literature, for example in "Greene's protective groups in organic synthesis", 4th Ed., Wiley (2007), p. 626-926, preferably $C_1$-$C_6$alkylcarbonyl, $C_1$-$C_6$alkoxycarbonyl, phenyl$C_1$-$C_5$alkoxycarbonyl, phenylcarbonyl, $C_1$-$C_6$alkylsulfonyl, phenylsulfonyl) using methods for removal these protecting groups that have been described in the literature, for example in "Greene's protective groups in organic synthesis", 4th Ed., Wiley (2007), p. 626-926.

Compounds of formula (XIIIa) may be prepared by reaction of an aldehyde of formula (XIIa) with a compound of the general formula (XVIII) and salts thereof, wherein $A^1$ and X are defined as above, for example hydroxylamine, O-alkyl hydroxylamines or alkyl hydrazines. Such reactions are carried out optionally in the presence of a base, for example an organic base, such as triethylamine, pyridine, or sodium acetate, or an inorganic base, such as sodium hydrogen carbonate, optionally in the presence of a solvent, for example an alcohol, such as methanol or ethanol, or water, or mixtures thereof. The reaction is carried out at a temperature of from 0° C. to 100° C., preferably from 15° C. to 30° C., in particular at ambient temperature. Compounds of formula (XVIII) are commercially available or can be made by methods known to a person skilled in the art.

Compounds of formula (IId) wherein X and $A^1$ are defined as above may be prepared from compounds of formula (XIIIb) (wherein $PG^1$, $PG^2$ and $PG^3$ stands independently of each other for hydrogen or a nitrogen protecting group ("PG") selected from those described in the literature, for example in "Greene's protective groups in organic synthesis", 4th Ed., Wiley (2007), p. 626-926, preferably $C_1$-$C_6$alkylcarbonyl, $C_1$-$C_6$alkoxycarbonyl, phenyl$C_1$-$C_5$alkoxycarbonyl, phenylcarbonyl, $C_1$-$C_6$alkylsulfonyl, phenylsulfonyl) using methods for removal these protecting groups that have been described in the literature, for example in "Greene's protective groups in organic synthesis", 4th Ed., Wiley (2007), p. 626-926.

Compounds of formula (XIIIb) may be prepared by reaction of a ketone of formula (XIIb) with a compound of the general formula (XVIII) and salts thereof, wherein $A^1$ and X are defined as above, for example hydroxylamine, O-alkyl hydroxylamines or alkyl hydrazines. Such reactions are carried out optionally in the presence of a base, for example an organic base, such as triethylamine, pyridine, or sodium acetate, or an inorganic base, such as sodium hydrogen carbonate, optionally in the presence of a solvent, for example an alcohol, such as methanol or ethanol, or water, or mixtures thereof. The reaction is carried out at a temperature of from 0° C. to 100° C., preferably from 15° C. to 30° C., in particular at ambient temperature. Compounds of formula (XVIII) are commercially available or can be made by methods known to a person skilled in the art.

Compounds of general formula (XIIb), wherein $A^2$ is defined as above may be prepared from aldehydes of general formula (XIIa) using methods described in the literature, for example Journal of Organic Chemistry (2009), 74, 3566-3568 or Journal of the American Chemical Society (2010), 132, 3266-3267. Specific examples are described in the experimental section.

Compounds of the general formula (XIIa) may be obtained by oxidation of alcohols of formula (XI) using methods known to persons skilled in the art. Specific examples are described in the experimental section.

Alcohols of the general formula (XI) may be prepared by selective removal of alcohol protecting group $PG^4$ of compounds (X) using methods selected from those described in the literature, for example in "Greene's protective groups in organic synthesis", 4th Ed., Wiley (2007), p. 13-366. Suitable protecting groups ($PG^4$) may be selected from those described in the literature, for example in "Greene's protective groups in organic synthesis", 4th Ed., Wiley (2007), p. 13-366, preferably phenyl$C_1$-$C_6$alkyl, wherein the phenyl group optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, most preferably benzyl.

Compounds of general formula (X) may be prepared from compounds of the general formula (IX) by using methods selected from those described in the literature, for example in "Greene's protective groups in organic synthesis", 4th Ed., Wiley (2007), p. 626-926.

Compounds of the general formula (IX) may be prepared in a similar way than compounds of general formula (IIa) as shown above. Specific examples are described in the experimental section.

Alternatively, triazinones of the general formula (IIe) (wherein $B^2$, $R^6$, $R^7$ are defined as above) wherein $R^1$ is $Q^2$ may be prepared by various methods from the intermediate of the general formula (XIIa) using procedures known in the art (Scheme 4).

Scheme 3.

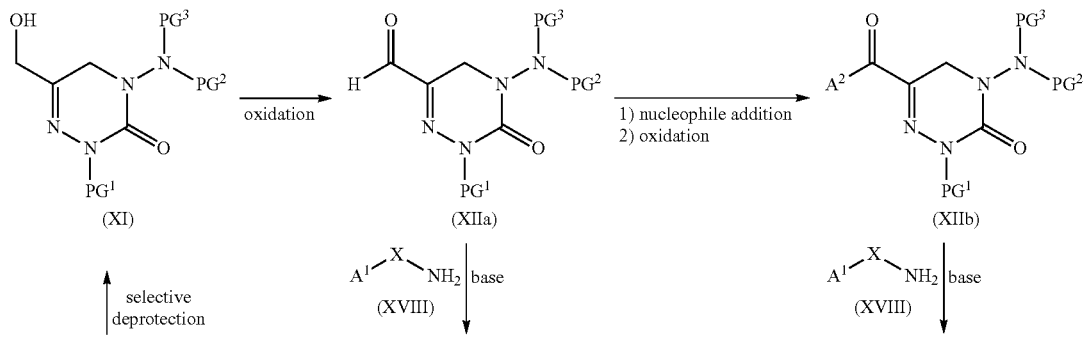

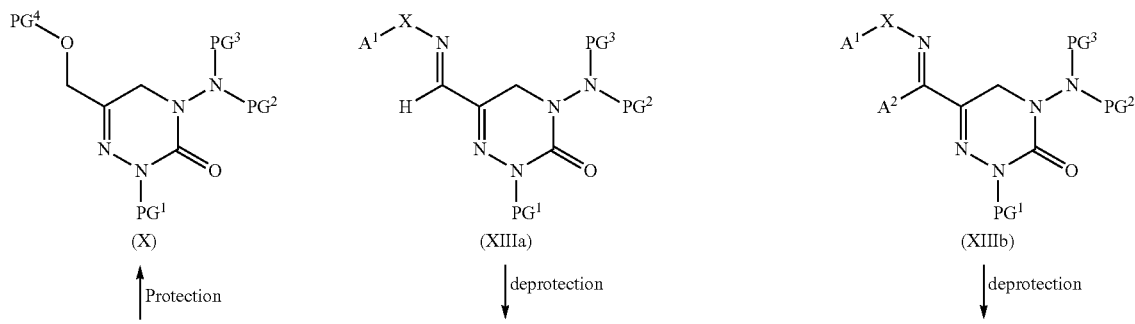

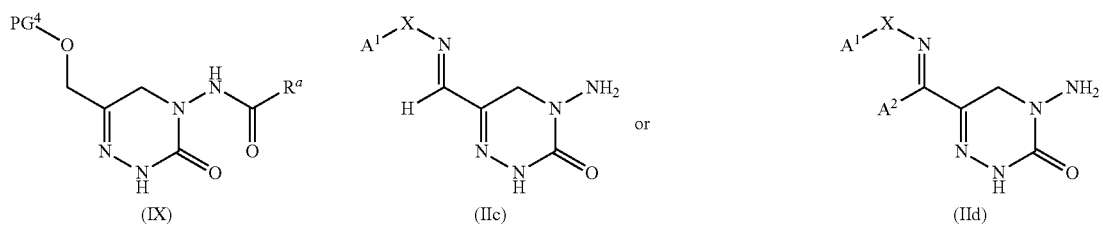

Scheme 4.

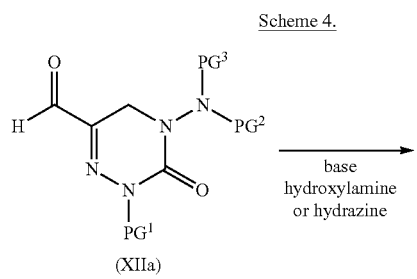

(XIIa)

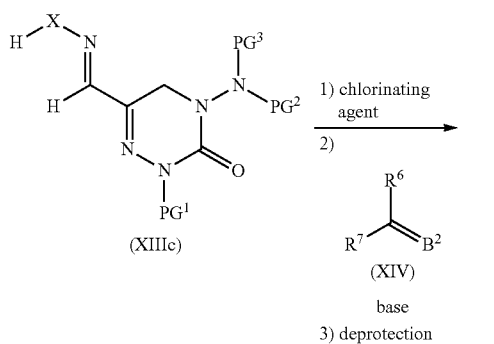

(XIIIc)

1) chlorinating agent
2) 
$$\underset{R^7}{\overset{R^6}{>}}\!\!=\!\!B^2$$
(XIV)
base
3) deprotection

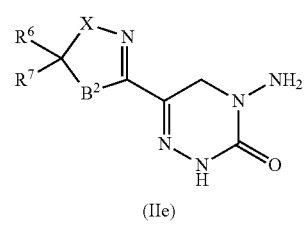

(IIe)

For example, compounds of formula (IIe) may be obtained from intermediate (XIIIc) in a two-step reaction. In the first step, the intermediate of formula (XIIIc), for example an oxime (X=O) is reacted with a halogenating agent, for example a succinimide, such as N-chlorosuccinimide ("NCS"), in the presence of a suitable solvent, for example a polar solvent, such as N,N-dimethylformamide. The first step is carried out at a temperature of from 0° C. to 100° C., preferably from 15° C. to 30° C., in particular at ambient temperature.

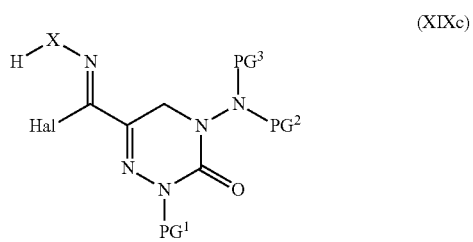

In the second step, the halogenated (Hal=halogen, preferably chloro or bromo) intermediate of formula (XIXc) is reacted with reactant (XIV) (wherein $B^2$, $R^6$, $R^7$ are defined as above), for example an olefin or imine, in the presence of a base, for example an organic base, such as triethylamine, or an inorganic base, such as sodium hydrogen carbonate, in the presence of a suitable solvent, for example a polar solvent, such as N,N-dimethylformamide or isopropanol. It is possible to conduct these two steps separately and optionally to isolate the intermediate (XIXc) or more conveniently to conduct these two steps successively in one reaction vessel without isolation of the intermediate. The second step is carried out at a temperature of from 0° C. to 100° C., preferably from 15° C. to 30° C., in particular at ambient temperature. Compounds of formula (XIV) are commercially available or can be prepared by methods known to a person skilled in the art.

Compounds (XIIIc) can be prepared from (XIIa) according to the procedures described for (XIIIa) and (XIIIb).

Alternatively, triazinones of the general formula (IIf) (wherein $R^{11}$, $R^{12}$, $R^{13}$, $R^{13}$ are defined as above) wherein $R^1$ is $Q^3$ may be prepared by various methods from the intermediate of the general formula (XIIa) using procedures known in the art (Scheme 5).

For example, compounds of general formula (IIf) may be prepared from compounds of formula (XVII), wherein (wherein $PG^1$, $PG^2$ and $PG^3$ stands independently of each other for hydrogen or a nitrogen protecting group ("PG", as defined above) selected from those described in the literature, for example in "Greene's protective groups in organic synthesis", 4th Ed., Wiley (2007), p. 626-926) using methods that have been described in the literature, for example in "Greene's protective groups in organic synthesis", 4th Ed., Wiley (2007), p. 626-926.

Compounds of general formula (XVII) may be prepared may be prepared by various methods known to persons skilled in the art. For example, a compound of the general formula (XVI) can be dehydrated using methods described in the literature, for example WO20070311213.

Compounds of general formula (XVI) may be prepared from compounds of the general formula (XV) and O-alkyl hydroxylamines (XX) using peptide coupling methods described in the literature, for example Journal of Medicinal Chemistry (2001), 44, 619-626. O-Alkyl hydroxylamines (XX) are either commercially available or may be prepared by methods known to a person skilled in the art.

Acids of general formula (XV) may be prepared by various methods from compounds of formula (XIIa) using known methods. For example, by reaction with an oxidizing reagent, e.g. sodium chlorite in the presence of an olefin, for example 2-methylbut-2-ene, in the presence of a suitable solvent mixture, for example tetrahydrofuran, tert-butanol and water. The reaction can be carried out at a temperature of from −50° C. to 50° C., preferably from −20° C. to 20° C., in particular at ambient temperature.

Compounds of general formula (XIIa) can be prepared as described above.

Scheme 5.

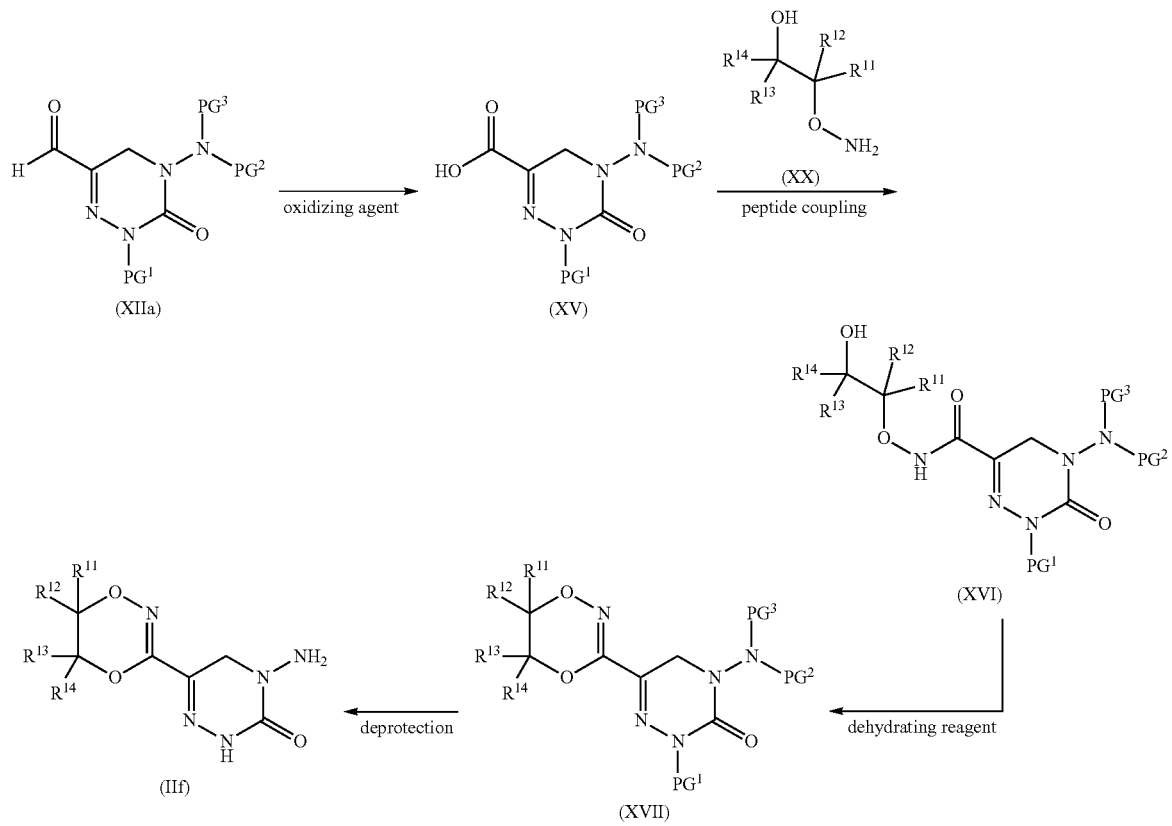

A compound (I) can be converted in a manner known per se into another compound (I) by replacing one or more substituents of the starting compound (I) in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds I can be converted in a manner known per se into other salts of compounds I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds I, which have salt-forming properties can be obtained in free form or in the form of salts.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables below can be prepared according to the methods described above. The examples which follow are intended to illustrate the invention and show preferred compounds of formula (I) or (I').

TABLE 1

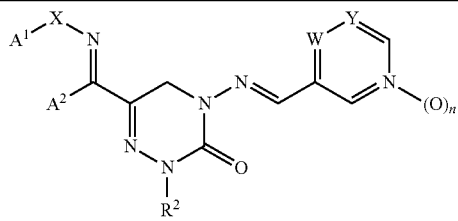

| | n | Y | W | X | $A^1$ | $A^2$ | $R^2$ |
|---|---|---|---|---|---|---|---|
| 1.001 | 0 | C—H | C—H | O | $CH_3$ | H | H |
| 1.002 | 0 | C—F | C—H | O | $CH_3$ | H | H |
| 1.003 | 1 | C—F | C—H | O | $CH_3$ | H | H |
| 1.004 | 0 | C—Cl | C—H | O | $CH_3$ | H | H |
| 1.005 | 0 | C—Br | C—H | O | $CH_3$ | H | H |
| 1.006 | 0 | C—$CH_3$ | C—H | O | $CH_3$ | H | H |
| 1.007 | 0 | C—$CF_3$ | C—H | O | $CH_3$ | H | H |
| 1.008 | 0 | C-cyclo-Pr | C—H | O | $CH_3$ | H | H |
| 1.009 | 0 | C—C≡N | C—H | O | $CH_3$ | H | H |
| 1.010 | 0 | C—C≡CH | C—H | O | $CH_3$ | H | H |
| 1.011 | 0 | C—CH=$CH_2$ | C—H | O | $CH_3$ | H | H |
| 1.012 | 1 | C—H | C—H | O | $CH_3$ | H | H |
| 1.013 | 0 | N | C—H | O | $CH_3$ | H | H |
| 1.014 | 0 | C—H | N | O | $CH_3$ | H | H |
| 1.015 | 0 | C—H | C—H | O | $CH_3$ | H | $C(O)CH_3$ |
| 1.016 | 0 | C—F | C—H | O | $CH_3$ | H | $C(O)CH_3$ |
| 1.017 | 1 | C—F | C—H | O | $CH_3$ | H | $C(O)CH_3$ |
| 1.018 | 1 | C—H | C—H | O | $CH_3$ | H | $C(O)CH_3$ |
| 1.019 | 0 | N | C—H | O | $CH_3$ | H | $C(O)CH_3$ |
| 1.020 | 0 | C—H | N | O | $CH_3$ | H | $C(O)CH_3$ |
| 1.021 | 0 | C—H | C—H | O | $CH_3$ | H | C(O)Ot-Bu |
| 1.022 | 0 | C—F | C—H | O | $CH_3$ | H | C(O)Ot-Bu |
| 1.023 | 1 | C—F | C—H | O | $CH_3$ | H | C(O)Ot-Bu |
| 1.024 | 1 | C—H | C—H | O | $CH_3$ | H | C(O)Ot-Bu |
| 1.025 | 0 | N | C—H | O | $CH_3$ | H | C(O)Ot-Bu |
| 1.026 | 0 | C—H | N | O | $CH_3$ | H | C(O)Ot-Bu |
| 1.027 | 0 | C—H | C—H | O | $CH_3$ | H | $C(O)OCH_2Ph$ |
| 1.028 | 0 | C—F | C—H | O | $CH_3$ | H | $C(O)OCH_2Ph$ |
| 1.029 | 1 | C—F | C—H | O | $CH_3$ | H | $C(O)OCH_2Ph$ |
| 1.030 | 1 | C—H | C—H | O | $CH_3$ | H | $C(O)OCH_2Ph$ |
| 1.031 | 0 | N | C—H | O | $CH_3$ | H | $C(O)OCH_2Ph$ |
| 1.032 | 0 | C—H | N | O | $CH_3$ | H | $C(O)OCH_2Ph$ |
| 1.033 | 0 | C—H | C—H | O | $CH_3$ | H | C(O)OEt |
| 1.034 | 0 | C—F | C—H | O | $CH_3$ | H | C(O)OEt |
| 1.035 | 1 | C—F | C—H | O | $CH_3$ | H | C(O)OEt |
| 1.036 | 1 | C—H | C—H | O | $CH_3$ | H | C(O)OEt |
| 1.037 | 0 | N | C—H | O | $CH_3$ | H | C(O)OEt |
| 1.038 | 0 | C—H | N | O | $CH_3$ | H | C(O)OEt |
| 1.039 | 0 | C—H | C—H | O | $CH_3$ | H | $C(O)O(CH_2)_2OCH_3$ |
| 1.040 | 0 | C—F | C—H | O | $CH_3$ | H | $C(O)O(CH_2)_2OCH_3$ |
| 1.041 | 1 | C—F | C—H | O | $CH_3$ | H | $C(O)O(CH_2)_2OCH_3$ |
| 1.042 | 1 | C—H | C—H | O | $CH_3$ | H | $C(O)O(CH_2)_2OCH_3$ |
| 1.043 | 0 | N | C—H | O | $CH_3$ | H | $C(O)O(CH_2)_2OCH_3$ |
| 1.044 | 0 | C—H | N | O | $CH_3$ | H | $C(O)O(CH_2)_2OCH_3$ |

TABLE 1-continued

| | n | Y | W | X | A¹ | A² | R² |
|---|---|---|---|---|---|---|---|
| 1.045 | 0 | C—H | C—H | O | CH₃ | H | C(O)iso-Butyl |
| 1.046 | 0 | C—F | C—H | O | CH₃ | H | C(O)iso-Butyl |
| 1.047 | 1 | C—F | C—H | O | CH₃ | H | C(O)iso-Butyl |
| 1.048 | 1 | C—H | C—H | O | CH₃ | H | C(O)iso-Butyl |
| 1.049 | 0 | N | C—H | O | CH₃ | H | C(O)iso-Butyl |
| 1.050 | 0 | C—H | N | O | CH₃ | H | C(O)iso-Butyl |
| 1.051 | 0 | C—H | C—H | O | CH₃ | H | C(O)iso-Propyl |
| 1.052 | 0 | C—F | C—H | O | CH₃ | H | C(O)iso-Propyl |
| 1.053 | 1 | C—F | C—H | O | CH₃ | H | C(O)iso-Propyl |
| 1.054 | 1 | C—H | C—H | O | CH₃ | H | C(O)iso-Propyl |
| 1.055 | 0 | N | C—H | O | CH₃ | H | C(O)iso-Propyl |
| 1.056 | 0 | C—H | N | O | CH₃ | H | C(O)iso-Propyl |
| 1.057 | 0 | C—H | C—H | O | CH₃ | H | C(O)cyclo-Pr |
| 1.058 | 0 | C—F | C—H | O | CH₃ | H | C(O)cyclo-Pr |
| 1.059 | 1 | C—F | C—H | O | CH₃ | H | C(O)cyclo-Pr |
| 1.060 | 1 | C—H | C—H | O | CH₃ | H | C(O)cyclo-Pr |
| 1.061 | 0 | N | C—H | O | CH₃ | H | C(O)cyclo-Pr |
| 1.062 | 0 | C—H | N | O | CH₃ | H | C(O)cyclo-Pr |
| 1.063 | 0 | C—H | C—H | O | CH₃ | CH₃ | H |
| 1.064 | 0 | C—F | C—H | O | CH₃ | CH₃ | H |
| 1.065 | 1 | C—F | C—H | O | CH₃ | CH₃ | H |
| 1.066 | 1 | C—H | C—H | O | CH₃ | CH₃ | H |
| 1.067 | 0 | N | C—H | O | CH₃ | CH₃ | H |
| 1.068 | 0 | C—H | N | O | CH₃ | CH₃ | H |
| 1.069 | 0 | C—H | C—H | O | CH₃ | CF₃ | H |
| 1.070 | 0 | C—F | C—H | O | CH₃ | CF₃ | H |
| 1.071 | 1 | C—F | C—H | O | CH₃ | CF₃ | H |
| 1.072 | 1 | C—H | C—H | O | CH₃ | CF₃ | H |
| 1.073 | 0 | N | C—H | O | CH₃ | CF₃ | H |
| 1.074 | 0 | C—H | N | O | CH₃ | CF₃ | H |
| 1.075 | 0 | C—H | C—H | O | Et | H | H |
| 1.076 | 0 | C—F | C—H | O | Et | H | H |
| 1.077 | 1 | C—F | C—H | O | Et | H | H |
| 1.078 | 1 | C—H | C—H | O | Et | H | H |
| 1.079 | 0 | N | C—H | O | Et | H | H |
| 1.080 | 0 | C—H | N | O | Et | H | H |
| 1.081 | 0 | C—H | C—H | O | CH₂CF₃ | H | H |
| 1.081 | 0 | C—F | C—H | O | CH₂CF₃ | H | H |
| 1.082 | 1 | C—F | C—H | O | CH₂CF₃ | H | H |
| 1.083 | 1 | C—H | C—H | O | CH₂CF₃ | H | H |
| 1.084 | 0 | N | C—H | O | CH₂CF₃ | H | H |
| 1.085 | 0 | C—H | N | O | CH₂CF₃ | H | H |
| 1.086 | 0 | C—H | C—H | O | i-Pr | H | H |
| 1.087 | 0 | C—F | C—H | O | i-Pr | H | H |
| 1.088 | 1 | C—F | C—H | O | i-Pr | H | H |
| 1.089 | 1 | C—H | C—H | O | i-Pr | H | H |
| 1.090 | 0 | N | C—H | O | i-Pr | H | H |
| 1.091 | 0 | C—H | N | O | i-Pr | H | H |
| 1.092 | 0 | C—H | C—H | O | t-Bu | H | H |
| 1.093 | 0 | C—F | C—H | O | t-Bu | H | H |
| 1.094 | 1 | C—F | C—H | O | t-Bu | H | H |
| 1.095 | 1 | C—H | C—H | O | t-Bu | H | H |
| 1.096 | 0 | N | C—H | O | t-Bu | H | H |
| 1.097 | 0 | C—H | N | O | t-Bu | H | H |
| 1.099 | 0 | C—H | C—H | O | 3,5-Cl₂C₆H₃ | H | H |
| 1.100 | 0 | C—F | C—H | O | 3,5-Cl₂C₆H₃ | H | H |
| 1.101 | 1 | C—F | C—H | O | 3,5-Cl₂C₆H₃ | H | H |
| 1.102 | 1 | C—H | C—H | O | 3,5-Cl₂C₆H₃ | H | H |
| 1.103 | 0 | N | C—H | O | 3,5-Cl₂C₆H₃ | H | H |
| 1.104 | 0 | CH | N | O | 3,5-Cl₂C₆H₃ | H | H |
| 1.105 | 0 | C—H | C—H | O | CH₂-2,6-Cl₂C₆H₃ | H | H |
| 1.106 | 0 | C—F | C—H | O | CH₂-2,6-Cl₂C₆H₃ | H | H |
| 1.107 | 1 | C—F | C—H | O | CH₂-2,6-Cl₂C₆H₃ | H | H |
| 1.108 | 1 | C—H | C—H | O | CH₂-2,6-Cl₂C₆H₃ | H | H |
| 1.109 | 0 | N | C—H | O | CH₂-2,6-Cl₂C₆H₃ | H | H |
| 1.110 | 0 | C—H | N | O | CH₂-2,6-Cl₂C₆H₃ | H | H |
| 1.111 | 0 | C—H | C—H | O | H | H | H |

TABLE 1-continued

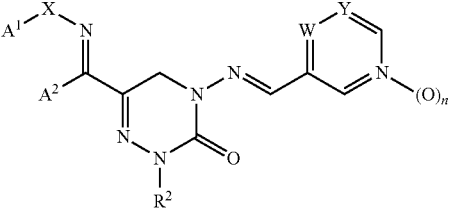

| | n | Y | W | X | A¹ | A² | R² |
|---|---|---|---|---|---|---|---|
| 1.112 | 0 | C—F | C—H | O | H | H | H |
| 1.113 | 1 | C—F | C—H | O | H | H | H |
| 1.114 | 1 | C—H | C—H | O | H | H | H |
| 1.115 | 0 | N | C—H | O | H | H | H |
| 1.116 | 0 | C—H | N | O | H | H | H |
| 1.117 | 0 | C—H | C—H | N—Me | Me | H | H |
| 1.118 | 0 | C—F | C—H | N—Me | Me | H | H |
| 1.119 | 1 | C—F | C—H | N—Me | Me | H | H |
| 1.120 | 1 | C—H | C—H | N—Me | Me | H | H |
| 1.121 | 0 | N | C—H | N—Me | Me | H | H |
| 1.122 | 0 | C—H | N | N—Me | Me | H | H |
| 1.123 | 0 | C—H | C—H | N—Me | Me | H | H |
| 1.124 | 0 | C—F | C—H | NH | Me | H | H |
| 1.125 | 1 | C—F | C—H | NH | Me | H | H |
| 1.126 | 1 | C—H | C—H | NH | Me | H | H |
| 1.127 | 0 | N | C—H | NH | Me | H | H |
| 1.128 | 0 | C—H | N | NH | Me | H | H |
| 1.129 | 0 | C—H | C—H | O | Me | t-Bu | H |
| 1.130 | 0 | C—F | C—H | O | Me | t-Bu | H |
| 1.131 | 1 | C—F | C—H | O | Me | t-Bu | H |
| 1.132 | 1 | C—H | C—H | O | Me | t-Bu | H |
| 1.133 | 0 | N | C—H | O | Me | t-Bu | H |
| 1.134 | 0 | C—H | N | O | Me | t-Bu | H |
| 1.135 | 0 | C—H | C—H | O | Me | 3,5-Cl₂C₆H₃ | H |
| 1.136 | 0 | C—F | C—H | O | Me | 3,5-Cl₂C₆H₃ | H |
| 1.137 | 1 | C—F | C—H | O | Me | 3,5-Cl₂C₆H₃ | H |
| 1.138 | 1 | C—H | C—H | O | Me | 3,5-Cl₂C₆H₃ | H |
| 1.139 | 0 | N | C—H | O | Me | 3,5-Cl₂C₆H₃ | H |
| 1.140 | 0 | C—H | N | O | Me | 3,5-Cl₂C₆H₃ | H |
| 1.141 | 0 | C—H | C—H | O | Me | Et | H |
| 1.142 | 0 | C—F | C—H | O | Me | Et | H |
| 1.143 | 1 | C—F | C—H | O | Me | Et | H |
| 1.144 | 1 | C—H | C—H | O | Me | Et | H |
| 1.145 | 0 | N | C—H | O | Me | Et | H |
| 1.146 | 0 | C—H | N | O | Me | Et | H |

TABLE 2

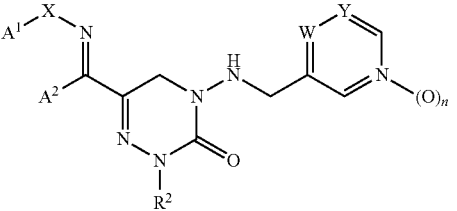

| | n | Y | W | X | A¹ | A² | R² |
|---|---|---|---|---|---|---|---|
| 2.001 | 0 | C—H | C—H | O | CH₃ | H | H |
| 2.002 | 0 | C—F | C—H | O | CH₃ | H | H |
| 2.003 | 1 | C—F | C—H | O | CH₃ | H | H |
| 2.004 | 0 | C—Cl | C—H | O | CH₃ | H | H |
| 2.005 | 0 | C—Br | C—H | O | CH₃ | H | H |
| 2.006 | 0 | C—CH₃ | C—H | O | CH₃ | H | H |
| 2.007 | 0 | C—CF₃ | C—H | O | CH₃ | H | H |
| 2.008 | 0 | C-cyclo-Pr | C—H | O | CH₃ | H | H |
| 2.009 | 0 | C—C≡N | C—H | O | CH₃ | H | H |
| 2.010 | 0 | C—C≡CH | C—H | O | CH₃ | H | H |
| 2.011 | 0 | C—CH═CH₂ | C—H | O | CH₃ | H | H |
| 2.012 | 1 | C—H | C—H | O | CH₃ | H | H |
| 2.013 | 0 | N | C—H | O | CH₃ | H | H |
| 2.014 | 0 | C—H | N | O | CH₃ | H | H |

TABLE 2-continued

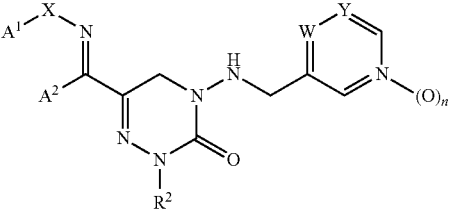

| | n | Y | W | X | $A^1$ | $A^2$ | $R^2$ |
|---|---|---|---|---|---|---|---|
| 2.015 | 0 | C—H | C—H | O | $CH_3$ | H | $C(O)CH_3$ |
| 2.016 | 0 | C—F | C—H | O | $CH_3$ | H | $C(O)CH_3$ |
| 2.017 | 1 | C—F | C—H | O | $CH_3$ | H | $C(O)CH_3$ |
| 2.018 | 1 | C—H | C—H | O | $CH_3$ | H | $C(O)CH_3$ |
| 2.019 | 0 | N | C—H | O | $CH_3$ | H | $C(O)CH_3$ |
| 2.020 | 0 | C—H | N | O | $CH_3$ | H | $C(O)CH_3$ |
| 2.021 | 0 | C—H | C—H | O | $CH_3$ | H | C(O)Ot-Bu |
| 2.022 | 0 | C—F | C—H | O | $CH_3$ | H | C(O)Ot-Bu |
| 2.023 | 1 | C—F | C—H | O | $CH_3$ | H | C(O)Ot-Bu |
| 2.024 | 1 | C—H | C—H | O | $CH_3$ | H | C(O)Ot-Bu |
| 2.025 | 0 | N | C—H | O | $CH_3$ | H | C(O)Ot-Bu |
| 2.026 | 0 | C—H | N | O | $CH_3$ | H | C(O)Ot-Bu |
| 2.027 | 0 | C—H | C—H | O | $CH_3$ | H | $C(O)OCH_2Ph$ |
| 2.028 | 0 | C—F | C—H | O | $CH_3$ | H | $C(O)OCH_2Ph$ |
| 2.029 | 1 | C—F | C—H | O | $CH_3$ | H | $C(O)OCH_2Ph$ |
| 2.030 | 1 | C—H | C—H | O | $CH_3$ | H | $C(O)OCH_2Ph$ |
| 2.031 | 0 | N | C—H | O | $CH_3$ | H | $C(O)OCH_2Ph$ |
| 2.032 | 0 | C—H | N | O | $CH_3$ | H | $C(O)OCH_2Ph$ |
| 2.033 | 0 | C—H | C—H | O | $CH_3$ | H | C(O)OEt |
| 2.034 | 0 | C—F | C—H | O | $CH_3$ | H | C(O)OEt |
| 2.035 | 1 | C—F | C—H | O | $CH_3$ | H | C(O)OEt |
| 2.036 | 1 | C—H | C—H | O | $CH_3$ | H | C(O)OEt |
| 2.037 | 0 | N | C—H | O | $CH_3$ | H | C(O)OEt |
| 2.038 | 0 | C—H | N | O | $CH_3$ | H | C(O)OEt |
| 2.039 | 0 | C—H | C—H | O | $CH_3$ | H | $C(O)O(CH_2)_2OCH_3$ |
| 2.040 | 0 | C—F | C—H | O | $CH_3$ | H | $C(O)O(CH_2)_2OCH_3$ |
| 2.041 | 1 | C—F | C—H | O | $CH_3$ | H | $C(O)O(CH_2)_2OCH_3$ |
| 2.042 | 1 | C—H | C—H | O | $CH_3$ | H | $C(O)O(CH_2)_2OCH_3$ |
| 2.043 | 0 | N | C—H | O | $CH_3$ | H | $C(O)O(CH_2)_2OCH_3$ |
| 2.044 | 0 | C—H | N | O | $CH_3$ | H | $C(O)O(CH_2)_2OCH_3$ |
| 2.045 | 0 | C—H | C—H | O | $CH_3$ | H | C(O)iso-Butyl |
| 2.046 | 0 | C—F | C—H | O | $CH_3$ | H | C(O)iso-Butyl |
| 2.047 | 1 | C—F | C—H | O | $CH_3$ | H | C(O)iso-Butyl |
| 2.048 | 1 | C—H | C—H | O | $CH_3$ | H | C(O)iso-Butyl |
| 2.049 | 0 | N | C—H | O | $CH_3$ | H | C(O)iso-Butyl |
| 2.050 | 0 | C—H | N | O | $CH_3$ | H | C(O)iso-Butyl |
| 2.051 | 0 | C—H | C—H | O | $CH_3$ | H | C(O)iso-Propyl |
| 2.052 | 0 | C—F | C—H | O | $CH_3$ | H | C(O)iso-Propyl |
| 2.053 | 1 | C—F | C—H | O | $CH_3$ | H | C(O)iso-Propyl |
| 2.054 | 1 | C—H | C—H | O | $CH_3$ | H | C(O)iso-Propyl |
| 2.055 | 0 | N | C—H | O | $CH_3$ | H | C(O)iso-Propyl |
| 2.056 | 0 | C—H | N | O | $CH_3$ | H | C(O)iso-Propyl |
| 2.057 | 0 | C—H | C—H | O | $CH_3$ | H | C(O)cyclo-Pr |
| 2.058 | 0 | C—F | C—H | O | $CH_3$ | H | C(O)cyclo-Pr |
| 2.059 | 1 | C—F | C—H | O | $CH_3$ | H | C(O)cyclo-Pr |
| 2.060 | 1 | C—H | C—H | O | $CH_3$ | H | C(O)cyclo-Pr |
| 2.061 | 0 | N | C—H | O | $CH_3$ | H | C(O)cyclo-Pr |
| 2.062 | 0 | C—H | N | O | $CH_3$ | H | C(O)cyclo-Pr |
| 2.063 | 0 | C—H | C—H | O | $CH_3$ | $CH_3$ | H |
| 2.064 | 0 | C—F | C—H | O | $CH_3$ | $CH_3$ | H |
| 2.065 | 1 | C—F | C—H | O | $CH_3$ | $CH_3$ | H |
| 2.066 | 1 | C—H | C—H | O | $CH_3$ | $CH_3$ | H |
| 2.067 | 0 | N | C—H | O | $CH_3$ | $CH_3$ | H |
| 2.068 | 0 | C—H | N | O | $CH_3$ | $CH_3$ | H |
| 2.069 | 0 | C—H | C—H | O | $CH_3$ | $CF_3$ | H |
| 2.070 | 0 | C—F | C—H | O | $CH_3$ | $CF_3$ | H |
| 2.071 | 1 | C—F | C—H | O | $CH_3$ | $CF_3$ | H |
| 2.072 | 1 | C—H | C—H | O | $CH_3$ | $CF_3$ | H |
| 2.073 | 0 | N | C—H | O | $CH_3$ | $CF_3$ | H |
| 2.074 | 0 | C—H | N | O | $CH_3$ | $CF_3$ | H |
| 2.075 | 0 | C—H | C—H | O | Et | H | H |
| 2.076 | 0 | C—F | C—H | O | Et | H | H |
| 2.077 | 1 | C—F | C—H | O | Et | H | H |
| 2.078 | 1 | C—H | C—H | O | Et | H | H |
| 2.079 | 0 | N | C—H | O | Et | H | H |
| 2.080 | 0 | C—H | N | O | Et | H | H |
| 2.081 | 0 | C—H | C—H | O | $CH_2CF_3$ | H | H |

TABLE 2-continued

|  | n | Y | W | X | A$^1$ | A$^2$ | R$^2$ |
|---|---|---|---|---|---|---|---|
| 2.081 | 0 | C—F | C—H | O | CH$_2$CF$_3$ | H | H |
| 2.082 | 1 | C—F | C—H | O | CH$_2$CF$_3$ | H | H |
| 2.083 | 1 | C—H | C—H | O | CH$_2$CF$_3$ | H | H |
| 2.084 | 0 | N | C—H | O | CH$_2$CF$_3$ | H | H |
| 2.085 | 0 | C—H | N | O | CH$_2$CF$_3$ | H | H |
| 2.086 | 0 | C—H | C—H | O | t-Bu | H | H |
| 2.087 | 0 | C—F | C—H | O | t-Bu | H | H |
| 2.088 | 1 | C—F | C—H | O | t-Bu | H | H |
| 2.089 | 1 | C—H | C—H | O | t-Bu | H | H |
| 2.090 | 0 | N | C—H | O | t-Bu | H | H |
| 2.091 | 0 | C—H | N | O | t-Bu | H | H |
| 2.092 | 0 | C—H | C—H | O | 3,5-Cl$_2$C$_6$H$_3$ | H | H |
| 2.093 | 0 | C—F | C—H | O | 3,5-Cl$_2$C$_6$H$_3$ | H | H |
| 2.094 | 1 | C—F | C—H | O | 3,5-Cl$_2$C$_6$H$_3$ | H | H |
| 2.095 | 1 | C—H | C—H | O | 3,5-Cl$_2$C$_6$H$_3$ | H | H |
| 2.096 | 0 | N | C—H | O | 3,5-Cl$_2$C$_6$H$_3$ | H | H |
| 2.097 | 0 | C—H | N | O | 3,5-Cl$_2$C$_6$H$_3$ | H | H |
| 2.099 | 0 | C—H | C—H | O | CH$_2$-2,6-Cl$_2$C$_6$H$_3$ | H | H |
| 2.100 | 0 | C—F | C—H | O | CH$_2$-2,6-Cl$_2$C$_6$H$_3$ | H | H |
| 2.101 | 1 | C—F | C—H | O | CH$_2$-2,6-Cl$_2$C$_6$H$_3$ | H | H |
| 2.102 | 1 | C—H | C—H | O | CH$_2$-2,6-Cl$_2$C$_6$H$_3$ | H | H |
| 2.103 | 0 | N | C—H | O | CH$_2$-2,6-Cl$_2$C$_6$H$_3$ | H | H |
| 2.104 | 0 | C—H | N | O | CH$_2$-2,6-Cl$_2$C$_6$H$_3$ | H | H |
| 2.105 | 0 | C—H | C—H | O | H | H | H |
| 2.106 | 0 | C—F | C—H | O | H | H | H |
| 2.107 | 1 | C—F | C—H | O | H | H | H |
| 2.108 | 1 | C—H | C—H | O | H | H | H |
| 2.109 | 0 | N | C—H | O | H | H | H |
| 2.110 | 0 | C—H | N | O | H | H | H |
| 2.111 | 0 | C—H | C—H | N—Me | Me | H | H |
| 2.112 | 0 | C—F | C—H | N—Me | Me | H | H |
| 2.113 | 1 | C—F | C—H | N—Me | Me | H | H |
| 2.114 | 1 | C—H | C—H | N—Me | Me | H | H |
| 2.115 | 0 | N | C—H | N—Me | Me | H | H |
| 2.116 | 0 | C—H | N | N—Me | Me | H | H |
| 2.117 | 0 | C—H | C—H | N—Me | Me | H | H |
| 2.118 | 0 | C—F | C—H | NH | Me | H | H |
| 2.119 | 1 | C—F | C—H | NH | Me | H | H |
| 2.120 | 1 | C—H | C—H | NH | Me | H | H |
| 2.121 | 0 | N | C—H | NH | Me | H | H |
| 2.122 | 0 | C—H | N | NH | Me | H | H |
| 2.123 | 0 | C—H | C—H | O | Me | t-Bu | H |
| 2.124 | 0 | C—F | C—H | O | Me | t-Bu | H |
| 2.125 | 1 | C—F | C—H | O | Me | t-Bu | H |
| 2.126 | 1 | C—H | C—H | O | Me | t-Bu | H |
| 2.127 | 0 | N | C—H | O | Me | t-Bu | H |
| 2.128 | 0 | C—H | N | O | Me | t-Bu | H |
| 2.129 | 0 | C—H | C—H | O | Me | 3,5-Cl$_2$C$_6$H$_3$ | H |
| 2.130 | 0 | C—F | C—H | O | Me | 3,5-Cl$_2$C$_6$H$_3$ | H |
| 2.131 | 1 | C—F | C—H | O | Me | 3,5-Cl$_2$C$_6$H$_3$ | H |
| 2.132 | 1 | C—H | C—H | O | Me | 3,5-Cl$_2$C$_6$H$_3$ | H |
| 2.133 | 0 | N | C—H | O | Me | 3,5-Cl$_2$C$_6$H$_3$ | H |
| 2.134 | 0 | C—H | N | O | Me | 3,5-Cl$_2$C$_6$H$_3$ | H |
| 2.135 | 0 | C—H | C—H | O | Me | Et | H |
| 2.136 | 0 | C—F | C—H | O | Me | Et | H |
| 2.137 | 1 | C—F | C—H | O | Me | Et | H |
| 2.138 | 1 | C—H | C—H | O | Me | Et | H |
| 2.139 | 0 | N | C—H | O | Me | Et | H |
| 2.140 | 0 | C—H | N | O | Me | Et | H |

TABLE 3

| | n | Y | W | X | B$^1$ | B$^2$ | R$^2$ |
|---|---|---|---|---|---|---|---|
| 3.001 | 0 | C—H | C—H | O | CMe$_2$ | CH$_2$ | H |
| 3.002 | 0 | C—F | C—H | O | CMe$_2$ | CH$_2$ | H |
| 3.003 | 1 | C—F | C—H | O | CMe$_2$ | CH$_2$ | H |
| 3.004 | 0 | C—Cl | C—H | O | CMe$_2$ | CH$_2$ | H |
| 3.005 | 0 | C—Br | C—H | O | CMe$_2$ | CH$_2$ | H |
| 3.006 | 0 | C—CH$_3$ | C—H | O | CMe$_2$ | CH$_2$ | H |
| 3.007 | 0 | C—CF$_3$ | C—H | O | CMe$_2$ | CH$_2$ | H |
| 3.008 | 0 | C-cyclo-Pr | C—H | O | CMe$_2$ | CH$_2$ | H |
| 3.009 | 0 | C—C≡N | C—H | O | CMe$_2$ | CH$_2$ | H |
| 3.010 | 0 | C—C≡CH | C—H | O | CMe$_2$ | CH$_2$ | H |
| 3.011 | 0 | C—CH=CH$_2$ | C—H | O | CMe$_2$ | CH$_2$ | H |
| 3.012 | 1 | C—H | C—H | O | CMe$_2$ | CH$_2$ | H |
| 3.013 | 0 | N | C—H | O | CMe$_2$ | CH$_2$ | H |
| 3.014 | 0 | C—H | N | O | CMe$_2$ | CH$_2$ | H |
| 3.015 | 0 | C—H | C—H | O | CMe$_2$ | CH$_2$ | C(O)CH$_3$ |
| 3.016 | 0 | C—F | C—H | O | CMe$_2$ | CH$_2$ | C(O)CH$_3$ |
| 3.017 | 1 | C—F | C—H | O | CMe$_2$ | CH$_2$ | C(O)CH$_3$ |
| 3.018 | 1 | C—H | C—H | O | CMe$_2$ | CH$_2$ | C(O)CH$_3$ |
| 3.019 | 0 | N | C—H | O | CMe$_2$ | CH$_2$ | C(O)CH$_3$ |
| 3.020 | 0 | C—H | N | O | CMe$_2$ | CH$_2$ | C(O)CH$_3$ |
| 3.021 | 0 | C—H | C—H | O | CMe$_2$ | CH$_2$ | C(O)Ot-Bu |
| 3.022 | 0 | C—F | C—H | O | CMe$_2$ | CH$_2$ | C(O)Ot-Bu |
| 3.023 | 1 | C—F | C—H | O | CMe$_2$ | CH$_2$ | C(O)Ot-Bu |
| 3.024 | 1 | C—H | C—H | O | CMe$_2$ | CH$_2$ | C(O)Ot-Bu |
| 3.025 | 0 | N | C—H | O | CMe$_2$ | CH$_2$ | C(O)Ot-Bu |
| 3.026 | 0 | C—H | N | O | CMe$_2$ | CH$_2$ | C(O)Ot-Bu |
| 3.027 | 0 | C—H | C—H | O | CMe$_2$ | CH$_2$ | C(O)OCH$_2$Ph |
| 3.028 | 0 | C—F | C—H | O | CMe$_2$ | CH$_2$ | C(O)OCH$_2$Ph |
| 3.029 | 1 | C—F | C—H | O | CMe$_2$ | CH$_2$ | C(O)OCH$_2$Ph |
| 3.030 | 1 | C—H | C—H | O | CMe$_2$ | CH$_2$ | C(O)OCH$_2$Ph |
| 3.031 | 0 | N | C—H | O | CMe$_2$ | CH$_2$ | C(O)OCH$_2$Ph |
| 3.032 | 0 | C—H | N | O | CMe$_2$ | CH$_2$ | C(O)OCH$_2$Ph |
| 3.033 | 0 | C—H | C—H | O | CMe$_2$ | CH$_2$ | C(O)OEt |
| 3.034 | 0 | C—F | C—H | O | CMe$_2$ | CH$_2$ | C(O)OEt |
| 3.035 | 1 | C—F | C—H | O | CMe$_2$ | CH$_2$ | C(O)OEt |
| 3.036 | 1 | C—H | C—H | O | CMe$_2$ | CH$_2$ | C(O)OEt |
| 3.037 | 0 | N | C—H | O | CMe$_2$ | CH$_2$ | C(O)OEt |
| 3.038 | 0 | C—H | N | O | CMe$_2$ | CH$_2$ | C(O)OEt |
| 3.039 | 0 | C—H | C—H | O | CMe$_2$ | CH$_2$ | C(O)O(CH$_2$)$_2$OCH$_3$ |
| 3.040 | 0 | C—F | C—H | O | CMe$_2$ | CH$_2$ | C(O)O(CH$_2$)$_2$OCH$_3$ |
| 3.041 | 1 | C—F | C—H | O | CMe$_2$ | CH$_2$ | C(O)O(CH$_2$)$_2$OCH$_3$ |
| 3.042 | 1 | C—H | C—H | O | CMe$_2$ | CH$_2$ | C(O)O(CH$_2$)$_2$OCH$_3$ |
| 3.043 | 0 | N | C—H | O | CMe$_2$ | CH$_2$ | C(O)O(CH$_2$)$_2$OCH$_3$ |
| 3.043 | 0 | C—H | N | O | CMe$_2$ | CH$_2$ | C(O)O(CH$_2$)$_2$OCH$_3$ |
| 3.044 | 0 | C—H | C—H | O | CMe$_2$ | CH$_2$ | C(O)iso-Butyl |
| 3.045 | 0 | C—F | C—H | O | CMe$_2$ | CH$_2$ | C(O)iso-Butyl |
| 3.046 | 1 | C—F | C—H | O | CMe$_2$ | CH$_2$ | C(O)iso-Butyl |
| 3.047 | 1 | C—H | C—H | O | CMe$_2$ | CH$_2$ | C(O)iso-Butyl |
| 3.048 | 0 | N | C—H | O | CMe$_2$ | CH$_2$ | C(O)iso-Butyl |
| 3.049 | 0 | C—H | N | O | CMe$_2$ | CH$_2$ | C(O)iso-Butyl |
| 3.050 | 0 | C—H | C—H | O | CMe$_2$ | CH$_2$ | C(O)iso-Propyl |
| 3.051 | 0 | C—F | C—H | O | CMe$_2$ | CH$_2$ | C(O)iso-Propyl |
| 3.052 | 1 | C—F | C—H | O | CMe$_2$ | CH$_2$ | C(O)iso-Propyl |
| 3.053 | 1 | C—H | C—H | O | CMe$_2$ | CH$_2$ | C(O)iso-Propyl |
| 3.054 | 0 | N | C—H | O | CMe$_2$ | CH$_2$ | C(O)iso-Propyl |
| 3.055 | 0 | CH | N | O | CMe$_2$ | CH$_2$ | C(O)iso-Propyl |
| 3.056 | 0 | C—H | C—H | O | CMe$_2$ | CH$_2$ | C(O)cyclo-Pr |
| 3.057 | 0 | C—F | C—H | O | CMe$_2$ | CH$_2$ | C(O)cyclo-Pr |
| 3.058 | 1 | C—F | C—H | O | CMe$_2$ | CH$_2$ | C(O)cyclo-Pr |
| 3.059 | 1 | C—H | C—H | O | CMe$_2$ | CH$_2$ | C(O)cyclo-Pr |
| 3.060 | 0 | N | C—H | O | CMe$_2$ | CH$_2$ | C(O)cyclo-Pr |
| 3.061 | 0 | C—H | N | O | CMe$_2$ | CH$_2$ | C(O)cyclo-Pr |
| 3.062 | 0 | C—H | C—H | O | CHMe | CH$_2$ | H |
| 3.063 | 0 | C—F | C—H | O | CHMe | CH$_2$ | H |
| 3.064 | 1 | C—F | C—H | O | CHMe | CH$_2$ | H |
| 3.065 | 1 | C—H | C—H | O | CHMe | CH$_2$ | H |
| 3.066 | 0 | N | C—H | O | CHMe | CH$_2$ | H |

TABLE 3-continued

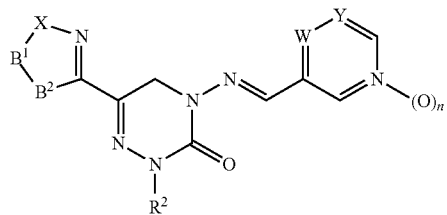

|  | n | Y | W | X | B¹ | B² | R² |
|---|---|---|---|---|---|---|---|
| 3.067 | 0 | C—H | N | O | CHMe | CH₂ | H |
| 3.068 | 0 | C—H | C—H | O | C(CF₃)Me | CH₂ | H |
| 3.069 | 0 | C—F | C—H | O | C(CF₃)Me | CH₂ | H |
| 3.070 | 1 | C—F | C—H | O | C(CF₃)Me | CH₂ | H |
| 3.071 | 1 | C—H | C—H | O | C(CF₃)Me | CH₂ | H |
| 3.072 | 0 | N | C—H | O | C(CF₃)Me | CH₂ | H |
| 3.073 | 0 | C—H | N | O | C(CF₃)Me | CH₂ | H |
| 3.074 | 0 | C—H | C—H | O | CEt₂ | CH₂ | H |
| 3.075 | 0 | C—F | C—H | O | CEt₂ | CH₂ | H |
| 3.076 | 1 | C—F | C—H | O | CEt₂ | CH₂ | H |
| 3.076 | 1 | C—H | C—H | O | CEt₂ | CH₂ | H |
| 3.077 | 0 | N | C—H | O | CEt₂ | CH₂ | H |
| 3.078 | 0 | C—H | N | O | CEt₂ | CH₂ | H |
| 3.079 | 0 | C—H | C—H | O | C(CF₃)₂ | CH₂ | H |
| 3.080 | 0 | C—F | C—H | O | C(CF₃)₂ | CH₂ | H |
| 3.081 | 1 | C—F | C—H | O | C(CF₃)₂ | CH₂ | H |
| 3.082 | 1 | C—H | C—H | O | C(CF₃)₂ | CH₂ | H |
| 3.083 | 0 | N | C—H | O | C(CF₃)₂ | CH₂ | H |
| 3.084 | 0 | C—H | N | O | C(CF₃)₂ | CH₂ | H |
| 3.085 | 0 | C—H | C—H | O | C(CF₃)₂ | CH₂ | C(O)CH₃ |
| 3.086 | 0 | C—F | C—H | O | C(CF₃)₂ | CH₂ | C(O)CH₃ |
| 3.087 | 0 | C—H | C—H | O | CH(CF₃) | CH₂ | H |
| 3.088 | 0 | C—F | C—H | O | CH(CF₃) | CH₂ | H |
| 3.089 | 1 | C—F | C—H | O | CH(CF₃) | CH₂ | H |
| 3.090 | 1 | C—H | C—H | O | CH(CF₃) | CH₂ | H |
| 3.091 | 0 | N | C—H | O | CH(CF₃) | CH₂ | H |
| 3.092 | 0 | C—H | N | O | CH(CF₃) | CH₂ | H |
| 3.093 | 0 | C—H | C—H | O | CH(3,5-Cl₂C₆H₃) | CH₂ | H |
| 3.094 | 0 | C—F | C—H | O | CH(3,5-Cl₂C₆H₃) | CH₂ | H |
| 3.095 | 1 | C—F | C—H | O | CH(3,5-Cl₂C₆H₃) | CH₂ | H |
| 3.096 | 1 | C—H | C—H | O | CH(3,5-Cl₂C₆H₃) | CH₂ | H |
| 3.097 | 0 | N | C—H | O | CH(3,5-Cl₂C₆H₃) | CH₂ | H |
| 3.098 | 0 | C—H | N | O | CH(3,5-Cl₂C₆H₃) | CH₂ | H |
| 3.099 | 0 | C—H | C—H | O | CH(2,6-Cl₂C₆H₃) | CH₂ | H |
| 3.100 | 0 | C—F | C—H | O | CH(2,6-Cl₂C₆H₃) | CH₂ | H |
| 3.101 | 1 | C—F | C—H | O | CH(2,6-Cl₂C₆H₃) | CH₂ | H |
| 3.102 | 1 | C—H | C—H | O | CH(2,6-Cl₂C₆H₃) | CH₂ | H |
| 3.103 | 0 | N | C—H | O | CH(2,6-Cl₂C₆H₃) | CH₂ | H |
| 3.104 | 0 | C—H | N | O | CH(2,6-Cl₂C₆H₃) | CH₂ | H |
| 3.105 | 0 | C—H | C—H | O | CH(2-pyridyl) | CH₂ | H |
| 3.106 | 0 | C—F | C—H | O | CH(2-pyridyl) | CH₂ | H |
| 3.107 | 1 | C—F | C—H | O | CH(2-pyridyl) | CH₂ | H |
| 3.108 | 1 | C—H | C—H | O | CH(2-pyridyl) | CH₂ | H |
| 3.109 | 0 | N | C—H | O | CH(2-pyridyl) | CH₂ | H |
| 3.110 | 0 | C—H | N | O | CH(2-pyridyl) | CH₂ | H |
| 3.111 | 0 | C—H | C—H | O | CMe(3,5-Cl₂C₆H₃) | CH₂ | H |
| 3.112 | 0 | C—F | C—H | O | CMe(3,5-Cl₂C₆H₃) | CH₂ | H |
| 3.113 | 1 | C—F | C—H | O | CMe(3,5-Cl₂C₆H₃) | CH₂ | H |
| 3.114 | 1 | C—H | C—H | O | CMe(3,5-Cl₂C₆H₃) | CH₂ | H |
| 3.115 | 0 | N | C—H | O | CMe(3,5-Cl₂C₆H₃) | CH₂ | H |
| 3.116 | 0 | C—H | N | O | CMe(3,5-Cl₂C₆H₃) | CH₂ | H |
| 3.117 | 0 | C—H | C—H | O | C(CF₃)(3,5-Cl₂C₆H₃) | CH₂ | H |
| 3.118 | 0 | C—F | C—H | O | C(CF₃)(3,5-Cl₂C₆H₃) | CH₂ | H |
| 3.119 | 1 | C—F | C—H | O | C(CF₃)(3,5-Cl₂C₆H₃) | CH₂ | H |
| 3.120 | 1 | C—H | C—H | O | C(CF₃)(3,5-Cl₂C₆H₃) | CH₂ | H |
| 3.121 | 0 | N | C—H | O | C(CF₃)(3,5-Cl₂C₆H₃) | CH₂ | H |
| 3.122 | 0 | C—H | N | O | C(CF₃)(3,5-Cl₂C₆H₃) | CH₂ | H |
| 3.123 | 0 | C—H | C—H | O | C(CH₂)₂ | CH₂ | H |
| 3.124 | 0 | C—F | C—H | O | C(CH₂)₂ | CH₂ | H |
| 3.125 | 1 | C—F | C—H | O | C(CH₂)₂ | CH₂ | H |
| 3.126 | 1 | C—H | C—H | O | C(CH₂)₂ | CH₂ | H |
| 3.127 | 0 | N | C—H | O | C(CH₂)₂ | CH₂ | H |
| 3.128 | 0 | C—H | N | O | C(CH₂)₂ | CH₂ | H |
| 3.129 | 0 | C—H | C—H | O | C(CH₂)₃ | CH₂ | H |
| 3.130 | 0 | C—F | C—H | O | C(CH₂)₃ | CH₂ | H |
| 3.131 | 1 | C—F | C—H | O | C(CH₂)₃ | CH₂ | H |
| 3.132 | 1 | C—H | C—H | O | C(CH₂)₃ | CH₂ | H |

TABLE 3-continued

| | n | Y | W | X | B¹ | B² | R² |
|---|---|---|---|---|---|---|---|
| 3.133 | 0 | N | C—H | O | C(CH$_2$)$_3$ | CH$_2$ | H |
| 3.134 | 0 | C—H | N | O | C(CH$_2$)$_3$ | CH$_2$ | H |
| 3.135 | 0 | C—H | C—H | O | C(CH$_2$)$_4$ | CH$_2$ | H |
| 3.136 | 0 | C—F | C—H | O | C(CH$_2$)$_4$ | CH$_2$ | H |
| 3.137 | 1 | C—F | C—H | O | C(CH$_2$)$_4$ | CH$_2$ | H |
| 3.138 | 1 | C—H | C—H | O | C(CH$_2$)$_4$ | CH$_2$ | H |
| 3.139 | 0 | N | C—H | O | C(CH$_2$)$_4$ | CH$_2$ | H |
| 3.140 | 0 | C—H | N | O | C(CH$_2$)$_4$ | CH$_2$ | H |
| 3.141 | 0 | C—H | C—H | O | CMeEt | CH$_2$ | H |
| 3.142 | 0 | C—F | C—H | O | CMeEt | CH$_2$ | H |
| 3.143 | 1 | C—F | C—H | O | CMeEt | CH$_2$ | H |
| 3.144 | 1 | C—H | C—H | O | CMeEt | CH$_2$ | H |
| 3.145 | 0 | N | C—H | O | CMeEt | CH$_2$ | H |
| 3.146 | 0 | C—H | N | O | CMeEt | CH$_2$ | H |
| 3.147 | 0 | C—H | C—H | O | CH(4-ClC$_6$H$_4$) | CH$_2$ | H |
| 3.148 | 0 | C—F | C—H | O | CH(4-ClC$_6$H$_4$) | CH$_2$ | H |
| 3.149 | 1 | C—F | C—H | O | CH(4-ClC$_6$H$_4$) | CH$_2$ | H |
| 3.150 | 1 | C—H | C—H | O | CH(4-ClC$_6$H$_4$) | CH$_2$ | H |
| 3.151 | 0 | N | C—H | O | CH(4-ClC$_6$H$_4$) | CH$_2$ | H |
| 3.152 | 0 | C—H | N | O | CH(4-ClC$_6$H$_4$) | CH$_2$ | H |
| 3.153 | 0 | C—H | C—H | NMe | CMe$_2$ | CH$_2$ | H |
| 3.154 | 0 | C—F | C—H | NMe | CMe$_2$ | CH$_2$ | H |
| 3.155 | 1 | C—F | C—H | NMe | CMe$_2$ | CH$_2$ | H |
| 3.156 | 1 | C—H | C—H | NMe | CMe$_2$ | CH$_2$ | H |
| 3.157 | 0 | N | C—H | NMe | CMe$_2$ | CH$_2$ | H |
| 3.158 | 0 | C—H | N | NMe | CMe$_2$ | CH$_2$ | H |
| 3.159 | 0 | C—H | C—H | O | CMe$_2$ | O | H |
| 3.160 | 0 | C—F | C—H | O | CMe$_2$ | O | H |
| 3.161 | 1 | C—F | C—H | O | CMe$_2$ | O | H |
| 3.162 | 1 | C—H | C—H | O | CMe$_2$ | O | H |
| 3.163 | 0 | N | C—H | O | CMe$_2$ | O | H |
| 3.164 | 0 | C—H | N | O | CMe$_2$ | O | H |
| 3.165 | 0 | C—H | C—H | O | CMe$_2$ | NH | H |
| 3.166 | 0 | C—F | C—H | O | CMe$_2$ | NH | H |
| 3.167 | 1 | C—F | C—H | O | CMe$_2$ | NH | H |
| 3.168 | 1 | C—H | C—H | O | CMe$_2$ | NH | H |
| 3.169 | 0 | N | C—H | O | CMe$_2$ | NH | H |
| 3.170 | 0 | C—H | N | O | CMe$_2$ | NH | H |
| 3.171 | 0 | C—C(O)OMe | C—H | O | CMe$_2$ | CH$_2$ | H |
| 3.172 | 0 | C—OH | C—H | O | CMe$_2$ | CH$_2$ | H |
| 3.173 | 0 | C—H | C—H | O | CMe$_2$ | CH$_2$ | prop-2-ynyl |
| 3.174 | 0 | C—F | C—H | O | CMe$_2$ | CH$_2$ | prop-2-ynyl |
| 3.175 | 1 | C—F | C—H | O | CMe$_2$ | CH$_2$ | prop-2-ynyl |
| 3.176 | 1 | C—H | C—H | O | CMe$_2$ | CH$_2$ | prop-2-ynyl |
| 3.176 | 0 | N | C—H | O | CMe$_2$ | CH$_2$ | prop-2-ynyl |
| 3.177 | 0 | C—H | N | O | CMe$_2$ | CH$_2$ | prop-2-ynyl |
| 3.178 | 0 | C—H | C—H | O | CMe$_2$ | CH$_2$ | allyl |
| 3.179 | 0 | C—F | C—H | O | CMe$_2$ | CH$_2$ | allyl |
| 3.180 | 1 | C—F | C—H | O | CMe$_2$ | CH$_2$ | allyl |
| 3.181 | 1 | C—H | C—H | O | CMe$_2$ | CH$_2$ | allyl |
| 3.182 | 0 | N | C—H | O | CMe$_2$ | CH$_2$ | allyl |
| 3.183 | 0 | C—H | N | O | CMe$_2$ | CH$_2$ | allyl |
| 3.184 | 0 | C—H | C—H | O | CMe$_2$ | CH$_2$ | cyanomethyl |
| 3.185 | 0 | C—F | C—H | O | CMe$_2$ | CH$_2$ | cyanomethyl |
| 3.186 | 1 | C—F | C—H | O | CMe$_2$ | CH$_2$ | cyanomethyl |
| 3.187 | 1 | C—H | C—H | O | CMe$_2$ | CH$_2$ | cyanomethyl |
| 3.188 | 0 | N | C—H | O | CMe$_2$ | CH$_2$ | cyanomethyl |
| 3.189 | 0 | C—H | N | O | CMe$_2$ | CH$_2$ | cyanomethyl |
| 3.190 | 0 | C—H | C—H | O | CMe$_2$ | CH$_2$ | CH$_2$C(O)OEt |
| 3.191 | 0 | C—F | C—H | O | CMe$_2$ | CH$_2$ | CH$_2$C(O)OEt |
| 3.192 | 1 | C—F | C—H | O | CMe$_2$ | CH$_2$ | CH$_2$C(O)OEt |
| 3.193 | 1 | C—H | C—H | O | CMe$_2$ | CH$_2$ | CH$_2$C(O)OEt |
| 3.194 | 0 | N | C—H | O | CMe$_2$ | CH$_2$ | CH$_2$C(O)OEt |
| 3.195 | 0 | C—H | N | O | CMe$_2$ | CH$_2$ | CH$_2$C(O)OEt |
| 3.196 | 0 | C—H | C—H | O | CMe$_2$ | CH$_2$ | ethoxymethyl |
| 3.197 | 0 | C—F | C—H | O | CMe$_2$ | CH$_2$ | ethoxymethyl |
| 3.198 | 1 | C—F | C—H | O | CMe$_2$ | CH$_2$ | ethoxymethyl |

TABLE 3-continued

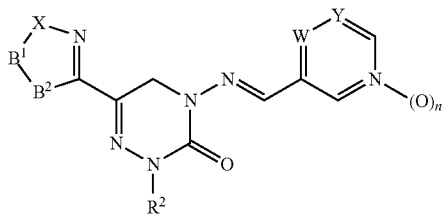

| | n | Y | W | X | B$^1$ | B$^2$ | R$^2$ |
|---|---|---|---|---|---|---|---|
| 3.199 | 1 | C—H | C—H | O | CMe$_2$ | CH$_2$ | ethoxymethyl |
| 3.200 | 0 | N | C—H | O | CMe$_2$ | CH$_2$ | ethoxymethyl |
| 3.201 | 0 | C—H | N | O | CMe$_2$ | CH$_2$ | ethoxymethyl |
| 3.202 | 0 | C—H | C—H | O | CMe$_2$ | CH$_2$ | C(O)(CH$_2$)$_2$CO$_2$Me |
| 3.203 | 0 | C—F | C—H | O | CMe$_2$ | CH$_2$ | C(O)(CH$_2$)$_2$CO$_2$Me |
| 3.204 | 1 | C—F | C—H | O | CMe$_2$ | CH$_2$ | C(O)(CH$_2$)$_2$CO$_2$Me |
| 3.205 | 1 | C—H | C—H | O | CMe$_2$ | CH$_2$ | C(O)(CH$_2$)$_2$CO$_2$Me |
| 3.206 | 0 | N | C—H | O | CMe$_2$ | CH$_2$ | C(O)(CH$_2$)$_2$CO$_2$Me |
| 3.207 | 0 | C—H | N | O | CMe$_2$ | CH$_2$ | C(O)(CH$_2$)$_2$CO$_2$Me |
| 3.208 | 0 | C—H | C—H | O | CMe$_2$ | CH$_2$ | 2-nitrobenzyl |
| 3.209 | 0 | C—F | C—H | O | CMe$_2$ | CH$_2$ | 2-nitrobenzyl |
| 3.210 | 1 | C—F | C—H | O | CMe$_2$ | CH$_2$ | 2-nitrobenzyl |
| 3.211 | 1 | C—H | C—H | O | CMe$_2$ | CH$_2$ | 2-nitrobenzyl |
| 3.212 | 0 | N | C—H | O | CMe$_2$ | CH$_2$ | 2-nitrobenzyl |
| 3.213 | 0 | C—H | N | O | CMe$_2$ | CH$_2$ | 2-nitrobenzyl |

TABLE 4

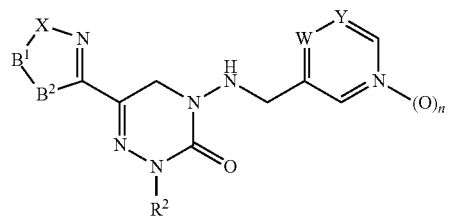

| | n | Y | W | X | B$^1$ | B$^2$ | R$^2$ |
|---|---|---|---|---|---|---|---|
| 4.001 | 0 | C—H | C—H | O | CMe$_2$ | CH$_2$ | H |
| 4.002 | 0 | C—F | C—H | O | CMe$_2$ | CH$_2$ | H |
| 4.003 | 1 | C—F | C—H | O | CMe$_2$ | CH$_2$ | H |
| 4.004 | 0 | C—Cl | C—H | O | CMe$_2$ | CH$_2$ | H |
| 4.005 | 0 | C—Br | C—H | O | CMe$_2$ | CH$_2$ | H |
| 4.006 | 0 | C—CH$_3$ | C—H | O | CMe$_2$ | CH$_2$ | H |
| 4.007 | 0 | C—CF$_3$ | C—H | O | CMe$_2$ | CH$_2$ | H |
| 4.008 | 0 | C-cyclo-Pr | C—H | O | CMe$_2$ | CH$_2$ | H |
| 4.009 | 0 | C—C≡N | C—H | O | CMe$_2$ | CH$_2$ | H |
| 4.010 | 0 | C—C≡CH | C—H | O | CMe$_2$ | CH$_2$ | H |
| 4.011 | 0 | C—CH=CH$_2$ | C—H | O | CMe$_2$ | CH$_2$ | H |
| 4.012 | 1 | C—H | C—H | O | CMe$_2$ | CH$_2$ | H |
| 4.013 | 0 | N | C—H | O | CMe$_2$ | CH$_2$ | H |
| 4.014 | 0 | C—H | N | O | CMe$_2$ | CH$_2$ | H |
| 4.015 | 0 | C—H | C—H | O | CMe$_2$ | CH$_2$ | C(O)CH$_3$ |
| 4.016 | 0 | C—F | C—H | O | CMe$_2$ | CH$_2$ | C(O)CH$_3$ |
| 4.017 | 1 | C—F | C—H | O | CMe$_2$ | CH$_2$ | C(O)CH$_3$ |
| 4.018 | 1 | C—H | C—H | O | CMe$_2$ | CH$_2$ | C(O)CH$_3$ |
| 4.019 | 0 | N | C—H | O | CMe$_2$ | CH$_2$ | C(O)CH$_3$ |
| 4.020 | 0 | C—H | N | O | CMe$_2$ | CH$_2$ | C(O)CH$_3$ |
| 4.021 | 0 | C—H | C—H | O | CMe$_2$ | CH$_2$ | C(O)Ot-Bu |
| 4.022 | 0 | C—F | C—H | O | CMe$_2$ | CH$_2$ | C(O)Ot-Bu |
| 4.023 | 1 | C—F | C—H | O | CMe$_2$ | CH$_2$ | C(O)Ot-Bu |
| 4.024 | 1 | C—H | C—H | O | CMe$_2$ | CH$_2$ | C(O)Ot-Bu |
| 4.025 | 0 | N | C—H | O | CMe$_2$ | CH$_2$ | C(O)Ot-Bu |
| 4.026 | 0 | C—H | N | O | CMe$_2$ | CH$_2$ | C(O)Ot-Bu |
| 4.027 | 0 | C—H | C—H | O | CMe$_2$ | CH$_2$ | C(O)OCH$_2$Ph |
| 4.028 | 0 | C—F | C—H | O | CMe$_2$ | CH$_2$ | C(O)OCH$_2$Ph |
| 4.029 | 1 | C—F | C—H | O | CMe$_2$ | CH$_2$ | C(O)OCH$_2$Ph |
| 4.030 | 1 | C—H | C—H | O | CMe$_2$ | CH$_2$ | C(O)OCH$_2$Ph |
| 4.031 | 0 | N | C—H | O | CMe$_2$ | CH$_2$ | C(O)OCH$_2$Ph |
| 4.032 | 0 | C—H | N | O | CMe$_2$ | CH$_2$ | C(O)OCH$_2$Ph |
| 4.033 | 0 | C—H | C—H | O | CMe$_2$ | CH$_2$ | C(O)OEt |
| 4.034 | 0 | C—F | C—H | O | CMe$_2$ | CH$_2$ | C(O)OEt |

TABLE 4-continued

|  | n | Y | W | X | B$^1$ | B$^2$ | R$^2$ |
|---|---|---|---|---|---|---|---|
| 4.035 | 1 | C—F | C—H | O | CMe$_2$ | CH$_2$ | C(O)OEt |
| 4.036 | 1 | C—H | C—H | O | CMe$_2$ | CH$_2$ | C(O)OEt |
| 4.037 | 0 | N | C—H | O | CMe$_2$ | CH$_2$ | C(O)OEt |
| 4.038 | 0 | C—H | N | O | CMe$_2$ | CH$_2$ | C(O)OEt |
| 4.039 | 0 | C—H | C—H | O | CMe$_2$ | CH$_2$ | C(O)O(CH$_2$)$_2$OCH$_3$ |
| 4.040 | 0 | C—F | C—H | O | CMe$_2$ | CH$_2$ | C(O)O(CH$_2$)$_2$OCH$_3$ |
| 4.041 | 1 | C—F | C—H | O | CMe$_2$ | CH$_2$ | C(O)O(CH$_2$)$_2$OCH$_3$ |
| 4.042 | 1 | C—H | C—H | O | CMe$_2$ | CH$_2$ | C(O)O(CH$_2$)$_2$OCH$_3$ |
| 4.043 | 0 | N | C—H | O | CMe$_2$ | CH$_2$ | C(O)O(CH$_2$)$_2$OCH$_3$ |
| 4.043 | 0 | C—H | N | O | CMe$_2$ | CH$_2$ | C(O)O(CH$_2$)$_2$OCH$_3$ |
| 4.044 | 0 | C—H | C—H | O | CMe$_2$ | CH$_2$ | C(O)iso-Butyl |
| 4.045 | 0 | C—F | C—H | O | CMe$_2$ | CH$_2$ | C(O)iso-Butyl |
| 4.046 | 1 | C—F | C—H | O | CMe$_2$ | CH$_2$ | C(O)iso-Butyl |
| 4.047 | 1 | C—H | C—H | O | CMe$_2$ | CH$_2$ | C(O)iso-Butyl |
| 4.048 | 0 | N | C—H | O | CMe$_2$ | CH$_2$ | C(O)iso-Butyl |
| 4.049 | 0 | C—H | N | O | CMe$_2$ | CH$_2$ | C(O)iso-Butyl |
| 4.050 | 0 | C—H | C—H | O | CMe$_2$ | CH$_2$ | C(O)iso-Propyl |
| 4.051 | 0 | C—F | C—H | O | CMe$_2$ | CH$_2$ | C(O)iso-Propyl |
| 4.052 | 1 | C—F | C—H | O | CMe$_2$ | CH$_2$ | C(O)iso-Propyl |
| 4.053 | 1 | C—H | C—H | O | CMe$_2$ | CH$_2$ | C(O)iso-Propyl |
| 4.054 | 0 | N | C—H | O | CMe$_2$ | CH$_2$ | C(O)iso-Propyl |
| 4.055 | 0 | C—H | N | O | CMe$_2$ | CH$_2$ | C(O)iso-Propyl |
| 4.056 | 0 | C—H | C—H | O | CMe$_2$ | CH$_2$ | C(O)cyclo-Pr |
| 4.057 | 0 | C—F | C—H | O | CMe$_2$ | CH$_2$ | C(O)cyclo-Pr |
| 4.058 | 1 | C—F | C—H | O | CMe$_2$ | CH$_2$ | C(O)cyclo-Pr |
| 4.059 | 1 | C—H | C—H | O | CMe$_2$ | CH$_2$ | C(O)cyclo-Pr |
| 4.060 | 0 | N | C—H | O | CMe$_2$ | CH$_2$ | C(O)cyclo-Pr |
| 4.061 | 0 | C—H | N | O | CMe$_2$ | CH$_2$ | C(O)cyclo-Pr |
| 4.062 | 0 | C—H | C—H | O | CHMe | CH$_2$ | H |
| 4.063 | 0 | C—F | C—H | O | CHMe | CH$_2$ | H |
| 4.064 | 1 | C—F | C—H | O | CHMe | CH$_2$ | H |
| 4.065 | 1 | C—H | C—H | O | CHMe | CH$_2$ | H |
| 4.066 | 0 | N | C—H | O | CHMe | CH$_2$ | H |
| 4.067 | 0 | C—H | N | O | CHMe | CH$_2$ | H |
| 4.068 | 0 | C—H | C—H | O | C(CF$_3$)Me | CH$_2$ | H |
| 4.069 | 0 | C—F | C—H | O | C(CF$_3$)Me | CH$_2$ | H |
| 4.070 | 1 | C—F | C—H | O | C(CF$_3$)Me | CH$_2$ | H |
| 4.071 | 1 | C—H | C—H | O | C(CF$_3$)Me | CH$_2$ | H |
| 4.072 | 0 | N | C—H | O | C(CF$_3$)Me | CH$_2$ | H |
| 4.073 | 0 | C—H | N | O | C(CF$_3$)Me | CH$_2$ | H |
| 4.074 | 0 | C—H | C—H | O | C(CF$_3$)$_2$ | CH$_2$ | H |
| 4.075 | 0 | C—F | C—H | O | C(CF$_3$)$_2$ | CH$_2$ | H |
| 4.076 | 1 | C—F | C—H | O | C(CF$_3$)$_2$ | CH$_2$ | H |
| 4.076 | 1 | C—H | C—H | O | C(CF$_3$)$_2$ | CH$_2$ | H |
| 4.077 | 0 | N | C—H | O | C(CF$_3$)$_2$ | CH$_2$ | H |
| 4.078 | 0 | C—H | N | O | C(CF$_3$)$_2$ | CH$_2$ | H |
| 4.079 | 0 | C—H | C—H | O | C(CF$_3$)$_2$ | CH$_2$ | C(O)CH$_3$ |
| 4.080 | 0 | C—F | C—H | O | C(CF$_3$)$_2$ | CH$_2$ | C(O)CH$_3$ |
| 4.081 | 0 | C—H | C—H | O | CH(CF$_3$) | CH$_2$ | H |
| 4.082 | 0 | C—H | C—H | O | CH(CF$_3$) | CH$_2$ | H |
| 4.083 | 1 | C—F | C—H | O | CH(CF$_3$) | CH$_2$ | H |
| 4.084 | 1 | C—H | C—H | O | CH(CF$_3$) | CH$_2$ | H |
| 4.085 | 0 | N | C—H | O | CH(CF$_3$) | CH$_2$ | H |
| 4.086 | 0 | C—H | N | O | CH(CF$_3$) | CH$_2$ | H |
| 4.087 | 0 | C—H | C—H | O | CH(3,5-Cl$_2$C$_6$H$_3$) | CH$_2$ | H |
| 4.088 | 0 | C—F | C—H | O | CH(3,5-Cl$_2$C$_6$H$_3$) | CH$_2$ | H |
| 4.089 | 1 | C—F | C—H | O | CH(3,5-Cl$_2$C$_6$H$_3$) | CH$_2$ | H |
| 4.090 | 1 | C—H | C—H | O | CH(3,5-Cl$_2$C$_6$H$_3$) | CH$_2$ | H |
| 4.091 | 0 | N | C—H | O | CH(3,5-Cl$_2$C$_6$H$_3$) | CH$_2$ | H |
| 4.092 | 0 | C—H | N | O | CH(3,5-Cl$_2$C$_6$H$_3$) | CH$_2$ | H |
| 4.093 | 0 | C—H | C—H | O | CH(2,6-Cl$_2$C$_6$H$_3$) | CH$_2$ | H |
| 4.094 | 0 | C—F | C—H | O | CH(2,6-Cl$_2$C$_6$H$_3$) | CH$_2$ | H |
| 4.095 | 1 | C—F | C—H | O | CH(2,6-Cl$_2$C$_6$H$_3$) | CH$_2$ | H |
| 4.096 | 1 | C—H | C—H | O | CH(2,6-Cl$_2$C$_6$H$_3$) | CH$_2$ | H |
| 4.097 | 0 | N | C—H | O | CH(2,6-Cl$_2$C$_6$H$_3$) | CH$_2$ | H |
| 4.098 | 0 | C—H | N | O | CH(2,6-Cl$_2$C$_6$H$_3$) | CH$_2$ | H |
| 4.099 | 0 | C—H | C—H | O | CMe(3,5-Cl$_2$C$_6$H$_3$) | CH$_2$ | H |

TABLE 4-continued

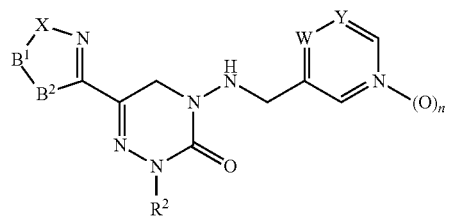

| | n | Y | W | X | B¹ | B² | R² |
|---|---|---|---|---|---|---|---|
| 4.100 | 0 | C—F | C—H | O | CMe(3,5-Cl$_2$C$_6$H$_3$) | CH$_2$ | H |
| 4.101 | 1 | C—F | C—H | O | CMe(3,5-Cl$_2$C$_6$H$_3$) | CH$_2$ | H |
| 4.102 | 1 | C—H | C—H | O | CMe(3,5-Cl$_2$C$_6$H$_3$) | CH$_2$ | H |
| 4.103 | 0 | N | C—H | O | CMe(3,5-Cl$_2$C$_6$H$_3$) | CH$_2$ | H |
| 4.104 | 0 | C—H | N | O | CMe(3,5-Cl$_2$C$_6$H$_3$) | CH$_2$ | H |
| 4.105 | 0 | C—H | C—H | O | C(CF$_3$)(3,5-Cl$_2$C$_6$H$_3$) | CH$_2$ | H |
| 4.106 | 0 | C—F | C—H | O | C(CF$_3$)(3,5-Cl$_2$C$_6$H$_3$) | CH$_2$ | H |
| 4.107 | 1 | C—F | C—H | O | C(CF$_3$)(3,5-Cl$_2$C$_6$H$_3$) | CH$_2$ | H |
| 4.108 | 1 | C—H | C—H | O | C(CF$_3$)(3,5-Cl$_2$C$_6$H$_3$) | CH$_2$ | H |
| 4.109 | 0 | N | C—H | O | C(CF$_3$)(3,5-Cl$_2$C$_6$H$_3$) | CH$_2$ | H |
| 4.110 | 0 | C—H | N | O | C(CF$_3$)(3,5-Cl$_2$C$_6$H$_3$) | CH$_2$ | H |
| 4.111 | 0 | C—H | C—H | O | C(CH$_2$)$_2$ | CH$_2$ | H |
| 4.112 | 0 | C—F | C—H | O | C(CH$_2$)$_2$ | CH$_2$ | H |
| 4.113 | 1 | C—F | C—H | O | C(CH$_2$)$_2$ | CH$_2$ | H |
| 4.114 | 1 | C—H | C—H | O | C(CH$_2$)$_2$ | CH$_2$ | H |
| 4.115 | 0 | N | C—H | O | C(CH$_2$)$_2$ | CH$_2$ | H |
| 4.116 | 0 | C—H | N | O | C(CH$_2$)$_2$ | CH$_2$ | H |
| 4.117 | 0 | C—H | C—H | NMe | CMe$_2$ | CH$_2$ | H |
| 4.118 | 0 | C—F | C—H | NMe | CMe$_2$ | CH$_2$ | H |
| 4.119 | 1 | C—F | C—H | NMe | CMe$_2$ | CH$_2$ | H |
| 4.120 | 1 | C—H | C—H | NMe | CMe$_2$ | CH$_2$ | H |
| 4.121 | 0 | N | C—H | NMe | CMe$_2$ | CH$_2$ | H |
| 4.122 | 0 | C—H | N | NMe | CMe$_2$ | CH$_2$ | H |
| 4.123 | 0 | C—H | C—H | O | CMe$_2$ | O | H |
| 4.124 | 0 | C—F | C—H | O | CMe$_2$ | O | H |
| 4.125 | 1 | C—F | C—H | O | CMe$_2$ | O | H |
| 4.126 | 1 | C—H | C—H | O | CMe$_2$ | O | H |
| 4.127 | 0 | N | C—H | O | CMe$_2$ | O | H |
| 4.128 | 0 | C—H | N | O | CMe$_2$ | O | H |
| 4.129 | 0 | C—H | C—H | O | CMe$_2$ | NH | H |
| 4.130 | 0 | C—F | C—H | O | CMe$_2$ | NH | H |
| 4.131 | 1 | C—F | C—H | O | CMe$_2$ | NH | H |
| 4.132 | 1 | C—H | C—H | O | CMe$_2$ | NH | H |
| 4.133 | 0 | N | C—H | O | CMe$_2$ | NH | H |
| 4.134 | 0 | C—H | N | O | CMe$_2$ | NH | H |

TABLE 5

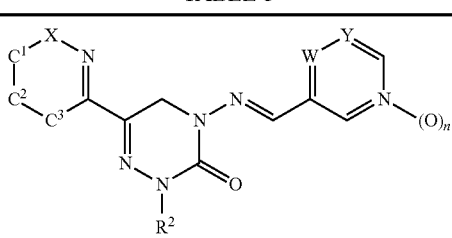

| | n | Y | W | X | C¹ | C² | C³ | R² |
|---|---|---|---|---|---|---|---|---|
| 5.001 | 0 | C—H | CH | O | CH$_2$ | CH$_2$ | O | H |
| 5.002 | 0 | C—F | CH | O | CH$_2$ | CH$_2$ | O | H |
| 5.003 | 1 | C—F | CH | O | CH$_2$ | CH$_2$ | O | H |
| 5.004 | 0 | C—Cl | CH | O | CH$_2$ | CH$_2$ | O | H |
| 5.005 | 0 | C—Br | CH | O | CH$_2$ | CH$_2$ | O | H |
| 5.006 | 0 | C—CH$_3$ | CH | O | CH$_2$ | CH$_2$ | O | H |
| 5.007 | 0 | C—CF$_3$ | CH | O | CH$_2$ | CH$_2$ | O | H |
| 5.008 | 0 | C-cyclo-Pr | CH | O | CH$_2$ | CH$_2$ | O | H |
| 5.009 | 0 | C—C≡N | CH | O | CH$_2$ | CH$_2$ | O | H |
| 5.010 | 0 | C—C≡CH | CH | O | CH$_2$ | CH$_2$ | O | H |
| 5.012 | 0 | C—CH═CH$_2$ | CH | O | CH$_2$ | CH$_2$ | O | H |
| 5.013 | 1 | C—H | CH | O | CH$_2$ | CH$_2$ | O | H |
| 5.014 | 0 | N | CH | O | CH$_2$ | CH$_2$ | O | H |

TABLE 5-continued

| | n | Y | W | X | C¹ | C² | C³ | R² |
|---|---|---|---|---|---|---|---|---|
| 5.015 | 0 | C—H | N | O | CH$_2$ | CH$_2$ | O | H |
| 5.016 | 0 | C—H | CH | O | CH$_2$ | CH$_2$ | O | C(O)CH$_3$ |
| 5.017 | 0 | C—F | CH | O | CH$_2$ | CH$_2$ | O | C(O)CH$_3$ |
| 5.018 | 1 | C—F | CH | O | CH$_2$ | CH$_2$ | O | C(O)CH$_3$ |
| 5.019 | 1 | C—H | CH | O | CH$_2$ | CH$_2$ | O | C(O)CH$_3$ |
| 5.020 | 0 | N | CH | O | CH$_2$ | CH$_2$ | O | C(O)CH$_3$ |
| 5.021 | 0 | C—H | N | O | CH$_2$ | CH$_2$ | O | C(O)CH$_3$ |
| 5.022 | 0 | C—H | CH | O | CH$_2$ | CH$_2$ | O | C(O)Ot-Bu |
| 5.023 | 0 | C—F | CH | O | CH$_2$ | CH$_2$ | O | C(O)Ot-Bu |
| 5.024 | 1 | C—F | CH | O | CH$_2$ | CH$_2$ | O | C(O)Ot-Bu |
| 5.025 | 1 | C—H | CH | O | CH$_2$ | CH$_2$ | O | C(O)Ot-Bu |
| 5.026 | 0 | N | CH | O | CH$_2$ | CH$_2$ | O | C(O)Ot-Bu |
| 5.027 | 0 | C—H | N | O | CH$_2$ | CH$_2$ | O | C(O)Ot-Bu |
| 5.028 | 0 | C—H | CH | O | CH$_2$ | CH$_2$ | O | C(O)OCH$_2$Ph |
| 5.029 | 0 | C—F | CH | O | CH$_2$ | CH$_2$ | O | C(O)OCH$_2$Ph |
| 5.030 | 1 | C—F | CH | O | CH$_2$ | CH$_2$ | O | C(O)OCH$_2$Ph |
| 5.031 | 1 | C—H | CH | O | CH$_2$ | CH$_2$ | O | C(O)OCH$_2$Ph |
| 5.033 | 0 | N | CH | O | CH$_2$ | CH$_2$ | O | C(O)OCH$_2$Ph |
| 5.034 | 0 | C—H | N | O | CH$_2$ | CH$_2$ | O | C(O)OCH$_2$Ph |
| 5.035 | 0 | C—H | CH | O | CH$_2$ | CH$_2$ | O | C(O)OEt |
| 5.036 | 0 | C—F | CH | O | CH$_2$ | CH$_2$ | O | C(O)OEt |
| 5.037 | 1 | C—F | CH | O | CH$_2$ | CH$_2$ | O | C(O)OEt |
| 5.038 | 1 | C—H | CH | O | CH$_2$ | CH$_2$ | O | C(O)OEt |
| 5.039 | 0 | N | CH | O | CH$_2$ | CH$_2$ | O | C(O)OEt |
| 5.040 | 0 | CH | N | O | CH$_2$ | CH$_2$ | O | C(O)OEt |
| 5.041 | 0 | C—H | CH | O | CH$_2$ | CH$_2$ | O | C(O)O(CH$_2$)$_2$OCH$_3$ |
| 5.042 | 0 | C—F | CH | O | CH$_2$ | CH$_2$ | O | C(O)O(CH$_2$)$_2$OCH$_3$ |
| 5.043 | 1 | C—F | CH | O | CH$_2$ | CH$_2$ | O | C(O)O(CH$_2$)$_2$OCH$_3$ |
| 5.044 | 1 | C—H | CH | O | CH$_2$ | CH$_2$ | O | C(O)O(CH$_2$)$_2$OCH$_3$ |
| 5.045 | 0 | N | CH | O | CH$_2$ | CH$_2$ | O | C(O)O(CH$_2$)$_2$OCH$_3$ |
| 5.046 | 0 | C—H | N | O | CH$_2$ | CH$_2$ | O | C(O)O(CH$_2$)$_2$OCH$_3$ |
| 5.047 | 0 | C—H | CH | O | CH$_2$ | CH$_2$ | O | C(O)iso-Butyl |
| 5.048 | 0 | C—F | CH | O | CH$_2$ | CH$_2$ | O | C(O)iso-Butyl |
| 5.049 | 1 | C—F | CH | O | CH$_2$ | CH$_2$ | O | C(O)iso-Butyl |
| 5.050 | 1 | C—H | CH | O | CH$_2$ | CH$_2$ | O | C(O)iso-Butyl |
| 5.051 | 0 | N | CH | O | CH$_2$ | CH$_2$ | O | C(O)iso-Butyl |
| 5.053 | 0 | CH | N | O | CH$_2$ | CH$_2$ | O | C(O)iso-Butyl |
| 5.054 | 0 | C—H | CH | O | CH$_2$ | CH$_2$ | O | C(O)iso-Propyl |
| 5.055 | 0 | C—F | CH | O | CH$_2$ | CH$_2$ | O | C(O)iso-Propyl |
| 5.056 | 1 | C—F | CH | O | CH$_2$ | CH$_2$ | O | C(O)iso-Propyl |
| 5.057 | 1 | C—H | CH | O | CH$_2$ | CH$_2$ | O | C(O)iso-Propyl |
| 5.058 | 0 | N | CH | O | CH$_2$ | CH$_2$ | O | C(O)iso-Propyl |
| 5.059 | 0 | CH | N | O | CH$_2$ | CH$_2$ | O | C(O)iso-Propyl |
| 5.060 | 0 | C—H | CH | O | CH$_2$ | CH$_2$ | O | C(O)cyclo-Pr |
| 5.061 | 0 | C—F | CH | O | CH$_2$ | CH$_2$ | O | C(O)cyclo-Pr |
| 5.062 | 1 | C—F | CH | O | CH$_2$ | CH$_2$ | O | C(O)cyclo-Pr |
| 5.063 | 1 | C—H | CH | O | CH$_2$ | CH$_2$ | O | C(O)cyclo-Pr |
| 5.064 | 0 | N | CH | O | CH$_2$ | CH$_2$ | O | C(O)cyclo-Pr |
| 5.065 | 0 | CH | N | O | CH$_2$ | CH$_2$ | O | C(O)cyclo-Pr |
| 5.066 | 0 | C—H | CH | NH | C(O) | CH$_2$ | CH$_2$ | H |
| 5.067 | 0 | C—F | CH | NH | C(O) | CH$_2$ | CH$_2$ | H |
| 5.068 | 1 | C—F | CH | NH | C(O) | CH$_2$ | CH$_2$ | H |
| 5.069 | 1 | C—H | CH | NH | C(O) | CH$_2$ | CH$_2$ | H |
| 5.070 | 0 | N | CH | NH | C(O) | CH$_2$ | CH$_2$ | H |
| 5.071 | 0 | CH | N | NH | C(O) | CH$_2$ | CH$_2$ | H |
| 5.072 | 0 | C—H | CH | NMe | C(O) | CH$_2$ | CH$_2$ | H |
| 5.073 | 0 | C—F | CH | NMe | C(O) | CH$_2$ | CH$_2$ | H |
| 5.074 | 1 | C—F | CH | NMe | C(O) | CH$_2$ | CH$_2$ | H |
| 5.075 | 1 | C—H | CH | NMe | C(O) | CH$_2$ | CH$_2$ | H |
| 5.076 | 0 | N | CH | NMe | C(O) | CH$_2$ | CH$_2$ | H |
| 5.076 | 0 | CH | N | NMe | C(O) | CH$_2$ | CH$_2$ | H |
| 5.077 | 0 | C—H | CH | NMe | C(O) | CH$_2$ | CH$_2$ | C(O)Me |
| 5.078 | 0 | C—F | CH | NMe | C(O) | CH$_2$ | CH$_2$ | C(O)Me |
| 5.079 | 1 | C—F | CH | NMe | C(O) | CH$_2$ | CH$_2$ | C(O)Me |
| 5.080 | 1 | C—H | CH | NMe | C(O) | CH$_2$ | CH$_2$ | C(O)Me |
| 5.081 | 0 | N | CH | NMe | C(O) | CH$_2$ | CH$_2$ | C(O)Me |
| 5.082 | 0 | CH | N | NMe | C(O) | CH$_2$ | CH$_2$ | C(O)Me |

TABLE 5-continued

| | n | Y | W | X | C¹ | C² | C³ | R² |
|---|---|---|---|---|---|---|---|---|
| 5.083 | 0 | C—H | CH | NH | C(O) | CH₂ | NH | H |
| 5.084 | 0 | C—F | CH | NH | C(O) | CH₂ | NH | H |
| 5.085 | 1 | C—F | CH | NH | C(O) | CH₂ | NH | H |
| 5.086 | 1 | C—H | CH | NH | C(O) | CH₂ | NH | H |
| 5.087 | 0 | N | CH | NH | C(O) | CH₂ | NH | H |
| 5.088 | 0 | CH | N | NH | C(O) | CH₂ | NH | H |
| 5.089 | 0 | C—H | CH | NMe | C(O) | CH₂ | NH | H |
| 5.090 | 0 | C—F | CH | NMe | C(O) | CH₂ | NH | H |
| 5.091 | 1 | C—F | CH | NMe | C(O) | CH₂ | NH | H |
| 5.092 | 1 | C—H | CH | NMe | C(O) | CH₂ | NH | H |
| 5.093 | 0 | N | CH | NMe | C(O) | CH₂ | NH | H |
| 5.094 | 0 | CH | N | NMe | C(O) | CH₂ | NH | H |
| 5.095 | 0 | C—H | CH | NMe | C(O) | CH₂ | NH | C(O)Me |
| 5.096 | 0 | C—F | CH | NMe | C(O) | CH₂ | NH | C(O)Me |
| 5.097 | 1 | C—F | CH | NMe | C(O) | CH₂ | NH | C(O)Me |
| 5.098 | 1 | C—H | CH | NMe | C(O) | CH₂ | NH | C(O)Me |
| 5.099 | 0 | N | CH | NMe | C(O) | CH₂ | NH | C(O)Me |
| 5.100 | 0 | CH | N | NMe | C(O) | CH₂ | NH | C(O)Me |
| 5.101 | 0 | C—H | CH | NH | C(O) | CH₂ | O | H |
| 5.102 | 0 | C—F | CH | NH | C(O) | CH₂ | O | H |
| 5.103 | 1 | C—F | CH | NH | C(O) | CH₂ | O | H |
| 5.104 | 1 | C—H | CH | NH | C(O) | CH₂ | O | H |
| 5.105 | 0 | N | CH | NH | C(O) | CH₂ | O | H |
| 5.106 | 0 | CH | N | NH | C(O) | CH₂ | O | H |
| 5.107 | 0 | C—H | CH | NMe | C(O) | CH₂ | O | H |
| 5.108 | 0 | C—F | CH | NMe | C(O) | CH₂ | O | H |
| 5.109 | 1 | C—F | CH | NMe | C(O) | CH₂ | O | H |
| 5.110 | 1 | C—H | CH | NMe | C(O) | CH₂ | O | H |
| 5.111 | 0 | N | CH | NMe | C(O) | CH₂ | O | H |
| 5.112 | 0 | CH | N | NMe | C(O) | CH₂ | O | H |
| 5.113 | 0 | C—H | CH | NMe | C(O) | CH₂ | O | C(O)Me |
| 5.114 | 0 | C—F | CH | NMe | C(O) | CH₂ | O | C(O)Me |
| 5.115 | 1 | C—F | CH | NMe | C(O) | CH₂ | O | C(O)Me |
| 5.116 | 1 | C—H | CH | NMe | C(O) | CH₂ | O | C(O)Me |
| 5.117 | 0 | N | CH | NMe | C(O) | CH₂ | O | C(O)Me |
| 5.118 | 0 | CH | N | NMe | C(O) | CH₂ | O | C(O)Me |

TABLE 6

| | n | Y | W | X | C¹ | C² | C³ | R² |
|---|---|---|---|---|---|---|---|---|
| 6.001 | 0 | C—H | CH | O | CH₂ | CH₂ | O | H |
| 6.002 | 0 | C—F | CH | O | CH₂ | CH₂ | O | H |
| 6.003 | 1 | C—F | CH | O | CH₂ | CH₂ | O | H |
| 6.004 | 0 | C—Cl | CH | O | CH₂ | CH₂ | O | H |
| 6.005 | 0 | C—Br | CH | O | CH₂ | CH₂ | O | H |
| 6.006 | 0 | C—CH₃ | CH | O | CH₂ | CH₂ | O | H |
| 6.007 | 0 | C—CF₃ | CH | O | CH₂ | CH₂ | O | H |
| 6.008 | 0 | C-cyclo-Pr | CH | O | CH₂ | CH₂ | O | H |
| 6.009 | 0 | C—C≡N | CH | O | CH₂ | CH₂ | O | H |
| 6.010 | 0 | C—C≡CH | CH | O | CH₂ | CH₂ | O | H |
| 6.012 | 0 | C—CH=CH₂ | CH | O | CH₂ | CH₂ | O | H |
| 6.013 | 1 | C—H | CH | O | CH₂ | CH₂ | O | H |

TABLE 6-continued

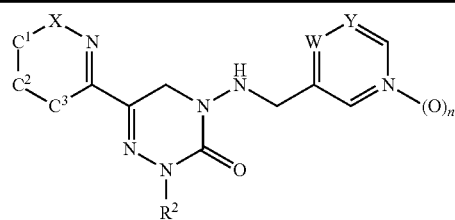

| | n | Y | W | X | C$^1$ | C$^2$ | C$^3$ | R$^2$ |
|---|---|---|---|---|---|---|---|---|
| 6.014 | 0 | N | CH | O | CH$_2$ | CH$_2$ | O | H |
| 6.015 | 0 | C—H | N | O | CH$_2$ | CH$_2$ | O | H |
| 6.016 | 0 | C—H | CH | O | CH$_2$ | CH$_2$ | O | C(O)CH$_3$ |
| 6.017 | 0 | C—F | CH | O | CH$_2$ | CH$_2$ | O | C(O)CH$_3$ |
| 6.018 | 1 | C—F | CH | O | CH$_2$ | CH$_2$ | O | C(O)CH$_3$ |
| 6.019 | 1 | C—H | CH | O | CH$_2$ | CH$_2$ | O | C(O)CH$_3$ |
| 6.020 | 0 | N | CH | O | CH$_2$ | CH$_2$ | O | C(O)CH$_3$ |
| 6.021 | 0 | C—H | N | O | CH$_2$ | CH$_2$ | O | C(O)CH$_3$ |
| 6.022 | 0 | C—H | CH | O | CH$_2$ | CH$_2$ | O | C(O)Ot-Bu |
| 6.023 | 0 | C—F | CH | O | CH$_2$ | CH$_2$ | O | C(O)Ot-Bu |
| 6.024 | 1 | C—F | CH | O | CH$_2$ | CH$_2$ | O | C(O)Ot-Bu |
| 6.025 | 1 | C—H | CH | O | CH$_2$ | CH$_2$ | O | C(O)Ot-Bu |
| 6.026 | 0 | N | CH | O | CH$_2$ | CH$_2$ | O | C(O)Ot-Bu |
| 6.027 | 0 | C—H | N | O | CH$_2$ | CH$_2$ | O | C(O)Ot-Bu |
| 6.028 | 0 | C—H | CH | O | CH$_2$ | CH$_2$ | O | C(O)OCH$_2$Ph |
| 6.029 | 0 | C—F | CH | O | CH$_2$ | CH$_2$ | O | C(O)OCH$_2$Ph |
| 6.030 | 1 | C—F | CH | O | CH$_2$ | CH$_2$ | O | C(O)OCH$_2$Ph |
| 6.031 | 1 | C—H | CH | O | CH$_2$ | CH$_2$ | O | C(O)OCH$_2$Ph |
| 6.033 | 0 | N | CH | O | CH$_2$ | CH$_2$ | O | C(O)OCH$_2$Ph |
| 6.034 | 0 | C—H | N | O | CH$_2$ | CH$_2$ | O | C(O)OCH$_2$Ph |
| 6.035 | 0 | C—H | CH | O | CH$_2$ | CH$_2$ | O | C(O)OEt |
| 6.036 | 0 | C—F | CH | O | CH$_2$ | CH$_2$ | O | C(O)OEt |
| 6.037 | 1 | C—F | CH | O | CH$_2$ | CH$_2$ | O | C(O)OEt |
| 6.038 | 1 | C—H | CH | O | CH$_2$ | CH$_2$ | O | C(O)OEt |
| 6.039 | 0 | N | CH | O | CH$_2$ | CH$_2$ | O | C(O)OEt |
| 6.040 | 0 | C—H | N | O | CH$_2$ | CH$_2$ | O | C(O)OEt |
| 6.041 | 0 | C—H | CH | O | CH$_2$ | CH$_2$ | O | C(O)O(CH$_2$)$_2$OCH$_3$ |
| 6.042 | 0 | C—F | CH | O | CH$_2$ | CH$_2$ | O | C(O)O(CH$_2$)$_2$OCH$_3$ |
| 6.043 | 1 | C—F | CH | O | CH$_2$ | CH$_2$ | O | C(O)O(CH$_2$)$_2$OCH$_3$ |
| 6.044 | 1 | C—H | CH | O | CH$_2$ | CH$_2$ | O | C(O)O(CH$_2$)$_2$OCH$_3$ |
| 6.045 | 0 | N | CH | O | CH$_2$ | CH$_2$ | O | C(O)O(CH$_2$)$_2$OH$_3$ |
| 6.046 | 0 | C—H | N | O | CH$_2$ | CH$_2$ | O | C(O)O(CH$_2$)$_2$OCH$_3$ |
| 6.047 | 0 | C—H | CH | O | CH$_2$ | CH$_2$ | O | C(O)iso-Butyl |
| 6.048 | 0 | C—F | CH | O | CH$_2$ | CH$_2$ | O | C(O)iso-Butyl |
| 6.049 | 1 | C—F | CH | O | CH$_2$ | CH$_2$ | O | C(O)iso-Butyl |
| 6.050 | 1 | C—H | CH | O | CH$_2$ | CH$_2$ | O | C(O)iso-Butyl |
| 6.051 | 0 | N | CH | O | CH$_2$ | CH$_2$ | O | C(O)iso-Butyl |
| 6.053 | 0 | C—H | N | O | CH$_2$ | CH$_2$ | O | C(O)iso-Butyl |
| 6.054 | 0 | C—H | CH | O | CH$_2$ | CH$_2$ | O | C(O)iso-Propyl |
| 6.055 | 0 | C—F | CH | O | CH$_2$ | CH$_2$ | O | C(O)iso-Propyl |
| 6.056 | 1 | C—F | CH | O | CH$_2$ | CH$_2$ | O | C(O)iso-Propyl |
| 6.057 | 1 | C—H | CH | O | CH$_2$ | CH$_2$ | O | C(O)iso-Propyl |
| 6.058 | 0 | N | CH | O | CH$_2$ | CH$_2$ | O | C(O)iso-Propyl |
| 6.059 | 0 | CH | N | O | CH$_2$ | CH$_2$ | O | C(O)iso-Propyl |
| 6.060 | 0 | C—H | CH | O | CH$_2$ | CH$_2$ | O | C(O)cyclo-Pr |
| 6.061 | 0 | C—F | CH | O | CH$_2$ | CH$_2$ | O | C(O)cyclo-Pr |
| 6.062 | 1 | C—F | CH | O | CH$_2$ | CH$_2$ | O | C(O)cyclo-Pr |
| 6.063 | 1 | C—H | CH | O | CH$_2$ | CH$_2$ | O | C(O)cyclo-Pr |
| 6.064 | 0 | N | CH | O | CH$_2$ | CH$_2$ | O | C(O)cyclo-Pr |
| 6.065 | 0 | C—H | N | O | CH$_2$ | CH$_2$ | O | C(O)cyclo-Pr |
| 6.066 | 0 | C—H | CH | NH | C(O) | CH$_2$ | CH$_2$ | H |
| 6.067 | 0 | C—F | CH | NH | C(O) | CH$_2$ | CH$_2$ | H |
| 6.068 | 1 | C—F | CH | NH | C(O) | CH$_2$ | CH$_2$ | H |
| 6.069 | 1 | C—H | CH | NH | C(O) | CH$_2$ | CH$_2$ | H |
| 6.070 | 0 | N | CH | NH | C(O) | CH$_2$ | CH$_2$ | H |
| 6.071 | 0 | C—H | N | NH | C(O) | CH$_2$ | CH$_2$ | H |
| 6.072 | 0 | C—H | CH | NMe | C(O) | CH$_2$ | CH$_2$ | H |
| 6.073 | 0 | C—F | CH | NMe | C(O) | CH$_2$ | CH$_2$ | H |
| 6.074 | 1 | C—F | CH | NMe | C(O) | CH$_2$ | CH$_2$ | H |
| 6.075 | 1 | C—H | CH | NMe | C(O) | CH$_2$ | CH$_2$ | H |
| 6.076 | 0 | N | CH | NMe | C(O) | CH$_2$ | CH$_2$ | H |
| 6.076 | 0 | C—H | N | NMe | C(O) | CH$_2$ | CH$_2$ | H |
| 6.077 | 0 | C—H | CH | NMe | C(O) | CH$_2$ | CH$_2$ | C(O)Me |
| 6.078 | 0 | C—F | CH | NMe | C(O) | CH$_2$ | CH$_2$ | C(O)Me |
| 6.079 | 1 | C—F | CH | NMe | C(O) | CH$_2$ | CH$_2$ | C(O)Me |
| 6.080 | 1 | C—H | CH | NMe | C(O) | CH$_2$ | CH$_2$ | C(O)Me |
| 6.081 | 0 | N | CH | NMe | C(O) | CH$_2$ | CH$_2$ | C(O)Me |

TABLE 6-continued

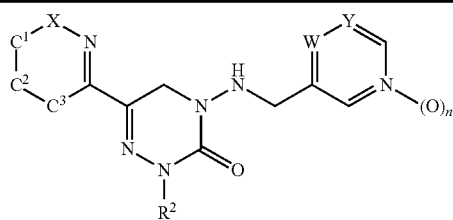

| | n | Y | W | X | C¹ | C² | C³ | R² |
|---|---|---|---|---|---|---|---|---|
| 6.082 | 0 | C—H | N | NMe | C(O) | CH₂ | CH₂ | C(O)Me |
| 6.083 | 0 | C—H | CH | NH | C(O) | CH₂ | NH | H |
| 6.084 | 0 | C—F | CH | NH | C(O) | CH₂ | NH | H |
| 6.085 | 1 | C—F | CH | NH | C(O) | CH₂ | NH | H |
| 6.086 | 1 | C—H | CH | NH | C(O) | CH₂ | NH | H |
| 6.087 | 0 | N | CH | NH | C(O) | CH₂ | NH | H |
| 6.088 | 0 | C—H | N | NH | C(O) | CH₂ | NH | H |
| 6.089 | 0 | C—H | CH | NMe | C(O) | CH₂ | NH | H |
| 6.090 | 0 | C—F | CH | NMe | C(O) | CH₂ | NH | H |
| 6.091 | 1 | C—F | CH | NMe | C(O) | CH₂ | NH | H |
| 6.092 | 1 | C—H | CH | NMe | C(O) | CH₂ | NH | H |
| 6.093 | 0 | N | CH | NMe | C(O) | CH₂ | NH | H |
| 6.094 | 0 | C—H | N | NMe | C(O) | CH₂ | NH | H |
| 6.095 | 0 | C—H | CH | NMe | C(O) | CH₂ | NH | C(O)Me |
| 6.096 | 0 | C—F | CH | NMe | C(O) | CH₂ | NH | C(O)Me |
| 6.097 | 1 | C—F | CH | NMe | C(O) | CH₂ | NH | C(O)Me |
| 6.098 | 1 | C—H | CH | NMe | C(O) | CH₂ | NH | C(O)Me |
| 6.099 | 0 | N | CH | NMe | C(O) | CH₂ | NH | C(O)Me |
| 6.100 | 0 | C—H | N | NMe | C(O) | CH₂ | NH | C(O)Me |
| 6.101 | 0 | C—H | CH | NH | C(O) | CH₂ | O | H |
| 6.102 | 0 | C—F | CH | NH | C(O) | CH₂ | O | H |
| 6.103 | 1 | C—F | CH | NH | C(O) | CH₂ | O | H |
| 6.104 | 1 | C—H | CH | NH | C(O) | CH₂ | O | H |
| 6.105 | 0 | N | CH | NH | C(O) | CH₂ | O | H |
| 6.106 | 0 | C—H | N | NH | C(O) | CH₂ | O | H |
| 6.107 | 0 | C—H | CH | NMe | C(O) | CH₂ | O | H |
| 6.108 | 0 | C—F | CH | NMe | C(O) | CH₂ | O | H |
| 6.109 | 1 | C—F | CH | NMe | C(O) | CH₂ | O | H |
| 6.110 | 1 | C—H | CH | NMe | C(O) | CH₂ | O | H |
| 6.111 | 0 | N | CH | NMe | C(O) | CH₂ | O | H |
| 6.112 | 0 | C—H | N | NMe | C(O) | CH₂ | O | H |
| 6.113 | 0 | C—H | CH | NMe | C(O) | CH₂ | O | C(O)Me |
| 6.114 | 0 | C—F | CH | NMe | C(O) | CH₂ | O | C(O)Me |
| 6.115 | 1 | C—F | CH | NMe | C(O) | CH₂ | O | C(O)Me |
| 6.116 | 1 | C—H | CH | NMe | C(O) | CH₂ | O | C(O)Me |
| 6.117 | 0 | N | CH | NMe | C(O) | CH₂ | O | C(O)Me |
| 6.118 | 0 | C—H | N | NMe | C(O) | CH₂ | O | C(O)Me |

TABLE 7

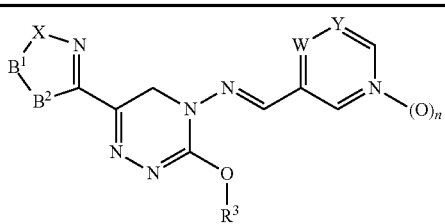

| | n | Y | W | X | B¹ | B² | R² |
|---|---|---|---|---|---|---|---|
| 7.001 | 0 | C—H | C—H | O | CMe₂ | CH₂ | Ac |
| 7.002 | 0 | C—F | C—H | O | CMe₂ | CH₂ | Ac |
| 7.003 | 1 | C—F | C—H | O | CMe₂ | CH₂ | Ac |
| 7.004 | 1 | C—H | C—H | O | CMe₂ | CH₂ | Ac |
| 7.005 | 0 | N | C—H | O | CMe₂ | CH₂ | Ac |
| 7.006 | 0 | C—H | N | O | CMe₂ | CH₂ | Ac |
| 7.007 | 0 | C—H | C—H | O | CMe₂ | CH₂ | C(O)Et |
| 7.008 | 0 | C—F | C—H | O | CMe₂ | CH₂ | C(O)Et |
| 7.009 | 1 | C—F | C—H | O | CMe₂ | CH₂ | C(O)Et |
| 7.010 | 1 | C—H | C—H | O | CMe₂ | CH₂ | C(O)Et |
| 7.012 | 0 | N | C—H | O | CMe₂ | CH₂ | C(O)Et |
| 7.013 | 0 | C—H | N | O | CMe₂ | CH₂ | C(O)Et |
| 7.014 | 0 | C—H | C—H | O | CMe₂ | CH₂ | C(O)i-Pr |
| 7.015 | 0 | C—F | C—H | O | CMe₂ | CH₂ | C(O)i-Pr |
| 7.016 | 1 | C—F | C—H | O | CMe₂ | CH₂ | C(O)i-Pr |
| 7.017 | 1 | C—H | C—H | O | CMe₂ | CH₂ | C(O)i-Pr |
| 7.018 | 0 | N | C—H | O | CMe₂ | CH₂ | C(O)i-Pr |
| 7.019 | 0 | C—H | N | O | CMe₂ | CH₂ | C(O)i-Pr |
| 7.020 | 0 | C—H | C—H | O | CMe₂ | CH₂ | C(O)cyclo-Pr |
| 7.021 | 0 | C—F | C—H | O | CMe₂ | CH₂ | C(O)cyclo-Pr |
| 7.022 | 1 | C—F | C—H | O | CMe₂ | CH₂ | C(O)cyclo-Pr |
| 7.023 | 1 | C—H | C—H | O | CMe₂ | CH₂ | C(O)cyclo-Pr |
| 7.024 | 0 | N | C—H | O | CMe₂ | CH₂ | C(O)cyclo-Pr |
| 7.025 | 0 | C—H | N | O | CMe₂ | CH₂ | C(O)cyclo-Pr |

TABLE 7-continued

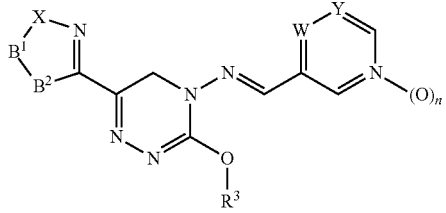

| n | Y | W | X | B¹ | B² | R² |
|---|---|---|---|----|----|-----|
| 7.026 | 0 | C—H | C—H | O | CMe₂ | CH₂ | C(O)cyclo-Bu |
| 7.027 | 0 | C—F | C—H | O | CMe₂ | CH₂ | C(O)cyclo-Bu |
| 7.028 | 1 | C—F | C—H | O | CMe₂ | CH₂ | C(O)cyclo-Bu |
| 7.029 | 1 | C—H | C—H | O | CMe₂ | CH₂ | C(O)cyclo-Bu |
| 7.030 | 0 | N | C—H | O | CMe₂ | CH₂ | C(O)cyclo-Bu |
| 7.031 | 0 | C—H | N | O | CMe₂ | CH₂ | C(O)cyclo-Bu |
| 7.033 | 0 | C—H | C—H | O | CMe₂ | CH₂ | C(O)i-Bu |
| 7.034 | 0 | C—F | C—H | O | CMe₂ | CH₂ | C(O)i-Bu |
| 7.035 | 1 | C—F | C—H | O | CMe₂ | CH₂ | C(O)i-Bu |
| 7.036 | 1 | C—H | C—H | O | CMe₂ | CH₂ | C(O)i-Bu |
| 7.037 | 0 | N | C—H | O | CMe₂ | CH₂ | C(O)i-Bu |
| 7.038 | 0 | C—H | N | O | CMe₂ | CH₂ | C(O)i-Bu |
| 7.039 | 0 | C—H | C—H | O | CMe₂ | CH₂ | C(O)OMe |
| 7.040 | 0 | C—F | C—H | O | CMe₂ | CH₂ | C(O)OMe |
| 7.041 | 1 | C—F | C—H | O | CMe₂ | CH₂ | C(O)OMe |
| 7.042 | 1 | C—H | C—H | O | CMe₂ | CH₂ | C(O)OMe |
| 7.043 | 0 | N | C—H | O | CMe₂ | CH₂ | C(O)OMe |
| 7.044 | 0 | C—H | N | O | CMe₂ | CH₂ | C(O)OMe |
| 7.045 | 0 | C—H | C—H | O | CMe₂ | CH₂ | C(O)OEt |
| 7.046 | 0 | C—F | C—H | O | CMe₂ | CH₂ | C(O)OEt |
| 7.047 | 1 | C—F | C—H | O | CMe₂ | CH₂ | C(O)OEt |
| 7.048 | 1 | C—H | C—H | O | CMe₂ | CH₂ | C(O)OEt |
| 7.049 | 0 | N | C—H | O | CMe₂ | CH₂ | C(O)OEt |
| 7.050 | 0 | C—H | N | O | CMe₂ | CH₂ | C(O)OEt |
| 7.051 | 0 | C—H | C—H | O | CMe₂ | CH₂ | 5-methylisoxazole-4-carbonyl |
| 7.053 | 0 | C—F | C—H | O | CMe₂ | CH₂ | 5-methylisoxazole-4-carbonyl |
| 7.054 | 1 | C—F | C—H | O | CMe₂ | CH₂ | 5-methylisoxazole-4-carbonyl |
| 7.055 | 1 | C—H | C—H | O | CMe₂ | CH₂ | 5-methylisoxazole-4-carbonyl |
| 7.056 | 0 | N | C—H | O | CMe₂ | CH₂ | 5-methylisoxazole-4-carbonyl |
| 7.057 | 0 | C—H | N | O | CMe₂ | CH₂ | 5-methylisoxazole-4-carbonyl |
| 7.058 | 0 | C—H | C—H | O | CMe₂ | CH₂ | C(O)OBn |
| 7.059 | 0 | C—F | C—H | O | CMe₂ | CH₂ | C(O)OBn |
| 7.060 | 1 | C—F | C—H | O | CMe₂ | CH₂ | C(O)OBn |
| 7.061 | 1 | C—H | C—H | O | CMe₂ | CH₂ | C(O)OBn |
| 7.062 | 0 | N | C—H | O | CMe₂ | CH₂ | C(O)OBn |
| 7.063 | 0 | C—H | N | O | CMe₂ | CH₂ | C(O)OBn |
| 7.064 | 0 | C—H | C—H | O | CMe₂ | CH₂ | C(O)O(CH₂)₂OMe |
| 7.065 | 0 | C—F | C—H | O | CMe₂ | CH₂ | C(O)O(CH₂)₂OMe |
| 7.066 | 1 | C—F | C—H | O | CMe₂ | CH₂ | C(O)O(CH₂)₂OMe |
| 7.067 | 1 | C—H | C—H | O | CMe₂ | CH₂ | C(O)O(CH₂)₂OMe |
| 7.068 | 0 | N | C—H | O | CMe₂ | CH₂ | C(O)O(CH₂)₂OMe |
| 7.069 | 0 | C—H | N | O | CMe₂ | CH₂ | C(O)O(CH₂)₂OMe |
| 7.070 | 0 | C—H | C—H | O | CMe₂ | CH₂ | C(O)Oi-Pr |
| 7.071 | 0 | C—F | C—H | O | CMe₂ | CH₂ | C(O)Oi-Pr |
| 7.072 | 1 | C—F | C—H | O | CMe₂ | CH₂ | C(O)Oi-Pr |
| 7.073 | 1 | C—H | C—H | O | CMe₂ | CH₂ | C(O)Oi-Pr |
| 7.074 | 0 | N | C—H | O | CMe₂ | CH₂ | C(O)Oi-Pr |
| 7.075 | 0 | C—H | N | O | CMe₂ | CH₂ | C(O)Oi-Pr |
| 7.076 | 0 | C—H | C—H | O | CMe₂ | CH₂ | tetrahydrofuran-3-carbonyl |
| 7.076 | 0 | C—F | C—H | O | CMe₂ | CH₂ | tetrahydrofuran-3-carbonyl |
| 7.077 | 1 | C—F | C—H | O | CMe₂ | CH₂ | tetrahydrofuran-3-carbonyl |
| 7.078 | 1 | C—H | C—H | O | CMe₂ | CH₂ | tetrahydrofuran-3-carbonyl |
| 7.079 | 0 | N | C—H | O | CMe₂ | CH₂ | tetrahydrofuran-3-carbonyl |
| 7.080 | 0 | C—H | N | O | CMe₂ | CH₂ | tetrahydrofuran-3-carbonyl |
| 7.081 | 0 | C—H | C—H | O | CMe₂ | CH₂ | tetrahydropyran-3-carbonyloxy |
| 7.082 | 0 | C—F | C—H | O | CMe₂ | CH₂ | tetrahydropyran-3-carbonyloxy |
| 7.083 | 1 | C—F | C—H | O | CMe₂ | CH₂ | tetrahydropyran-3-carbonyloxy |
| 7.084 | 1 | C—H | C—H | O | CMe₂ | CH₂ | tetrahydropyran-3-carbonyloxy |
| 7.085 | 0 | N | C—H | O | CMe₂ | CH₂ | tetrahydropyran-3-carbonyloxy |
| 7.086 | 0 | C—H | N | O | CMe₂ | CH₂ | tetrahydropyran-3-carbonyloxy |

The compounds according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also commonly occurring resistant species, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

The compounds of formula (I) or (I') can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) or (I') include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus*, and *R. santonensis*) and the *Termitidae* (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

Further examples of the above mentioned pests are:
from the order Acarina, for example,
*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;
from the order Anoplura, for example,
*Haematopinus* spp., *Linognathus* spp., *Pediculus* spp., *Pemphigus* spp. and *Phylloxera* spp.;
from the order Coleoptera, for example,
*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemLineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., Scarabeidae, *Sitophilus* spp., *Sitotroga* spp., *Tenebrio* spp., *Tribolium* spp. and *Trogoderma* spp.;
from the order Diptera, for example,
*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;
from the order Heteroptera, for example,
*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;
from the order Homoptera, for example,
*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*;
from the order Hymenoptera, for example,
*Acromyrmex, Atta* spp., *Cephus* spp., *Diprion* spp., Diprionidae, *Gilpinia polytoma, Hoplocampa* spp., *Lasius* spp., *Monomorium pharaonis, Neodiprion* spp., *Solenopsis* spp. and *Vespa* spp.;
from the order Isoptera, for example,
*Reticulitermes* spp.;
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiela, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;
from the order Mallophaga, for example,
*Damalinea* spp. and *Trichodectes* spp.;
from the order Orthoptera, for example,
*Blatta* spp., *Blattella* spp., *Gryllotalpa* spp., *Leucophaea maderae, Locusta* spp., *Periplaneta* spp. and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis*;
from the order Thysanoptera, for example,
*Frankliniella* spp., *Hercinothrips* spp., *Scirtothrips aurantii, Taeniothrips* spp., *Thrips palmi* and *Thrips tabaci*; and
from the order Thysanura, for example,
*Lepisma saccharina*.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is also to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonizing nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein CryIF for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003.

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Crops may also be modified for enhanced resistance to fungal (for example *Fusarium, Anthracnose,* or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Crops that exhibit enhanced yield or quality include those with improved flowering or fruit ripening properties (such as delayed ripening); modified oil, starch, amino acid, fatty acid, vitamin, phenolic or other content (such as Vistive™ soybean variety); enhanced nutrient utilisation (such as improved nitrogen assimilation); and enhanced quality plant product (such as higher quality cotton fibre).

Further areas of use of the compounds and compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compounds and compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compounds and compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharine*.

The invention therefore provides a method of combating and controlling insects, acarines, nematodes or molluscs which comprises applying an insecticidally, acaricidally, nematicidally or molluscicidally effective amount of a compound of formula (I) or (I'), or a composition containing a compound of formula (I) or (I'), to a pest, a locus of pest, or to a plant susceptible to attack by a pest, The compounds of formula (I) or (I') are preferably used against insects or acarines.

The term "plant" as used herein includes seedlings, bushes and trees.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions C8 to C12 of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopo¬lypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylpheno¬xypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl¬ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutyl¬naphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids. Further suitable phosphates are tris-esters of phosphoric acid with aliphatic or aromatic alcohols and/or bis-esters of alkyl phosphonic acids with aliphatic or aromatic alcohols, which are a high performance oil-type adjuvant. These tris-esters have been described, for example, in WO0147356, WO0056146, EP-A-0579052 or EP-A-1018299 or are commercially available under their chemical name. Preferred tris-esters of phosphoric acid for use in the new compositions are tris-(2-ethylhexyl)phosphate, tris-n-octyl phosphate and tris-butoxyethyl phosphate, where tris-(2-ethylhexyl)phosphate is most preferred. Suitable bis-ester of alkyl phosphonic acids are bis-(2-ethylhexyl)-(2-ethylhexyl)-phosphonate, bis-(2-ethylhexyl)-(n-octyl)-phosphonate, dibutyl-butyl phosphonate and bis(2-ethylhexyl)-tripropylene-phosphonate, where bis-(2-ethylhexyl)-(n-octyl)-phosphonate is particularly preferred.

The compositions according to the invention can preferably additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil such as ADIGOR® and MERO®, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000. Also, alkoxylated fatty acids can be used as additives in the inventive compositions as well as polymethylsiloxane based additives, which have been described in WO08/037,373.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

As a rule, the compositions comprise 0.1 to 99%, especially 0.1 to 95%, of active ingredient of three formula (I) or (I') and 1 to 99.9%, especially 5 to 99.9%, of at least one solid or liquid adjuvant, it being possible as a rule for 0 to 25%, especially 0.1 to 20%, of the composition to be surfactants(% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:

| active ingredient: | 1 to 95%, preferably 5 to 50%, more preferably 5 to 20% |
| --- | --- |
| surfactant: | 1 to 30%, preferably 10 to 20% |
| solvent: | 5 to 98%, preferably 70 to 85% |

Dusts:

| active ingredient: | 0.1 to 10%, preferably 2 to 5%, |
| --- | --- |
| solid carrier: | 99.9 to 90%, preferably 99.9 to 99% |

Suspension Concentrates:

| active ingredient: | 5 to 75%, preferably 10 to 50%, more preferably 10 to 40% |
| --- | --- |
| water: | 94 to 24%, preferably 88 to 30% |
| surfactant: | 1 to 40%, preferably 2 to 30% |

Oil-Based Suspension Concentrates:

| active ingredient: | 2 to 75%, preferably 5 to 50%, more preferably 10 to 25% |
| --- | --- |
| oil: | 94 to 24%, preferably 88 to 30% |
| surfactant: | 1 to 40%, preferably 2 to 30% |

Wettable Powders:

| active ingredient: | 0.5 to 90%, preferably 1 to 80%, more preferably 25 to 75% |
| --- | --- |
| surfactant: | 0.5 to 20%, preferably 1 to 15% |
| solid carrier: | 5 to 99%, preferably 15 to 98% |

Granulates:

| active ingredient: | 0.5 to 30%, preferably 3 to 25%, more preferably 3 to 15% |
| --- | --- |
| solid carrier: | 99.5 to 70%, preferably 97 to 85% |

Preferably, the term "active ingredient" refers to one of the compounds selected from Tables 1 to 7 shown above. It also refers to mixtures of the compound of formula (I) or (I'), in particular a compound selected from said Tables 1 to 7, with other insecticides, fungicides, herbicides, safeners, adjuvants and the like, which mixtures are specifically disclosed below.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers; fertilizers, in particular nitrogen containing fertilizers such as ammonium nitrates and urea as described in WO08/017,388, which can enhance the efficacy of the inventive compounds; or other active ingredients for achieving specific effects, for example ammonium or phosphonium salts, in particular halides, (hydrogen)sulphates, nitrates, (hydrogen) carbonates, citrates, tartrates, formiates and acetates, as described in WO07/068,427 and WO07/068,428, which also can enhance the efficacy of the inventive compounds and which can be used in combination with penetration enhancers such as alkoxalated fatty acids; bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. A plant propagation material comprising a compound of formula (I) or (I') is a further object of the invention.

Further methods of application of the compositions according to the invention comprise drip application onto the soil, dipping of parts of plants such as roots bulbs or tubers, drenching the soil, as well as soil injection. These methods are known in the art.

In order to apply a compound of formula (I) or (I') as an insecticide, acaricide, nematicide or molluscicide to a pest, a locus of pest, or to a plant susceptible to attack by a pest, a compound of formula (I) or (I') is usually formulated into a composition which includes, in addition to the compound of formula (I) or (I'), a suitable inert diluent or carrier and, optionally, a formulation adjuvant in form of a surface active agent (SFA) as described herein or, for example, in EP-B-1062217. SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I) or (I'). The composition is generally used for the control of pests such that a compound of formula (I) or (I') is applied at a rate of from 0.1 g to 10 kg per hectare, preferably from 1 g to 6 kg per hectare, more preferably from 1 g to 1 kg per hectare.

When used in a seed dressing, a compound of formula (I) or (I') is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) or (I') and a suitable carrier or diluent therefor.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I) or (I').

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), oil-based suspension concentrate (OD), aerosols, fogging/smoke formulations, capsule suspensions (CS) and seed treatment formulations. The formulation type chosen in any instance will depend upon the particular purpose en-visaged and the physical, chemical and biological properties of the compound of formula (I) or (I').

Dustable powders (DP) may be prepared by mixing a compound of formula (I) or (I') with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) or (I') with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) or (I') with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) or (I') and one or more powdered solid diluents or carriers, or from pre-formed blank granules by absorbing a compound of formula (I) or (I') (or a solution thereof, in a suitable agent) in a porous granular material (such as pumice, attapulgite clays, fuller's earth, kieselguhr, diatomaceous earths or ground corn cobs) or by adsorbing a compound of formula (I) or (I') (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) or (I') in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) or (I') in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) or (I') either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) or (I') is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I) or (I'). SCs may be prepared by ball or bead milling the solid compound of formula (I) or (I') in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) or (I') may be dry milled and added to water, containing agents hereinbefore described, to produce the desired end product.

Oil-based suspension concentrate (OD) may be prepared similarly by suspending finely divided insoluble solid particles of a compound of formula (I) or (I') in an organic fluid (for example at least one mineral oil or vegetable oil). ODs may further comprise at least one penetration promoter (for example an alcohol ethoxylate or a related compound), at least one non-ionic surfactants and/or at least one anionic surfactant, and optionally at least one additive from the group of emulsifiers, foam-inhibiting agents, preservatives, antioxidants, dyestuffs, and/or inert filler materials. An OD is intended and suitable for dilution with water before use to produce a spray solution with sufficient stability to allow spray application through appropriate equipment.

Aerosol formulations comprise a compound of formula (I) or (I') and a suitable propellant (for example n-butane). A compound of formula (I) or (I') may also be dissolved or dispersed in a suitable medium (for example water or a water miscible liquid, such as n-propanol) to provide compositions for use in non-pressurised, hand-actuated spray pumps.

A compound of formula (I) or (I') may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) or (I') and, optionally, a carrier or diluent therefor. The polymeric shell may be produced by either an interfacial polycondensation reaction or by a coacervation procedure. The compositions may provide for controlled release of the compound of formula (I) or (I') and they may be used for seed treatment. A compound of formula (I) or (I') may also be formulated in a biodegradable polymeric matrix to provide a slow, controlled release of the compound.

A compound of formula (I) or (I') may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC, OD and DC compositions described above. Compositions for treating seed may include an agent for assisting the adhesion of the composition to the seed (for example a mineral oil or a film-forming barrier).

A composition of the present invention may include one or more additives to improve the biological performance of the composition (for example by improving wetting, retention or distribution on surfaces; resistance to rain on treated surfaces; or uptake or mobility of a compound of formula (I) or (I')).

Such additives include surface active agents (SFAs), spray additives based on oils, for example certain mineral oils, vegetable oils or natural plant oils (such as soy bean and rape seed oil), and blends of these with other bio-enhancing adjuvants (ingredients which may aid or modify the action of a compound of formula (I) or (I')). Increasing the effect of a compound of formula (I) or (I') may for example be achieved by adding ammonium and/or phosphonium salts, and/or optionally at least one penetration promoter such as fatty alcohol alkoxylates (for example rape oil methyl ester) or vegetable oil esters.

Wetting agents, dispersing agents and emulsifying agents may be surface active agents (SFAs) of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as ° leyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) or (I') may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) or (I') may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ODs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) or (I') (for example 0.0001 to 10%, by weight) depending upon the purpose for which they are to be used.

A compound of formula (I) or (I') may be used in mixtures with fertilizers (for example nitrogen-, potassium- or phosphorus-containing fertilizers, and more particularly ammonium nitrate and/or urea fertilizers). Suitable formulation types include granules of fertiliser. The mixtures suitably contain up to 25% by weight of the compound of formula (I) or (I').

The invention therefore also provides a fertiliser composition comprising a fertiliser and a compound of formula (I) or (I').

The compositions of this invention may contain other compounds having biological activity, for example micronutrients or compounds having fungicidal activity or which possess plant growth regulating, herbicidal, safening, insecticidal, nematicidal or acaricidal activity.

The compound of formula (I) or (I') may be the sole active ingredient of the composition or it may be admixed with one or more additional active ingredients such as a pesticide (insect, acarine, mollusc and nematode pesticide), fungicide, synergist, herbicide, safener or plant growth regulator where appropriate. The activity of the compositions according to the invention may thereby be broadened considerably and may have surprising advantages which can also be described, in a wider sense, as synergistic activity. An additional active ingredient may: provide a composition having a broader spectrum of activity or increased persistence at a locus; provide a composition demonstrating better plant/crop tolerance by reducing phytotoxicity; provide a composition controlling insects in their different development stages; synergise the activity or complement the activity (for example by increasing the speed of effect or overcoming repellency) of the compound of formula (I) or (I'); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-($\underline{E}$)-(1R,3S)-2,2-dimethyl-3-(2-oxothiolan-3-ylidenemethyl) cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, or spinosad, spinetoram or azadirachtin;
h) Hormones or pheromones;
i) Organochlorine compounds such as endosulfan, benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds such as imidacloprid, thiacloprid, acetamiprid, clothianidin, nitenpyram, dinotefuran or thiamethoxam;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr;
q) Pymetrozine compounds different from the compound of formula (I) or (I') or pyrifluquinazon;
r) Spirotetramat, spirodiclofen or spiromesifen;
s) Flubendiamide, chloranthraliniprole, or cyanthraniliprole;
t) Cyenopyrafen or cyflumetofen; or
u) Sulfoxaflor.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

The following mixtures of the compounds of formula I or I' with active ingredients are preferred, wherein, preferably, the term "COMPOUND OF FORMULA I OR I'" refers to a compound selected from the Tables 1 to 7 above:
an adjuvant selected from the group of substances consisting of an oil of vegetable or animal origin, a mineral oil, alkyl esters of such oils or mixtures of such oils, and petroleum oils (alternative name) (628)+COMPOUND OF FORMULA I OR I',
an acaricide selected from the group of substances consisting of 1,1-bis(4-chlorophenyl)-2-ethoxyethanol (IUPAC name) (910)+COMPOUND OF FORMULA I OR I', 2,4-dichlorophenyl benzenesulfonate (IUPAC/Chemical Abstracts name) (1059)+COMPOUND OF FORMULA I OR I', 2-fluoro-N-methyl-N-1-naphthylacetamide (IUPAC name) (1295)+COMPOUND OF FORMULA I OR 4-chlorophenyl phenyl sulfone (IUPAC name) (981)+COMPOUND OF FORMULA I OR I', abamectin (1)+COMPOUND OF FORMULA I OR I', acequinocyl (3)+COMPOUND OF FORMULA I OR I', acetoprole [CCN]+COMPOUND OF FORMULA I OR I', acrinathrin (9)+COMPOUND OF FORMULA I OR I', aldicarb (16)+COMPOUND OF FORMULA I OR I', aldoxycarb (863)+COMPOUND OF FORMULA I OR I', alpha-cypermethrin (202)+COMPOUND OF FORMULA I OR I', amidithion (870)+COMPOUND OF FORMULA I OR I', amidoflumet [CCN]+COMPOUND OF FORMULA I OR I', amidothioate (872)+COMPOUND OF FORMULA I OR I', amiton (875)+COMPOUND OF FORMULA I OR I', amiton hydrogen oxalate (875)+COMPOUND OF FORMULA I OR I', amitraz (24)+COMPOUND OF FORMULA I OR I', aramite (881)+COMPOUND OF FORMULA I OR I', arsenous oxide (882)+COMPOUND OF FORMULA I OR I', AVI 382 (compound code)+COMPOUND OF FORMULA I OR I', AZ 60541 (compound code)+COMPOUND OF FORMULA I OR I', azinphos-ethyl (44)+COMPOUND OF FORMULA I OR I', azinphos-methyl (45)+COMPOUND OF FORMULA I OR I', azobenzene (IUPAC name) (888)+COMPOUND OF FORMULA I OR I', azocyclotin (46)+COMPOUND OF FORMULA I OR I', azothoate (889)+COMPOUND OF FORMULA I OR I', benomyl (62)+COMPOUND OF FORMULA I OR I', benoxafos (alternative name) [CCN]+COMPOUND OF FORMULA I OR I', benzoximate (71)+COMPOUND OF FORMULA I OR I', benzyl benzoate (IUPAC name) [CCN]+COMPOUND OF FORMULA I OR I', bifenazate (74)+COMPOUND OF FORMULA I OR I', bifenthrin (76)+COMPOUND OF FORMULA I OR I', binapacryl (907)+COMPOUND OF FORMULA I OR I', brofenvalerate (alternative name)+COMPOUND OF FORMULA I OR I', bromocyclen (918)+COMPOUND OF FORMULA I OR I', bromophos (920)+COMPOUND OF FORMULA I OR I', bromophos-ethyl (921)+COMPOUND OF FORMULA I OR I', bromopropylate (94)+COMPOUND OF FORMULA I OR I', buprofezin (99)+COMPOUND OF FORMULA I OR I', butocarboxim (103)+COMPOUND OF FORMULA I OR I', butoxycarboxim (104)+COMPOUND OF FORMULA I OR I', butylpyridaben (alternative name)+COMPOUND OF FORMULA I OR I', calcium polysulfide (IUPAC name) (111)+COMPOUND OF FORMULA I OR I', camphechlor (941)+COMPOUND OF FORMULA I OR I', carbanolate (943)+COMPOUND OF FORMULA I OR I', carbaryl (115)+COMPOUND OF FORMULA I OR I', carbofuran (118)+COMPOUND OF FORMULA I OR I', carbophenothion (947)+COMPOUND OF FORMULA I OR I', *CGA* 50'439 (development code) (125)+COMPOUND OF FORMULA I OR I', chinomethionat (126)+COMPOUND OF FORMULA I OR I', chlorbenside (959)+COMPOUND OF FORMULA I OR I', chlordimeform (964)+COMPOUND OF FORMULA I OR I', chlordimeform hydrochloride (964)+COMPOUND OF FORMULA I OR I', chlorfenapyr (130)+COMPOUND OF FORMULA I OR I', chlorfenethol (968)+COMPOUND OF FORMULA I OR I', chlorfenson (970)+COMPOUND OF FORMULA I OR I', chlorfensulphide (971)+COMPOUND OF FORMULA I OR I', chlorfenvinphos (131)+COMPOUND OF FORMULA I OR I', chlorobenzilate (975)+COMPOUND OF FORMULA I OR I', chloromebuform (977)+COMPOUND OF FORMULA I OR I', chloromethiuron (978)+COMPOUND OF FORMULA I OR I', chloropropylate (983)+COMPOUND OF FORMULA I OR I', chlorpyrifos (145)+COMPOUND OF FORMULA I OR I', chlorpyrifos-methyl (146)+COMPOUND OF FORMULA I OR I', chlorthiophos (994)+COMPOUND OF FORMULA I OR I', cinerin I (696)+COMPOUND OF FORMULA I OR I', cinerin II (696)+COMPOUND OF FORMULA I OR I', cinerins (696)+COMPOUND OF FORMULA I OR I', clofentezine (158)+COMPOUND OF FORMULA I OR I', closantel (alternative name) [CCN]+COMPOUND OF FORMULA I OR I', coumaphos (174)+COMPOUND OF FORMULA I OR I', crotamiton (alternative name) [CCN]+COMPOUND OF FORMULA I OR I', crotoxyphos (1010)+COMPOUND OF FORMULA I OR I', cufraneb (1013)+COMPOUND OF FORMULA I OR I', cyanthoate (1020)+COMPOUND OF FORMULA I OR I', cyenopyrafen [CCN]+COMPOUND OF FORMULA I OR I', cyflumetofen (CAS Reg. No.: 400882-07-7)+COMPOUND OF FORMULA I OR I', cyhalothrin (196)+COMPOUND OF FORMULA I OR I', cyhexatin (199)+COMPOUND OF FORMULA I OR I', cypermethrin (201)+COMPOUND OF FORMULA I OR I', DCPM (1032)+COMPOUND OF FORMULA I OR I', DDT (219)+COMPOUND OF FORMULA I OR I', demephion (1037)+COMPOUND OF FORMULA I OR demephion-O (1037)+COMPOUND OF FORMULA I OR I', demephion-S (1037)+COMPOUND OF FORMULA I OR I', demeton (1038)+COMPOUND OF FORMULA I OR I', demeton-methyl (224)+COMPOUND OF FORMULA I OR I', demeton-O (1038)+COMPOUND OF FORMULA I OR I', demeton-O-methyl (224)+COMPOUND OF FORMULA I OR I', demeton-S (1038)+COMPOUND OF FORMULA I OR I', demeton-S-methyl (224)+COMPOUND OF FORMULA I OR I', demeton-S-methylsulphon (1039)+COMPOUND OF FORMULA I OR I', diafenthiuron (226)+COMPOUND OF FORMULA I OR I', dialifos (1042)+COMPOUND OF FORMULA I OR I', diazinon (227)+COMPOUND OF FORMULA I OR I', dichlofluanid (230)+COMPOUND OF FORMULA I OR I', dichlorvos (236)+COMPOUND OF FORMULA I OR I', dicliphos (alternative name)+COMPOUND OF FORMULA I OR I', dicofol (242)+COMPOUND OF FORMULA I OR I', dicrotophos (243)+COMPOUND OF FORMULA I OR I', dienochlor (1071)+COMPOUND OF FORMULA I OR I', diflovidazin [CCN]+COMPOUND OF FORMULA I OR I', dimefox (1081)+COMPOUND OF FORMULA I OR I', dimethoate (262)+COMPOUND OF FORMULA I OR I', dinactin (alternative name) (653)+COMPOUND OF FORMULA I OR I', dinex (1089)+COMPOUND OF FORMULA I OR I', dinex-diclexine (1089)+COMPOUND OF FORMULA I OR I', dinobuton (269)+COMPOUND OF FORMULA I OR I', dinocap (270)+COMPOUND OF FORMULA I OR I', dinocap-4 [CCN]+COMPOUND OF FORMULA I OR I', dinocap-6 [CCN]+COMPOUND OF FORMULA I OR I', dinocton (1090)+COMPOUND OF FORMULA I OR I', dino-penton (1092)+COMPOUND OF FORMULA I OR I', dinosulfon (1097)+COMPOUND OF FORMULA I OR I', dinoterbon (1098)+COMPOUND OF FORMULA I OR I', dioxathion (1102)+COMPOUND OF FORMULA I OR I', diphenyl sulfone (IUPAC name) (1103)+COMPOUND OF FORMULA I OR I', disulfuram (alternative name) [CCN]+COMPOUND OF FORMULA I OR I', disulfoton (278)+COMPOUND OF FORMULA I OR I', DNOC (282)+COMPOUND OF FORMULA I OR I', dofenapyn (1113)+COMPOUND OF FORMULA I OR I', doramectin (alternative name) [CCN]+COMPOUND OF FORMULA I OR I', endosulfan (294)+COMPOUND OF FORMULA I OR endothion (1121)+COMPOUND OF FORMULA I OR I', EPN (297)+COMPOUND OF FORMULA I OR I', eprinomectin (alternative name) [CCN]+COMPOUND OF FORMULA I OR I', ethion (309)+COMPOUND OF FORMULA I OR I', ethoate-methyl (1134)+COMPOUND OF FORMULA I OR I', etoxazole (320)+COMPOUND OF FORMULA I OR I', etrimfos (1142)+COMPOUND OF FORMULA I OR I', fenazaflor (1147)+COMPOUND OF FORMULA I OR I', fenazaquin (328)+COMPOUND OF FORMULA I OR I', fenbutatin oxide (330)+COMPOUND OF FORMULA I OR I', fenothiocarb (337)+COMPOUND OF FORMULA I OR I', fenpropathrin (342)+COMPOUND OF FORMULA I OR I', fenpyrad (alternative name)+COMPOUND OF FORMULA I OR fenpyroximate (345)+COMPOUND OF FORMULA I OR I', fenson (1157)+COMPOUND OF FORMULA I OR I', fentrifanil (1161)+COMPOUND OF FORMULA I OR I', fenvalerate (349)+COMPOUND OF FORMULA I OR I', fipronil (354)+COMPOUND OF FORMULA I OR I', fluacrypyrim (360)+COMPOUND OF FORMULA I OR I', fluazuron (1166)+COMPOUND OF FORMULA I OR I', flubenzimine (1167)+COMPOUND OF FORMULA I OR I', flucycloxuron (366)+COMPOUND OF FORMULA I OR I', flucythrinate (367)+COMPOUND OF FORMULA I OR I', fluenetil (1169)+COMPOUND OF FORMULA I OR I', flufenoxuron (370)+COMPOUND OF FORMULA I OR I', flumethrin (372)+COMPOUND OF FORMULA I OR I', fluorbenside (1174)+COMPOUND OF FORMULA I OR I', fluvalinate (1184)+COMPOUND OF FORMULA I OR I', FMC 1137 (development code) (1185)+COMPOUND OF FORMULA I OR I', formetanate (405)+COMPOUND OF FORMULA I OR I', formetanate hydrochloride (405)+COMPOUND OF FORMULA I OR I', formothion (1192)+COMPOUND OF FORMULA I OR I', formparanate (1193)+COMPOUND OF FORMULA I OR I', gamma-HCH (430)+COMPOUND OF FORMULA I OR I', glyodin (1205)+COMPOUND OF FORMULA I OR I', halfenprox (424)+COMPOUND OF FORMULA I OR I', heptenophos (432)+COMPOUND OF FORMULA I OR I', hexadecyl cyclopropanecarboxylate (IUPAC/Chemical Abstracts name) (1216)+COMPOUND OF FORMULA I OR hexythiazox (441)+COMPOUND OF FORMULA I OR I', IKA 2002 (CAS Reg. No.: 211923-74-9)+COMPOUND OF FORMULA I OR I', iodomethane (IUPAC name) (542)+COMPOUND OF FORMULA I OR I', isocarbophos (alternative name) (473)+COMPOUND OF FORMULA I OR I', isopropyl O-(methoxyaminothiophosphoryl)salicylate (IUPAC name) (473)+COMPOUND OF FORMULA I OR I', ivermectin (alternative name) [CCN]+COMPOUND OF FORMULA I OR I', jasmolin I (696)+COMPOUND OF FORMULA I OR I', jasmolin II (696)+COMPOUND OF FORMULA I OR I', jodfenphos (1248)+COMPOUND OF FORMULA I OR I', lindane (430)+COMPOUND OF FORMULA I OR I', lufenuron (490)+COMPOUND OF FORMULA I OR I', malathion (492)+COMPOUND OF FORMULA I OR I', malonoben (1254)+COMPOUND OF FORMULA I OR I', mecarbam (502)+COMPOUND OF FORMULA I OR I', mephosfolan (1261)+COMPOUND OF FORMULA I OR I', mesulfen (alternative name) [CCN]+COMPOUND OF FORMULA I OR I', methacrifos (1266)+COMPOUND OF FORMULA I OR I', methamidophos (527)+COMPOUND OF FORMULA I OR I', methidathion (529)+COMPOUND OF FORMULA I OR I', methiocarb (530)+COMPOUND OF FORMULA I OR I', methomyl (531)+COMPOUND OF FORMULA I OR I', methyl bromide (537)+COMPOUND OF FORMULA I OR I', metolcarb (550)+COMPOUND OF FORMULA I OR I', mevinphos (556)+COMPOUND OF FORMULA I OR I', mexacarbate (1290)+COMPOUND OF FORMULA I OR I', milbemectin (557)+COMPOUND OF FORMULA I OR I', milbemycin oxime (alternative name) [CCN]+COMPOUND OF FORMULA I OR I', mipafox (1293)+COMPOUND OF FORMULA I OR I', monocrotophos (561)+COMPOUND OF FORMULA I OR I', morphothion (1300)+COMPOUND OF FORMULA I OR I', moxidectin (alternative name) [CCN]+COMPOUND OF FORMULA I OR I', naled (567)+COMPOUND OF FORMULA I OR I', NC-184 (compound code)+COMPOUND OF FORMULA I OR I', NC-512 (compound code)+COMPOUND OF FORMULA I OR I', nifluridide (1309)+COMPOUND OF FORMULA I OR I', nikkomycins (alternative name) [CCN]+COMPOUND OF FORMULA I OR I', nitrilacarb (1313)+COMPOUND OF FORMULA I OR I', nitrilacarb 1:1 zinc chloride complex (1313)+COMPOUND OF FORMULA I OR I', NNI-0101 (compound code)+COMPOUND OF FORMULA I OR I', NNI-0250 (compound code)+COMPOUND OF FORMULA I OR I', omethoate (594)+COMPOUND OF FORMULA I OR I', oxamyl (602)+COMPOUND OF FORMULA I OR I', oxydeprofos (1324)+COMPOUND OF FORMULA I OR I', oxydisulfoton (1325)+COMPOUND OF FORMULA I OR I', pp'-DDT (219)+COMPOUND OF FORMULA I OR I', parathion (615)+COMPOUND OF FORMULA I OR I', permethrin (626)+COMPOUND OF FORMULA I OR I', petroleum oils (alternative name) (628)+COMPOUND OF FORMULA I OR I', phenkapton (1330)+COMPOUND OF FORMULA I OR I', phenthoate (631)+COMPOUND OF FORMULA I OR I', phorate (636)+COMPOUND OF FORMULA I OR I', phosalone (637)+COMPOUND OF FORMULA I OR I', phosfolan (1338)+COMPOUND OF FORMULA I OR I', phosmet (638)+COMPOUND OF FORMULA I OR I', phosphamidon (639)+COMPOUND OF FORMULA I OR I', phoxim (642)+COMPOUND OF FORMULA I OR I', pirimiphos-methyl (652)+COMPOUND OF FORMULA I OR I', polychloroterpenes (traditional name) (1347)+COMPOUND OF FORMULA I OR I', polynactins (alternative name) (653)+COMPOUND OF FORMULA I OR I', proclonol (1350)+COMPOUND OF FORMULA I OR I', profenofos (662)+COMPOUND OF FORMULA I OR I', promacyl (1354)+COMPOUND OF FORMULA I OR I', propargite (671)+COMPOUND OF FORMULA I OR I', propetamphos (673)+COMPOUND OF FORMULA I OR I', propoxur (678)+COMPOUND OF FORMULA I OR I', prothidathion (1360)+COMPOUND OF FORMULA I OR I', prothoate (1362)+COMPOUND OF FORMULA I OR I', pyrethrin I (696)+COMPOUND OF FORMULA I OR I', pyrethrin II (696)+COMPOUND OF FORMULA I OR I', pyrethrins (696)+COMPOUND OF FORMULA I OR I', pyridaben (699)+COMPOUND OF FORMULA I OR I', pyridaphenthion (701)+COMPOUND OF FORMULA I OR I', pyrimidifen (706)+COMPOUND OF FORMULA I OR I', pyrimitate (1370)+COMPOUND OF FORMULA I OR I', quinalphos (711)+COMPOUND OF FORMULA I OR I', quintiofos (1381)+COMPOUND OF FORMULA I OR I', R-1492 (development code) (1382)+COMPOUND OF FORMULA I OR I', RA-17 (development code) (1383)+COMPOUND OF FORMULA I OR I', rotenone (722)+COMPOUND OF FORMULA I OR I', schradan (1389)+COMPOUND OF FORMULA I OR I', sebufos (alternative name)+COMPOUND OF FORMULA I OR I', selamectin (alternative name) [CCN]+COMPOUND OF FORMULA I OR I', SI-0009 (compound code)+COMPOUND OF FORMULA I OR I', sophamide (1402)+COMPOUND OF FORMULA I OR I', spirodiclofen (738)+COMPOUND OF FORMULA I OR I', spiromesifen (739)+COMPOUND OF FORMULA I OR I', SSI-121 (development code) (1404)+COMPOUND OF FORMULA I OR I', sulfuram (alternative name) [CCN]+COMPOUND OF FORMULA I OR I', sulfluramid (750)+COMPOUND OF FORMULA I OR I', sulfotep (753)+COMPOUND OF FORMULA I OR I', sulfur (754)+COMPOUND OF FORMULA I OR I', SZI-121 (development code) (757)+COMPOUND OF FORMULA I OR I', tau-fluvalinate (398)+COMPOUND OF FORMULA I OR I', tebufenpyrad (763)+COMPOUND OF FORMULA I OR I', TEPP (1417)+COMPOUND OF FORMULA I OR I', terbam (alternative name)+COMPOUND OF FORMULA I OR I', tetrachlorvinphos (777)+COMPOUND OF FORMULA I OR I', tetradifon (786)+COMPOUND OF FORMULA I OR I', tetranactin (alternative name) (653)+COMPOUND OF FORMULA I OR I', tetrasul (1425)+COMPOUND OF FORMULA I OR I', thiafenox (alternative name)+COMPOUND OF FORMULA I OR I', thiocarboxime (1431)+COMPOUND OF FORMULA I OR I', thiofanox (800)+COMPOUND OF FORMULA I OR I', thiometon (801)+COMPOUND OF FORMULA I OR I', thioquinox (1436)+COMPOUND OF FORMULA I OR I', thuringiensin (alternative name) [CCN]+COMPOUND OF FORMULA I OR I', triamiphos (1441)+COMPOUND OF FORMULA I OR I', triarathene (1443)+COMPOUND OF FORMULA I OR I', triazophos (820)+COMPOUND OF FORMULA I OR I', triazuron (alternative name)+COMPOUND OF FORMULA I OR I', trichlorfon (824)+COMPOUND OF FORMULA I OR I', trifenofos (1455)+COMPOUND OF FORMULA I OR I', trinactin (alternative name) (653)+COMPOUND OF FORMULA I OR I', vamidothion (847)+COMPOUND OF FORMULA I OR I', vaniliprole [CCN] and YI-5302 (compound code)+COMPOUND OF FORMULA I OR I', an algicide selected from the group of substances consisting of bethoxazin [CCN]+COMPOUND OF FORMULA I OR I', copper dioctanoate (IUPAC name) (170)+COMPOUND OF FORMULA I OR I', copper sulfate (172)+COMPOUND OF FORMULA I OR I', cybutryne [CCN]+COMPOUND OF FORMULA I OR I', dichlone (1052)+COMPOUND OF FORMULA I OR I', dichlorophen (232)+COMPOUND OF FORMULA I OR I', endothal (295)+COMPOUND OF FORMULA I OR I', fentin (347)+COMPOUND OF FORMULA I OR I', hydrated lime [CCN]+COMPOUND OF FORMULA I OR I', nabam (566)+COMPOUND OF FORMULA I OR I', quinoclamine (714)+COMPOUND OF FORMULA I OR I', quinonamid (1379)+COMPOUND OF FORMULA I OR I', simazine (730)+COMPOUND OF FORMULA I OR I', triphenyltin acetate (IUPAC name)

(347) and triphenyltin hydroxide (IUPAC name) (347)+COMPOUND OF FORMULA I OR I', an anthelmintic selected from the group of substances consisting of abamectin (1)+COMPOUND OF FORMULA I OR I', crufomate (1011)+COMPOUND OF FORMULA I OR I', doramectin (alternative name) [CCN]+COMPOUND OF FORMULA I OR I', emamectin (291)+COMPOUND OF FORMULA I OR I', emamectin benzoate (291)+COMPOUND OF FORMULA I OR I', eprinomectin (alternative name) [CCN]+COMPOUND OF FORMULA I OR I', ivermectin (alternative name) [CCN]+COMPOUND OF FORMULA I OR I', milbemycin oxime (alternative name) [CCN]+COMPOUND OF FORMULA I OR I', moxidectin (alternative name) [CCN]+COMPOUND OF FORMULA I OR I', piperazine [CCN]+COMPOUND OF FORMULA I OR I', selamectin (alternative name) [CCN]+COMPOUND OF FORMULA I OR I', spinosad (737) and thiophanate (1435)+COMPOUND OF FORMULA I OR I', an avicide selected from the group of substances consisting of chloralose (127)+COMPOUND OF FORMULA I OR I', endrin (1122)+COMPOUND OF FORMULA I OR I', fenthion (346)+COMPOUND OF FORMULA I OR I', pyridin-4-amine (IUPAC name) (23) and strychnine (745)+COMPOUND OF FORMULA I OR I', a bactericide selected from the group of substances consisting of 1-hydroxy-1H-pyridine-2-thione (IUPAC name) (1222)+COMPOUND OF FORMULA I OR I', 4-(quinoxalin-2-ylamino)benzenesulfonamide (IUPAC name) (748)+COMPOUND OF FORMULA I OR I', 8-hydroxyquinoline sulfate (446)+COMPOUND OF FORMULA I OR I', bronopol (97)+COMPOUND OF FORMULA I OR I', copper dioctanoate (IUPAC name) (170)+COMPOUND OF FORMULA I OR I', copper hydroxide (IUPAC name) (169)+COMPOUND OF FORMULA I OR I', cresol [CCN]+COMPOUND OF FORMULA I OR I', dichlorophen (232)+COMPOUND OF FORMULA I OR I', dipyrithione (1105)+COMPOUND OF FORMULA I OR I', dodicin (1112)+COMPOUND OF FORMULA I OR I', fenaminosulf (1144)+COMPOUND OF FORMULA I OR I', formaldehyde (404)+COMPOUND OF FORMULA I OR I', hydrargaphen (alternative name) [CCN]+COMPOUND OF FORMULA I OR I', kasugamycin (483)+COMPOUND OF FORMULA I OR I', kasugamycin hydrochloride hydrate (483)+COMPOUND OF FORMULA I OR I', nickel bis(dimethyldithiocarbamate) (IUPAC name) (1308)+COMPOUND OF FORMULA I OR I', nitrapyrin (580)+COMPOUND OF FORMULA I OR I', octhilinone (590)+COMPOUND OF FORMULA I OR I', oxolinic acid (606)+COMPOUND OF FORMULA I OR I', oxytetracycline (611)+COMPOUND OF FORMULA I OR I', potassium hydroxyquinoline sulfate (446)+COMPOUND OF FORMULA I OR I', probenazole (658)+COMPOUND OF FORMULA I OR I', streptomycin (744)+COMPOUND OF FORMULA I OR I', streptomycin sesquisulfate (744)+COMPOUND OF FORMULA I OR I', tecloftalam (766)+COMPOUND OF FORMULA I OR I', and thiomersal (alternative name) [CCN]+COMPOUND OF FORMULA I OR I', a biological agent selected from the group of substances consisting of *Adoxophyes orana* GV (alternative name) (12)+COMPOUND OF FORMULA I OR *Agrobacterium* radiobacter (alternative name) (13)+COMPOUND OF FORMULA I OR I', *Amblyseius* spp. (alternative name) (19)+COMPOUND OF FORMULA I OR I', *Anagrapha falcifera* NPV (alternative name) (28)+COMPOUND OF FORMULA I OR I', *Anagrus atomus* (alternative name) (29)+COMPOUND OF FORMULA I OR I', *Aphelinus abdominalis* (alternative name) (33)+COMPOUND OF FORMULA I OR I', *Aphidius colemani* (alternative name) (34)+COMPOUND OF FORMULA I OR I', *Aphidoletes aphidimyza* (alternative name) (35)+COMPOUND OF FORMULA I OR *Autographa californica* NPV (alternative name) (38)+COMPOUND OF FORMULA I OR I', *Bacillus firmus* (alternative name) (48)+COMPOUND OF FORMULA I OR I', *Bacillus sphaericus* Neide (scientific name) (49)+COMPOUND OF FORMULA I OR I', *Bacillus thuringiensis* Berliner (scientific name) (51)+COMPOUND OF FORMULA I OR I', *Bacillus thuringiensis* subsp. *aizawai* (scientific name) (51)+COMPOUND OF FORMULA I OR I', *Bacillus thuringiensis* subsp. *israelensis* (scientific name) (51)+COMPOUND OF FORMULA I OR I', *Bacillus thuringiensis* subsp. *japonensis* (scientific name) (51)+COMPOUND OF FORMULA I OR I', *Bacillus thuringiensis* subsp. *kurstaki* (scientific name) (51)+COMPOUND OF FORMULA I OR I', *Bacillus thuringiensis* subsp. *tenebrionis* (scientific name) (51)+COMPOUND OF FORMULA I OR I', *Beauveria bassiana* (alternative name) (53)+COMPOUND OF FORMULA I OR I', *Beauveria brongniartii* (alternative name) (54)+COMPOUND OF FORMULA I OR I', *Chrysoperla carnea* (alternative name) (151)+COMPOUND OF FORMULA I OR I', *Cryptolaemus montrouzieri* (alternative name) (178)+COMPOUND OF FORMULA I OR *Cydia pomonella* GV (alternative name) (191)+COMPOUND OF FORMULA I OR *Dacnusa sibirica* (alternative name) (212)+COMPOUND OF FORMULA I OR I', *Diglyphus isaea* (alternative name) (254)+COMPOUND OF FORMULA I OR I', *Encarsia formosa* (scientific name) (293)+COMPOUND OF FORMULA I OR I', *Eretmocerus eremicus* (alternative name) (300)+COMPOUND OF FORMULA I OR I', *Helicoverpa zea* NPV (alternative name) (431)+COMPOUND OF FORMULA I OR I', *Heterorhabditis bacteriophora* and *H. megidis* (alternative name) (433)+COMPOUND OF FORMULA I OR I', *Hippodamia convergens* (alternative name) (442)+COMPOUND OF FORMULA I OR I', *Leptomastix dactylopii* (alternative name) (488)+COMPOUND OF FORMULA I OR I', *Macrolophus caliginosus* (alternative name) (491)+COMPOUND OF FORMULA I OR *Mamestra brassicae* NPV (alternative name) (494)+COMPOUND OF FORMULA I OR I', *Metaphycus helvolus* (alternative name) (522)+COMPOUND OF FORMULA I OR *Metarhizium anisopliae* var. *acridum* (scientific name) (523)+COMPOUND OF FORMULA I OR *Metarhizium anisopliae* var. *anisopliae* (scientific name) (523)+COMPOUND OF FORMULA I OR *Neodiprion sertifer* NPV and *N. lecontei* NPV (alternative name) (575)+COMPOUND OF FORMULA I OR I', *Orius* spp. (alternative name) (596)+COMPOUND OF FORMULA I OR I', *Paecilomyces fumosoroseus* (alternative name) (613)+COMPOUND OF FORMULA I OR I', *Phytoseiulus persimilis* (alternative name) (644)+COMPOUND OF FORMULA I OR *Spodoptera exigua* multicapsid nuclear polyhedrosis virus (scientific name) (741)+COMPOUND OF FORMULA I OR I', *Steinernema bibionis* (alternative name) (742)+COMPOUND OF FORMULA I OR I', *Steinernema carpocapsae* (alternative name) (742)+COMPOUND OF FORMULA I OR I', *Steinernema feltiae* (alternative name) (742)+COMPOUND OF FORMULA I OR I', *Steinernema glaseri* (alternative name) (742)+COMPOUND OF FORMULA I OR I', *Steinernema riobrave* (alternative name) (742)+COMPOUND OF FORMULA I OR I', *Steinernema riobravis* (alternative name) (742)+COMPOUND OF FORMULA I OR I', *Steinernema scapterisci* (alternative name) (742)+COMPOUND OF FORMULA I OR I', *Steinernema* spp. (alternative name) (742)+COMPOUND OF FORMULA I OR I', *Trichogramma* spp. (alternative name) (826)+COMPOUND OF FORMULA I OR I', *Typhlodromus occidentalis* (alternative name) (844) and *Verticillium lecanii* (alternative name) (848)+COMPOUND OF FORMULA I OR I', a soil sterilant selected from the group of substances consisting of iodomethane (IUPAC name) (542) and methyl bromide (537)+COMPOUND OF FORMULA I OR I', a chemosterilant selected from the group of substances consisting of apholate [CCN]+COMPOUND OF FORMULA I OR I', bisazir (alternative name) [CCN]+COMPOUND OF FORMULA I OR I', busulfan (alternative name) [CCN]+COMPOUND OF FORMULA I OR I', diflubenzuron (250)+COMPOUND OF FORMULA I OR I', dimatif (alternative name) [CCN]+COMPOUND OF FORMULA I OR I', hemel [CCN]+COMPOUND OF FORMULA I OR I', hempa [CCN]+COMPOUND OF FORMULA I OR I', metepa [CCN]+COMPOUND OF FORMULA I OR I', methiotepa [CCN]+COMPOUND OF FORMULA I OR I', methyl apholate [CCN]+COMPOUND OF FORMULA I OR I', morzid [CCN]+COMPOUND OF FORMULA I OR I', penfluoron (alternative name) [CCN]+COMPOUND OF FORMULA I OR I', tepa [CCN]+COMPOUND OF FORMULA I OR I', thiohempa (alternative name) [CCN]+COMPOUND OF FORMULA I OR I', thiotepa (alternative name) [CCN]+COMPOUND OF FORMULA I OR I', tretamine (alternative name) [CCN] and uredepa (alternative name) [CCN]+COMPOUND OF FORMULA I OR I', an insect pheromone selected from the group of substances consisting of (E)-dec-5-en-1-yl acetate with (E)-dec-5-en-1-ol (IUPAC name) (222)+COMPOUND OF FORMULA I OR I', (E)-tridec-4-en-1-yl acetate (IUPAC name) (829)+COMPOUND OF FORMULA I OR I', (E)-6-methylhept-2-en-4-ol (IUPAC name) (541)+COMPOUND OF FORMULA I OR I', (E,Z)-tetradeca-4,10-dien-1-yl acetate (IUPAC name) (779)+COMPOUND OF FORMULA I OR I', (Z)-dodec-7-en-1-yl acetate (IUPAC name) (285)+COMPOUND OF FORMULA I OR I', (Z)-hexadec-11-enal (IUPAC name) (436)+COMPOUND OF FORMULA I OR I', (Z)-hexadec-11-en-1-yl acetate (IUPAC name) (437)+COMPOUND OF FORMULA I OR I', (Z)-hexadec-13-en-11-yn-1-yl acetate (IUPAC name) (438)+COMPOUND OF FORMULA I OR I', (Z)-icos-13-en-10-one (IUPAC name) (448)+COMPOUND OF FORMULA I OR I', (Z)-tetradec-7-en-1-al (IUPAC name) (782)+COMPOUND OF FORMULA I OR I', (Z)-tetradec-9-en-1-ol (IUPAC name) (783)+COMPOUND OF FORMULA I OR I', (Z)-tetradec-9-en-1-yl acetate (IUPAC name) (784)+COMPOUND OF FORMULA I OR I', (7E,9Z)-dodeca-7,9-dien-1-yl acetate (IUPAC name) (283)+COMPOUND OF FORMULA I OR I', (9Z,11E)-tetradeca-9,11-dien-1-yl acetate (IUPAC name) (780)+COMPOUND OF FORMULA I OR I', (9Z,12E)-tetradeca-9,12-dien-1-yl acetate (IUPAC name) (781)+COMPOUND OF FORMULA I OR I', 14-methyloctadec-1-ene (IUPAC name) (545)+COMPOUND OF FORMULA I OR I', 4-methylnonan-5-ol with 4-methylnonan-5-one (IUPAC name) (544)+COMPOUND OF FORMULA I OR I', alpha-multistriatin (alternative name) [CCN]+COMPOUND OF FORMULA I OR I', brevicomin (alternative name) [CCN]+COMPOUND OF FORMULA I OR I', codlelure (alternative name) [CCN]+COMPOUND OF FORMULA I OR I', codlemone (alternative name) (167)+COMPOUND OF FORMULA I OR I', cuelure (alternative name) (179)+COMPOUND OF FORMULA I OR I', disparlure (277)+COMPOUND OF FORMULA I OR I', dodec-8-en-1-yl acetate (IUPAC name) (286)+COMPOUND OF FORMULA I OR I', dodec-9-en-1-yl acetate (IUPAC name) (287)+COMPOUND OF FORMULA I OR I', dodeca-8+COMPOUND OF FORMULA I OR I', 10-dien-1-yl acetate (IUPAC name) (284)+COMPOUND OF FORMULA I OR I', dominicalure (alternative name) [CCN]+COMPOUND OF FORMULA I OR I', ethyl 4-methyloctanoate (IUPAC name) (317)+COMPOUND OF FORMULA I OR I', eugenol (alternative name) [CCN]+COMPOUND OF FORMULA I OR I', frontalin (alternative name) [CCN]+COMPOUND OF FORMULA I OR I', gossyplure (alternative name) (420)+COMPOUND OF FORMULA I OR I', grandlure (421)+COMPOUND OF FORMULA I OR I', grandlure I (alternative name) (421)+COMPOUND OF FORMULA I OR I', grandlure II (alternative name) (421)+COMPOUND OF FORMULA I OR I', grandlure III (alternative name) (421)+COMPOUND OF FORMULA I OR I', grandlure IV (alternative name) (421)+COMPOUND OF FORMULA I OR I', hexylure [CCN]+COMPOUND OF FORMULA I OR I', ipsdienol (alternative name) [CCN]+COMPOUND OF FORMULA I OR I', ipsenol (alternative name) [CCN]+COMPOUND OF FORMULA I OR I', japonilure (alternative name) (481)+COMPOUND OF FORMULA I OR I', lineatin (alternative name) [CCN]+COMPOUND OF FORMULA I OR I', litlure (alternative name) [CCN]+COMPOUND OF FORMULA I OR I', looplure (alternative name) [CCN]+COMPOUND OF FORMULA I OR I', medlure [CCN]+COMPOUND OF FORMULA I OR I', megatomoic acid (alternative name) [CCN]+COMPOUND OF FORMULA I OR I', methyl eugenol (alternative name) (540)+COMPOUND OF FORMULA I OR I', muscalure (563)+COMPOUND OF FORMULA I OR I', octadeca-2,13-dien-1-yl acetate (IUPAC name) (588)+COMPOUND OF FORMULA I OR I', octadeca-3,13-dien-1-yl acetate (IUPAC name) (589)+COMPOUND OF FORMULA I OR I', orfralure (alternative name) [CCN]+COMPOUND OF FORMULA I OR I', oryctalure (alternative name) (317)+COMPOUND OF FORMULA I OR I', ostramone (alternative name) [CCN]+COMPOUND OF FORMULA I OR I', siglure [CCN]+COMPOUND OF FORMULA I OR I', sordidin (alternative name) (736)+COMPOUND OF FORMULA I OR I', sulcatol (alternative name) [CCN]+COMPOUND OF FORMULA I OR I', tetradec-11-en-1-yl acetate (IUPAC name) (785)+COMPOUND OF FORMULA I OR I', trimedlure (839)+COMPOUND OF FORMULA I OR I', trimedlure A (alternative name) (839)+COMPOUND OF FORMULA I OR I', trimedlure $B_1$ (alternative name) (839)+COMPOUND OF FORMULA I OR I', trimedlure $B_2$ (alternative name)

(839)+COMPOUND OF FORMULA I OR I', trimedlure C (alternative name) (839) and trunc-call (alternative name) [CCN]+COMPOUND OF FORMULA I OR I', an insect repellent selected from the group of substances consisting of 2-(octylthio)ethanol (IUPAC name) (591)+COMPOUND OF FORMULA I OR I', butopyronoxyl (933)+COMPOUND OF FORMULA I OR I', butoxy(polypropylene glycol) (936)+COMPOUND OF FORMULA I OR I', dibutyl adipate (IUPAC name) (1046)+COMPOUND OF FORMULA I OR I', dibutyl phthalate (1047)+COMPOUND OF FORMULA I OR I', dibutyl succinate (IUPAC name) (1048)+COMPOUND OF FORMULA I OR I', diethyltoluamide [CCN]+COMPOUND OF FORMULA I OR I', dimethyl carbate [CCN]+COMPOUND OF FORMULA I OR I', dimethyl phthalate [CCN]+COMPOUND OF FORMULA I OR I', ethyl hexanediol (1137)+COMPOUND OF FORMULA I OR I', hexamide [CCN]+COMPOUND OF FORMULA I OR I', methoquin-butyl (1276)+COMPOUND OF FORMULA I OR I', methyl-neodecanamide [CCN]+COMPOUND OF FORMULA I OR I', oxamate [CCN] and picaridin [CCN]+COMPOUND OF FORMULA I OR I', an insecticide selected from the group of substances consisting of 1-dichloro-1-nitroethane (IUPAC/Chemical Abstracts name) (1058)+COMPOUND OF FORMULA I OR I', 1,1-dichloro-2,2-bis(4-ethylphenyl)ethane (IUPAC name) (1056), +COMPOUND OF FORMULA I OR I', 1,2-dichloropropane (IUPAC/Chemical Abstracts name) (1062)+COMPOUND OF FORMULA I OR I', 1,2-dichloropropane with 1,3-dichloropropene (IUPAC name) (1063)+COMPOUND OF FORMULA I OR I', 1-bromo-2-chloroethane (IUPAC/Chemical Abstracts name) (916)+COMPOUND OF FORMULA I OR I', 2,2,2-trichloro-1-(3,4-dichlorophenyl)ethyl acetate (IUPAC name) (1451)+COMPOUND OF FORMULA I OR I', 2,2-dichlorovinyl 2-ethylsulfinylethyl methyl phosphate (IUPAC name) (1066)+COMPOUND OF FORMULA I OR I', 2-(1,3-dithiolan-2-yl)phenyl dimethylcarbamate (IUPAC/Chemical Abstracts name) (1109)+COMPOUND OF FORMULA I OR I', 2-(2-butoxyethoxy)ethyl thiocyanate (IUPAC/Chemical Abstracts name) (935)+COMPOUND OF FORMULA I OR I', 2-(4,5-dimethyl-1,3-dioxolan-2-yl)phenyl methylcarbamate (IUPAC/Chemical Abstracts name) (1084)+COMPOUND OF FORMULA I OR I', 2-(4-chloro-3,5-xylyloxy)ethanol (IUPAC name) (986)+COMPOUND OF FORMULA I OR I', 2-chlorovinyl diethyl phosphate (IUPAC name) (984)+COMPOUND OF FORMULA I OR I', 2-imidazolidone (IUPAC name) (1225)+COMPOUND OF FORMULA I OR I', 2-isovalerylindan-1,3-dione (IUPAC name) (1246)+COMPOUND OF FORMULA I OR I', 2-methyl(prop-2-ynyl)aminophenyl methylcarbamate (IUPAC name) (1284)+COMPOUND OF FORMULA I OR I', 2-thiocyanatoethyl laurate (IUPAC name) (1433)+COMPOUND OF FORMULA I OR I', 3-bromo-1-chloroprop-1-ene (IUPAC name) (917)+COMPOUND OF FORMULA I OR I', 3-methyl-1-phenylpyrazol-5-yl dimethylcarbamate (IUPAC name) (1283)+COMPOUND OF FORMULA I OR I', 4-methyl(prop-2-ynyl)amino-3,5-xylyl methylcarbamate (IUPAC name) (1285)+COMPOUND OF FORMULA I OR I', 5,5-dimethyl-3-oxocyclohex-1-enyl dimethylcarbamate (IUPAC name) (1085)+COMPOUND OF FORMULA I OR I', abamectin (1)+COMPOUND OF FORMULA I OR I', acephate (2)+COMPOUND OF FORMULA I OR I', acetamiprid (4)+COMPOUND OF FORMULA I OR I', acethion (alternative name) [CCN]+COMPOUND OF FORMULA I OR I', acetoprole [CCN]+COMPOUND OF FORMULA I OR I', acrinathrin (9)+COMPOUND OF FORMULA I OR I', acrylonitrile (IUPAC name) (861)+COMPOUND OF FORMULA I OR I', alanycarb (15)+COMPOUND OF FORMULA I OR I', aldicarb (16)+COMPOUND OF FORMULA I OR I', aldoxycarb (863)+COMPOUND OF FORMULA I OR I', aldrin (864)+COMPOUND OF FORMULA I OR I', allethrin (17)+COMPOUND OF FORMULA I OR I', allosamidin (alternative name) [CCN]+COMPOUND OF FORMULA I OR I', allyxycarb (866)+COMPOUND OF FORMULA I OR I', alpha-cypermethrin (202)+COMPOUND OF FORMULA I OR I', alpha-ecdysone (alternative name) [CCN]+COMPOUND OF FORMULA I OR I', alpha-endosulfan [CCN]+COMPOUND OF FORMULA I OR I', aluminium phosphide (640)+COMPOUND OF FORMULA I OR I', amidithion (870)+COMPOUND OF FORMULA I OR I', amidothioate (872)+COMPOUND OF FORMULA I OR I', aminocarb (873)+COMPOUND OF FORMULA I OR I', amiton (875)+COMPOUND OF FORMULA I OR I', amiton hydrogen oxalate (875)+COMPOUND OF FORMULA I OR I', amitraz (24)+COMPOUND OF FORMULA I OR I', anabasine (877)+COMPOUND OF FORMULA I OR I', athidathion (883)+COMPOUND OF FORMULA I OR I', AVI 382 (compound code)+COMPOUND OF FORMULA I OR I', AZ 60541 (compound code)+COMPOUND OF FORMULA I OR I', azadirachtin (alternative name) (41)+COMPOUND OF FORMULA I OR I', azamethiphos (42)+COMPOUND OF FORMULA I OR I', azinphos-ethyl (44)+COMPOUND OF FORMULA I OR I', azinphos-methyl (45)+COMPOUND OF FORMULA I OR I', azothoate (889)+COMPOUND OF FORMULA I OR I', *Bacillus thuringiensis* delta endotoxins (alternative name) (52)+COMPOUND OF FORMULA I OR I', barium hexafluorosilicate (alternative name) [CCN]+COMPOUND OF FORMULA I OR I', barium polysulfide (IUPAC/Chemical Abstracts name) (892)+COMPOUND OF FORMULA I OR I', barthrin [CCN]+COMPOUND OF FORMULA I OR I', Bayer 22/190 (development code) (893)+COMPOUND OF FORMULA I OR I', Bayer 22408 (development code) (894)+COMPOUND OF FORMULA I OR I', bendiocarb (58)+COMPOUND OF FORMULA I OR I', benfuracarb (60)+COMPOUND OF FORMULA I OR I', bensultap (66)+COMPOUND OF FORMULA I OR I', beta-cyfluthrin (194)+COMPOUND OF FORMULA I OR I', beta-cypermethrin (203)+COMPOUND OF FORMULA I OR I', bifenthrin (76)+COMPOUND OF FORMULA I OR I', bioallethrin (78)+COMPOUND OF FORMULA I OR I', bioallethrin S-cyclopentenyl isomer (alternative name) (79)+COMPOUND OF FORMULA I OR I', bioethanomethrin [CCN]+COMPOUND OF FORMULA I OR I', biopermethrin (908)+COMPOUND OF FORMULA I OR I', bioresmethrin (80)+COMPOUND OF FORMULA I OR I', bis(2-chloroethyl)ether (IUPAC name) (909)+COMPOUND OF FORMULA I OR I', bistrifluron (83)+COMPOUND OF FORMULA I OR I', borax (86)+COMPOUND OF FORMULA I OR I', brofenvalerate (alternative name)+COMPOUND OF FORMULA I OR I', bromfenvinfos (914)+COMPOUND OF FORMULA I OR I', bromocyclen (918)+COMPOUND OF FORMULA I OR I', bromo-DDT (alternative name) [CCN]+COMPOUND OF FORMULA I OR I', bromophos (920)+COMPOUND OF FORMULA I OR I', bromophos-ethyl (921)+COMPOUND OF FORMULA I OR I', bufencarb (924)+COMPOUND OF FORMULA I OR I', buprofezin (99)+COMPOUND OF FORMULA I OR I', butacarb (926)+COMPOUND OF FORMULA I OR I', butathiofos (927)+COMPOUND OF FORMULA I OR I', butocarboxim (103)+COMPOUND OF FORMULA I OR I', butonate (932)+COMPOUND OF FORMULA I OR I', butoxycarboxim (104)+COMPOUND OF FORMULA I OR I', butylpyridaben (alternative name)+COMPOUND OF FORMULA I OR I', cadusafos (109)+COMPOUND OF FORMULA I OR I', calcium arsenate [CCN]+COMPOUND OF FORMULA I OR I', calcium cyanide (444)+COMPOUND OF FORMULA I OR I', calcium polysulfide (IUPAC name) (111)+COMPOUND OF FORMULA I OR I', camphechlor (941)+COMPOUND OF FORMULA I OR I', carbanolate (943)+COMPOUND OF FORMULA I OR I', carbaryl (115)+COMPOUND OF FORMULA I OR I', carbofuran (118)+COMPOUND OF FORMULA I OR I', carbon disulfide (IUPAC/Chemical Abstracts name) (945)+COMPOUND OF FORMULA I OR I', carbon tetrachloride (IUPAC name) (946)+COMPOUND OF FORMULA I OR I', carbophenothion (947)+COMPOUND OF FORMULA I OR I', carbosulfan (119)+COMPOUND OF FORMULA I OR I', cartap (123)+COMPOUND OF FORMULA I OR I', cartap hydrochloride (123)+COMPOUND OF FORMULA I OR I', cevadine (alternative name) (725)+COMPOUND OF FORMULA I OR I', chlorantraniliprole [CCN]+COMPOUND OF FORMULA I OR I', chlorbicyclen (960)+COMPOUND OF FORMULA I OR I', chlordane (128)+COMPOUND OF FORMULA I OR I', chlordecone (963)+COMPOUND OF FORMULA I OR I', chlordimeform (964)+COMPOUND OF FORMULA I OR I', chlordimeform hydrochloride (964)+COMPOUND OF FORMULA I OR I', chlorethoxyfos (129)+COMPOUND OF FORMULA I OR I', chlorfenapyr (130)+COMPOUND OF FORMULA I OR I', chlorfenvinphos (131)+COMPOUND OF FORMULA I OR I', chlorfluazuron (132)+COMPOUND OF FORMULA I OR I', chlormephos (136)+COMPOUND OF FORMULA I OR I', chloroform [CCN]+COMPOUND OF FORMULA I OR I', chloropicrin (141)+COMPOUND OF FORMULA I OR I', chlorphoxim (989)+COMPOUND OF FORMULA I OR I', chlorprazophos (990)+COMPOUND OF FORMULA I OR I', chlorpyrifos (145)+COMPOUND OF FORMULA I OR I', chlorpyrifos-methyl (146)+COMPOUND OF FORMULA I OR I', chlorthiophos (994)+COMPOUND OF FORMULA I OR I', chromafenozide (150)+COMPOUND OF FORMULA I OR I', cinerin I (696)+COMPOUND OF FORMULA I OR I', cinerin II (696)+COMPOUND OF FORMULA I OR I', cinerins (696)+COMPOUND OF FORMULA I OR I', cis-resmethrin (alternative name)+COMPOUND OF FORMULA I OR I', cismethrin (80)+COMPOUND OF FORMULA I OR I', clocythrin (alternative name)+COMPOUND OF FORMULA I OR I', cloethocarb (999)+COMPOUND OF FORMULA I OR I', closantel (alternative name) [CCN]+COMPOUND OF FORMULA I OR I', clothianidin (165)+COMPOUND OF FORMULA I OR I', copper acetoarsenite [CCN]+COMPOUND OF FORMULA I OR I', copper arsenate [CCN]+COMPOUND OF FORMULA I OR I', copper oleate [CCN]+COMPOUND OF FORMULA I OR I', coumaphos (174)+COMPOUND OF FORMULA I OR I', coumithoate (1006)+COMPOUND OF FORMULA I OR I', crotamiton (alternative name) [CCN]+COMPOUND OF FORMULA I OR I', crotoxyphos (1010)+COMPOUND OF FORMULA I OR I', crufomate (1011)+COMPOUND OF FORMULA I OR I', cryolite (alternative name) (177)+COMPOUND OF FORMULA I OR I', CS 708 (development code) (1012)+COMPOUND OF FORMULA I OR I', cyanofenphos (1019)+COMPOUND OF FORMULA I OR I', cyanophos (184)+COMPOUND OF FORMULA I OR I', cyanthoate (1020)+COMPOUND OF FORMULA I OR I', cyantraniliprole [CCN]+COMPOUND OF FORMULA I OR I', cyclethrin [CCN]+COMPOUND OF FORMULA I OR I', cycloprothrin (188)+COMPOUND OF FORMULA I OR I', cyfluthrin (193)+COMPOUND OF FORMULA I OR I', cyhalothrin (196)+COMPOUND OF FORMULA I OR I', cypermethrin (201)+COMPOUND OF FORMULA I OR I', cyphenothrin (206)+COMPOUND OF FORMULA I OR I', cyromazine (209)+COMPOUND OF FORMULA I OR I', cythioate (alternative name) [CCN]+COMPOUND OF FORMULA I OR I', d-limonene (alternative name) [CCN]+COMPOUND OF FORMULA I OR I', d-tetramethrin (alternative name) (788)+COMPOUND OF FORMULA I OR I', DAEP (1031)+COMPOUND OF FORMULA I OR I', dazomet (216)+COMPOUND OF FORMULA I OR I', DDT (219)+COMPOUND OF FORMULA I OR I', decarbofuran (1034)+COMPOUND OF FORMULA I OR I', deltamethrin (223)+COMPOUND OF FORMULA I OR I', demephion (1037)+COMPOUND OF FORMULA I OR I', demephion-O (1037)+COMPOUND OF FORMULA I OR I', demephion-S (1037)+COMPOUND OF FORMULA I OR I', demeton (1038)+COMPOUND OF FORMULA I OR I', demeton-methyl (224)+COMPOUND OF FORMULA I OR I', demeton-O (1038)+COMPOUND OF FORMULA I OR I', demeton-O-methyl (224)+COMPOUND OF FORMULA I OR I', demeton-S (1038)+COMPOUND OF FORMULA I OR I', demeton-S-methyl (224)+COMPOUND OF FORMULA I OR I', demeton-S-methylsulphon (1039)+COMPOUND OF FORMULA I OR I', diafenthiuron (226)+COMPOUND OF FORMULA I OR I', dialifos (1042)+COMPOUND OF FORMULA I OR I', diamidafos (1044)+COMPOUND OF FORMULA I OR I', diazinon (227)+COMPOUND OF FORMULA I OR I', dicapthon (1050)+COMPOUND OF FORMULA I OR I', dichlofenthion (1051)+COMPOUND OF FORMULA I OR I', dichlorvos (236)+COMPOUND OF FORMULA I OR I', dicliphos (alternative name)+COMPOUND OF FORMULA I OR I', dicresyl (alternative name) [CCN]+COMPOUND OF FORMULA I OR I', dicrotophos (243)+COMPOUND OF FORMULA I OR I', dicyclanil (244)+COMPOUND OF FORMULA I OR I', dieldrin (1070)+COMPOUND OF FORMULA I OR I', diethyl 5-methylpyrazol-3-yl phosphate (IUPAC name) (1076)+COMPOUND OF FORMULA I OR I', diflubenzuron (250)+COMPOUND OF FORMULA I OR I', dilor (alternative name) [CCN]+COMPOUND OF FORMULA I OR I', dimefluthrin [CCN]+COMPOUND OF FORMULA I OR I', dimefox (1081)+COMPOUND OF FORMULA I OR I', dimetan (1085)+COMPOUND OF FORMULA I OR I', dimethoate (262)+COMPOUND OF FORMULA I OR I', dimethrin (1083)+COMPOUND OF FORMULA I OR I', dimethylvinphos (265)+COMPOUND OF FORMULA I OR I', dimetilan (1086)+COMPOUND OF FORMULA I OR I', dinex (1089)+COMPOUND OF FORMULA I OR I', dinex-diclexine (1089)+COMPOUND OF FORMULA I OR I', dinoprop (1093)+COMPOUND OF FORMULA I OR I', dinosam (1094)+COMPOUND OF FORMULA I OR I', dinoseb (1095)+COMPOUND OF FORMULA I OR I', dinotefuran (271)+COMPOUND OF FORMULA I OR I', diofenolan (1099)+COMPOUND OF FORMULA I OR I', dioxabenzofos (1100)+COMPOUND OF FORMULA I OR I', dioxacarb (1101)+COMPOUND OF FORMULA I OR I', dioxathion (1102)+COMPOUND OF FORMULA I OR I', disulfoton (278)+COMPOUND OF FORMULA I OR I', dithicrofos (1108)+COMPOUND OF FORMULA I OR I', DNOC (282)+COMPOUND OF FORMULA I OR I', doramectin (alternative name) [CCN]+COMPOUND OF FORMULA I OR I', DSP (1115)+COMPOUND OF FORMULA I OR I', ecdysterone (alternative name) [CCN]+COMPOUND OF FORMULA I OR I', EI 1642 (development code) (1118)+COMPOUND OF FORMULA I OR I', emamectin (291)+COMPOUND OF FORMULA I OR I', emamectin benzoate (291)+COMPOUND OF FORMULA I OR I', EMPC (1120)+COMPOUND OF FORMULA I OR I', empenthrin (292)+COMPOUND OF FORMULA I OR I', endosulfan (294)+COMPOUND OF FORMULA I OR I', endothion (1121)+COMPOUND OF FORMULA I OR I', endrin (1122)+COMPOUND OF FORMULA I OR I', EPBP (1123)+COMPOUND OF FORMULA I OR I', EPN (297)+COMPOUND OF FORMULA I OR I', epofenonane (1124)+COMPOUND OF FORMULA I OR I', eprinomectin (alternative name) [CCN]+COMPOUND OF FORMULA I OR I', esfenvalerate (302)+COMPOUND OF FORMULA I OR I', etaphos (alternative name) [CCN]+COMPOUND OF FORMULA I OR I', ethiofencarb (308)+COMPOUND OF FORMULA I OR I', ethion (309)+COMPOUND OF FORMULA I OR I', ethiprole (310)+COMPOUND OF FORMULA I OR I', ethoate-methyl (1134)+COMPOUND OF FORMULA I OR I', ethoprophos (312)+COMPOUND OF FORMULA I OR I', ethyl formate (IUPAC name) [CCN]+COMPOUND OF FORMULA I OR I', ethyl-DDD (alternative name) (1056)+COMPOUND OF FORMULA I OR I', ethylene dibromide (316)+COMPOUND OF FORMULA I OR I', ethylene dichloride (chemical name) (1136)+COMPOUND OF FORMULA I OR I', ethylene oxide [CCN]+COMPOUND OF FORMULA I OR I', etofenprox (319)+COMPOUND OF FORMULA I OR I', etrimfos (1142)+COMPOUND OF FORMULA I OR I', EXD (1143)+COMPOUND OF FORMULA I OR I', famphur (323)+COMPOUND OF FORMULA I OR I', fenamiphos (326)+COMPOUND OF FORMULA I OR I', fenazaflor (1147)+COMPOUND OF FORMULA I OR I', fenchlorphos (1148)+COMPOUND OF FORMULA I OR I', fenethacarb (1149)+COMPOUND OF FORMULA I OR I', fenfluthrin (1150)+COMPOUND OF FORMULA I OR I', fenitrothion (335)+COMPOUND OF FORMULA I OR I', fenobucarb (336)+COMPOUND OF FORMULA I OR I', fenoxacrim (1153)+COMPOUND OF FORMULA I OR I', fenoxycarb (340)+COMPOUND OF FORMULA I OR I', fenpirithrin (1155)+COMPOUND OF FORMULA I OR I', fenpropathrin (342)+COMPOUND OF FORMULA I OR I', fenpyrad (alternative name)+COMPOUND OF FORMULA I OR I', fensulfothion (1158)+COMPOUND OF FORMULA I OR I', fenthion (346)+COMPOUND OF FORMULA I OR I', fenthion-ethyl [CCN]+COMPOUND OF FORMULA I OR I', fenvalerate (349)+COMPOUND OF FORMULA I OR I', fipronil (354)+COMPOUND OF FORMULA I OR I', flonicamid (358)+COMPOUND OF FORMULA I OR I', flubendiamide (CAS. Reg. No.: 272451-65-7)+COMPOUND OF FORMULA I OR I', flucofuron (1168)+COMPOUND OF FORMULA I OR I', flucycloxuron (366)+COMPOUND OF FORMULA I OR I', flucythrinate (367)+COMPOUND OF FORMULA I OR I', fluenetil (1169)+COMPOUND OF FORMULA I OR I', flufenerim [CCN]+COMPOUND OF FORMULA I OR I', flufenoxuron (370)+COMPOUND OF FORMULA I OR I', flufenprox (1171)+COMPOUND OF FORMULA I OR I', flumethrin (372)+COMPOUND OF FORMULA I OR I', fluvalinate (1184)+COMPOUND OF FORMULA I OR I', FMC 1137 (development code) (1185)+COMPOUND OF FORMULA I OR I', fonofos (1191)+COMPOUND OF FORMULA I OR I', formetanate (405)+COMPOUND OF FORMULA I OR I', formetanate hydrochloride (405)+COMPOUND OF FORMULA I OR I', formothion (1192)+COMPOUND OF FORMULA I OR I', formparanate (1193)+COMPOUND OF FORMULA I OR I', fosmethilan (1194)+COMPOUND OF FORMULA I OR I', fospirate (1195)+COMPOUND OF FORMULA I OR I', fosthiazate (408)+COMPOUND OF FORMULA I OR I', fosthietan (1196)+COMPOUND OF FORMULA I OR I', furathiocarb (412)+COMPOUND OF FORMULA I OR I', furethrin (1200)+COMPOUND OF FORMULA I OR I', gamma-cyhalothrin (197)+COMPOUND OF FORMULA I OR I', gamma-HCH (430)+COMPOUND OF FORMULA I OR I', guazatine (422)+COMPOUND OF FORMULA I OR I', guazatine acetates (422)+COMPOUND OF FORMULA I OR I', GY-81 (development code) (423)+COMPOUND OF FORMULA I OR I', halfenprox (424)+COMPOUND OF FORMULA I OR I', halofenozide (425)+COMPOUND OF FORMULA I OR I', HCH (430)+COMPOUND OF FORMULA I OR I', HEOD (1070)+COMPOUND OF FORMULA I OR I', heptachlor (1211)+COMPOUND OF FORMULA I OR I', heptenophos (432)+COMPOUND OF FORMULA I OR I', heterophos [CCN]+COMPOUND OF FORMULA I OR I', hexaflumuron (439)+COMPOUND OF FORMULA I OR I', HHDN (864)+COMPOUND OF FORMULA I OR I', hydramethylnon (443)+COMPOUND OF FORMULA I OR I', hydrogen cyanide (444)+COMPOUND OF FORMULA I OR I', hydroprene (445)+COMPOUND OF FORMULA I OR I', hyquincarb (1223)+COMPOUND OF FORMULA I OR I', imidacloprid (458)+COMPOUND OF FORMULA I OR I', imiprothrin (460)+COMPOUND OF FORMULA I OR I', indoxacarb (465)+COMPOUND OF FORMULA I OR I', iodomethane (IUPAC name) (542)+COMPOUND OF FORMULA I OR I', IPSP (1229)+COMPOUND OF FORMULA I OR I', isazofos (1231)+COMPOUND OF FORMULA I OR I', isobenzan (1232)+COMPOUND OF FORMULA I OR I', isocarbophos (alternative name) (473)+COMPOUND OF FORMULA I OR I', isodrin (1235)+COMPOUND OF FORMULA I OR I', isofenphos (1236)+COMPOUND OF FORMULA I OR I', isolane (1237)+COMPOUND OF FORMULA I OR I', isoprocarb (472)+COMPOUND OF FORMULA I OR I', isopropyl O-(methoxyaminothiophosphoryl)salicylate (IUPAC name) (473)+COMPOUND OF FORMULA I OR I', isoprothiolane (474)+COMPOUND OF FORMULA I OR I', isothioate (1244)+COMPOUND OF FORMULA I OR I', isoxathion (480)+COMPOUND OF FORMULA I OR I', ivermectin (alternative name) [CCN]+COMPOUND OF FORMULA I OR I', jasmolin I (696)+COMPOUND OF FORMULA I OR I', jasmolin II (696)+COMPOUND OF FORMULA I OR I', jodfenphos (1248)+COMPOUND OF FORMULA I OR I', juvenile hormone I (alternative name) [CCN]+COMPOUND OF FORMULA I OR I', juvenile hormone II (alternative name) [CCN]+COMPOUND OF FORMULA I OR I', juvenile hormone III (alternative name) [CCN]+COMPOUND OF FORMULA I OR I', kelevan (1249)+COMPOUND OF FORMULA I OR I', kinoprene (484)+COMPOUND OF FORMULA I OR I', lambda-cyhalothrin (198)+COMPOUND OF FORMULA I OR I', lead arsenate [CCN]+COMPOUND OF FORMULA I OR I', lepimectin (CCN)+COMPOUND OF FORMULA I OR I', leptophos (1250)+COMPOUND OF FORMULA I OR I', lindane (430)+COMPOUND OF FORMULA I OR I', lirimfos (1251)+COMPOUND OF FORMULA I OR I', lufenuron (490)+COMPOUND OF FORMULA I OR I', lythidathion (1253)+COMPOUND OF FORMULA I OR I', m-cumenyl methylcarbamate (IUPAC name) (1014)+COMPOUND OF FORMULA I OR I', magnesium phosphide (IUPAC name) (640)+COMPOUND OF FORMULA I OR I', malathion (492)+COMPOUND OF FORMULA I OR I', malonoben (1254)+COMPOUND OF FORMULA I OR I', mazidox (1255)+COMPOUND OF FORMULA I OR I', mecarbam (502)+COMPOUND OF FORMULA I OR I', mecarphon (1258)+COMPOUND OF FORMULA I OR I', menazon (1260)+COMPOUND OF FORMULA I OR I', mephosfolan (1261)+COMPOUND OF FORMULA I OR I', mercurous chloride (513)+COMPOUND OF FORMULA I OR I', mesulfenfos (1263)+COMPOUND OF FORMULA I OR I', metaflumizone (CCN)+COMPOUND OF FORMULA I OR I', metam (519)+COMPOUND OF FORMULA I OR I', metam-potassium (alternative name) (519)+COMPOUND OF FORMULA I OR I', metam-sodium (519)+COMPOUND OF FORMULA I OR I', methacrifos (1266)+COMPOUND OF FORMULA I OR I', methamidophos (527)+COMPOUND OF FORMULA I OR I', methanesulfonyl fluoride (IUPAC/Chemical Abstracts name) (1268)+COMPOUND OF FORMULA I OR I', methidathion (529)+COMPOUND OF FORMULA I OR I', methiocarb (530)+COMPOUND OF FORMULA I OR I', methocrotophos (1273)+COMPOUND OF FORMULA I OR I', methomyl (531)+COMPOUND OF FORMULA I OR I', methoprene (532)+COMPOUND OF FORMULA I OR I', methoquin-butyl (1276)+COMPOUND OF FORMULA I OR I', methothrin (alternative name) (533)+COMPOUND OF FORMULA I OR I', methoxychlor (534)+COMPOUND OF FORMULA I OR I', methoxyfenozide (535)+COMPOUND OF FORMULA I OR I', methyl bromide (537)+COMPOUND OF FORMULA I OR I', methyl isothiocyanate (543)+COMPOUND OF FORMULA I OR I', methylchloroform (alternative name) [CCN]+COMPOUND OF FORMULA I OR I', methylene chloride [CCN]+COMPOUND OF FORMULA I OR I', metofluthrin [CCN]+COMPOUND OF FORMULA I OR I', metolcarb (550)+COMPOUND OF FORMULA I OR I', metoxadiazone (1288)+COMPOUND OF FORMULA I OR I', mevinphos (556)+COMPOUND OF FORMULA I OR I', mexacarbate (1290)+COMPOUND OF FORMULA I OR I', milbemectin (557)+COMPOUND OF FORMULA I OR I', milbemycin oxime (alternative name) [CCN]+COMPOUND OF FORMULA I OR I', mipafox (1293)+COMPOUND OF FORMULA I OR I', mirex (1294)+COMPOUND OF FORMULA I OR I', monocrotophos (561)+COMPOUND OF FORMULA I OR I', morphothion (1300)+COMPOUND OF FORMULA I OR I', moxidectin (alternative name) [CCN]+COMPOUND OF FORMULA I OR I', naftalofos (alternative name) [CCN]+COMPOUND OF FORMULA I OR I', naled (567)+COMPOUND OF FORMULA I OR I', naphthalene (IUPAC/Chemical Abstracts name) (1303)+COMPOUND OF FORMULA I OR I', NC-170 (development code) (1306)+COMPOUND OF FORMULA I OR I', NC-184 (compound code)+COMPOUND OF FORMULA I OR I', nicotine (578)+COMPOUND OF FORMULA I OR I', nicotine sulfate (578)+COMPOUND OF FORMULA I OR I', nifluridide (1309)+COMPOUND OF FORMULA I OR I', nitenpyram (579)+COMPOUND OF FORMULA I OR I', nithiazine (1311)+COMPOUND OF FORMULA I OR I', nitrilacarb (1313)+COMPOUND OF FORMULA I OR I', nitrilacarb 1:1 zinc chloride complex (1313)+COMPOUND OF FORMULA I OR I', NNI-0101 (compound code)+COMPOUND OF FORMULA I OR I', NNI-0250 (compound code)+COMPOUND OF FORMULA I OR I', nornicotine (traditional name) (1319)+COMPOUND OF FORMULA I OR I', novaluron (585)+COMPOUND OF FORMULA I OR I', noviflumuron (586)+COMPOUND OF FORMULA I OR I', O-5-dichloro-4-iodophenyl O-ethyl ethylphosphonothioate (IUPAC name) (1057)+COMPOUND OF FORMULA I OR I', 0,0-diethyl 0-4-methyl-2-oxo-2H-chromen-7-yl phosphorothioate (IUPAC name) (1074)+COMPOUND OF FORMULA I OR I', O,O-diethyl O-6-methyl-2-propylpyrimidin-4-yl phosphorothioate (IUPAC name) (1075)+COMPOUND OF FORMULA I OR I', O,O,O',O'-tetrapropyl dithiopyrophosphate (IUPAC name) (1424)+COMPOUND OF FORMULA I OR I', oleic acid (IUPAC name) (593)+COMPOUND OF FORMULA I OR I', omethoate (594)+COMPOUND OF FORMULA I OR I', oxamyl (602)+COMPOUND OF FORMULA I OR I', oxydemeton-methyl (609)+COMPOUND OF FORMULA I OR I', oxydeprofos (1324)+COMPOUND OF FORMULA I OR I', oxydisulfoton (1325)+COMPOUND OF FORMULA I OR I', pp'-DDT (219)+COMPOUND OF FORMULA I OR I', para-dichlorobenzene [CCN]+COMPOUND OF FORMULA I OR I', parathion (615)+COMPOUND OF FORMULA I OR I', parathion-methyl (616)+COMPOUND OF FORMULA I OR I', penfluoron (alternative name) [CCN]+COMPOUND OF FORMULA I OR I', pentachlorophenol (623)+COMPOUND OF FORMULA I OR I', pentachlorophenyl laurate (IUPAC name) (623)+COMPOUND OF FORMULA I OR I', permethrin (626)+COMPOUND OF FORMULA I OR I', petroleum oils (alternative name) (628)+COMPOUND OF FORMULA I OR I', PH 60-38 (development code) (1328)+COMPOUND OF FORMULA I OR I', phenkapton (1330)+COMPOUND OF FORMULA I OR I', phenothrin (630)+COMPOUND OF FORMULA I OR I', phenthoate (631)+COMPOUND OF FORMULA I OR I', phorate (636)+COMPOUND OF FORMULA I OR I', phosalone (637)+COMPOUND OF FORMULA I OR I', phosfolan (1338)+COMPOUND OF FORMULA I OR I', phosmet (638)+COMPOUND OF FORMULA I OR I', phosnichlor (1339)+COMPOUND OF FORMULA I OR I', phosphamidon (639)+COMPOUND OF FORMULA I OR I', phosphine (IUPAC name) (640)+COMPOUND OF FORMULA I OR I', phoxim (642)+COMPOUND OF FORMULA I OR I', phoxim-methyl (1340)+COMPOUND OF FORMULA I OR I', pirimetaphos (1344)+COMPOUND OF FORMULA I OR I', pirimicarb (651)+COMPOUND OF FORMULA I OR I', pirimiphos-ethyl (1345)+COMPOUND OF FORMULA I OR I', pirimiphos-methyl (652)+COMPOUND OF FORMULA I OR I', polychlorodicyclopentadiene isomers (IUPAC name) (1346)+COMPOUND OF FORMULA I OR I', polychloroterpenes (traditional name) (1347)+COMPOUND OF FORMULA I OR I', potassium arsenite [CCN]+COMPOUND OF FORMULA I OR I', potassium thiocyanate [CCN]+COMPOUND OF FORMULA I OR I', prallethrin (655)+COMPOUND OF FORMULA I OR I', precocene I (alternative name) [CCN]+COMPOUND OF FORMULA I OR I', precocene II (alternative name) [CCN]+COMPOUND OF FORMULA I OR I', precocene III (alternative name) [CCN]+COMPOUND OF FORMULA I OR I', primidophos (1349)+COMPOUND OF FORMULA I OR I', profenofos (662)+COMPOUND OF FORMULA I OR I', profluthrin [CCN]+COMPOUND OF FORMULA I OR I', promacyl (1354)+COMPOUND OF FORMULA I OR I', promecarb (1355)+COMPOUND OF FORMULA I OR I', propaphos (1356)+COMPOUND OF FORMULA I OR I', propetamphos (673)+COMPOUND OF FORMULA I OR I', propoxur (678)+COMPOUND OF FORMULA I OR I', prothidathion (1360)+COMPOUND OF FORMULA I OR I', prothiofos (686)+COMPOUND OF FORMULA I OR I', prothoate (1362)+COMPOUND OF FORMULA I OR I', protrifenbute [CCN]+COMPOUND OF FORMULA I OR I', pymetrozine (688)+COMPOUND OF FORMULA I OR I', pyraclofos (689)+COMPOUND OF FORMULA I OR I', pyrafluprole [CCN]+COMPOUND OF FORMULA I OR I', pyrazophos (693)+COMPOUND OF FORMULA I OR I', pyresmethrin (1367)+COMPOUND OF FORMULA I OR I', pyrethrin I (696)+COMPOUND OF FORMULA I OR I', pyrethrin II (696)+COMPOUND OF FORMULA I OR I', pyrethrins (696)+COMPOUND OF FORMULA I OR I', pyridaben (699)+COMPOUND OF FORMULA I OR I', pyridalyl (700)+COMPOUND OF FORMULA I OR I', pyridaphenthion (701)+COMPOUND OF FORMULA I OR I', pyrifluquinazon [CCN]+COMPOUND OF FORMULA I OR I', pyrimidifen (706)+COMPOUND OF FORMULA I OR I', pyrimitate (1370)+COMPOUND OF FORMULA I OR I', pyriprole [CCN]+COMPOUND OF FORMULA I OR I', pyriproxyfen (708)+COMPOUND OF FORMULA I OR I', quassia (alternative name) [CCN]+COMPOUND OF FORMULA I OR I', quinalphos (711)+COMPOUND OF FORMULA I OR I', quinalphos-methyl (1376)+COMPOUND OF FORMULA I OR I', quinothion (1380)+COMPOUND OF FORMULA I OR I', quintiofos (1381)+COMPOUND OF FORMULA I OR I', R-1492 (development code) (1382)+COMPOUND OF FORMULA I OR I', rafoxanide (alternative name) [CCN]+COMPOUND OF FORMULA I OR I', resmethrin (719)+COMPOUND OF FORMULA I OR I', rotenone (722)+COMPOUND OF FORMULA I OR I', RU 15525 (development code) (723)+COMPOUND OF FORMULA I OR I', RU 25475 (development code) (1386)+COMPOUND OF FORMULA I OR I', ryania (alternative name) (1387)+COMPOUND OF FORMULA I OR I', ryanodine (traditional name) (1387)+COMPOUND OF FORMULA I OR I', sabadilla (alternative name) (725)+COMPOUND OF FORMULA I OR I', schradan (1389)+COMPOUND OF FORMULA I OR I', sebufos (alternative name)+COMPOUND OF FORMULA I OR I', selamectin (alternative name) [CCN]+COMPOUND OF FORMULA I OR I', SI-0009 (compound code)+COMPOUND OF FORMULA I OR I', SI-0205 (compound code)+COMPOUND OF FORMULA I OR I', SI-0404 (compound code)+COMPOUND OF FORMULA I OR I', SI-0405 (compound code)+COMPOUND OF FORMULA I OR I', silafluofen (728)+COMPOUND OF FORMULA I OR I', SN 72129 (development code) (1397)+COMPOUND OF FORMULA I OR I', sodium arsenite [CCN]+COMPOUND OF FORMULA I OR I', sodium cyanide (444)+COMPOUND OF FORMULA I OR I', sodium fluoride (IUPAC/Chemical Abstracts name) (1399)+COMPOUND OF FORMULA I OR I', sodium hexafluorosilicate (1400)+COMPOUND OF FORMULA I OR I', sodium pentachlorophenoxide (623)+COMPOUND OF FORMULA I OR I', sodium selenate (IUPAC name) (1401)+COMPOUND OF FORMULA I OR I', sodium thiocyanate [CCN]+COMPOUND OF FORMULA I OR I', sophamide (1402)+COMPOUND OF FORMULA I OR I', spinetoram [CCN]+COMPOUND OF FORMULA I OR I', spinosad (737)+COMPOUND OF FORMULA I OR I', spiromesifen (739)+COMPOUND OF FORMULA I OR I', spirotetramat [CCN]+COMPOUND OF FORMULA I OR I', sulcofuron (746)+COMPOUND OF FORMULA I OR I', sulcofuron-sodium (746)+COMPOUND OF FORMULA I OR I', sulfluramid (750)+COMPOUND OF FORMULA I OR I', sulfotep (753)+COMPOUND OF FORMULA I OR I', sulfoxaflor [CCN]+COMPOUND OF FORMULA I OR I', sulfuryl fluoride (756)+COMPOUND OF FORMULA I OR I', sulprofos (1408)+COMPOUND OF FORMULA I OR I', tar oils (alternative name) (758)+COMPOUND OF FORMULA I OR I', tau-fluvalinate (398)+COMPOUND OF FORMULA I OR I', tazimcarb (1412)+COMPOUND OF FORMULA I OR I', TDE (1414)+COMPOUND OF FORMULA I OR I', tebufenozide (762)+COMPOUND OF FORMULA I OR I', tebufenpyrad (763)+COMPOUND OF FORMULA I OR I', tebupirimfos (764)+COMPOUND OF FORMULA I OR I', teflubenzuron (768)+COMPOUND OF FORMULA I OR I', tefluthrin (769)+COMPOUND OF FORMULA I OR I', temephos (770)+COMPOUND OF FORMULA I OR I', TEPP (1417)+COMPOUND OF FORMULA I OR I', terallethrin (1418)+COMPOUND OF FORMULA I OR I', terbam (alternative name)+COMPOUND OF FORMULA I OR I', terbufos (773)+COMPOUND OF FORMULA I OR I', tetrachloroethane [CCN]+COMPOUND OF FORMULA I OR I', tetrachlorvinphos (777)+COMPOUND OF FORMULA I OR I', tetramethrin (787)+COMPOUND OF FORMULA I OR I', tetramethylfluthrin (CAS. Reg. No.: 84937-88-2)+COMPOUND OF FORMULA I OR I', theta-cypermethrin (204)+COMPOUND OF FORMULA I OR I', thiacloprid (791)+COMPOUND OF FORMULA I OR I', thiafenox (alternative name)+COMPOUND OF FORMULA I OR I', thiamethoxam (792)+COMPOUND OF FORMULA I OR I', thicrofos (1428)+COMPOUND OF FORMULA I OR I', thiocarboxime (1431)+COMPOUND OF FORMULA I OR I', thiocyclam (798)+COMPOUND OF FORMULA I OR I', thiocyclam hydrogen oxalate (798)+COMPOUND OF FORMULA I OR I', thiodicarb (799)+COMPOUND OF FORMULA I OR I', thiofanox (800)+COMPOUND OF FORMULA I OR I', thiometon (801)+COMPOUND OF FORMULA I OR I', thionazin (1434)+COMPOUND OF FORMULA I OR I', thiosultap (803)+COMPOUND OF FORMULA I OR I', thiosultap-sodium (803)+COMPOUND OF FORMULA I OR I', thuringiensin (alternative name) [CCN]+COMPOUND OF FORMULA I OR I', tolfenpyrad (809)+COMPOUND OF FORMULA I OR I', tralomethrin (812)+COMPOUND OF FORMULA I OR I', transfluthrin (813)+COMPOUND OF FORMULA I OR I', transpermethrin (1440)+COMPOUND OF FORMULA I OR I', triamiphos (1441)+COMPOUND OF FORMULA I OR I', triazamate (818)+COMPOUND OF FORMULA I OR I', triazophos (820)+COMPOUND OF FORMULA I OR I', triazuron (alternative name)+COMPOUND OF FORMULA I OR I', trichlorfon (824)+COMPOUND OF FORMULA I OR I', trichlormetaphos-3 (alternative name) [CCN]+COMPOUND OF FORMULA I OR I', trichloronat (1452)+COMPOUND OF FORMULA I OR I', trifenofos (1455)+COMPOUND OF FORMULA I OR I', triflumuron (835)+COMPOUND OF FORMULA I OR I', trimethacarb (840)+COMPOUND OF FORMULA I OR I', triprene (1459)+COMPOUND OF FORMULA I OR I', vamidothion (847)+COMPOUND OF FORMULA I OR I', vaniliprole [CCN]+COMPOUND OF FORMULA I OR I', veratridine (alternative name) (725)+COMPOUND OF FORMULA I OR I', veratrine (alternative name) (725)+COMPOUND OF FORMULA I OR I', XMC (853)+COMPOUND OF FORMULA I OR I', xylylcarb (854)+COMPOUND OF FORMULA I OR I', YI-5302 (compound code)+COMPOUND OF FORMULA I OR I', zeta-cypermethrin (205)+COMPOUND OF FORMULA I OR I', zetamethrin (alternative name)+COMPOUND OF FORMULA I OR I', zinc phosphide (640)+COMPOUND OF FORMULA I OR I', zolaprofos (1469) and ZXI 8901 (development code) (858)+COMPOUND OF FORMULA I OR I', a molluscicide selected from the group of substances consisting of bis(tributyltin) oxide (IUPAC name) (913)+COMPOUND OF FORMULA I OR I', bromoacetamide [CCN]+COMPOUND OF FORMULA I OR I', calcium arsenate [CCN]+COMPOUND OF FORMULA I OR I', cloethocarb (999)+COMPOUND OF FORMULA I OR I', copper acetoarsenite [CCN]+COMPOUND OF FORMULA I OR I', copper sulfate (172)+COMPOUND OF FORMULA I OR I', fentin (347)+COMPOUND OF FORMULA I OR I', ferric phosphate (IUPAC name) (352)+COMPOUND OF FORMULA I OR I', metaldehyde (518)+COMPOUND OF FORMULA I OR I', methiocarb (530)+COMPOUND OF FORMULA I OR I', niclosamide (576)+COMPOUND OF FORMULA I OR I', niclosamide-olamine (576)+COMPOUND OF FORMULA I OR I', pentachlorophenol (623)+COMPOUND OF FORMULA I OR I', sodium pentachlorophenoxide (623)+COMPOUND OF FORMULA I OR I', tazimcarb (1412)+COMPOUND OF FORMULA I OR I', thiodicarb (799)+COMPOUND OF FORMULA I OR I', tralopyril [CCN]+COMPOUND OF FORMULA I OR I', tributyltin oxide (913)+COMPOUND OF FORMULA I OR I', trifenmorph (1454)+COMPOUND OF FORMULA I OR I', trimethacarb (840)+COMPOUND OF FORMULA I OR I', triphenyltin acetate (IUPAC name) (347) and triphenyltin hydroxide (IUPAC name) (347)+COMPOUND OF FORMULA I OR I', a nematicide selected from the group of substances consisting of AKD-3088 (compound code)+COMPOUND OF FORMULA I OR I', 1,2-dibromo-3-chloropropane (IUPAC/Chemical Abstracts name) (1045)+COMPOUND OF FORMULA I OR I', 1,2-dichloropropane (IUPAC/Chemical Abstracts name) (1062)+COMPOUND OF FORMULA I OR I', 1,2-dichloropropane with 1,3-dichloropropene (IUPAC name) (1063)+COMPOUND OF FORMULA I OR I', 1,3-dichloropropene (233)+COMPOUND OF FORMULA I OR I', 3,4-dichlorotetrahydrothiophene 1,1-dioxide (IUPAC/Chemical Abstracts name) (1065)+COMPOUND OF FORMULA I OR I', 3-(4-chlorophenyl)-5-methylrhodanine (IUPAC name) (980)+COMPOUND OF FORMULA I OR I', 5-methyl-6-thioxo-1,3,5-thiadiazinan-3-ylacetic acid (IUPAC name) (1286)+COMPOUND OF FORMULA I OR I', 6-isopentenylaminopurine (alternative name) (210)+COMPOUND OF FORMULA I OR I', abamectin (1)+COMPOUND OF FORMULA I OR I', acetoprole [CCN]+COMPOUND OF FORMULA I OR I', alanycarb (15)+COMPOUND OF FORMULA I OR I', aldicarb (16)+COMPOUND OF FORMULA I OR I', aldoxycarb (863)+COMPOUND OF FORMULA I OR I', AZ 60541 (compound code)+COMPOUND OF FORMULA I OR I', benclothiaz [CCN]+COMPOUND OF FORMULA I OR I', benomyl (62)+COMPOUND OF FORMULA I OR I', butylpyridaben (alternative name)+COMPOUND OF FORMULA I OR I', cadusafos (109)+COMPOUND OF FORMULA I OR I', carbofuran (118)+COMPOUND OF FORMULA I OR I', carbon disulfide (945)+COMPOUND OF FORMULA I OR I', carbosulfan (119)+COMPOUND OF FORMULA I OR I', chloropicrin (141)+COMPOUND OF FORMULA I OR I', chlorpyrifos (145)+COMPOUND OF FORMULA I OR I', cloethocarb (999)+COMPOUND OF FORMULA I OR I', cytokinins (alternative name) (210)+COMPOUND OF FORMULA I OR I', dazomet (216)+COMPOUND OF FORMULA I OR I', DBCP (1045)+COMPOUND OF FORMULA I OR I', DCIP (218)+COMPOUND OF FORMULA I OR I', diamidafos (1044)+COMPOUND OF FORMULA I OR I', dichlofenthion (1051)+COMPOUND OF FORMULA I OR I', dicliphos (alternative name)+COMPOUND OF FORMULA I OR I', dimethoate (262)+COMPOUND OF FORMULA I OR I', doramectin (alternative name) [CCN]+COMPOUND OF FORMULA I OR I', emamectin (291)+COMPOUND OF FORMULA I OR I', emamectin benzoate (291)+COMPOUND OF FORMULA I OR I', eprinomectin (alternative name) [CCN]+COMPOUND OF FORMULA I OR I', ethoprophos (312)+COMPOUND OF FORMULA I OR I', ethylene dibromide (316)+COMPOUND OF FORMULA I OR I', fenamiphos (326)+COMPOUND OF FORMULA I OR I', fenpyrad (alternative name)+COMPOUND OF FORMULA I OR I', fensulfothion (1158)+COMPOUND OF FORMULA I OR I', fluensulfone (CAS. Reg. No.: 318290-98-1)+COMPOUND OF FORMULA I OR I', fosthiazate (408)+COMPOUND OF FORMULA I OR I', fosthietan (1196)+COMPOUND OF FORMULA I OR I', furfural (alternative name) [CCN]+COMPOUND OF FORMULA I OR I', GY-81 (development code) (423)+COMPOUND OF FORMULA I OR I', heterophos [CCN]+COMPOUND OF FORMULA I OR I', imicyafos [CCN]+COMPOUND OF FORMULA I OR I', iodomethane (IUPAC name) (542)+COMPOUND OF FORMULA I OR I', isamidofos (1230)+COMPOUND OF FORMULA I OR I', isazofos (1231)+COMPOUND OF FORMULA I OR I', ivermectin (alternative name) [CCN]+COMPOUND OF FORMULA I OR I', kinetin (alternative name) (210)+COMPOUND OF FORMULA I OR I', mecarphon (1258)+COMPOUND OF FORMULA I OR I', metam (519)+COMPOUND OF FORMULA I OR I', metam-potassium (alternative name) (519)+COMPOUND OF FORMULA I OR I', metam-sodium (519)+COMPOUND OF FORMULA I OR I', methyl bromide (537)+COMPOUND OF FORMULA I OR I', methyl isothiocyanate (543)+COMPOUND OF FORMULA I OR I', milbemycin oxime (alternative name) [CCN]+COMPOUND OF FORMULA I OR I', moxidectin (alternative name) [CCN]+COMPOUND OF FORMULA I OR I', *Myrothecium verrucaria* composition (alternative name) (565)+COMPOUND OF FORMULA I OR I', NC-184 (compound code)+COMPOUND OF FORMULA I OR I', oxamyl (602)+COMPOUND OF FORMULA I OR I', phorate (636)+COMPOUND OF FORMULA I OR I', phosphamidon (639)+COMPOUND OF FORMULA I OR I', phosphocarb [CCN]+COMPOUND OF FORMULA I OR I', sebufos (alternative name)+COMPOUND OF FORMULA I OR I', selamectin (alternative name) [CCN]+COMPOUND OF FORMULA I OR I', spinosad (737)+COMPOUND OF FORMULA I OR I', terbam (alternative name)+COMPOUND OF FORMULA I OR I', terbufos (773)+COMPOUND OF FORMULA I OR I', tetrachlorothiophene (IUPAC/Chemical Abstracts name) (1422)+COMPOUND OF FORMULA I OR I', thiafenox (alternative name)+COMPOUND OF FORMULA I OR I', thionazin (1434)+COMPOUND OF FORMULA I OR I', triazophos (820)+COMPOUND OF FORMULA I OR I', triazuron (alternative name)+COMPOUND OF FORMULA I OR I', xylenols [CCN]+COMPOUND OF FORMULA I OR I', YI-5302 (compound code) and zeatin (alternative name) (210)+COMPOUND OF FORMULA I OR I', a nitrification inhibitor selected from the group of substances consisting of potassium ethylxanthate [CCN] and nitrapyrin (580)+COMPOUND OF FORMULA I OR I', a plant activator selected from the group of substances consisting of acibenzolar (6)+COMPOUND OF FORMULA I OR I', acibenzolar-5-methyl (6)+COMPOUND OF FORMULA I OR I', probenazole (658) and *Reynoutria sachalinensis* extract (alternative name) (720)+COMPOUND OF FORMULA I OR I', a rodenticide selected from the group of substances consisting of 2-isovalerylindan-1,3-dione (IUPAC name) (1246)+COMPOUND OF FORMULA I OR I', 4-(quinoxalin-2-ylamino)benzenesulfonamide (IUPAC name) (748)+COMPOUND OF FORMULA I OR I', alpha-chlorohydrin [CCN]+COMPOUND OF FORMULA I OR I', aluminium phosphide (640)+COMPOUND OF FORMULA I OR I', antu (880)+COMPOUND OF FORMULA I OR I', arsenous oxide (882)+COMPOUND OF FORMULA I OR I', barium carbonate (891)+COMPOUND OF FORMULA I OR I', bisthiosemi (912)+COMPOUND OF FORMULA I OR I', brodifacoum (89)+COMPOUND OF FORMULA I OR I', bromadiolone (91)+COMPOUND OF FORMULA I OR I', bromethalin (92)+COMPOUND OF FORMULA I OR I', calcium cyanide (444)+COMPOUND OF FORMULA I OR I', chloralose (127)+COMPOUND OF FORMULA I OR I', chlorophacinone (140)+COMPOUND OF FORMULA I OR I', cholecalciferol (alternative name) (850)+COMPOUND OF FORMULA I OR I', coumachlor (1004)+COMPOUND OF FORMULA I OR I', coumafuryl (1005)+COMPOUND OF FORMULA I OR I', coumatetralyl (175)+COMPOUND OF FORMULA I OR I', crimidine (1009)+COMPOUND OF FORMULA I OR I', difenacoum (246)+COMPOUND OF FORMULA I OR I', difethialone (249)+COMPOUND OF FORMULA I OR I', diphacinone (273)+COMPOUND OF FORMULA I OR I', ergocalciferol (301)+COMPOUND OF FORMULA I OR I', flocoumafen (357)+COMPOUND OF FORMULA I OR I', fluoroacetamide (379)+COMPOUND OF FORMULA I OR I', flupropadine (1183)+COMPOUND OF FORMULA I OR I', flupropadine hydrochloride (1183)+COMPOUND OF FORMULA I OR I', gamma-HCH (430)+COMPOUND OF FORMULA I OR I', HCH (430)+COMPOUND OF FORMULA I OR I', hydrogen cyanide (444)+COMPOUND OF FORMULA I OR I', iodomethane (IUPAC name) (542)+COMPOUND OF FORMULA I OR I', lindane (430)+COMPOUND OF FORMULA I OR I', magnesium phosphide (IUPAC name) (640)+COMPOUND OF FORMULA I OR I', methyl bromide (537)+COMPOUND OF FORMULA I OR I', norbormide (1318)+COMPOUND OF FORMULA I OR I', phosacetim (1336)+COMPOUND OF FORMULA I OR I', phosphine (IUPAC name) (640)+COMPOUND OF FORMULA I OR I', phosphorus [CCN]+COMPOUND OF FORMULA I OR I', pindone (1341)+COMPOUND OF FORMULA I OR I', potassium arsenite [CCN]+COMPOUND OF FORMULA I OR I', pyrinuron (1371)+COMPOUND OF FORMULA I OR I', scilliroside (1390)+COMPOUND OF FORMULA I OR I', sodium arsenite [CCN]+COMPOUND OF FORMULA I OR I', sodium cyanide (444)+COMPOUND OF FORMULA I OR I', sodium fluoroacetate (735)+COMPOUND OF FORMULA I OR I', strychnine (745)+COMPOUND OF FORMULA I OR I', thallium sulfate [CCN]+COMPOUND OF FORMULA I OR I', warfarin (851) and zinc phosphide (640)+COMPOUND OF FORMULA I OR I', a synergist selected from the group of substances consisting of 2-(2-butoxyethoxy)ethyl piperonylate (IUPAC name) (934)+COMPOUND OF FORMULA I OR I', 5-(1,3-benzodioxol-5-yl)-3-hexylcyclohex-2-enone (IUPAC name) (903)+COMPOUND OF FORMULA I OR I', farnesol with nerolidol (alternative name) (324)+COMPOUND OF FORMULA I OR I', MB-599 (development code) (498)+COMPOUND OF FORMULA I OR I', MGK 264 (development code) (296)+COMPOUND OF FORMULA I OR I', piperonyl butoxide (649)+COMPOUND OF FORMULA I OR I', piprotal (1343)+COMPOUND OF FORMULA I OR I', propyl isomer (1358)+COMPOUND OF FORMULA I OR I', S421 (development code) (724)+COMPOUND OF FORMULA I OR I', sesamex (1393)+COMPOUND OF FORMULA I OR I', sesasmolin (1394) and sulfoxide (1406)+COMPOUND OF FORMULA I OR I', an animal repellent selected from the group of substances consisting of anthraquinone (32)+COMPOUND OF FORMULA I OR I', chloralose (127)+COMPOUND OF FORMULA I OR I', copper naphthenate [CCN]+COMPOUND OF FORMULA I OR I', copper oxychloride (171)+COMPOUND OF FORMULA I OR I', diazinon (227)+COMPOUND OF FORMULA I OR I', dicyclopentadiene (chemical name) (1069)+COMPOUND OF FORMULA I OR I', guazatine (422)+COMPOUND OF FORMULA I OR I', guazatine acetates (422)+COMPOUND OF FORMULA I OR I', methiocarb (530)+COMPOUND OF FORMULA I OR I', pyridin-4-amine (IUPAC name) (23)+COMPOUND OF FORMULA I OR I', thiram (804)+COMPOUND OF FORMULA I OR I', trimethacarb (840)+COMPOUND OF FORMULA I OR I', zinc naphthenate [CCN] and ziram (856)+COMPOUND OF FORMULA I OR I', a virucide selected from the group of substances consisting of imanin (alternative name) [CCN] and ribavirin (alternative name) [CCN]+COMPOUND OF FORMULA I OR I', a wound protectant selected from the group of substances consisting of mercuric oxide (512)+COMPOUND OF FORMULA I OR I', octhilinone (590) and thiophanate-methyl (802)+COMPOUND OF FORMULA I OR I', an insecticide selected from the group consisting of the compound of the formula A-1

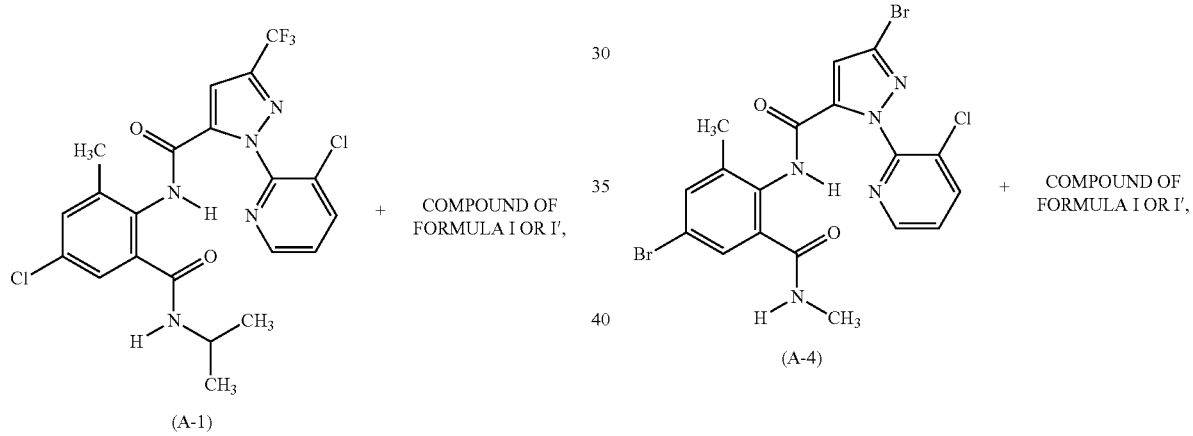

(A-1)

the formula A-2

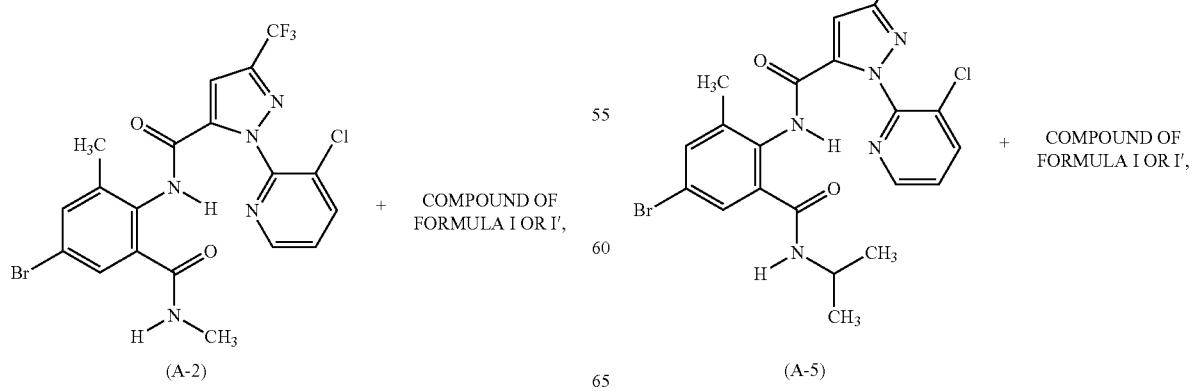

(A-2)

the formula A-3

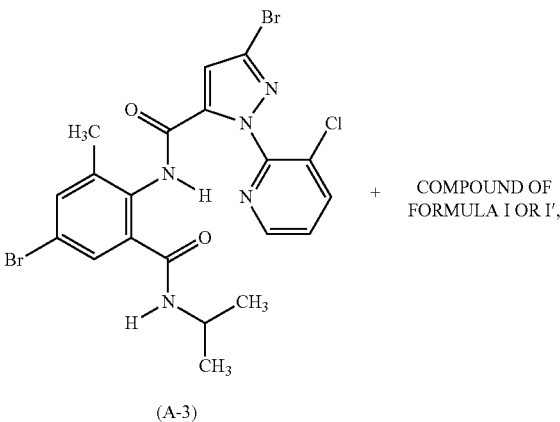 [SMILES: Cc1cc(Br)cc(C(=O)NC(C)C)c1NC(=O)c1cc(Br)nn1-c1ncccc1Cl ; "(A-3)"]

(A-3)

the formula A-4

(A-4)

the formula A-5

(A-5)

the formula A-6
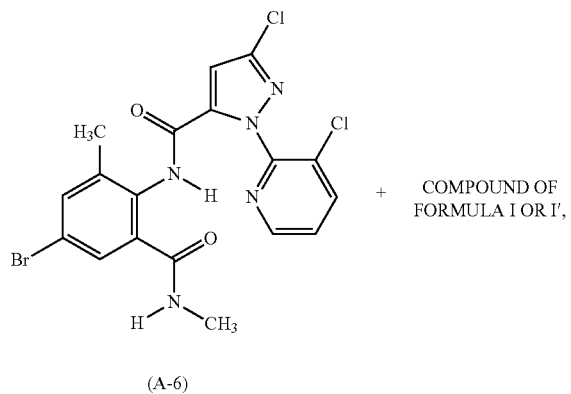 [SMILES: CNC(=O)c1cc(Br)cc(C)c1NC(=O)c1cc(Cl)nn1-c1ncccc1Cl ; "(A-6)"]
(A-6)
+ COMPOUND OF FORMULA I OR I',
the formula A-7
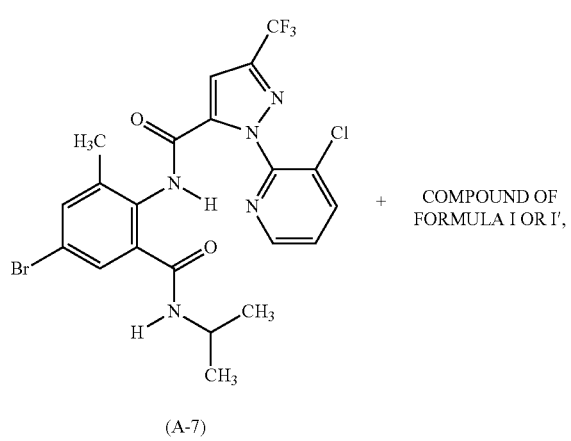 [SMILES: Cc1cc(Br)cc(C(=O)NC(C)C)c1NC(=O)c1cc(C(F)(F)F)nn1-c1ncccc1Cl ; "(A-7)"]
(A-7)
+ COMPOUND OF FORMULA I OR I',
the formula A-8
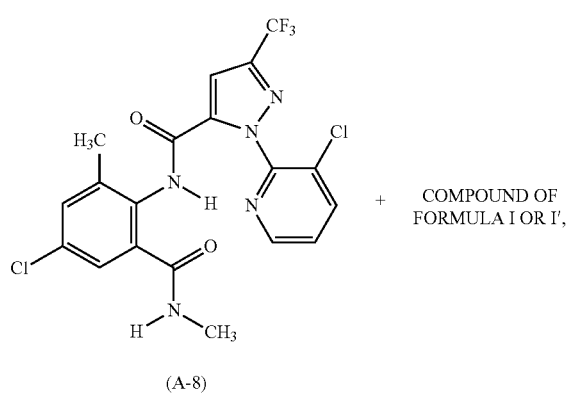 [SMILES: CNC(=O)c1cc(Cl)cc(C)c1NC(=O)c1cc(C(F)(F)F)nn1-c1ncccc1Cl ; "(A-8)"]
(A-8)
+ COMPOUND OF FORMULA I OR I',
the formula A-9
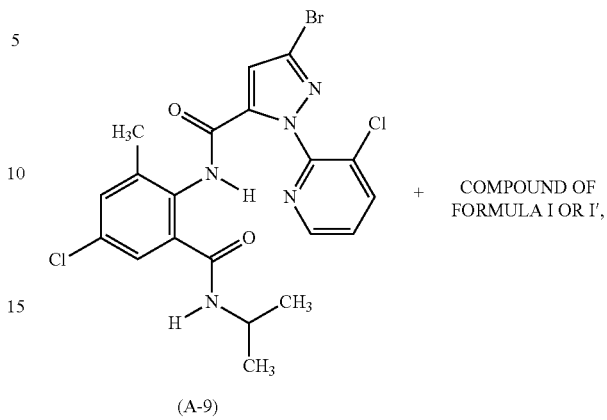
(A-9)
+ COMPOUND OF FORMULA I OR I',
the formula A-1C
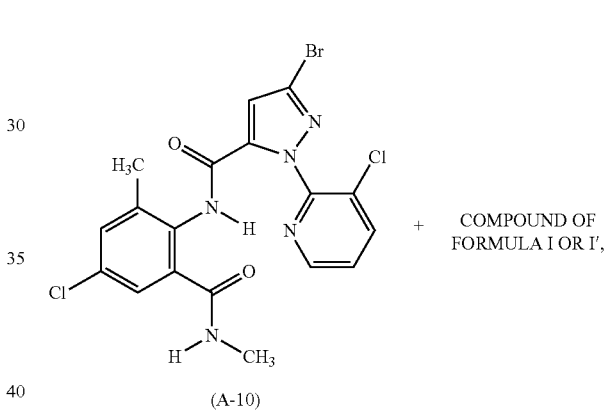
(A-10)
+ COMPOUND OF FORMULA I OR I',
the formula A-11
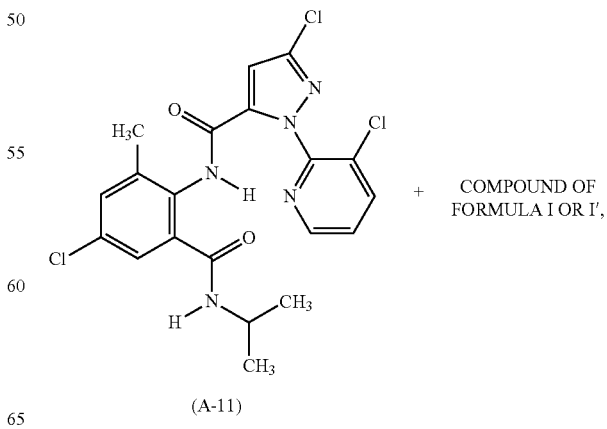
(A-11)
+ COMPOUND OF FORMULA I OR I', the formula A-12
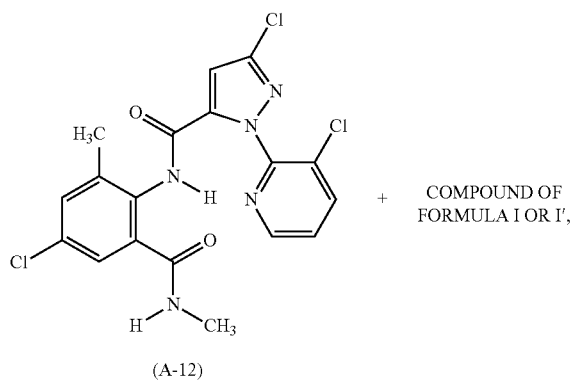
(A-12) + COMPOUND OF FORMULA I OR I',
the formula A-13
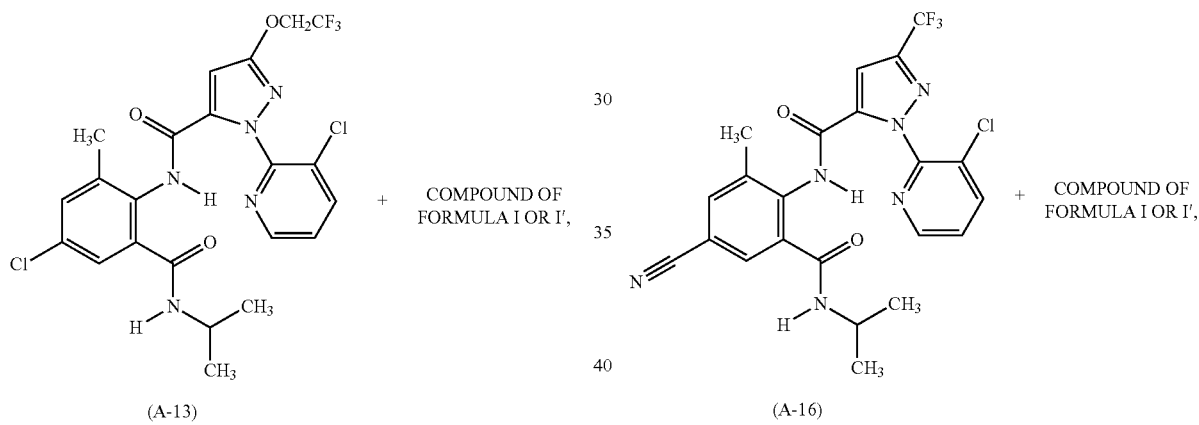
(A-13) + COMPOUND OF FORMULA I OR I',
the formula A-14
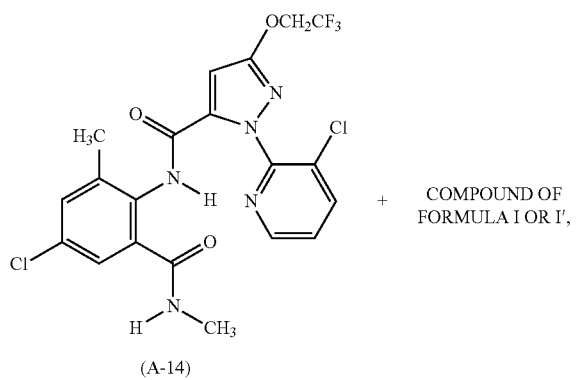
(A-14) + COMPOUND OF FORMULA I OR I',
the formula A-15
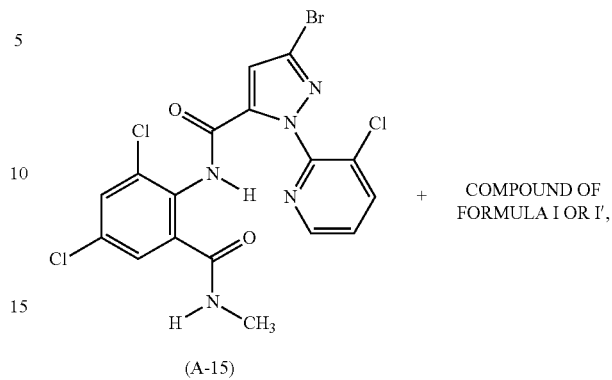
(A-15) + COMPOUND OF FORMULA I OR I',
the formula A-16
(A-16) + COMPOUND OF FORMULA I OR I',
the formula A-17
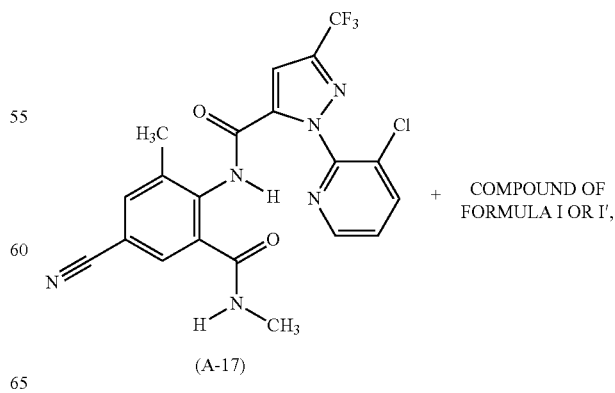
(A-17) + COMPOUND OF FORMULA I OR I', the formula A-18
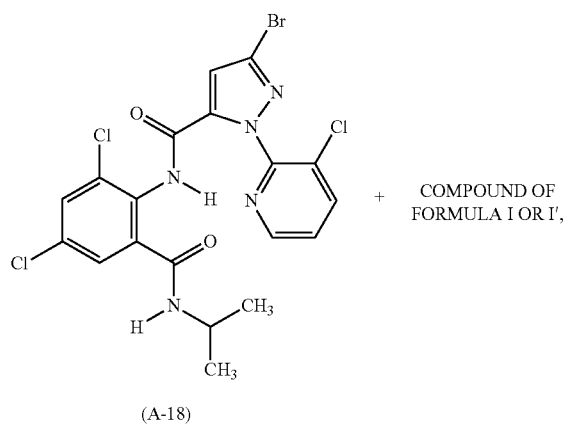 [SMILES: CC(C)NC(=O)c1cc(Cl)cc(Cl)c1NC(=O)c1cc(Br)nn1-c1ncccc1Cl ; "(A-18)"]
(A-18) + COMPOUND OF FORMULA I OR I',
the formula A-19
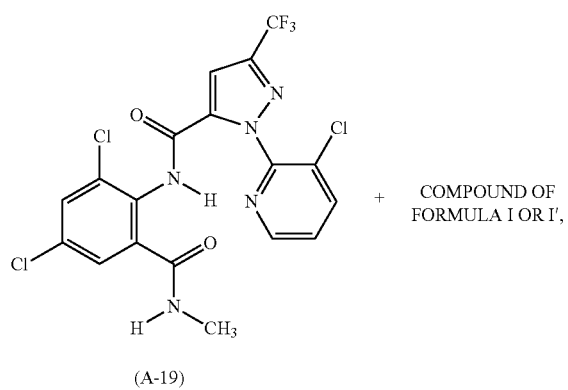
(A-19) + COMPOUND OF FORMULA I OR I',
the formula A-20
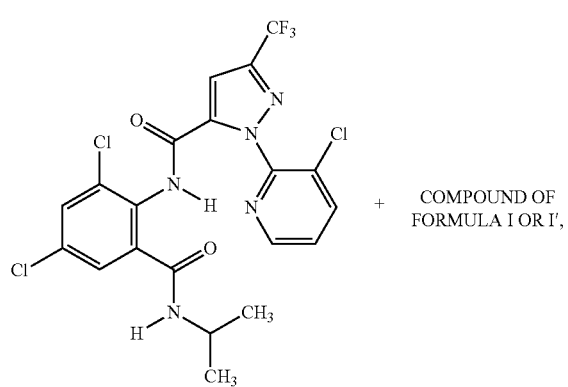
(A-20) + COMPOUND OF FORMULA I OR I',
the formula A-21
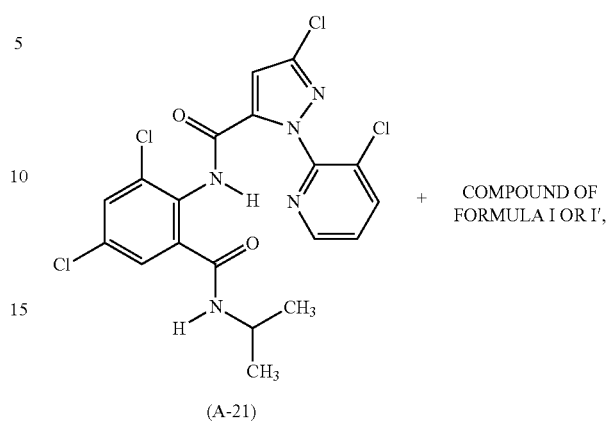
(A-21) + COMPOUND OF FORMULA I OR I',
the formula A-22
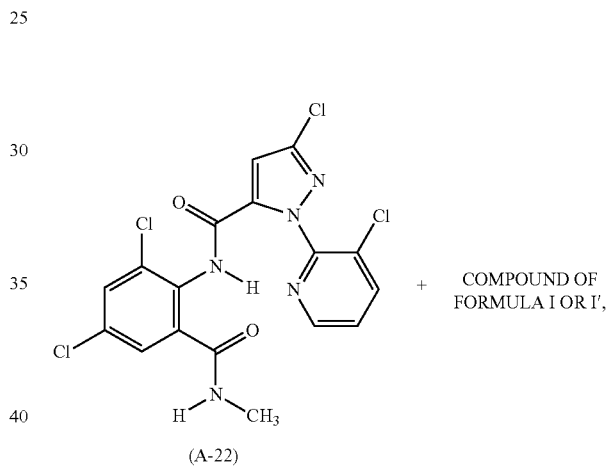
(A-22) + COMPOUND OF FORMULA I OR I',
the formula A-23
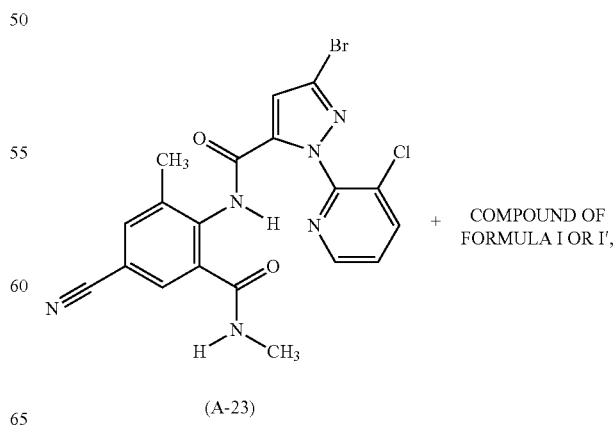
(A-23) + COMPOUND OF FORMULA I OR I', the formula A-24

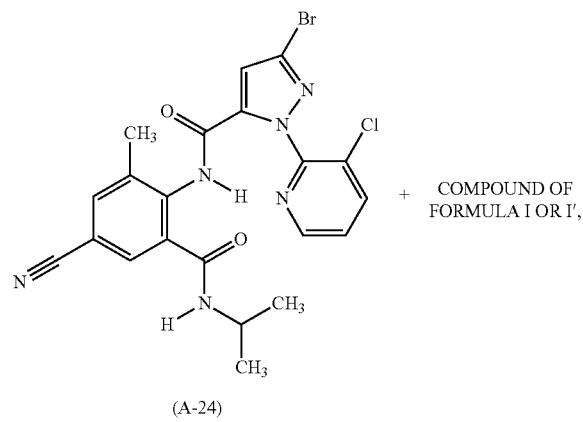 [SMILES: Cc1cc(C#N)cc(C(=O)NC(C)C)c1NC(=O)c1cc(Br)nn1-c1ncccc1Cl ; "(A-24)"]

(A-24)

the formula A-25

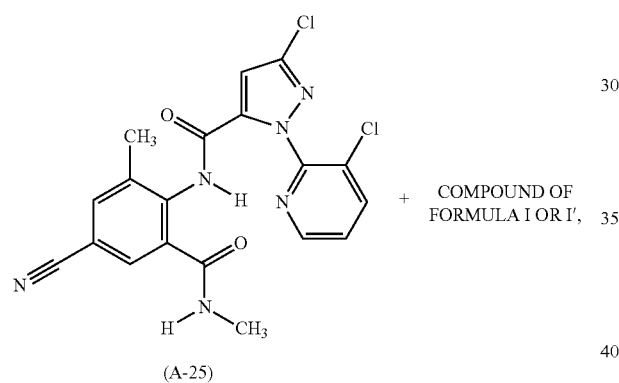

(A-25)

the formula A-26

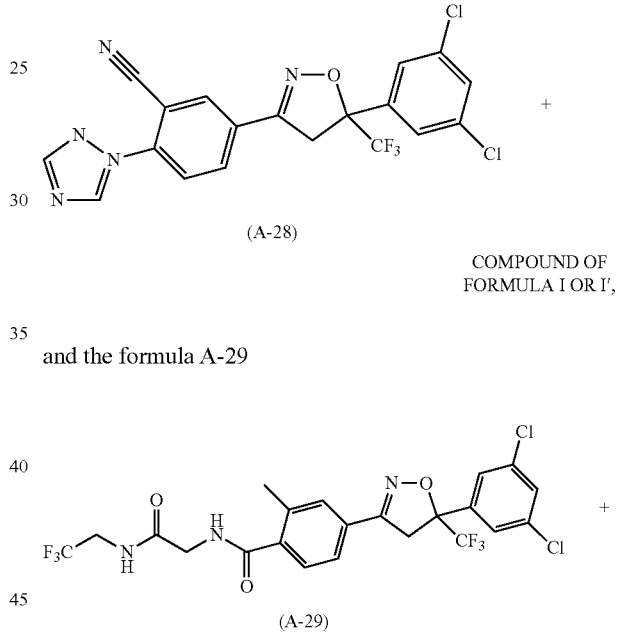

(A-26)

+ COMPOUND OF FORMULA I OR I', and the formula A-27

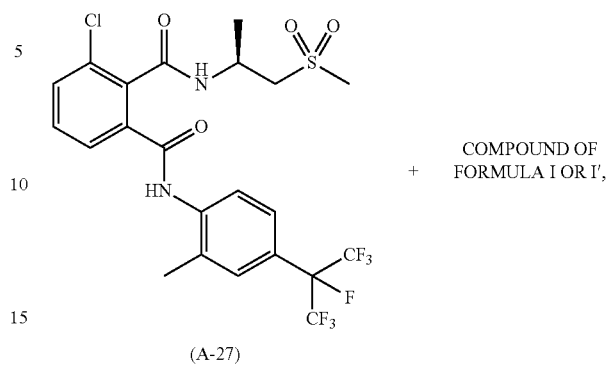

(A-27)

+ COMPOUND OF FORMULA I OR I', an insecticide selected from the group consisting of the compound of the formula A-28

(A-28)

+ COMPOUND OF FORMULA I OR I', and the formula A-29

(A-29)

+ COMPOUND OF FORMULA I OR I', and the formula A-30

(A-30)

+ COMPOUND OF FORMULA I OR I', an insecticide selected from the group consisting of the compound of the formula A-31

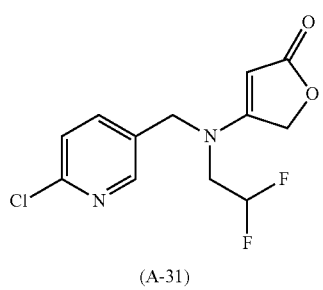

(A-31)

the formula A-32

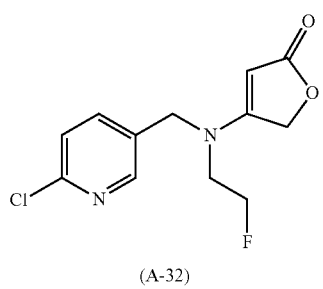

(A-32)

and the formula A-33

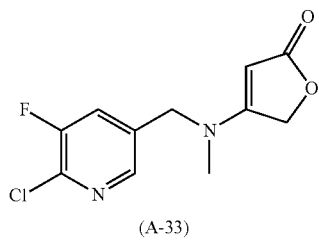

(A-33)

+ COMPOUND OF FORMULA I OR I',

+ COMPOUND OF FORMULA I OR I',

+ COMPOUND OF FORMULA I OR I',

The references in brackets behind the active ingredients, e.g. [3878-19-1] refer to the Chemical Abstracts Registry number. The compounds of the formula A-1 to A-26 are described in WO 03/015518 or in WO 04/067528. The compound of the formula A-27 is described in WO 06/022225 and in WO 07/112,844. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright © 1995-2004]; for example, the compound "acetoprole" is described under the internet address http://www.alanwood.net/pesticides/acetoprole.htmL. Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The compounds of formula I or I' according to the invention can also be used in combination with one or more fungicides. In particular, in the following mixtures of the compounds of formula I or I' with fungicides, the term COMPOUND OF FORMULA I OR I' preferably refers to a compound selected from one of the Tables 1 to 7:

COMPOUND OF FORMULA I OR I'+(E)-N-methyl-2-[2-(2,5-dimethylphenoxymethyl)phenyl]-2-methoxy-iminoacetamide (SSF-129), COMPOUND OF FORMULA I OR I'+4-bromo-2-cyano-N,N-dimethyl-6-trifluoromethyl benzimidazole-1-sulphonamide, COMPOUND OF FORMULA I OR I'+α-[N-(3-chloro-2,6-xylyl)-2-methoxyacetamido]-γ-butyrolactone, COMPOUND OF FORMULA I OR I'+4-chloro-2-cyano-N,N-dimethyl-5-p-tolylimidazole-1-sulfonamide (IKF-916, cyamidazosulfamid), COMPOUND OF FORMULA I OR I'+3-5-dichloro-N-(3-chloro-1-ethyl-1-methyl-2-oxopropyl)-4-methylbenzamide (RH-7281, zoxamide), COMPOUND OF FORMULA I OR I'+N-allyl-4,5,-dimethyl-2-trimethylsilylthiophene-3-carboxamide (MON65500), COMPOUND OF FORMULA I OR I'+N-(1-cyano-1,2-dimethylpropyl)-2-(2,4-dichlorophenoxy)propionamide (AC382042), COMPOUND OF FORMULA I OR I'+N-(2-methoxy-5-pyridyl)-cyclopropane carboxamide, COMPOUND OF FORMULA I OR I'+acibenzolar, COMPOUND OF FORMULA I OR I'+alanycarb, COMPOUND OF FORMULA I OR I'+aldimorph, COMPOUND OF FORMULA I OR I'+ametoctradin, COMPOUND OF FORMULA I OR I'+amisulbrom, COMPOUND OF FORMULA I OR I'+anilazine, COMPOUND OF FORMULA I OR I'+azaconazole, COMPOUND OF FORMULA I OR I'+azoxystrobin, COMPOUND OF FORMULA I OR I'+benalaxyl, COMPOUND OF FORMULA I OR I'+benalaxyl-M, COMPOUND OF FORMULA I OR I'+benomyl, COMPOUND OF FORMULA I OR I'+benthiavalicarb, COMPOUND OF FORMULA I OR I'+biloxazol, COMPOUND OF FORMULA I OR I'+bitertanol, COMPOUND OF FORMULA I OR I'+bixafen, COMPOUND OF FORMULA I OR I'+blasticidin S, COMPOUND OF FORMULA I OR I'+boscalid, COMPOUND OF FORMULA I OR I'+bromuconazole, COMPOUND OF FORMULA I OR I'+bupirimate, COMPOUND OF FORMULA I OR I'+captafol, COMPOUND OF FORMULA I OR I'+captan, COMPOUND OF FORMULA I OR I'+carbendazim, COMPOUND OF FORMULA I OR I'+carbendazim chlorhydrate, COMPOUND OF FORMULA I OR I'+carboxin, COMPOUND OF FORMULA I OR I'+carpropamid, carvone, COMPOUND OF FORMULA I OR I'+CGA41396, COMPOUND OF FORMULA I OR I'+CGA41397, COMPOUND OF FORMULA I OR I'+chinomethionate, COMPOUND OF FORMULA I OR I'+chlazafenone, COMPOUND OF FORMULA I OR I'+chlorothalonil, COMPOUND OF FORMULA I OR I'+chlorozolinate, COMPOUND OF FORMULA I OR I'+clozylacon, COMPOUND OF FORMULA I OR I'+copper containing compounds such as copper oxychloride, copper oxyquinolate, copper sulphate, copper tallate and Bordeaux mixture, COMPOUND OF FORMULA I OR I'+cyazofamid, COMPOUND OF FORMULA I OR I'+cyflufenamid, COMPOUND OF FORMULA I OR I'+cymoxanil, COMPOUND OF FORMULA I OR I'+cyproconazole, COMPOUND OF FORMULA I OR I'+cyprodinil, COMPOUND OF FOR- MULA I OR I'+debacarb, COMPOUND OF FORMULA I OR I'+di-2-pyridyl disulphide 1,1'-dioxide, COMPOUND OF FORMULA I OR I'+dichlofluanid, COMPOUND OF FORMULA I OR I'+diclomezine, COMPOUND OF FORMULA I OR I'+dicloran, COMPOUND OF FORMULA I OR I'+diethofencarb, COMPOUND OF FORMULA I OR I'+difenoconazole, COMPOUND OF FORMULA I OR I'+difenzoquat, COMPOUND OF FORMULA I OR I'+diflumetorim, COMPOUND OF FORMULA I OR I'+O,O-di-isopropyl-5-benzyl thiophosphate, COMPOUND OF FORMULA I OR I'+dimefluazole, COMPOUND OF FORMULA I OR I'+dimetconazole, COMPOUND OF FORMULA I OR I'+dimethomorph, COMPOUND OF FORMULA I OR I'+dimethirimol, COMPOUND OF FORMULA I OR I'+dimoxystrobin, COMPOUND OF FORMULA I OR I'+diniconazole, COMPOUND OF FORMULA I OR I'+dinocap, COMPOUND OF FORMULA I OR I'+dithianon, COMPOUND OF FORMULA I OR I'+dodecyl dimethyl ammonium chloride, COMPOUND OF FORMULA I OR I'+dodemorph, COMPOUND OF FORMULA I OR I'+dodine, COMPOUND OF FORMULA I OR I'+doguadine, COMPOUND OF FORMULA I OR I'+edifenphos, COMPOUND OF FORMULA I OR I'+epoxiconazole, COMPOUND OF FORMULA I OR I'+ethirimol, COMPOUND OF FORMULA I OR I'+ethyl(Z)—N-benzyl-N([methyl(methyl-thio-ethylideneaminooxycarbonyl)amino]thio)-β-alaninate, COMPOUND OF FORMULA I OR I'+etridiazole, COMPOUND OF FORMULA I OR I'+famoxadone, COMPOUND OF FORMULA I OR I'+fenamidone (RPA407213), COMPOUND OF FORMULA I OR I'+fenarimol, COMPOUND OF FORMULA I OR I'+fenbuconazole, COMPOUND OF FORMULA I OR I'+fenfuram, COMPOUND OF FORMULA I OR I'+fenhexamid (KBR2738), COMPOUND OF FORMULA I OR I'+fenoxanil, COMPOUND OF FORMULA I OR I'+fenpiclonil, COMPOUND OF FORMULA I OR I'+fenpropidin, COMPOUND OF FORMULA I OR I'+fenpropimorph, COMPOUND OF FORMULA I OR I'+fenpyrazamine/ipfenpyrazolone, COMPOUND OF FORMULA I OR I'+fentin acetate, COMPOUND OF FORMULA I OR I'+fentin hydroxide, COMPOUND OF FORMULA I OR I'+ferbam, COMPOUND OF FORMULA I OR I'+ferimzone, COMPOUND OF FORMULA I OR I'+fluazinam, COMPOUND OF FORMULA I OR I'+fludioxonil, COMPOUND OF FORMULA I OR I'+flumetover, COMPOUND OF FORMULA I OR I'+flumorph, COMPOUND OF FORMULA I OR I'+fluopicolide, COMPOUND OF FORMULA I OR I'+fluopyram, COMPOUND OF FORMULA I OR I'+fluoxastrobin, COMPOUND OF FORMULA I OR I'+fluoroimide, COMPOUND OF FORMULA I OR I'+fluquinconazole, COMPOUND OF FORMULA I OR I'+flusilazole, COMPOUND OF FORMULA I OR I'+flutianil, COMPOUND OF FORMULA I OR I'+flutolanil, COMPOUND OF FORMULA I OR I'+flutriafol, COMPOUND OF FORMULA I OR I'+fluxapyroxad, COMPOUND OF FORMULA I OR I'+folpet, COMPOUND OF FORMULA I OR I'+fuberidazole, COMPOUND OF FORMULA I OR I'+furalaxyl, COMPOUND OF FORMULA I OR I'+furametpyr, COMPOUND OF FORMULA I OR I'+guazatine, COMPOUND OF FORMULA I OR I'+hexaconazole, COMPOUND OF FORMULA I OR I'+hydroxyisoxazole, COMPOUND OF FORMULA I OR I'+hymexazole, COMPOUND OF FORMULA I OR I'+imazalil, COMPOUND OF FORMULA I OR I'+imibenconazole, COMPOUND OF FORMULA I OR I'+iminoctadine, COMPOUND OF FORMULA I OR I'+iminoctadine triacetate, COMPOUND OF FORMULA I OR I'+ipconazole, COMPOUND OF FORMULA I OR I'+iprobenfos, COMPOUND OF FORMULA I OR I'+iprodione, COMPOUND OF FORMULA I OR I'+iprovalicarb (SZX0722), COMPOUND OF FORMULA I OR I'+isopropanyl butyl carbamate, COMPOUND OF FORMULA I OR I'+isoprothiolane, COMPOUND OF FORMULA I OR I'+isopyrazam, COMPOUND OF FORMULA I OR I'+isotianil, COMPOUND OF FORMULA I OR I'+kasugamycin, COMPOUND OF FORMULA I OR I'+kresoxim-methyl, COMPOUND OF FORMULA I OR I'+LY186054, COMPOUND OF FORMULA I OR I'+LY211795, COMPOUND OF FORMULA I OR I'+LY248908, COMPOUND OF FORMULA I OR I'+mancozeb, COMPOUND OF FORMULA I OR I'+mandipropamid, COMPOUND OF FORMULA I OR I'+maneb, COMPOUND OF FORMULA I OR I'+mefenoxam, COMPOUND OF FORMULA I OR I'+mepanipyrim, COMPOUND OF FORMULA I OR I'+mepronil, COMPOUND OF FORMULA I OR I'+meptyldinocap, COMPOUND OF FORMULA I OR I'+metalaxyl, COMPOUND OF FORMULA I OR I'+metconazole, COMPOUND OF FORMULA I OR I'+metiram, COMPOUND OF FORMULA I OR I'+metiram-zinc, COMPOUND OF FORMULA I OR I'+metominostrobin, COMPOUND OF FORMULA I OR I'+metrafenone, COMPOUND OF FORMULA I OR I'+myclobutanil, COMPOUND OF FORMULA I OR I'+neoasozin, COMPOUND OF FORMULA I OR I'+nickel dimethyldithiocarbamate, COMPOUND OF FORMULA I OR I'+nicobifen, COMPOUND OF FORMULA I OR I'+nitrothal-isopropyl, COMPOUND OF FORMULA I OR I'+nuarimol, COMPOUND OF FORMULA I OR I'+ofurace, COMPOUND OF FORMULA I OR I'+organomercury compounds, COMPOUND OF FORMULA I OR I'+orysastrobin, COMPOUND OF FORMULA I OR I'+oxadixyl, COMPOUND OF FORMULA I OR I'+oxasulfuron, COMPOUND OF FORMULA I OR I'+oxolinic acid, COMPOUND OF FORMULA I OR I'+oxpoconazole, COMPOUND OF FORMULA I OR I'+oxycarboxin, COMPOUND OF FORMULA I OR I'+pefurazoate, COMPOUND OF FORMULA I OR I'+penconazole, COMPOUND OF FORMULA I OR I'+pencycuron, COMPOUND OF FORMULA I OR I'+penflufen, COMPOUND OF FORMULA I OR I'+penthiopyrad, COMPOUND OF FORMULA I OR I'+phenazin oxide, COMPOUND OF FORMULA I OR I'+phosetyl-Al, COMPOUND OF FORMULA I OR I'+phosphorus acids, COMPOUND OF FORMULA I OR I'+phthalide, COMPOUND OF FORMULA I OR I'+picoxystrobin (ZA1963), COMPOUND OF FORMULA I OR I'+polyoxin D, COMPOUND OF FORMULA I OR I'+polyram, COMPOUND OF FORMULA I OR I'+probenazole, COMPOUND OF FORMULA I OR I'+prochloraz, COMPOUND OF FORMULA I OR I'+procymidone, COMPOUND OF FORMULA I OR I'+propamocarb, COMPOUND OF FORMULA I OR I'+propiconazole, COMPOUND OF FORMULA I OR I'+propineb, COMPOUND OF FORMULA I OR I'+propionic acid, COMPOUND OF FORMULA I OR I'+proquinazid, COMPOUND OF FORMULA I OR I'+prothioconazole, COMPOUND OF FORMULA I OR I'+pyraclostrobin, COMPOUND OF FORMULA I OR I'+pyrazophos, COMPOUND OF FORMULA I OR I'+pyribencarb, COMPOUND OF FORMULA I OR I'+pyrifenox, COMPOUND OF FORMULA I OR I'+pyrimethanil, COMPOUND OF FORMULA I OR I'+pyroquilon, COMPOUND OF FORMULA I OR I'+pyroxyfur, COMPOUND OF FORMULA I OR I'+pyrrolnitrin, COMPOUND OF FORMULA I OR I'+quaternary ammonium compounds, COMPOUND OF FORMULA I OR I'+quinomethionate, COMPOUND OF FORMULA I OR I'+quinoxyfen, COMPOUND OF FORMULA I OR I'+quintozene, COMPOUND OF FORMULA I OR I'+sedaxane, COMPOUND OF FORMULA I OR I'+sipconazole (F-155), COMPOUND OF FORMULA I OR I'+sodium pentachlorophenate, COMPOUND OF FORMULA I OR I'+spiroxamine, COMPOUND OF FORMULA I OR I'+streptomycin, COMPOUND OF FORMULA I OR I'+sulphur, COMPOUND OF FORMULA I OR I'+tebuconazole, COMPOUND OF FORMULA I OR I'+tecloftalam, COMPOUND OF FORMULA I OR I'+tecnazene, COMPOUND OF FORMULA I OR I'+terbufloquin, COMPOUND OF FORMULA I OR I'+tetraconazole, COMPOUND OF FORMULA I OR I'+thiabendazole, COMPOUND OF FORMULA I OR I'+thifluzamid, COMPOUND OF FORMULA I OR I'+2-(thiocyanomethylthio)benzothiazole, COMPOUND OF FORMULA I OR I'+thiophanate-methyl, COMPOUND OF FORMULA I OR I'+thiram, COMPOUND OF FORMULA I OR I'+tiadinil, COMPOUND OF FORMULA I OR I'+timibenconazole, COMPOUND OF FORMULA I OR I'+tolclofos-methyl, COMPOUND OF FORMULA I OR I'+tolylfluanid, COMPOUND OF FORMULA I OR I'+triadimefon, COMPOUND OF FORMULA I OR I'+triadimenol, COMPOUND OF FORMULA I OR I'+triazbutil, COMPOUND OF FORMULA I OR I'+triazoxide, COMPOUND OF FORMULA I OR I'+tricyclazole, COMPOUND OF FORMULA I OR I'+tridemorph, COMPOUND OF FORMULA I OR I'+trifloxystrobin, COMPOUND OF FORMULA I OR I'+triforine, COMPOUND OF FORMULA I OR I'+triflumizole, COMPOUND OF FORMULA I OR I'+triticonazole, COMPOUND OF FORMULA I OR I'+validamycin A, COMPOUND OF FORMULA I OR I'+valiphenal, COMPOUND OF FORMULA I OR I'+vapam, COMPOUND OF FORMULA I OR I'+vinclozolin, COMPOUND OF FORMULA I OR I'+zineb and COMPOUND OF FORMULA I OR I'+ziram.

The compounds of formula I or I' may be mixed with soil, peat or other rooting media for the protection of plants against seed-borne, soil-borne or foliar fungal diseases.

The compounds of formula I or I' according to the invention can also be used in combination with one or more other synergists. In particular, the following mixtures of the COMPOUND OF FORMULA I OR I', where this term preferably refers to a compound selected from one of the Tables 1 to 7, are important:
COMPOUND OF FORMULA I OR I'+piperonyl butoxide, COMPOUND OF FORMULA I OR I'+sesamex, COMPOUND OF FORMULA I OR I'+safroxan and COMPOUND OF FORMULA I OR I'+dodecyl imidazole.

The compounds of formula I or I' according to the invention can also be used in combination with one or more other herbicides. In particular, the following mixtures of the COMPOUND OF FORMULA I OR I', where this term preferably refers to a compound selected from one of the Tables 1 to 7, are important:
COMPOUND OF FORMULA I OR I'+acetochlor, COMPOUND OF FORMULA I OR I'+acifluorfen, COMPOUND OF FORMULA I OR I'+acifluorfen-sodium, COMPOUND OF FORMULA I OR I'+aclonifen, COMPOUND OF FORMULA I OR I'+acrolein, COMPOUND OF FORMULA I OR I'+alachlor, COMPOUND OF FORMULA I OR I'+alloxydim, COMPOUND OF FORMULA I OR I'+allyl alcohol, COMPOUND OF FORMULA I OR I'+ametryn, COMPOUND OF FORMULA I OR I'+amicarbazone, COMPOUND OF FORMULA I OR I'+amidosulfuron, COMPOUND OF FORMULA I OR I'+aminocyclopyrachlor, COMPOUND OF FORMULA I OR I'+aminopyralid, COMPOUND OF FORMULA I OR I'+amitrole, COMPOUND OF FORMULA I OR I'+ammonium sulfamate, COMPOUND OF FORMULA I OR I'+anilofos, COMPOUND OF FORMULA I OR I'+asulam, COMPOUND OF FORMULA I OR I'+atraton, COMPOUND OF FORMULA I OR I'+atrazine, COMPOUND OF FORMULA I OR I'+azimsulfuron, COMPOUND OF FORMULA I OR I'+BCPC, COMPOUND OF FORMULA I OR I'+beflubutamid, COMPOUND OF FORMULA I OR I'+benazolin, COMPOUND OF FORMULA I OR I'+bencarbazone, COMPOUND OF FORMULA I OR I'+benfluralin, COMPOUND OF FORMULA I OR I'+benfuresate, COMPOUND OF FORMULA I OR I'+bensulfuron, COMPOUND OF FORMULA I OR I'+bensulfuron-methyl, COMPOUND OF FORMULA I OR I'+bensulide, COMPOUND OF FORMULA I OR I'+bentazone, COMPOUND OF FORMULA I OR I'+benzfendizone, COMPOUND OF FORMULA I OR I'+benzobicyclon, COMPOUND OF FORMULA I OR I'+benzofenap, COMPOUND OF THE FORMULA I OR I'+bicyclopyrone, COMPOUND OF FORMULA I OR I'+bifenox, COMPOUND OF FORMULA I OR I'+bilanafos, COMPOUND OF FORMULA I OR I'+bispyribac, COMPOUND OF FORMULA I OR I'+bispyribac-sodium, COMPOUND OF FORMULA I OR I'+borax, COMPOUND OF FORMULA I OR I'+bromacil, COMPOUND OF FORMULA I OR I'+bromobutide, COMPOUND OF FORMULA I OR I'+bromoxynil, COMPOUND OF FORMULA I OR I'+butachlor, COMPOUND OF FORMULA I OR I'+butafenacil, COMPOUND OF FORMULA I OR I'+butamifos, COMPOUND OF FORMULA I OR I'+butralin, COMPOUND OF FORMULA I OR I'+butroxydim, COMPOUND OF FORMULA I OR I'+butylate, COMPOUND OF FORMULA I OR I'+cacodylic acid, COMPOUND OF FORMULA I OR I'+calcium chlorate, COMPOUND OF FORMULA I OR I'+cafenstrole, COMPOUND OF FORMULA I OR I'+carbetamide, COMPOUND OF FORMULA I OR I'+carfentrazone, COMPOUND OF FORMULA I OR I'+carfentrazone-ethyl, COMPOUND OF FORMULA I OR I'+CDEA, COMPOUND OF FORMULA I OR I'+CEPC, COMPOUND OF FORMULA I OR I'+chlorflurenol, COMPOUND OF FORMULA I OR I'+chlorflurenol-methyl, COMPOUND OF FORMULA I OR I'+chloridazon, COMPOUND OF FORMULA I OR I'+chlorimuron, COMPOUND OF FORMULA I OR I'+chlorimuron-ethyl, COMPOUND OF FORMULA I OR I'+chloroacetic acid, COMPOUND OF FORMULA I OR I'+chlorotoluron, COMPOUND OF FORMULA I OR I'+chlorpropham, COMPOUND OF FORMULA I OR I'+chlorsulfuron, COMPOUND OF FORMULA I OR I'+chlorthal, COMPOUND OF FORMULA I OR I'+chlorthal-dimethyl, COMPOUND OF FORMULA I OR I'+cinidon-ethyl, COMPOUND OF FORMULA I OR I'+cinmethylin, COMPOUND OF FORMULA I OR I'+cinosulfuron, COMPOUND OF FORMULA I OR I'+cisanilide, COMPOUND OF FORMULA I OR I'+clethodim, COMPOUND OF FORMULA I OR I'+clodinafop, COMPOUND OF FORMULA I OR I'+clodinafop-propargyl, COMPOUND OF FORMULA I OR I'+clomazone, COMPOUND OF FORMULA I OR I'+clomeprop, COMPOUND OF FORMULA I OR I'+clopyralid, COMPOUND OF FORMULA I OR I'+cloransulam, COMPOUND OF FORMULA I OR I'+cloransulam-methyl, COMPOUND OF FORMULA I OR I'+CMA, COMPOUND OF FORMULA I OR I'+4-CPB, COMPOUND OF FORMULA I OR I'+CPMF, COMPOUND OF FORMULA I OR I'+4-CPP, COMPOUND OF FORMULA I OR I'+CPPC, COMPOUND OF FORMULA I OR I'+cresol, COMPOUND OF FORMULA I OR I'+cumyluron, COMPOUND OF FORMULA I OR I'+cyanamide, COMPOUND OF FORMULA I OR I'+cyanazine, COMPOUND OF FORMULA I OR I'+cycloate, COMPOUND OF FORMULA I OR I'+cyclosulfamuron, COMPOUND OF FORMULA I OR I'+cycloxydim, COMPOUND OF FORMULA I OR I'+cyhalofop, COMPOUND OF FORMULA I OR I'+cyhalofop-butyl, COMPOUND OF FORMULA I OR I'+2,4-D, COMPOUND OF FORMULA I OR I'+3,4-DA, COMPOUND OF FORMULA I OR I'+daimuron, COMPOUND OF FORMULA I OR I'+dalapon, COMPOUND OF FORMULA I OR I'+dazomet, COMPOUND OF FORMULA I OR I'+2,4-DB, COMPOUND OF FORMULA I OR I'+3,4-DB, COMPOUND OF FORMULA I OR I'+2,4-DEB, COMPOUND OF FORMULA I OR I'+desmedipham, COMPOUND OF FORMULA I OR I'+dicamba, COMPOUND OF FORMULA I OR I'+dichlobenil, COMPOUND OF FORMULA I OR I'+ortho-dichlorobenzene, COMPOUND OF FORMULA I OR I'+para-dichlorobenzene, COMPOUND OF FORMULA I OR I'+dichlorprop, COMPOUND OF FORMULA I OR I'+dichlorprop-P, COMPOUND OF FORMULA I OR I'+diclofop, COMPOUND OF FORMULA I OR I'+diclofop-methyl, COMPOUND OF FORMULA I OR I'+diclosulam, COMPOUND OF FORMULA I OR I'+difenzoquat, COMPOUND OF FORMULA I OR I'+difenzoquat metilsulfate, COMPOUND OF FORMULA I OR I'+diflufenican, COMPOUND OF FORMULA I OR I'+diflufenzopyr, COMPOUND OF FORMULA I OR I'+dimefuron, COMPOUND OF FORMULA I OR I'+dimepiperate, COMPOUND OF FORMULA I OR I'+dimethachlor, COMPOUND OF FORMULA I OR I'+dimethametryn, COMPOUND OF FORMULA I OR I'+dimethenamid, COMPOUND OF FORMULA I OR I'+dimethenamid-P, COMPOUND OF FORMULA I OR I'+dimethipin, COMPOUND OF FORMULA I OR I'+dimethylarsinic acid, COMPOUND OF FORMULA I OR I'+dinitramine, COMPOUND OF FORMULA I OR I'+dinoterb, COMPOUND OF FORMULA I OR I'+diphenamid, COMPOUND OF FORMULA I OR I'+diquat, COMPOUND OF FORMULA I OR I'+diquat dibromide, COMPOUND OF FORMULA I OR I'+dithiopyr, COMPOUND OF FORMULA I OR I'+diuron, COMPOUND OF FORMULA I OR I'+DNOC, COMPOUND OF FORMULA I OR I'+3,4-DP, COMPOUND OF FORMULA I OR I'+DSMA, COMPOUND OF FORMULA I OR I'+EBEP, COMPOUND OF FORMULA I OR I'+endothal, COMPOUND OF FORMULA I OR I'+EPTC, COMPOUND OF FORMULA I OR I'+esprocarb, COMPOUND OF FORMULA I OR I'+ethalfluralin, COMPOUND OF FORMULA I OR I'+ethametsulfuron, COMPOUND OF FORMULA I OR I'+ethametsulfuron-methyl, COMPOUND OF FORMULA I OR I'+ethofumesate, COMPOUND OF FORMULA I OR I'+ethoxyfen, COMPOUND OF FORMULA I OR I'+ethoxysulfuron, COMPOUND OF FORMULA I OR I'+etobenzanid, COMPOUND OF FORMULA I OR I'+fenoxaprop-P, COMPOUND OF FORMULA I OR I'+fenoxaprop-P-ethyl, COMPOUND OF FORMULA I OR I'+fentrazamide, COMPOUND OF FORMULA I OR I'+ferrous sulfate, COMPOUND OF FORMULA I OR I'+flamprop-M, COMPOUND OF FORMULA I OR I'+flazasulfuron, COMPOUND OF FORMULA I OR I'+florasulam, COMPOUND OF FORMULA I OR I'+fluazifop, COMPOUND OF FORMULA I OR I'+fluazifop-butyl, COMPOUND OF FORMULA I OR I'+fluazifop-P, COMPOUND OF FORMULA I OR I'+fluazifop-P-butyl, COMPOUND OF FORMULA I OR I'+flucarbazone, COMPOUND OF FORMULA I OR I'+flucarbazone-sodium, COMPOUND OF FORMULA I OR I'+flucetosulfuron, COMPOUND OF FORMULA I OR I'+fluchloralin, COMPOUND OF FORMULA I OR I'+flufenacet, COMPOUND OF FORMULA I OR I'+flufenpyr, COMPOUND OF FORMULA I OR I'+flufenpyr-ethyl, COMPOUND OF FORMULA I OR I'+flumetsulam, COMPOUND OF FORMULA I OR I'+flumiclorac, COMPOUND OF FORMULA I OR I'+flumiclorac-pentyl, COMPOUND OF FORMULA I OR I'+flumioxazin, COMPOUND OF FORMULA I OR I'+fluometuron, COMPOUND OF FORMULA I OR I'+fluoroglycofen, COMPOUND OF FORMULA I OR I'+fluoroglycofen-ethyl, COMPOUND OF FORMULA I OR I'+flupropanate, COMPOUND OF FORMULA I OR I'+flupyrsulfuron, COMPOUND OF FORMULA I OR I'+flupyrsulfuron-methyl-sodium, COMPOUND OF FORMULA I OR I'+flurenol, COMPOUND OF FORMULA I OR I'+fluridone, COMPOUND OF FORMULA I OR I'+fluorochloridone, COMPOUND OF FORMULA I OR I'+fluoroxypyr, COMPOUND OF FORMULA I OR I'+flurtamone, COMPOUND OF FORMULA I OR I'+fluthiacet, COMPOUND OF FORMULA I OR I'+fluthiacet-methyl, COMPOUND OF FORMULA I OR I'+fomesafen, COMPOUND OF FORMULA I OR I'+foramsulfuron, COMPOUND OF FORMULA I OR I'+fosamine, COMPOUND OF FORMULA I OR I'+glufosinate, COMPOUND OF FORMULA I OR I'+glufosinate-ammonium, COMPOUND OF FORMULA I OR I'+glufosinate-P, COMPOUND OF FORMULA I OR I'+glyphosate, COMPOUND OF FORMULA I OR I'+glyphosate-trimesium, COMPOUND OF FORMULA I OR I'+halosulfuron, COMPOUND OF FORMULA I OR I'+halosulfuron-methyl, COMPOUND OF FORMULA I OR I'+haloxyfop, COMPOUND OF FORMULA I OR I'+haloxyfop-P, COMPOUND OF FORMULA I OR I'+HC-252, COMPOUND OF FORMULA I OR I'+hexazinone, COMPOUND OF FORMULA I OR I'+imazamethabenz, COMPOUND OF FORMULA I OR I'+imazamethabenz-methyl, COMPOUND OF FORMULA I OR I'+imazamox, COMPOUND OF FORMULA I OR I'+imazapic, COMPOUND OF FORMULA I OR I'+imazapyr, COMPOUND OF FORMULA I OR I'+imazaquin, COMPOUND OF FORMULA I OR I'+imazethapyr, COMPOUND OF FORMULA I OR I'+imazosulfuron, COMPOUND OF FORMULA I OR I'+indanofan, COMPOUND OF FORMULA I OR I'+indaziflam, COMPOUND OF FORMULA I OR I'+iodomethane, COMPOUND OF FORMULA I OR I'+iodosulfuron, COMPOUND OF FORMULA I OR I'+iodosulfuron-methyl-sodium, COMPOUND OF FORMULA I OR I'+ioxynil, COMPOUND OF FORMULA I OR I'+ipfencarbazone, COMPOUND OF FORMULA I OR I'+isoproturon, COMPOUND OF FORMULA I OR I'+isouron, COMPOUND OF FORMULA I OR I'+isoxaben, COMPOUND OF FORMULA I OR I'+isoxachlortole, COMPOUND OF FORMULA I OR I'+isoxaflutole, COMPOUND OF FORMULA I OR I'+karbutilate, COMPOUND OF FORMULA I OR I'+lactofen, COMPOUND OF FORMULA I OR I'+lenacil, COMPOUND OF FORMULA I OR I'+linuron, COMPOUND OF FORMULA I OR I'+MAA, COMPOUND OF FORMULA I OR I'+MAMA, COMPOUND OF FORMULA I OR I'+MCPA, COMPOUND OF FORMULA I OR I'+MCPA-thioethyl, COMPOUND OF FORMULA I OR I'+MCPB, COMPOUND OF FORMULA I OR I'+mecoprop, COMPOUND OF FORMULA I OR I'+mecoprop-P, COMPOUND OF FORMULA I OR I'+mefenacet, COMPOUND OF FORMULA I OR I'+mefluidide, COMPOUND OF FORMULA I OR I'+mesosulfuron, COMPOUND OF FORMULA I OR I'+mesosulfuron-methyl, COMPOUND OF FORMULA I OR I'+mesotrione, COMPOUND OF FORMULA I OR I'+metam, COMPOUND OF FORMULA I OR I'+metamifop, COMPOUND OF FORMULA I OR I'+metamitron, COMPOUND OF FORMULA I OR I'+metazachlor, COMPOUND OF FORMULA I OR I'+methabenzthiazuron, COMPOUND OF FORMULA I OR I'+methylarsonic acid, COMPOUND OF FORMULA I OR I'+methyldymron, COMPOUND OF FORMULA I OR I'+methyl isothiocyanate, COMPOUND OF FORMULA I OR I'+metobenzuron, COMPOUND OF FORMULA I OR I'+metolachlor, COMPOUND OF FORMULA I OR I'+S-metolachlor, COMPOUND OF FORMULA I OR I'+metosulam, COMPOUND OF FORMULA I OR I'+metoxuron, COMPOUND OF FORMULA I OR I'+metribuzin, COMPOUND OF FORMULA I OR I'+metsulfuron, COMPOUND OF FORMULA I OR I'+metsulfuron-methyl, COMPOUND OF FORMULA I OR I'+MK-616, COMPOUND OF FORMULA I OR I'+molinate, COMPOUND OF FORMULA I OR I'+monolinuron, COMPOUND OF FORMULA I OR I'+MSMA, COMPOUND OF FORMULA I OR I'+naproanilide, COMPOUND OF FORMULA I OR I'+napropamide, COMPOUND OF FORMULA I OR I'+naptalam, COMPOUND OF FORMULA I OR I'+neburon, COMPOUND OF FORMULA I OR I'+nicosulfuron, COMPOUND OF FORMULA I OR I'+nonanoic acid, COMPOUND OF FORMULA I OR I'+norflurazon, COMPOUND OF FORMULA I OR I'+oleic acid (fatty acids), COMPOUND OF FORMULA I OR I'+orbencarb, COMPOUND OF FORMULA I OR I'+orthosulfamuron, COMPOUND OF FORMULA I OR I'+oryzalin, COMPOUND OF FORMULA I OR I'+oxadiargyl, COMPOUND OF FORMULA I OR I'+oxadiazon, COMPOUND OF FORMULA I OR I'+oxasulfuron, COMPOUND OF FORMULA I OR I'+oxaziclomefone, COMPOUND OF FORMULA I OR I'+oxyfluorfen, COMPOUND OF FORMULA I OR I'+paraquat, COMPOUND OF FORMULA I OR I'+paraquat dichloride, COMPOUND OF FORMULA I OR I'+pebulate, COMPOUND OF FORMULA I OR I'+pendimethalin, COMPOUND OF FORMULA I OR I'+penoxsulam, COMPOUND OF FORMULA I OR I'+pentachlorophenol, COMPOUND OF FORMULA I OR I'+pentanochlor, COMPOUND OF FORMULA I OR I'+pentoxazone, COMPOUND OF FORMULA I OR I'+pethoxamid, COMPOUND OF FORMULA I OR I'+petrolium oils, COMPOUND OF FORMULA I OR I'+phenmedipham, COMPOUND OF FORMULA I OR I'+phenmedipham-ethyl, COMPOUND OF FORMULA I OR I'+picloram, COMPOUND OF FORMULA I OR I'+picolinafen, COMPOUND OF FORMULA I OR I'+pinoxaden, COMPOUND OF FORMULA I OR I'+piperophos, COMPOUND OF FORMULA I OR I'+potassium arsenite, COMPOUND OF FORMULA I OR I'+potassium azide, COMPOUND OF FORMULA I OR I'+pretilachlor, COMPOUND OF FORMULA I OR I'+primisulfuron, COMPOUND OF FORMULA I OR I'+primisulfuron-methyl, COMPOUND OF FORMULA I OR I'+prodiamine, COMPOUND OF FORMULA I OR I'+profluazol, COMPOUND OF FORMULA I OR I'+profoxydim, COMPOUND OF FORMULA I OR I'+prometon, COMPOUND OF FORMULA I OR I'+prometryn, COMPOUND OF FORMULA I OR I'+propachlor, COMPOUND OF FORMULA I OR I'+propanil, COMPOUND OF FORMULA I OR I'+propaquizafop, COMPOUND OF FORMULA I OR I'+propazine, COMPOUND OF FORMULA I OR I'+propham, COMPOUND OF FORMULA I OR I'+propisochlor, COMPOUND OF FORMULA I OR I'+propoxycarbazone, COMPOUND OF FORMULA I OR I'+propoxycarbazone-sodium, COMPOUND OF FORMULA I OR I'+propyrisulfuron, COMPOUND OF FORMULA I OR I'+propyzamide, COMPOUND OF FORMULA I OR I'+prosulfocarb, COMPOUND OF FORMULA I OR I'+prosulfuron, COMPOUND OF FORMULA I OR I'+pyraclonil, COMPOUND OF FORMULA I OR I'+pyraflufen, COMPOUND OF FORMULA I OR I'+pyraflufen-ethyl, COMPOUND OF FORMULA I OR I'+pyrasulfutole, COMPOUND OF FORMULA I OR I'+pyrazolynate, COMPOUND OF FORMULA I OR I'+pyrazosulfuron, COMPOUND OF FORMULA I OR I'+pyrazosulfuron-ethyl, COMPOUND OF FORMULA I OR I'+pyrazoxyfen, COMPOUND OF FORMULA I OR I'+pyribenzoxim, COMPOUND OF FORMULA I OR I'+pyributicarb, COMPOUND OF FORMULA I OR I'+pyridafol, COMPOUND OF FORMULA I OR I'+pyridate, COMPOUND OF FORMULA I OR I'+pyriftalid, COMPOUND OF FORMULA I OR I'+pyriminobac, COMPOUND OF FORMULA I OR I'+pyriminobac-methyl, COMPOUND OF FORMULA I OR I'+pyrimisulfan, COMPOUND OF FORMULA I OR I'+pyrithiobac, COMPOUND OF FORMULA I OR I'+pyrithiobac-sodium, COMPOUND OF FORMULA I OR I'+pyroxsulam, COMPOUND OF FORMULA I OR I'+pyroxasulfone, COMPOUND OF FORMULA I OR I'+quinclorac, COMPOUND OF FORMULA I OR I'+quinmerac, COMPOUND OF FORMULA I OR I'+quinoclamine, COMPOUND OF FORMULA I OR I'+quizalofop, COMPOUND OF FORMULA I OR I'+quizalofop-P, COMPOUND OF FORMULA I OR I'+rimsulfuron, COMPOUND OF FORMULA I OR I'+saflufenacil, COMPOUND OF FORMULA I OR I'+sethoxydim, COMPOUND OF FORMULA I OR I'+siduron, COMPOUND OF FORMULA I OR I'+simazine, COMPOUND OF FORMULA I OR I'+simetryn, COMPOUND OF FORMULA I OR I'+SMA, COMPOUND OF FORMULA I OR I'+sodium arsenite, COMPOUND OF FORMULA I OR I'+sodium azide, COMPOUND OF FORMULA I OR I'+sodium chlorate, COMPOUND OF FORMULA I OR I'+sulcotrione, COMPOUND OF FORMULA I OR I'+sulfentrazone, COMPOUND OF FORMULA I OR I'+sulfometuron, COMPOUND OF FORMULA I OR I'+sulfometuron-methyl, COMPOUND OF FORMULA I OR I'+sulfosate, COMPOUND OF FORMULA I OR I'+sulfosulfuron, COMPOUND OF FORMULA I OR I'+sulfuric acid, COMPOUND OF FORMULA I OR I'+tar oils, COMPOUND OF FORMULA I OR I'+2,3,6-TBA, COMPOUND OF FORMULA I OR I'+TCA, COMPOUND OF FORMULA I OR I'+TCA-sodium, COMPOUND OF FORMULA I OR I'+tebuthiuron, COMPOUND OF FORMULA I OR I'+tefuryltrione, COMPOUND OF FORMULA I OR I'+tembotrione, COMPOUND OF FORMULA I OR I'+tepraloxydim, COMPOUND OF FORMULA I OR I'+terbacil, COMPOUND OF FORMULA I OR I'+terbumeton, COMPOUND OF FORMULA I OR I'+terbuthylazine, COMPOUND OF FORMULA I OR I'+terbutryn, COMPOUND OF FORMULA I OR I'+thenylchlor, COMPOUND OF FORMULA I OR I'+thiazopyr, COMPOUND OF FORMULA I OR I'+thiencarbazone, COMPOUND OF FORMULA I OR I'+thifensulfuron, COMPOUND OF FORMULA I OR I'+thifensulfuron-methyl, COMPOUND OF FORMULA I OR I'+thiobencarb, COMPOUND OF FORMULA I OR I'+tiocarbazil, COMPOUND OF FORMULA I OR I'+topramezone, COMPOUND OF FORMULA I OR I'+tralkoxydim, COMPOUND OF FORMULA I OR I'+tri-allate, COMPOUND OF FORMULA I OR I'+triasulfuron, COMPOUND OF FORMULA I OR I'+triaziflam, COMPOUND OF FORMULA I OR I'+tribenuron, COMPOUND OF FORMULA I OR I'+tribenuron-methyl, COMPOUND OF FORMULA I OR I'+tricamba, COMPOUND OF FORMULA I OR I'+triclopyr, COMPOUND OF FORMULA I OR I'+trietazine, COMPOUND OF FORMULA I OR I'+trifloxysulfuron, COMPOUND OF FORMULA I OR I'+trifloxysulfuron-sodium, COMPOUND OF FORMULA I OR I'+trifluralin, COMPOUND OF FORMULA I OR I'+triflusulfuron, COMPOUND OF FORMULA I OR I'+triflusulfuron-methyl, COMPOUND OF FORMULA I OR I'+trihydroxytriazine, COMPOUND OF FORMULA I OR I'+tritosulfuron, COMPOUND OF FORMULA I OR I'+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), COMPOUND OF FORMULA I OR I'+4-[(4,5-dihydro-3-methoxy-4-methyl-5-oxo)-1H-1,2,4-triazol-1-ylcarbonylsulfamoyl]-5-methylthiophene-3-carboxylic acid (BAY636), COMPOUND OF FORMULA I OR I'+BAY747 (CAS RN 335104-84-2), COMPOUND OF FORMULA I OR I'+topramezone (CAS RN 210631-68-8), COMPOUND OF FORMULA I OR I'+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and COMPOUND OF FORMULA I OR I'+4-hydroxy-3-[[2-(3-methoxypropyl)-6-(difluoromethyl)-3-pyridinyl]carbonyl]-bicyclo[3.2.1]oct-3-en-2-one.

The compounds of formula I or I' according to the invention can also be used in combination with safeners. Preferably, in these mixtures, the compound of the formula I or I' is one of those compounds listed in Tables 1 to 7 above. The following mixtures with safeners, especially, come into consideration:
compound of formula I or I'+cloquintocet-mexyl, compound of formula I or I'+cloquintocet acid and salts thereof, compound of formula I or I'+fenchlorazole-ethyl, compound of formula I or I'+fenchlorazole acid and salts thereof, compound of formula I or I'+mefenpyr-diethyl, compound of formula I or I'+mefenpyr diacid, compound of formula I or I'+isoxadifen-ethyl, compound of formula I or I'+isoxadifen acid, compound of formula I or I'+furilazole, compound of formula I or I'+furilazole R isomer, compound of formula I or I'+benoxacor, compound of formula I or I'+dichlormid, compound of formula I or I'+AD-67, compound of formula I or I'+oxabetrinil, compound of formula I or I'+cyometrinil, compound of formula I or I'+cyometrinil Z-isomer, compound of formula I or I'+fenclorim, compound of formula I or I'+cyprosulfamide, compound of formula I or I'+naphthalic anhydride, compound of formula I or I'+flurazole, compound of formula I or I'+N-(2-methoxybenzoyl)-4-[(methylaminocarbonyl)amino]benzenesulfonamide, compound of formula I or I'+CL 304,415, compound of formula I or +dicyclonon, compound of formula I or +fluxofenim, compound of formula I or +DKA-24, compound of formula I or I'+R-29148 and compound of formula I or I'+PPG-1292. A safening effect can also be observed for the mixtures compound of the formula I or I'+dymron, compound of the formula I or I'+MCPA, compound of the formula I or I'+mecopropand compound of the formula I or I'+mecoprop-P.

The mixing partners of the compound of formula I or I' may also be in the form of esters or salts, as mentioned e.g. in The Pesticide Manual, 12th Edition (BCPC), 2000.

In the above different lists of active ingredients to be mixed with a COMPOUND OF FORMULA I OR I', the compound of the formula I or I' is preferably a compound of Tables 1 to 7, whereby G can be hydrogen, C(O)OEt or C(O)OiPr.

In the above-mentioned mixtures of compounds of formula I or I', in particular a compound selected from said Tables 1 to 7, with other insecticides, fungicides, herbicides, safeners, adjuvants and the like, the mixing ratios can vary over a large range and are, preferably 100:1 to 1:6000, especially 50:1 to 1:50, more especially 20:1 to 1:20, even more especially 10:1 to 1:10. Those mixing ratios are understood to include, on the one hand, ratios by weight and also, on other hand, molar ratios.

The mixtures can advantageously be used in the above-mentioned formulations (in which case "active ingredient" relates to the respective mixture of compound of formula I or I' with the mixing partner).

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The mixtures comprising a compound of formula I or I' selected from Tables 1 to 7 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I or I' selected from Tables 1 to 7 and the active ingredients as described above is not essential for working the present invention.

In a further aspect of the invention, there is provided a method of combating and controlling insects from the order Hemiptera which are resistant to a neonicotinoid insecticide (IRAC mode of action classification: Group 4, including groups 4A & 4C), which method comprises applying a compound of the formula (I) or (I') in free form or in agrochemically acceptable salt form to said neonicotinoid resistant insects.

By virtue of the ability of a compound of the formula (I) or (I') to control such neonicotinoid resistant insects, the invention also provides a method of protecting a crop of useful plants, wherein said crop is susceptible to and/or under attack from such insects from the order Hemiptera. Such a method involves applying to said crop, treating a plant propagation material of said crop with, and/or applying to said insects, a compound of the formula (I) or (I') in free form or in agrochemically acceptable salt form.

Since a compound of the formula (I) or (I') does not exhibit cross-resistance to neonicotinoid resistant Hemiptera (e.g. *Myzus persicae, Bemisia tabaci* & *Nilaparvata lugens*), it may be used in a resistance management strategy with a view to controlling resistance to the neonicotinoid class of insecticides. Such a strategy may involve alternating applications of a compound of the formula (I) or (I') and a neonicotinoid insecticide, to said insects or to a crop of useful plants susceptible to and/or under attack from said insects. Such a strategy can be applied either on an application by application alternation (including different types of application, such as treatment of plant propagation material and foliar spray), or seasonal/crop alternation basis (e.g. use of a compound according to claim 1 on a first crop/for control in a first growing season, and use a neonicotinoid insecticide for a subsequent crop/growing season, or vice versa), and this forms yet a further aspect of the invention.

As mentioned herein, not only are insects from the order Hemiptera pests of a number of commercially important crops, the viruses that these insects carry also pose a threat. With the emergence of resistance to neonicotinoid insecticides, the severity of this threat has increased. Thus, a further aspect of the invention provides a method of controlling a plant virus in a crop of useful plants susceptible to and/or under attack by neonicotinoid resistant insects which carry said plant virus, which method comprises applying to said crop, treating a plant propagation material of said crop with, and/or applying to said insects, the compound of the formula (I) or (I') in free form or in agrochemically acceptable salt form. Examples of plant viruses that may be controlled according to this aspect of the invention include Sobemovirus, Caulimovirus (Caulimoviridae), Closterovirus (Closteroviridae), Sequivirus (Sequiviridae), Enamovirus (Luteoviridae), Luteovirus (Luteoviridae), Polerovirus (Luteoviridae), Umbravirus, Nanovirus (Nanoviridae), Cytorhabdovirus (Rhabdoviridae), Nucleorhabdovirus (Rhabdoviridae).

Methods of the invention as described herein may also involve a step of assessing whether insects are resistant to neonicotinoid insecticides and/or whether said insects carry a plant virus. This step will in general involve collecting a sample of insects from the area (e.g. crop, field, habitat) to be treated, before actually applying the compound of the formula (I) or (I'), and testing (for example using any suitable phenotypic, biochemical or molecular biological technique applicable) for resistance/sensitivity and/or the presence or absence of a virus.

The term neonicotinoid insecticide as used herein refers to any insecticidal compound that acts at the insect nicotinic acetylcholine receptor, and in particular refers to those compounds classified as neonicotinoid insectides according to Yamamoto (1996, Agrochem Jpn 68:14-15). Examples of neonicotinoid insecticides include those in Group 4A & 4C of the IRAC (insecticide resistance action committee, Crop Life) mode of action classification scheme, e.g. acetamiprid, clothianidin, dinotefuran, imidacloprid, nitenpyram, thiacloprid, thiamethoxam and sulfoxaflor, as well as any compound having the same mode of action.

By the terms "control" or "controlling" as applied to insects, it is meant that the targeted insects are repelled from or less attracted to the crops to be protected. Additionally, as applied to insects, the terms "control" or "controlling" may also refer to the inability, or reduced ability, of the insects to feed or lay eggs. These terms may further include that the targeted insects are killed.

Thus the method of the invention may involve the use of an amount of the active ingredient that is sufficient to repel insects (i.e. a repellently effective amount of active ingredient), an amount of the active ingredient that is sufficient to stop insects feeding, or it may involve the use of an insecticidally effective amount of active ingredient (i.e. an amount sufficient to kill insects), or any combination of the above effects. Where the terms "control" or "controlling" are applied to viruses it is meant that the level of viral infection of a crop of useful plants is lower than would be observed in the absence of any application of the compound of the formula (I) or (I').

The terms "applying" and "application" are understood to mean direct application to the insect to be controlled, as well as indirect application to said insect, for example through application to the crop or plant on which the insect acts as pest, or to the locus of said crop or insect, or indeed through treatment of the plant propagation material of said crop of plant.

Thus the compound of the formula (I) or (I') may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the plant propagation material, such as seed, before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

The methods of the invention are particularly applicable to the control of neonicotinoid resistant insects (and neonicotinoid resistance in insects) of the family Aphididae, such as: *Acyrthosiphum pisum, Aphis citricola, Aphis craccivora, Aphis fabae, Aphis frangulae, Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi* F., *Myzus nicotianae, Myzus persicae, Nasonovia ribisnigri, Pemphigus bursarius, Phorodon humuli, Rhopalosiphum insertum* Wa, *Rhopalosiphum maidis* Fitch, *Rhopalosiphum padi* L., *Schizaphis graminum* Rond., *Sitobion avenae, Toxoptera aurantii, Toxoptera citricola, Phylloxera vitifoliae, Acyrthosiphon dirhodum, Acyrthosiphon solani, Aphis forbesi, Aphis grossulariae, Aphis idaei, Aphis illinoisensis, Aphis maidiradicis, Aphis ruborum, Aphis schneideri, Brachycaudus persicaecola, Cavariella aegopodii* Scop., *Cryptomyzus galeopsidis, Cryptomyzus ribis, Hyadaphis pseudobrassicae, Hyalopterus amygdali, Hyperomyzus pallidus, Macrosiphoniella sanborni, Metopolophium dirhodum, Myzus malisuctus, Myzus varians, Neotoxoptera* sp, *Nippolachnus piri* Mats., *Oregma lanigera* Zehnter, *Rhopalosiphum fitchii* Sand., *Rhopalosiphum nymphaeae, Rhopalosiphum sacchari* Ze, *Sappaphis piricola* Okam.+T, *Schizaphis piricola, Toxoptera theobromae* Sch, and *Phylloxera coccinea.*

Specific examples of neonicotinoid resistant aphids include *Aphis gossypii Myzus nicotianae Myzus persicae Phorodon humuli*

In an embodiment, the neonicotinoid resistant aphids are one or more of *Aphis gossypii* and *Myzus nicotianae, Myzus persicae* & *Phorodon humuli.*

Table below lists key aphids and crops they target.

| PEST | COMMON NAME | EXAMPLES OF CROPS |
| --- | --- | --- |
| *Acyrthosiphum pisum* | Pea aphid | pea |
| *Aphis citricola* | Citrus aphid | citrus |
| *Aphis craccivora* | Cowpea aphid | vegetables, beans, sugarbeet |
| *Aphis fabae* | Black bean aphid | vegetables, beans, sugarbeet |
| *Aphis frangulae* | Breaking buckthorn aphid | Cotton, potato, vegetables |
| *Aphis glycines* | Soybean aphid | soybean |

| PEST | COMMON NAME | EXAMPLES OF CROPS |
|---|---|---|
| *Aphis gossypii* | Cotton aphid | cotton, vegetables, citrus, potato, melon, cucurbits |
| *Aphis nasturtii* | Buckthorn aphid | potato |
| *Aphis pomi* | Green apple aphid | apple |
| *Aphis spiraecola* | Green citurs aphis | apple, citrus, papaya |
| *Aulacorthum solani* | Foxglove aphid | citrus, sugar beet |
| *Brachycaudus helichrysi* | Plum aphid | peach, stone fruits |
| *Brevicoryne brassicae* | Cabbage aphid | *brassica* |
| *Diuraphis noxia* | Russion wheat aphid | cereals |
| *Dysaphis devecta* | Leaf-curling aphid | pome fruits |
| *Dysaphis plantaginea* | Rosy apple aphid | pome fruits, stone fruits |
| *Eriosoma lanigerum* | Wooly apple aphid | pome fruits, stone fruits |
| *Hyalopterus pruni* | Mealy plum aphid | stone fruits |
| *Lipaphis erysimi* | False cabbage aphid | *brassica* |
| *Macrosiphum avenae* | Grain aphid | cereals |
| *Macrosiphum euphorbiae* | Potato aphid | potato, sugar beet, vegetables |
| Macrosiphum rosae | Rose aphid | ornamentals |
| *Myzus cerasi* F. | Black cherry aphid | cherry, stone fruits |
| *Myzus nicotianae* | Tobacco aphid | tobacco |
| *Myzus persicae* | Peach aphid | peach, deciduous fruits, vegetables, sugarbeet, potato, cereals, sugarcane, maize, ornamentals |
| *Myzus persicae* | Green peach aphid | peach, deciduous fruits, vegetables, sugarbeet, potato, cereals, sugarcane, maize, ornamentals |
| *Nasonovia ribisnigri* | Lettuce aphid | vegetables |
| *Pemphigus bursarius* | Lettuce root aphid | vegetables |
| *Phorodon humuli* | Hop aphid | hops |
| *Rhopalosiphum insertum* Wa | Apple-grass aphid | Deciduous fruits, ornamentals |
| *Rhopalosiphum maidis* Fitch | Corn leaf aphid | Maize, cereals |
| *Rhopalosiphum padi* L. | Wheat aphid | Maize, cereals |
| *Schizaphis graminum* Rond. | Spring grain aphid | cereals |
| *Sitobion avenae* | Wheat aphid | cereals |
| *Toxoptera aurantii* | Citrus aphid | citrus |
| *Toxoptera citricola* | Black citrus aphid | citrus |
| *Phylloxera vitifoliae* | Grape Phylloxera | vine |

The methods of the invention are also particularly applicable to the control of neonicotinoid resistant insects (and neonicotinoid resistance in insects) of the family Aleyrodidae, such as: *Aleurocanthus spiniferus, Aleurocanthus woglumi, Aleurodicus cocois, Aleurodicus destructor, Aleurodicus disperses, Aleurodicus pulvinatus, Aleurothrixus floccosus, Aleurotrachelus socialis, Bemisia tabaci, Dialeurodes citri, Dialeurodes citrifolii, Lecanoideus floccissimus, Parabemisia myricae, Trialeurodes ricini, Trialeurodes vaporariorum.*

In an embodiment, the neonicotinoid resistant whitefly are one or more of *Bemisia tabaci* and *Trialeurodes vaporariorum.*

Table below lists key whitefly and crops they target.

The methods of the invention are also particularly applicable to the control of neonicotinoid resistant insects (and neonicotinoid resistance in insects) of the family Delpacidae, such as: *Laodelphax striatellus, Nilaparvata lugens, Peregrinus maidis, Perkinsiella saccharicida, Perkinsiella vastatrix, Sogatella furcifera, Tagosodes orizicolus, Tarophagus colocasiae, Tarophagus persephone, Tarophagus Proserpina.*

In an embodiment, the neonicotinoid resistant planthoppers are one or more of *Nilaparvata lugens* and *Laodelphax striatellus.*

| PEST | COMMON NAME | EXAMPLES OF CROPS |
|---|---|---|
| *Aleurocanthus spiniferus* | Orange spiney whitefly | Citrus |
| *Aleurocanthus woglumi* | Citrus blackfly | Citrus, Coffee |
| *Aleurodicus cocois* | Coconut whitefly | Coconut, Cashew |
| *Aleurodicus destructor* | Coconut whitefly | Coconut, Pepper |
| *Aleurodicus disperses* | Spiralling whitefly | Citrus, Coconut, Soybean, Cassava, Stone Fruit, Coffee, vegetables |
| *Aleurothrixus floccosus* | Wooly whitefly | Citrus, Mango, Coffee |
| *Bemisia tabaci* | Tobacco whitefly Silverleaf whitefly | Vegetables, Cotton, Crucifera, Legunes, Soyabean, Tobacco, Potato. |
| *Dialeurodes citri* | Citrus whitelfy | Citrus |
| *Parabemisia myricae* | Bayberry whitefly | Citrus, vegetables |
| *Trialeurodes vaporariorum* | Glasshouse whitefly | Melon, vegetables, Legumes, Roses |

Table below lists key planthoppers and crops they target.

| PEST | COMMON NAME | EXAMPLES OF CROPS |
|---|---|---|
| *Laodelphax striatellus* | Small brown planthopper | Rice |
| *Nilaparvata lugens* | Brown planthopper | Rice |
| *Sogatella furcifera* | White backed planthopper | Rice |

The term "plant propagation material" is understood to denote all the generative parts of the plant, such as seeds, which can be used for the multiplication of the latter and vegetative plant materials such as cuttings and tubers (for example, potatoes). Accordingly, as used herein, part of a plant includes propagation material. There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

Parts of plant and plant organs that grow at later point in time are any sections of a plant that develop from a plant propagation material, such as a seed. Parts of plant, plant organs, and plants can also benefit from the pest damage protection achieved by the application of the compound on to the plant propagation material. In an embodiment, certain parts of a plant and certain plant organs that grow at later point in time can also be considered as plant propagation material, which can themselves be applied (or treated) with the compound; and consequently, the plant, further parts of the plant and further plant organs that develop from the treated parts of plant and treated plant organs can also benefit from the pest damage protection achieved by the application of the compound on to the certain parts of plant and certain plant organs.

Methods for applying or treating pesticidal active ingredients on to plant propagation material, especially seeds, are known in the art, and include dressing, coating, pelleting and soaking application methods of the propagation material. It is preferred that the plant propagation material is a seed.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the compound and adherence thereof to the seeds is desired during propagation material treatment. Treatment could vary from a thin film (dressing) of a formulation containing the compound, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognisable.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the compound. In particular, seed coating or seed pelleting are preferred in the treatment of the compound. As a result of the treatment, the compound is adhered on to the seed and therefore available for pest control.

The treated seeds can be stored, handled, sowed and tilled in the same manner as any other active ingredient treated seed.

The following Examples illustrate, but do not limit, the invention.

The following LC-MS methods were used to characterize the compounds:

Method H

| | |
|---|---|
| MS | ZMD Mass Spectrometer from Waters (Single quadrupole mass spectrometer) Instrument Parameter: Ionisation method: Electrospray, polarity: positive (negative) ions; capillary (kV) 3.80, Cone (V) 30.00, Extractor (V) 3.00, Source Temperature (° C.) 150, Desolvation Temperature (° C.) 350, Cone Gas Flow (L/h) OFF, Desolvation Gas Flow (L/h) 600, mass range: 100 to 900 Da |
| LC | HP 1100 HPLC from Agilent: solvent degasser, binary pump, heated column compartment and diode-array detector. Column: Phenomenex Gemini C18, 3 µm, 30 × 3 mm, Temp: 60° C. DAD Wavelength range (nm): 200 to 500 Solvent Gradient: A = water + 0.05% HCOOH B = Acetonitrile/Methanol (4:1, v:v) + 0.04% HCOOH |

| Time (min) | A % | B % | Flow (mL/min) |
|---|---|---|---|
| 0.00 | 95.0 | 5.0 | 1.700 |
| 2.00 | 0.00 | 100.0 | 1.700 |
| 2.80 | 0.00 | 100.0 | 1.700 |
| 2.90 | 95.0 | 5.0 | 1.700 |
| 3.00 | 95.0 | 5.0 | 1.700 |

Method I

| | |
|---|---|
| MS | ZQ Mass Spectrometer from Waters (Single quadrupole mass spectrometer) Instrument Parameter: Ionisation method: Electrospray, Polarity: positive (negative) ions, capillary (kV) 3.00, Cone (V) 30.00, Extractor (V) 2.00, Source Temperature (° C.) 100, Desolvation Temperature (° C.) 250, Cone Gas Flow (L/h) 50, Desolvation Gas Flow (L/h) 400, Mass range: 100 to 900 Da |
| LC | HP 1100 HPLC from Agilent: solvent degasser, quaternary pump (ZCQ)/binary pump (ZDQ), heated column compartment and diode-array detector. Column: Phenomenex Gemini C18, 3 μm, 30 × 3 mm, Temp: 60° C. DAD Wavelength range (nm): 200 to 500 Solvent Gradient: A = water + 0.05% HCOOH B = Acetonitrile/Methanol (4:1, v:v) + 0.04% HCOOH |

| Time (min) | A % | B % | Flow (mL/min) |
|---|---|---|---|
| 0.00 | 95.0 | 5.0 | 1.700 |
| 2.00 | 0.00 | 100.0 | 1.700 |
| 2.80 | 0.00 | 100.0 | 1.700 |
| 2.90 | 95.0 | 5.0 | 1.700 |
| 3.00 | 95.0 | 5.0 | 1.700 |

Method J

| | |
|---|---|
| MS | ZQ Mass Spectrometer from Waters (Single quadrupole mass spectrometer) Instrument Parameter: Ionisation method: Electrospray, Polarity: positive ions, capillary (kV) 3.00, Cone (V) 30.00, Extractor (V) 2.00, Source Temperature (° C.) 100, Desolvation Temperature (° C.) 250, Cone Gas Flow (L/h) 50, Desolvation Gas Flow (L/h) 400, Mass range: 100 to 900 Da |
| LC | HP 1100 HPLC from Agilent: solvent degasser, quaternary pump (ZCQ)/binary pump (ZDQ), heated column compartment and diode-array detector. Column: Column: Hypercarb, 3 μm, 50 × 4.6 mm Temp: 60° C. DAD Wavelength range (nm): 200 to 500 Solvent Gradient: A = water + 0.05% HCOOH B = Acetonitrile/Methanol (4:1, v:v) + 0.04% HCOOH |

| Time (min) | A % | B % | Flow (mL/min) |
|---|---|---|---|
| 0.00 | 95.0 | 5.0 | 1.700 |
| 6.00 | 0.00 | 100.0 | 1.700 |
| 7.70 | 0.00 | 100.0 | 1.700 |
| 7.80 | 95.0 | 5.0 | 1.700 |
| 8.00 | 95.0 | 5.0 | 1.700 |

Method K

| | |
|---|---|
| MS | SQD Mass Spectrometer from Waters (Single quadrupole mass spectrometer) Instrument Parameter: Ionisation method: Electrospray, Polarity: positive and negative ions, Capillary (kV) 3.00, Cone (V) 30, Extractor (V) 2.00, Source Temperature (° C.) 150, Desolvation Temperature (° C.) 250, Cone Gas Flow (L/h) 0, Desolvation Gas Flow (L/h) 650, Mass range: 100 to 900 Da |
| LC | Acquity UPLC from Waters with binary pump, heated column compartment and diode-array detector. Column: Phenomenex Gemini C18, 3 μm, 30 × 2 mm, Temp: 60° C. DAD Wavelength range (nm): 210 to 500 Solvent Gradient: A = H2O + 5% MeOH + 0.05% HCOOH B = Acetonitrile + 0.05% HCOOH |

| Time (min) | A % | B % | Flow (mL/min) |
|---|---|---|---|
| 0.00 | 100.0 | 0.00 | 0.850 |
| 1.20 | 0.00 | 100.0 | 0.850 |
| 1.50 | 0.00 | 100.0 | 0.850 |

Method L

| | |
|---|---|
| MS | Agilent Mass spectrometer (Triple Quad mass spectrometer) 6410 series<br>Instrument parameter: Ionization method: Electrospray, polarity: positive (negative) ions, Source parameters: source temperature: (° C.) 350, Gas Flow: (L/min) 11, Nebulizer: (psi) 35, Capillary Voltage: (V) 4000, Mass Range: 110 to 1000 Da |
| LC | Agilent Technologies 1200 series: solvent degasser, quaternary pump, autosampler, Agilent Technologies 1260 series: Thermostatted column controller, Diode Array detector. Column: Xterra C18, 3.5µ, 30 × 4.6 mm.<br>DAD Wavelength (nm): 190 to 400, Column Temperature: 30° C.<br>Solvent Gradient:<br>A = Water + 0.1% HCOOH<br>B = Acetonitrile + 0.1% HCOOH |

Gradient:

| Time (min) | A % | B % | Flow (mL/min) |
|---|---|---|---|
| 0.00 | 90 | 10 | 1.8 |
| 2.00 | 0 | 100 | 1.8 |
| 3.00 | 0 | 100 | 1.8 |
| 3.20 | 90 | 10 | 1.8 |
| 4.00 | 90 | 10 | 1.8 |

EXAMPLE 1

Preparation of 6-[(E)-Methoxyiminomethyl]-4-[(E)-3-pyridylmethyleneamino]-2,5-dihydro-1,2,4-triazin-3-one (Compound 1.001)

Step A: 1-benzyloxy-3-chloro-propan-2-one

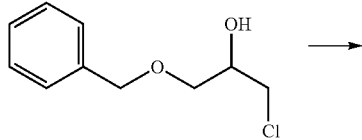

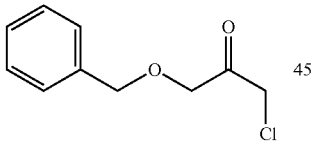

To a solution of 1-benzyloxy-3-chloro-propan-2-ol (10.0 g, 50.0 mmol) [prepared according to Journal of Organic Chemistry (1990), 55, 4897] in ethyl acetate (125 mL) was added a solution of NaHCO$_3$ (12.6 g, 150 mmol) and NaBr (5.66 g, 55.0 mmol) in water (75 mL). After cooling of the biphasic mixture to 0° C., 2,2,6,6-Tetramethyl-piperidin-1-yl)oxyl ("TEMPO") (391 mg, 2.50 mmol) was added in one portion followed by dropwise addition of NaOCl (6 wt % in water, 85.4 mL, 75.0 mmol) to the vigorously stirred solution. After completion of the addition, stirring at 0° C. was continued for 30 min. Subsequently, a solution of aqueous Na$_2$SO$_3$ was added until the reaction mixture had completely discolored. Additional solid Na$_2$SO$_3$ was added to saturate the aqueous phase. The mixture was transferred to a separation funnel and the layers were separated. The organic layer was washed with brine (100 mL), dried (Na$_2$SO$_4$), filtered and concentrated under reduced pressure (at 20° C.). The remaining oil was used without further purification. $^1$H NMR (400 MHz, CDCl$_3$) 4.26 (s, 2H), 4.33 (s, 2H), 4.62 (s, 2H), 7.31-7.45 (m, 5H).

Step B: 3-(3-benzyloxy-2-oxo-propyl)-5-methyl-1,3,4-oxadiazol-2-one

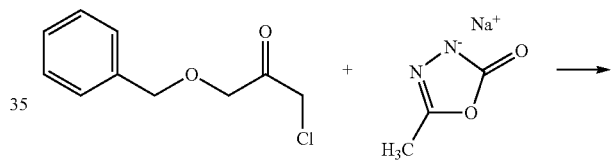

To a stirred suspension of 5-methyl-1,3,4-oxadiazol-2-one sodium salt (34.6 g, 284 mmol) in DMF (200 mL) at 0° C. was added dropwise a solution of 1-benzyloxy-3-chloro-propan-2-one (56.4 g, 284 mmol) in DMF (80 mL). After completion of the addition, the reaction mixture was allowed to warm to room temperature and stirring was continued for 16 h. The obtained reaction mixture was diluted with water and brine and extracted with EtOAc. The combined organic layers were washed with water, brine, and dried (Na$_2$SO$_4$). After evaporation of the solvent the desired product was obtained as a brown oil. Purification by flash chromatography (25% EtOAc/heptane) furnished the desired product as a yellowish oil. ¹H NMR (400 MHz, CDCl₃) 2.27 (s, 3H), 4.27 (s, 2H), 4.62 (s, 2H), 4.75 (s, 2H), 7.30-7.46 (m, 5H).

Step C: N-[6-(benzyloxymethyl)-3-oxo-2,5-dihydro-1,2,4-triazin-4-yl]acetamide

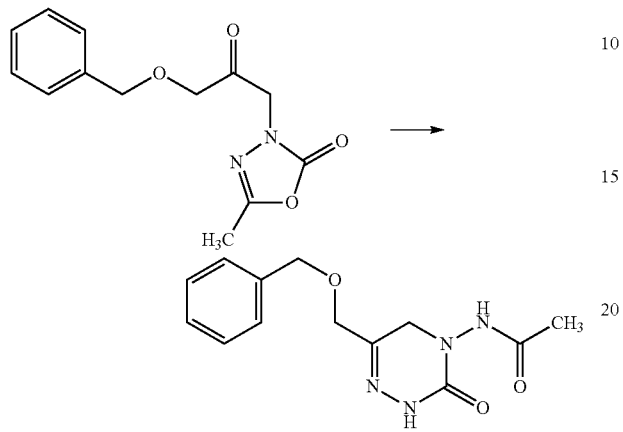

To a solution of 3-(3-benzyloxy-2-oxo-propyl)-5-methyl-1,3,4-oxadiazol-2-one (36.4 g, 139 mmol) in isopropanol (140 mL) was added hydrazine hydrate (62 wt % in water, 11.8 mL, 152 mmol) in at room temperature in one portion. The mixture was heated to 75° C. for 24 h. The volatiles were removed under reduced pressure, and the remaining brown oil was purified by flash chromatography (7% MeOH/dichloromethane) to furnish the desired product as a yellowish solid. ¹H NMR (400 MHz, CDCl₃) 2.04 (s, 3H), 4.12 (s, 2H), 4.23 (s, 2H), 4.54 (s, 2H), 7.24-7.44 (m, 5H), 8.25 (s, 1H), 8.69 (s, 1H).

Step D: tert-butyl 4-[acetyl(tert-butoxycarbonyl)amino]-6-(benzyloxymethyl)-3-oxo-5H-1,2,4-triazine-2-carboxylate

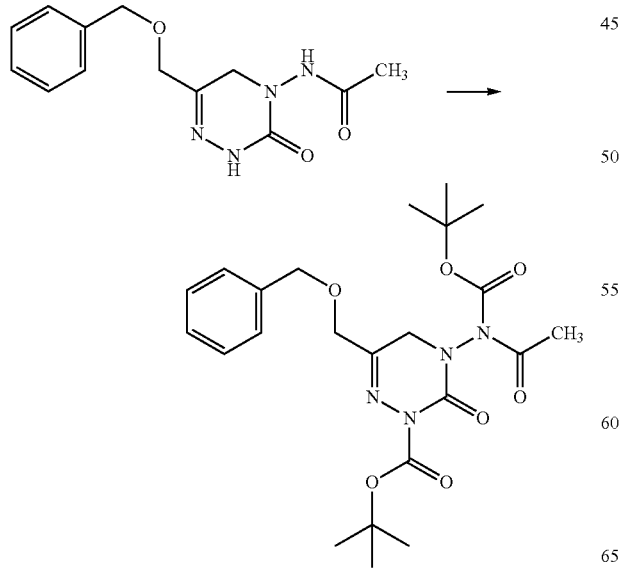

To a stirred solution of N-[6-(benzyloxymethyl)-3-oxo-2,5-dihydro-1,2,4-triazin-4-yl]acetamide (20.7 g, 75.0 mmol) in DMF (120 mL) at room temperature was added di-tert-butyl dicarbonate (65.5 g, 300 mmol) in several portions. After completion of the addition, 4-dimethylaminopyridine (0.46 g, 3.8 mmol) was added in one portion and the mixture was stirred for 24 h. The reaction mixture was diluted with water and brine and extracted with EtOAc. The combined organic layers were washed with brine and dried (Na₂SO₄). Evaporation of the solvent and purification by flash chromatography (30 to 40% EtOAc/heptane) furnished the desired product as a yellow sticky oil. LCMS (Method I) RT 1.98 min. [M+H]⁺ 477.

Step E: tert-butyl 4-[acetyl(tert-butoxycarbonyl)amino]-6-(hydroxymethyl)-3-oxo-5H-1,2,4-triazine-2-carboxylate

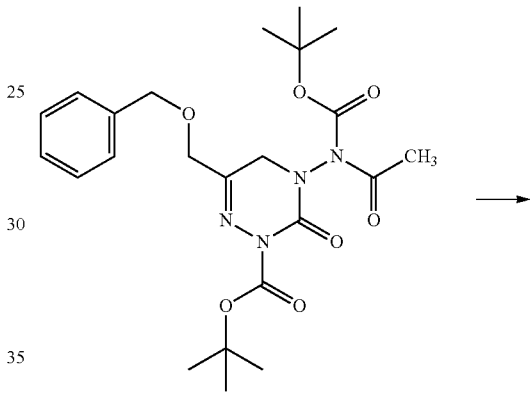

To a stirred solution of tert-butyl 4-[acetyl(tert-butoxycarbonyl)amino]-6-(benzyloxymethyl)-3-oxo-5H-1,2,4-triazine-2-carboxylate (38.0 g, 79.7 mmol) in EtOH (400 mL) under argon atmosphere was added palladium on charcoal (dry, 5 wt % Pd, 8.00 g). The reaction mixture was purged with hydrogen and heated to 60° C. At this temperature, the reaction mixture was stirred 24 h under H₂-atmosphere (approx. 1 atm). The mixture was purged with argon and then filtered using a short plug of silica gel followed by rinsing with additional EtOAc. Evaporation of the solvent furnished the desired product as a sticky oil. LCMS (Method I) RT 1.57 min. [M+H]⁺ 387.

Step F: tert-butyl 4-[acetyl(tert-butoxycarbonyl)amino]-6-formyl-3-oxo-5H-1,2,4-triazine-2-carboxylate

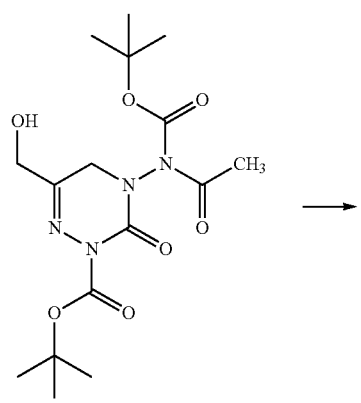

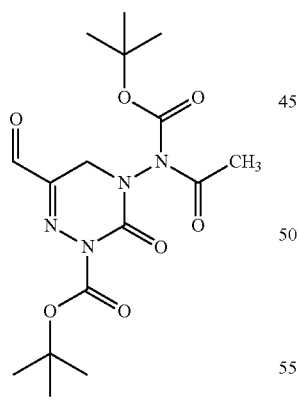

To a stirred solution of tert-butyl 4-[acetyl(tert-butoxycarbonyl)amino]-6-(hydroxymethyl)-3-oxo-5H-1,2,4-triazine-2-carboxylate (3.01 g, 7.78 mmol) in CHCl₃ (47 mL) was added manganese(IV) oxide (7.96 g, 77.8 mmol) and the obtained mixture was heated under reflux for 20 h. The obtained reaction mixture was filtered over Celite and followed by rinsing with 20% MeOH/CHCl₃. Removal of the solvent in vacuo furnished the desired product as a sticky oil which was used directly in the next step without further purification. ¹H NMR (400 MHz, CDCl₃) 1.43 (s, 9H), 1.52 (s, 9H), 2.48 (s, 3H), 4.26 (d$_{AB}$, 1H), 4.34 (d$_{AB}$, 1H), 9.58 (s, 1H).

Step G: tert-butyl 4-(tert-butoxycarbonylamino)-6-[(E)-methoxyiminomethyl]-3-oxo-5H-1,2,4-triazine-2-carboxylate

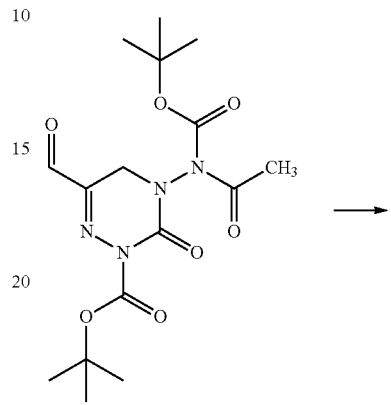

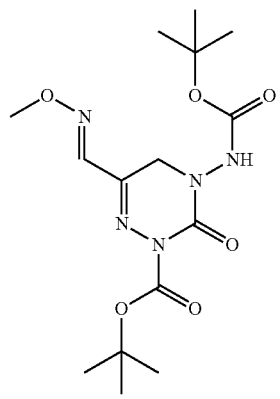

To a solution of tert-butyl 4-[acetyl(tert-butoxycarbonyl)amino]-6-formyl-3-oxo-5H-1,2,4-triazine-2-carboxylate (1.15 g, 3.00 mmol) in MeOH (1.8 mL) at room temperature was added pyridine (0.88 mL, 10.9 mmol) followed by O-methylhydroxylamine HCl salt (376 mg, 4.50 mmol). The obtained mixture was stirred for 20 h at room temperature and then concentrated under reduced pressure. The residual was redissolved in EtOAc, washed with water and dried (Na₂SO₄). After evaporation of the solvent, the crude product was obtained as a viscous oil which was used in the subsequent step without further purification. LCMS (Method I) RT 1.77 min. [M+H]⁺ 372.

Step H: 4-amino-6-[(E)-methoxyiminomethyl]-2,5-dihydro-1,2,4-triazin-3-one

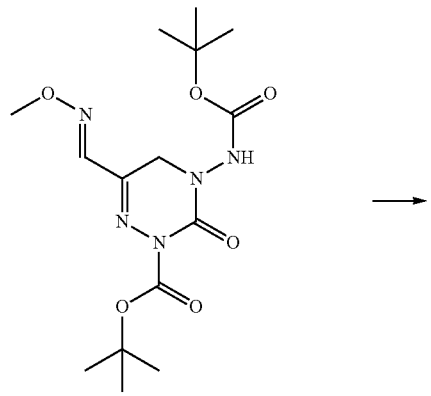

To a solution of tert-butyl 4-(tert-butoxycarbonylamino)-6-[(E)-methoxyiminomethyl]-3-oxo-5H-1,2,4-triazine-2-carboxylate (12.4 g, 30.0 mmol) in MeOH (120 mL) at 0° C. was slowly added acetyl chloride (10.7 mL, 150 mmol). After completion of the addition, the reaction mixture was stirred at this temperature for another 30 min before it was allowed to warm to room temperature. After additional 20 h stirring at room temperature, the reaction mixture was carefully neutralized with sat. NaHCO₃. The volatiles were removed in vacuo and the residual was repeatedly diluted with acetonitrile and evaporated. The remaining material were stirred for 10 min with hot acetonitrile and filtered. Concentration of the filtrate furnished the desired product as an off-white solid. LCMS (Method K) RT 0.42 min. [M+H]⁺ 172.

Step I: 6-[(E)-methoxyiminomethyl]-4-[(E)-3-pyridylmethyleneamino]-2,5-dihydro-1,2,4-triazin-3-one (Compound 1.001)

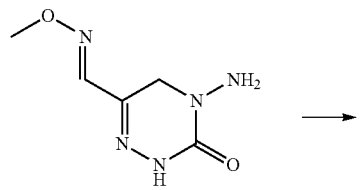

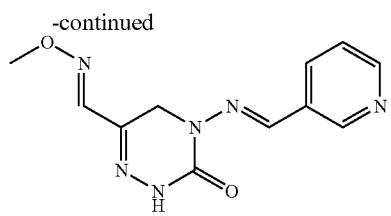

To a solution of 4-amino-6-[(E)-methoxyiminomethyl]-2,5-dihydro-1,2,4-triazin-3-one (2.57 g, 15.0 mmol) in EtOH was added pyridine-3-carbaldehyde (1.41 mL, 15.0 mmol), followed by addition of 1 drop conc. HCl. The mixture was heated to 60° C. for 3 h and then allowed to cool to room temperature. After addition of silica gel, the reaction mixture was evaporated and purified by flash chromatography (5% MeOH/CH₂Cl₂) to give compound I-001 as a white solid. LCMS (Method H) RT 0.97 min. [M+H]⁺ 261. M.p. 237-238° C.

EXAMPLE 2

Preparation of 4-[(E)-(5-fluoro-3-pyridyl)methyleneamino]-6-[(E)-methoxyiminomethyl]-2,5-dihydro-1,2,4-triazin-3-one (Compound 1.002)

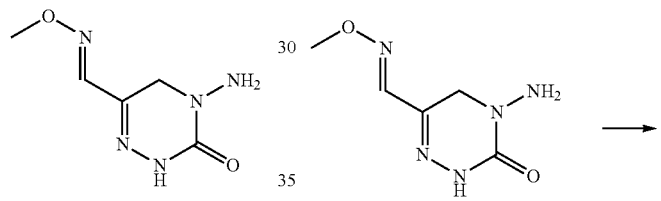

The title compound was obtained from 4-amino-6-[(E)-methoxyiminomethyl]-2,5-dihydro-1,2,4-triazin-3-one and 5-fluoropyridine-3-carbaldehyde following the procedure described in Example 1, step I. LCMS (Method K) RT 0.63 min. [M+H]⁺ 279. M.p. 226-227° C.

EXAMPLE 3

6-[(E)-methoxyiminomethyl]-4-[(E)-(1-oxidopyridin-1-ium-3-yl)methyleneamino]-2,5-dihydro-1,2,4-triazin-3-one (Compound 1.012)

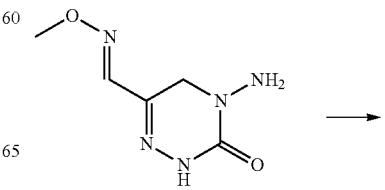

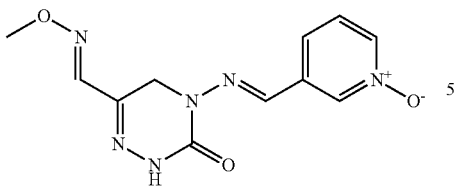

The title compound was obtained from 4-amino-6-[(E)-methoxyiminomethyl]-2,5-dihydro-1,2,4-triazin-3-one and 1-oxidopyridin-1-ium-3-carbaldehyde following the procedure described in Example 1, step I. LCMS (Method K) RT 0.48 min. [M+H]$^+$ 277. M.p. 229° C. (decomp.).

EXAMPLE 4

6-[(E)-methoxyiminomethyl]-4-[(E)-pyrimidin-5-ylmethyleneamino]-2,5-dihydro-1,2,4-triazin-3-one (Compound 1.013)

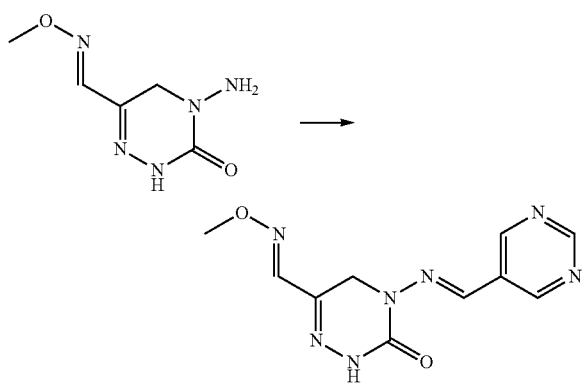

The title compound was obtained from 4-amino-6-[(E)-methoxyiminomethyl]-2,5-dihydro-1,2,4-triazin-3-one and pyrimidin-5-carbaldehyde following the procedure described in Example 1, step I. LCMS (Method H) RT 1.09 min. [M+H]$^+$ 262. M.p. 244-245° C.

EXAMPLE 5

6-[(E)-methoxyiminomethyl]-4-[(E)-pyrazin-2-ylmethyleneamino]-2,5-dihydro-1,2,4-triazin-3-one (Compound 1.014)

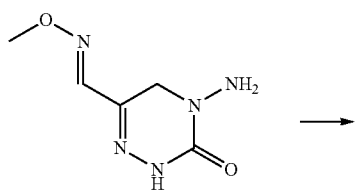

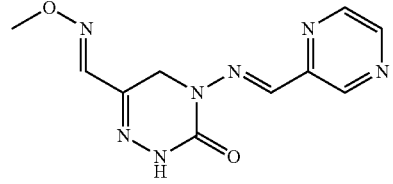

The title compound was obtained from 4-amino-6-[(E)-methoxyiminomethyl]-2,5-dihydro-1,2,4-triazin-3-one and pyrazine-2-carbaldehyde following the procedure described in Example 1, step I. LCMS (Method H) RT 1.15 min. [M+H]$^+$ 262. M.p. 233-234° C.

EXAMPLE 6

6-[(E)-N-methoxy-C-methyl-carbonimidoyl]-4-[(E)-3-pyridylmethyleneamino]-2,5-dihydro-1,2,4-triazin-3-one (Compound 1.063)

Step A: tert-butyl 4-acetamido-6-(1-hydroxyethyl)-3-oxo-5H-1,2,4-triazine-2-carboxylate

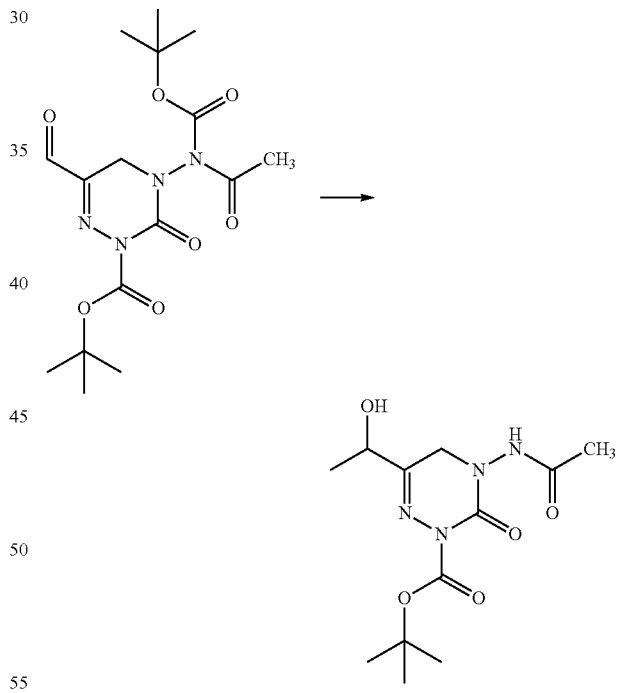

To a solution of tert-butyl 4-[acetyl(tert-butoxycarbonyl)amino]-6-formyl-3-oxo-5H-1,2,4-triazine-2-carboxylate (1.15 g, 3.00 mmol) [prepared according to Example 1, Step F] in THF (11.0 mL) at 0° C. was slowly added MeMgBr (3M solution in Et$_2$O, 1.50 mL, 4.50 mmol) via syringe. The reaction mixture was allowed to warm to room temperature and stirred for another 20 h. The reaction mixture was quenched with sat NH$_4$Cl solution and the aqueous layer extracted EtOAc. After washing of the combined organic layers with brine and drying (Na$_2$SO$_4$), the solvent was removed in vacuo to give the desired product as a viscous oil. LCMS (Method I) RT 1.19 min. [M+Na]+ 323.

Step B: tert-butyl 4-acetamido-6-acetyl-3-oxo-5H-1,2,4-triazine-2-carboxylate

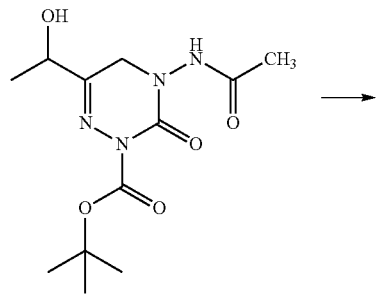

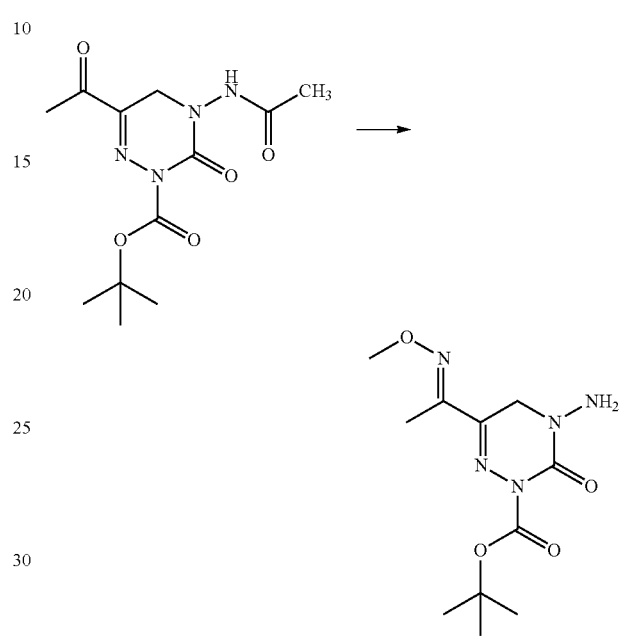

To a solution of tert-butyl 4-acetamido-6-(1-hydroxyethyl)-3-oxo-5H-1,2,4-triazine-2-carboxylate (601 mg, 1.50 mmol) in ethyl acetate (3.9 mL) was added a solution of NaHCO₃ (378 mg, 4.50 mmol) and NaBr (170 mg, 1.65 mmol) in water (2.6 mL). After cooling of the biphasic mixture to 0° C., 2,2,6,6-Tetramethyl-piperidin-1-yl)oxyl ("TEMPO") (12.0 mg, 0.0750 mmol) was added in one portion followed by dropwise addition of NaOCl (6 wt % in water, 2.79 mL, 2.25 mmol) to the vigorously stirred solution. After completion of the addition, stirring at 0° C. was continued for 30 min. Subsequently, a solution of aqueous Na₂SO₃ was added until the reaction mixture had completely discolored. Additional solid Na₂SO₃ was added to saturate the aqueous phase. The mixture was transferred to a separation funnel and the layers were separated. The organic layer was washed with brine (100 mL), dried (Na₂SO₄), filtered and concentrated under reduced pressure. LCMS (Method I) RT 1.42 min. [(M-Boc)+Na]+ 221.

Step C: tert-butyl 4-amino-6-[(E)-N-methoxy-C-methyl-carbonimidoyl]-3-oxo-5H-1,2,4-triazine-2-carboxylate The title compound was obtained from tert-butyl 4-acetamido-6-acetyl-3-oxo-5H-1,2,4-triazine-2-carboxylate and O-methylhydroxylamine HCl salt following the procedure described in Example 1, step G. LCMS (Method H) RT 1.50 min. [M+H]+ 286.

Step D: 4-amino-6-[(E)-N-methoxy-C-methyl-carbonimidoyl]-2,5-dihydro-1,2,4-triazin-3-one

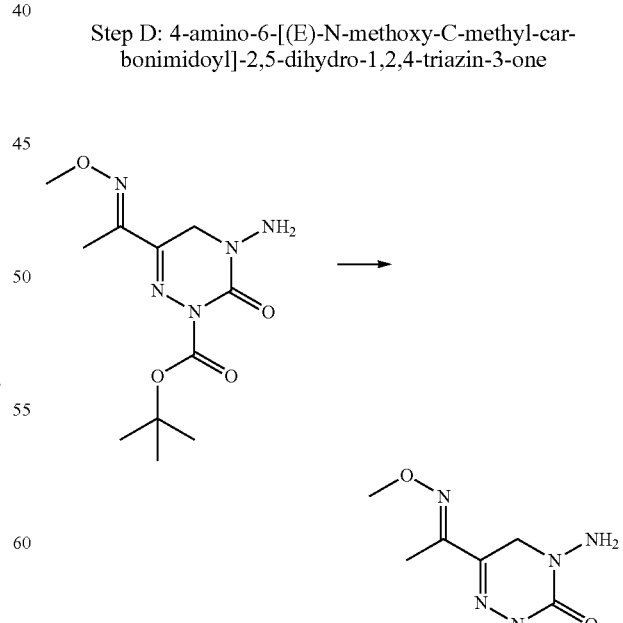

The title compound was obtained from tert-butyl 4-amino-6-[(E)-N-methoxy-C-methyl-carbonimidoyl]-3-oxo-5H-1,2, 4-triazine-2-carboxylate following the procedure described in Example 1, step H. LCMS (Method H) RT 1.01 min. [M+H]+ 186.

Step E: 6-[(E)-N-methoxy-C-methyl-carbonimidoyl]-4-[(E)-3-pyridylmethyleneamino]-2,5-dihydro-1,2,4-triazin-3-one (Compound 1.063)

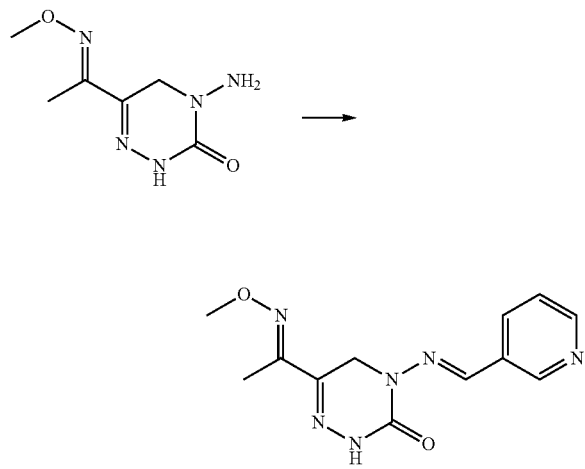

The title compound was obtained from 4-amino-6-[(E)-N-methoxy-C-methyl-carbonimidoyl]-2,5-dihydro-1,2,4-triazin-3-one and pyridine-3-carbaldehyde following the procedure described in Example 1, step I. LCMS (Method K) RT 0.53 min. [M+H]+ 275. M.p. 230-231° C.

EXAMPLE 7

6-[(E)-ethoxyiminomethyl]-4-[(E)-3-pyridylmethyleneamino]-2,5-dihydro-1,2,4-triazin-3-one (Compound 1.075)

Step A: tert-butyl 4-[acetyl(tert-butoxycarbonyl)amino]-6-[(E)-ethoxyiminomethyl]-3-oxo-5H-1,2,4-triazine-2-carboxylate

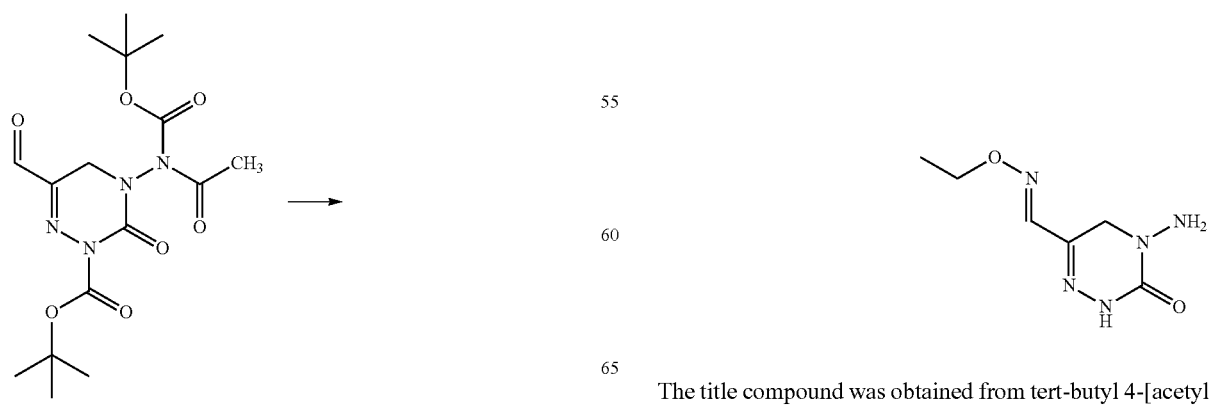

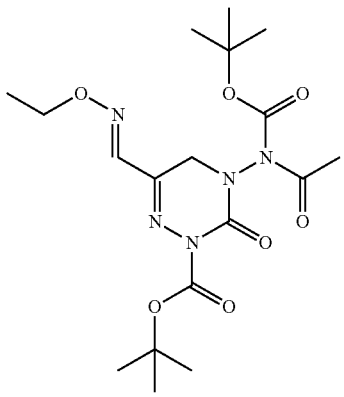

To a solution of tert-butyl 4-[acetyl(tert-butoxycarbonyl)amino]-6-formyl-3-oxo-5H-1,2,4-triazine-2-carboxylate (192 mg, 0.500 mmol) and sodium acetate (45 mg, 0.55 mmol) in EtOH (1.0 mL) at room temperature was added O-ethylhydroxylamine HCl-salt (54 mg, 0.55 mmol). The mixture was heated to 70° C. and stirred for 2 h. The obtained reaction mixture was filtered hot and the solid residual washed with EtOH. The filtrate was concentrated to give the desired product which was used without further purification. LCMS (Method I) RT 1.94 min. [M+Na]+ 450.

Step B: 4-amino-6-[(E)-ethoxyiminomethyl]-2,5-dihydro-1,2,4-triazin-3-one

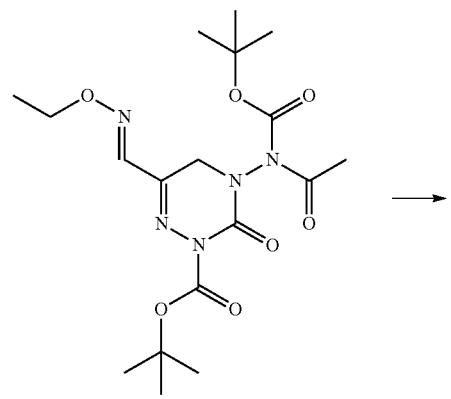

The title compound was obtained from tert-butyl 4-[acetyl(tert-butoxycarbonyl)amino]-6-[(E)-ethoxyiminomethyl]-3- oxo-5H-1,2,4-triazine-2-carboxylate following the procedure described in Example 1, Step H. LCMS (Method J) RT 4.98 min. [M+H]+ 186.

Step C: 6-[(E)-ethoxyiminomethyl]-4-[(E)-3-pyridyl-methyleneamino]-2,5-dihydro-1,2,4-triazin-3-one (Compound 1.075)

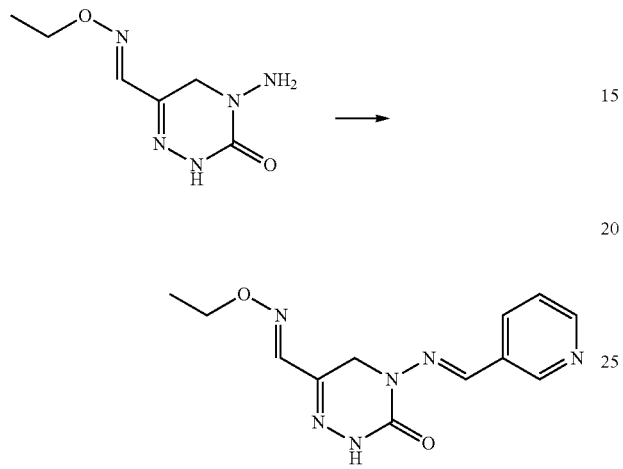

The title compound was obtained from 4-amino-6-[(E)-ethoxyiminomethyl]-2,5-dihydro-1,2,4-triazin-3-one and pyridine-3-carbaldehyde following the procedure described in Example 1, step I. LCMS (Method I) RT 1.10 min. [M+H]+ 275. M.p. 233-234° C.

EXAMPLE 8

(6E)-3-oxo-4-[(E)-3-pyridylmethyleneamino]-2,5-dihydro-1,2,4-triazine-6-carbaldehyde oxime (Compound I-105)

Step A: tert-butyl 4-(tert-butoxycarbonylamino)-6-[(E)-hydroxyiminomethyl]-3-oxo-5H-1,2,4-triazine-2-carboxylate

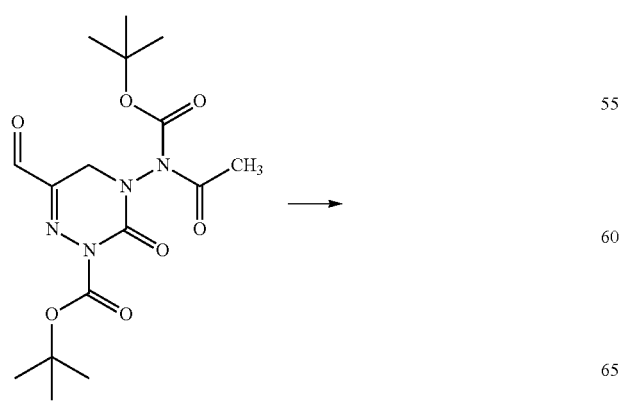

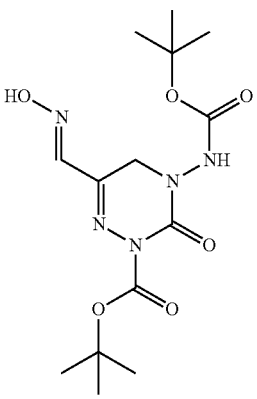

The title compound was obtained from tert-butyl 4-[acetyl (tert-butoxycarbonyl)amino]-6-formyl-3-oxo-5H-1,2,4-triazine-2-carboxylate and hydroxylamine HCl-salt following the procedure described in Example 1, Step G. LCMS (Method I) RT 1.55 min. [M+Na]+ 380.

Step B: (6E)-4-amino-3-oxo-2,5-dihydro-1,2,4-triazine-6-carbaldehyde oxime

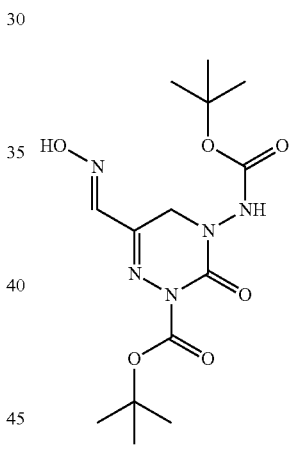

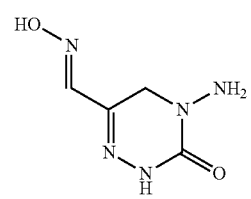

The title compound was obtained from tert-butyl 4-(tert-butoxycarbonylamino)-6-[(E)-hydroxyiminomethyl]-3-oxo- 5H-1,2,4-triazine-2-carboxylate following the procedure described in Example 1, Step H. LCMS (Method J) RT 2.83 min. [M+H]⁺ 158.

Step C: (6E)-3-oxo-4-[(E)-3-pyridylmethylene-amino]-2,5-dihydro-1,2,4-triazine-6-carbaldehyde oxime (Compound 1.111)

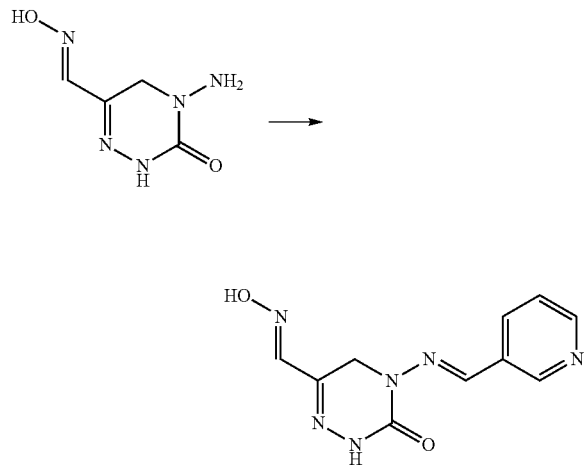

The title compound was obtained from (6E)-4-amino-3-oxo-2,5-dihydro-1,2,4-triazine-6-carbaldehyde oxime and pyridine-3-carbaldehyde following the procedure described in Example 1, step I. LCMS (Method I) RT 0.23 min. [M+H]⁺ 247. M.p. 272° C. (decomp.).

EXAMPLE 9

6-[(E)-(dimethylhydrazono)methyl]-4-[(E)-3-pyridylmethyleneamino]-2,5-dihydro-1,2,4-triazin-3-one (Compound 1.117)

Step A: tert-butyl 4-[acetyl(tert-butoxycarbonyl)amino]-6-[(E)-(dimethylhydrazono)methyl]-3-oxo-5H-1,2,4-triazine-2-carboxylate

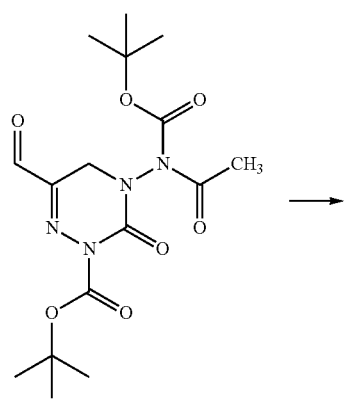

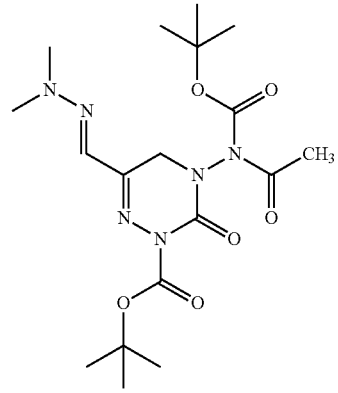

To a solution of tert-butyl 4-[acetyl(tert-butoxycarbonyl)amino]-6-formyl-3-oxo-5H-1,2,4-triazine-2-carboxylate (461 mg, 1.20 mmol) in EtOH was added N,N-dimethylhydrazine (0.110 mL, 1.44 mmol), followed by addition of 1 droplet of conc. HCl. The mixture was stirred at room temperature for 20 h followed by evaporation of the volatiles to give the title compound as a viscous oil. LCMS (Method K) RT 0.99 min. [M+H]⁺ 427.

Step B: 4-amino-6-[(E)-(dimethylhydrazono)methyl]-2,5-dihydro-1,2,4-triazin-3-one

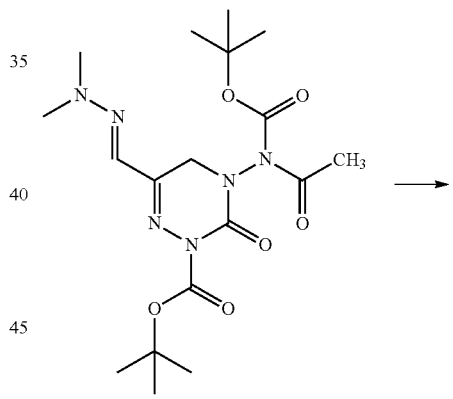

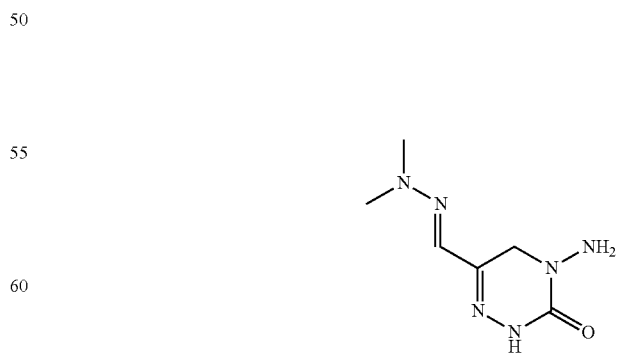

The title compound was obtained from tert-butyl 4-[acetyl(tert-butoxycarbonyl)amino]-6-[(E)-(dimethylhydrazono)methyl]-3-oxo-5H-1,2,4-triazine-2-carboxylate following the procedure described in Example 1, Step H. LCMS (Method K) RT 0.45 min. [M+H]⁺ 185.

Step C: 6-[(E)-(dimethyl hydrazono)methyl]-4-[(E)-3-pyridylmethyleneamino]-2,5-dihydro-1,2,4-triazin-3-one (Compound 1.117)

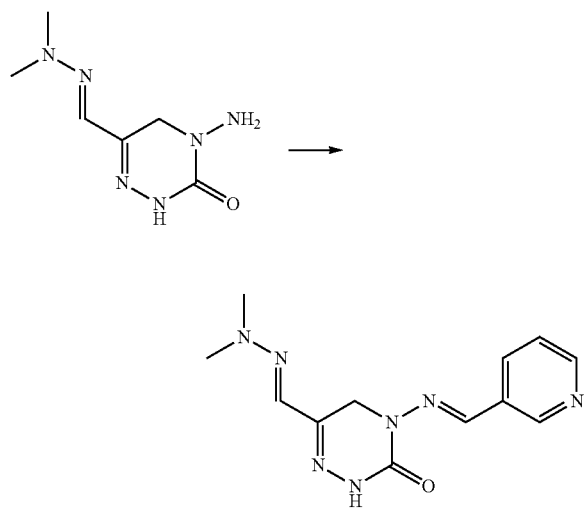 [SMILES: CN(C)/N=C/C1=NNC(=O)N(N)C1 ; CN(C)/N=C/C1=NNC(=O)N(/N=C/c2cccnc2)C1]

The title compound was obtained from 4-amino-6-[(E)-(dimethylhydrazono)methyl]-2,5-dihydro-1,2,4-triazin-3-one and pyridine-3-carbaldehyde following the procedure described in Example 1, step I. LCMS (Method K) RT 0.48 min. [M+H]⁺ 274. M.p. 229° C. (decomp.).

EXAMPLE 10

6-(5,5-dimethyl-4H-isoxazol-3-yl)-4-[(E)-3-pyridyl-methyleneamino]-2,5-dihydro-1,2,4-triazin-3-one (Compound 3.001)

Step A: tert-butyl 4-(tert-butoxycarbonylamino)-6-[(Z)—C-chloro-N-hydroxy-carbonimidoyl]-3-oxo-5H-1,2,4-triazine-2-carboxylate

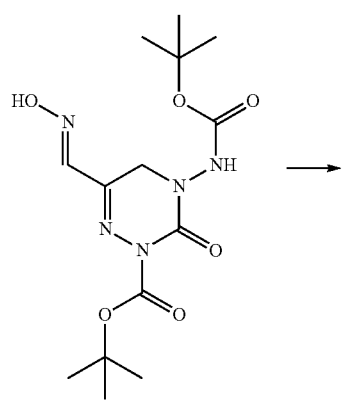

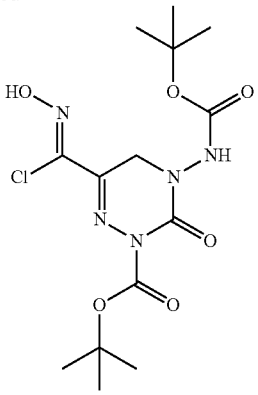

To a solution of tert-butyl 4-(tert-butoxycarbonylamino)-6-[(E)-hydroxyiminomethyl]-3-oxo-5H-1,2,4-triazine-2-carboxylate (3.20 g, 8.00 mmol) in DMF (11 mL) at room temperature was slowly added N-chlorosuccinimide ("NCS")) (1.39 g, 10.4 mmol) and the obtained solution was stirred for 20 h at room temperature. After addition of ice water, the mixture was extracted with diethyl ether and the combined organic layers were washed with brine. Drying (Na₂SO₄) and evaporation under reduced pressure furnished the desired product as a viscous oil which was used as obtained. ¹H NMR (400 MHz, CDCl₃) 1.48 (s, 9H), 1.62 (s, 9H), 4.60 (s, 2H), 8.05 (s, 1H).

Step B: tert-butyl 4-(tert-butoxycarbonylamino)-6-(5,5-dimethyl-4H-isoxazol-3-yl)-3-oxo-5H-1,2,4-triazine-2-carboxylate

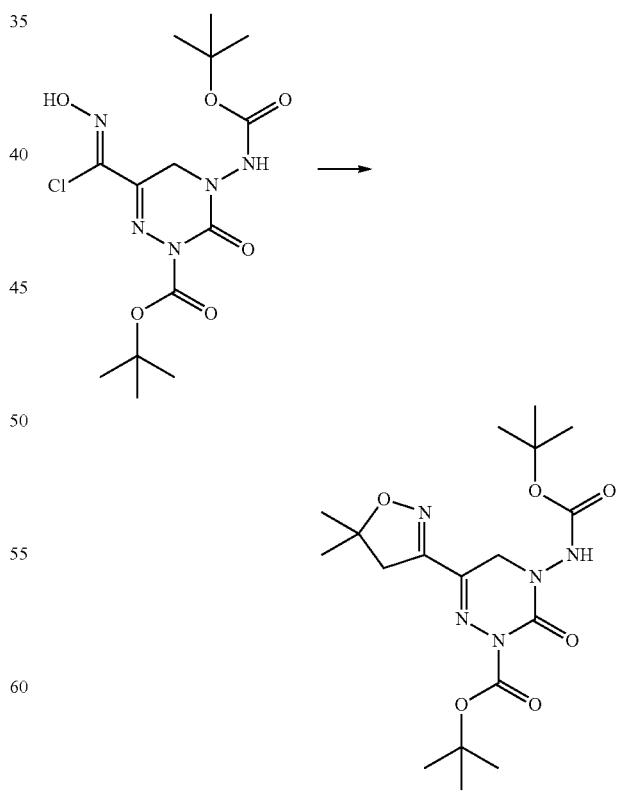

Into an argon-flushed round-bottom flask equipped with rubber septa and argon balloon at −78° C. was condensed gaseous 2-methylprop-1-ene (2.97 g, 53.0 mmol) via cannula. After addition of a solution of tert-butyl 4-(tert-butoxycarbonylamino)-6-[(Z)—C-chloro-N-hydroxy-carbonimidoyl]-3-oxo-5H-1,2,4-triazine-2-carboxylate (2.30 g, 5.30 mmol) in CHCl₃ (10.0 mL), triethylamine (0.747 mL, 5.30 mmol) was slowly added via syringe. After completion of the addition, the reaction mixture was allowed to slowly warm up to room temperature overnight. After 20 h stirring, the reaction mixture was quenched with sat. NH₄Cl, and the aqueous layer extracted with EtOAc. The combined organic layers were dried (Na₂SO₄) and concentrated in vacuo. The obtained sticky oil was used as obtained. LCMS (Method K) RT 0.96 min. [M–H]⁻ 410.

Step C: 4-amino-6-(5,5-dimethyl-4H-isoxazol-3-yl)-2,5-dihydro-1,2,4-triazin-3-one

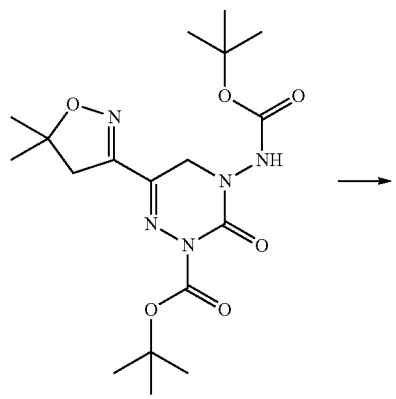

To a solution of tert-butyl 4-(tert-butoxycarbonylamino)-6-(5,5-dimethyl-4H-isoxazol-3-yl)-3-oxo-5H-1,2,4-triazine-2-carboxylate (2.50 g, 5.51 mmol) in EtOH (30 mL) at 0° C. was slowly added acetyl chloride (2.16 mL, 27.6 mmol). After completion of the addition, the reaction mixture was allowed to warm to room temperature and stirring was continued for an additional 20 h. The reaction mixture was cooled to 0° C. and carefully treated with NaOMe in MeOH until pH 7 was reached. The volatiles were removed in vacuo and the residual was repeatedly diluted with acetonitrile and evaporated. The remaining solids were stirred for 10 min with hot acetonitrile and filtered. Concentration of the filtrate furnished the desired product as an off-white solid. LCMS (Method K) RT 0.47 min. [M+H]⁺ 212.

Step D: 6-(5,5-dimethyl-4H-isoxazol-3-yl)-4-[(E)-3-pyridylmethyleneamino]-2,5-dihydro-1,2,4-triazin-3-one (Compound 3.001)

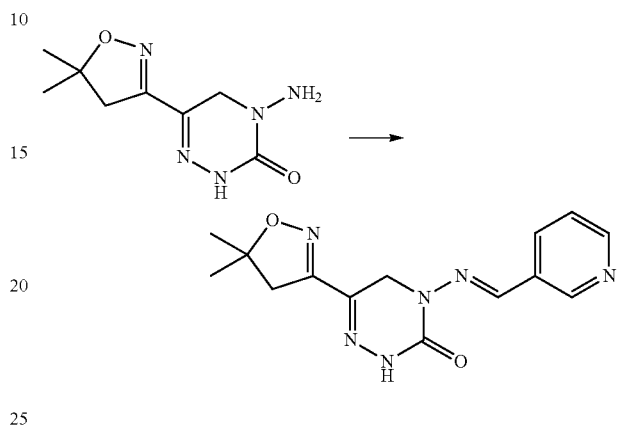

The title compound was obtained from 4-amino-6-(5,5-dimethyl-4H-isoxazol-3-yl)-2,5-dihydro-1,2,4-triazin-3-one and pyridine-3-carbaldehyde following the procedure described in Example 1, step I. LCMS (Method K) RT 0.52 min. [M+H]⁺ 301. M.p. 212° C. (decomp.).

EXAMPLE 11

6-(5,5-dimethyl-4H-isoxazol-3-yl)-4-[(E)-(5-fluoro-3-pyridyl)methyleneamino]-2,5-dihydro-1,2,4-triazin-3-one (Compound 3.002)

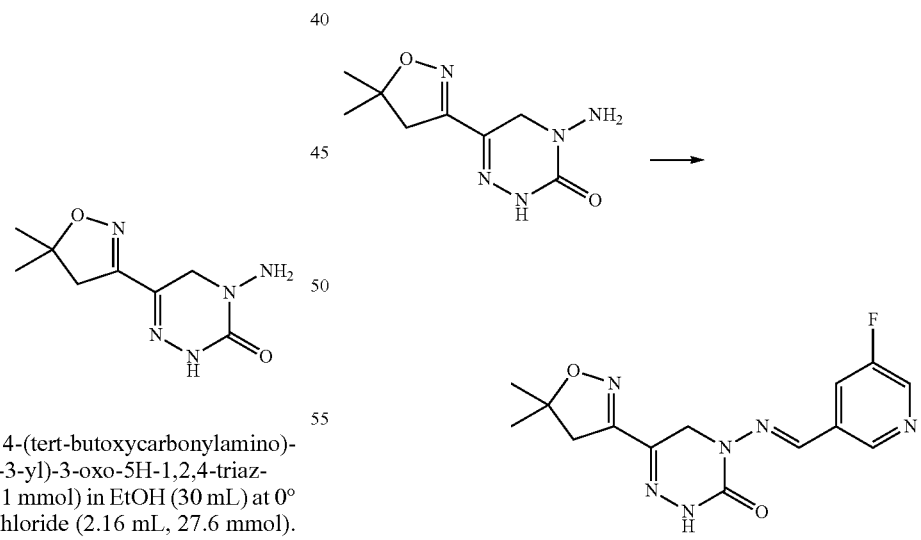

To a solution of 4-amino-6-(5,5-dimethyl-4H-isoxazol-3-yl)-2,5-dihydro-1,2,4-triazin-3-one (238 mg, 1.01 mmol) in EtOH at 60° C. was added pyridine-3-carbaldehyde (0.141 mL, 1.50 mmol), followed by addition of 1 droplet conc. HCl. The mixture stirred at this temperature for 30 min. After cooling to room temperature, the formed precipitate was filtered, washed with ether and dried to give the desired product as a white solid. LCMS (Method I) RT 1.39 min. [M+H]+ 319. M.p. 260° C. (decomp.).

EXAMPLE 12

6-[5,5-bis(trifluoromethyl)-4H-isoxazol-3-yl]-4-[(E)-3-pyridylmethyleneamino]-2,5-dihydro-1,2,4-triazin-3-one (Compound 3.079)

Step A: tert-butyl 6-[5,5-bis(trifluoromethyl)-4H-isoxazol-3-yl]-4-(tert-butoxycarbonylamino)-3-oxo-5H-1,2,4-triazine-2-carboxylate

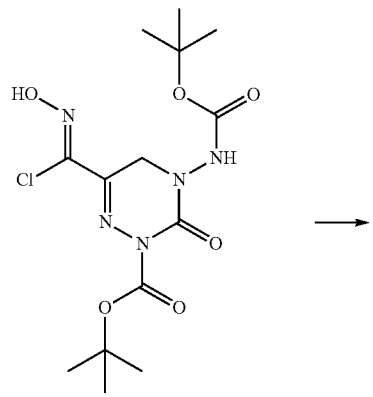

The title compound was obtained from tert-butyl 4-(tert-butoxycarbonylamino)-6-[(Z)—C-chloro-N-hydroxy-carbonimidoyl]-3-oxo-5H-1,2,4-triazine-2-carboxylate and 3,3,3-trifluoro-2-(trifluoromethyl)prop-1-ene following the procedure described in Example 10, step B. LCMS (Method K) RT 1.10 min. [M−H]− 518.

Step B: 4-amino-6-[5,5-bis(trifluoromethyl)-4H-isoxazol-3-yl]-2,5-dihydro-1,2,4-triazin-3-one

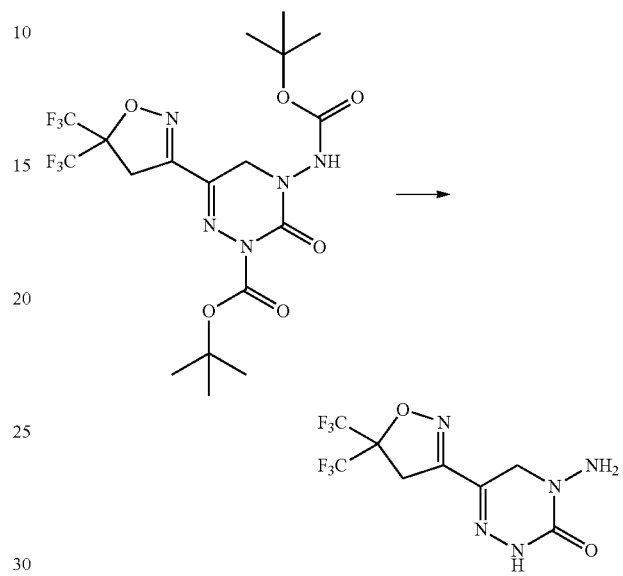

The title compound was obtained from tert-butyl 6-[5,5-bis(trifluoromethyl)-4H-isoxazol-3-yl]-4-(tert-butoxycarbonylamino)-3-oxo-5H-1,2,4-triazine-2-carboxylate following the procedure described in Example 1, Step H. LCMS (Method K) RT 0.75 min. [M+H]+ 320.

Step C: 6-[5,5-bis(trifluoromethyl)-4H-isoxazol-3-yl]-4-[(E)-3-pyridylmethyleneamino]-2,5-dihydro-1,2,4-triazin-3-one (Compound 3.079)

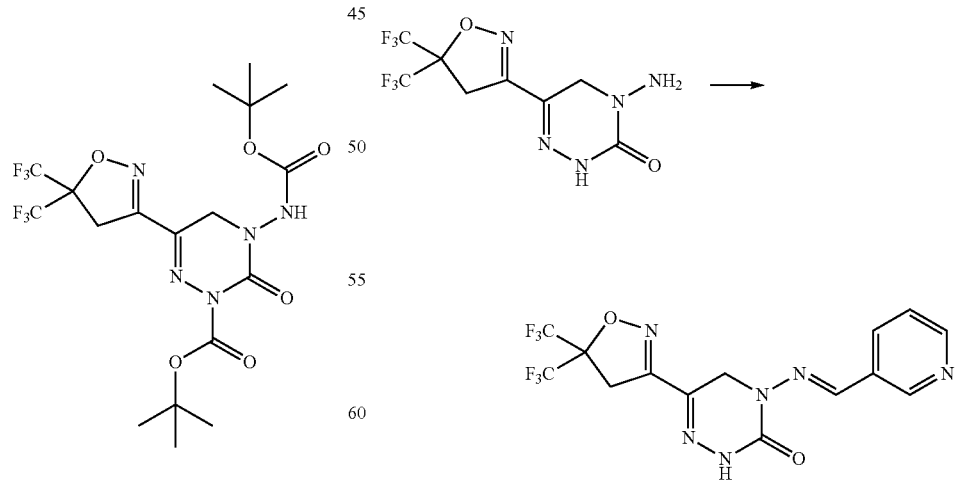

The title compound was obtained from 4-amino-6-[5,5-bis(trifluoromethyl)-4H-isoxazol-3-yl]-2,5-dihydro-1,2,4-triazin-3-one and pyridine-3-carbaldehyde following the procedure described in Example 1, step I. LCMS (Method K) RT 0.75 min. [M+H]+ 409. M.p. 270° C. (decomp.)

EXAMPLE 13

6-[5,5-bis(trifluoromethyl)-4H-isoxazol-3-yl]-4-[(E)-(5-fluoro-3-pyridyl)methyleneamino]-2,5-dihydro-1,2,4-triazin-3-one (Compound 3.080)

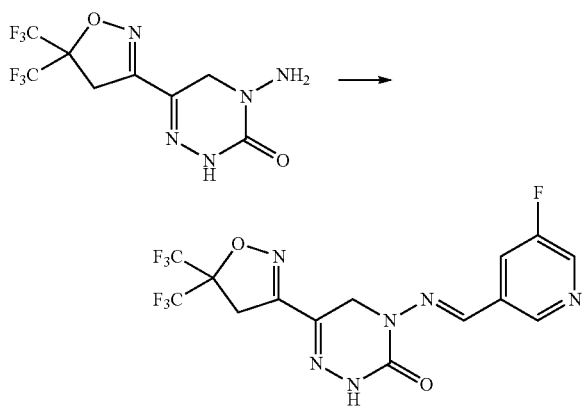

The title compound was obtained from 4-amino-6-[5,5-bis(trifluoromethyl)-4H-isoxazol-3-yl]-2,5-dihydro-1,2,4-triazin-3-one and 5-fluoropyridine-3-carbaldehyde following the procedure described in Example 1, step I. LCMS (Method K) RT 0.87 min. [M+H]+ 427. M.p. 290° C. (decomp.)

EXAMPLE 14

2-[6-(5,5-dimethyl-4H-isoxazol-3-yl)-4-[(E)-(5-fluoro-3-pyridyl)methylene amino]-3-oxo-5H-1,2,4-triazin-2-yl]acetonitrile (Compound 3.185)

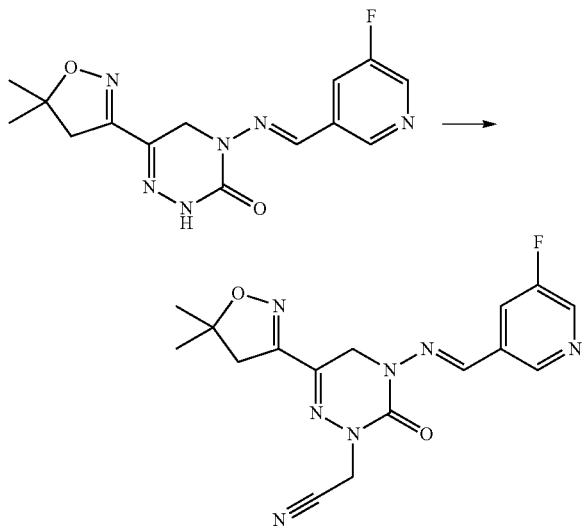

To a solution of 6-(5,5-dimethyl-4H-isoxazol-3-yl)-4-[(E)-(5-fluoro-3-pyridyl)methyleneamino]-2,5-dihydro-1,2,4-triazin-3-one (150 mg, 0.471 mmol) in anhydrous THF (8.0 mL) was added NaH (28.2 mg, 0.707 mmol) at 0° C. under nitrogen atmosphere. The reaction mixture was stirred at 0° C. for 10 min followed by dropwise addition of 2-bromoacetonitrile (36.2 μL, 62.2 mg, 0.518 mmol). The reaction mixture was allowed to warm to room temp. and stirring was continued for 2 h. The reaction mixture was quenched by addition of methanol followed by ice. The organic layer was evaporated in rotavap and aqueous layer extracted with ethyl acetate. The combined organic layers were washed with brine, dried (Na$_2$SO$_4$) and concentrated to furnish the crude product. Purification by flash chromatography (60-70% EtOAc/hexanes) provided the desired product as a white solid. M.p. 195-197° C.

EXAMPLE 15

[6-(5,5-dimethyl-4H-isoxazol-3-yl)-4-[(E)-(5-fluoro-3-pyridyl)methyleneamino]-5H-1,2,4-triazin-3-yl] isopropyl carbonate (Compound 7.071)

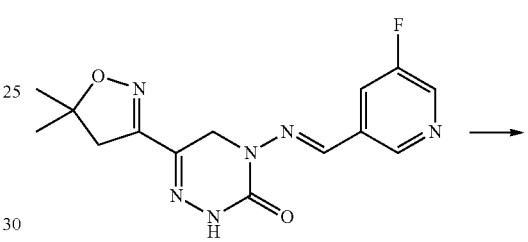

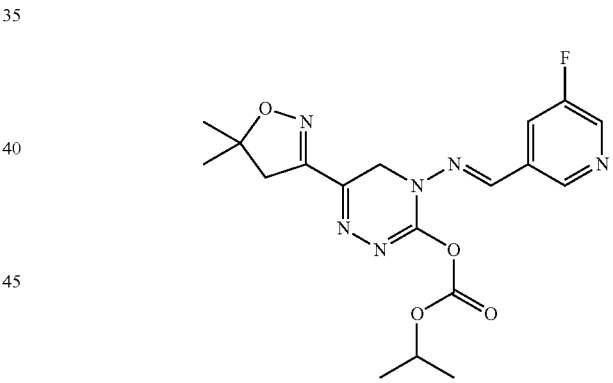

To a suspension of NaH (60 wt % in mineral oil, 15.1 mg, 0.377 mmol) in anhydrous THF (20 mL) at 0° C. was added 6-(5,5-dimethyl-4H-isoxazol-3-yl)-4-[(E)-(5-fluoro-3-pyridyl)methyleneamino]-2,5-dihydro-1,2,4-triazin-3-one (100 mg, 0.314 mmol) under nitrogen atmosphere. The reaction mixture was stirred at 0° C. for 10 min followed by dropwise addition of isopropyl chloroformate (1 M solution in toluene, 0.32 mL, 0.32 mmol). The reaction mixture was allowed to warm to room temp. and stirring was continued for 2 h. The reaction mixture was quenched by addition of methanol followed by ice. The organic layer was evaporated in rotavap and aqueous layer extracted with ethyl acetate. The combined organic layers were washed with brine, dried (Na$_2$SO$_4$) and concentrated to furnish the crude product. Purification by flash chromatography (60-70% EtOAc/hexanes) provided the desired product as a white solid. M.p. 153-155° C.

TABLE 8

Physical data of compounds of formula I or I'

| No. | | LCMS | | | Melting point (° C.) |
|---|---|---|---|---|---|
| | No. | Method | RT (min) | m/z | |
| E.001 | 1.001 | H | 0.97 | 261 [M + H]+ | 237-238 |
| E.002 | 1.002 | K | 0.63 | 279 [M + H]+ | 226-227 |
| E.003 | 1.012 | K | 0.48 | 277 [M + H]+ | 229 (dec) |
| E.004 | 1.013 | H | 1.09 | 262 [M + H]+ | 244-245 |
| E.005 | 1.014 | H | 1.15 | 262 [M + H]+ | 233-234 |
| E.006 | 1.063 | K | 0.53 | 275 [M + H]+ | 230-231 |
| E.007 | 1.075 | I | 1.10 | 275 [M + H]+ | 233-234 |
| E.008 | 1.086 | | | | 222-223 |
| E.009 | 1.087 | | | | 255-256 |
| E.010 | 1.090 | | | | 236-237 |
| E.011 | 1.092 | | | | 231-232 |
| E.012 | 1.093 | | | | 184-185 |
| E.013 | 1.096 | | | | 209-210 |
| E.014 | 1.106 | | | | 248-249 |
| E.015 | 1.111 | I | 0.23 | 247 [M + H]+ | 272 (dec) |
| E.016 | 1.117 | K | 0.48 | 274 [M + H]+ | 229 (dec) |
| E.017 | 3.001 | K | 0.52 | 301 [M + H]+ | 212 (dec) |
| E.018 | 3.002 | I | 1.39 | 319 [M + H]+ | 260 (dec) |
| E.019 | 3.004 | | | | 273-274 |
| E.020 | 3.005 | K | 0.81 | 379 [M + H]+ | >250 (dec) |
| E.021 | 3.006 | | | | 247-248 |
| E.022 | 3.007 | K | 0.85 | 369 [M + H]+ | >250 (dec) |
| E.023 | 3.012 | | | | 257-258 |
| E.024 | 3.013 | | | | 270-271 |
| E.025 | 3.014 | | | | 247-248 |
| E.026 | 3.022 | | | | 174-175 |
| E.027 | 3.062 | | | | 200-204 |
| E.028 | 3.063 | | | | 266-270 |
| E.029 | 3.066 | | | | 256-260 |
| E.030 | 3.068 | | | | 253-255 |
| E.031 | 3.069 | | | | 296-298 |
| E.032 | 3.072 | | | | 266-268 |
| E.033 | 3.074 | | | | 237-239 |
| E.034 | 3.075 | | | | 233-235 |
| E.035 | 3.077 | | | | 238-240 |
| E.036 | 3.079 | K | 0.75 | 409 [M + H]+ | 270 (dec) |
| E.037 | 3.080 | K | 0.87 | 427 [M + H]+ | 290 (dec) |
| E.038 | 3.083 | | | | 277-278 |
| E.039 | 3.088 | | | | 250-251 |
| E.040 | 3.091 | | | | 200-201 |
| E.041 | 3.099 | | | | 279-281 |
| E.042 | 3.100 | | | | 291-293 |
| E.043 | 3.103 | | | | 284-286 |
| E.044 | 3.105 | | | | 230-232 |
| E.045 | 3.106 | | | | 240-242 |
| E.046 | 3.109 | | | | 225-227 |
| E.047 | 3.117 | | | | 277-279 |
| E.048 | 3.118 | | | | 297-299 |
| E.049 | 3.121 | | | | 287-289 |
| E.050 | 3.123 | | | | 253-255 |
| E.051 | 3.124 | | | | 231-233 |
| E.052 | 3.127 | | | | 234-236 |
| E.053 | 3.129 | | | | 269-271 |
| E.054 | 3.130 | | | | 231-233 |
| E.055 | 3.133 | | | | 234-236 |
| E.056 | 3.135 | | | | 224-226 |
| E.057 | 3.136 | | | | 249-251 |
| E.058 | 3.139 | | | | 284-286 |
| E.059 | 3.141 | | | | 224-226 |
| E.060 | 3.142 | | | | 258-260 |
| E.061 | 3.145 | | | | 244-246 |
| E.062 | 3.147 | | | | 280-281 |
| E.063 | 3.148 | | | | 271-274 |
| E.064 | 3.151 | | | | 269-271 |
| E.065 | 3.171 | | | | 255-256 |
| E.066 | 3.172 | K | 0.56 | 317 [M + H]+ | >250 (dec) |
| E.067 | 3.173 | L | 1.40 | 339 [M + H]+ | oil |
| E.068 | 3.174 | | | | 109-111 |
| E.069 | 3.178 | L | 1.47 | 341 [M + H]+ | oil |
| E.070 | 3.179 | | | | 111-113 |
| E.071 | 3.184 | | | | 162-164 |
| E.072 | 3.185 | | | | 195-197 |
| E.073 | 3.190 | | | | 144-147 |
| E.074 | 3.191 | | | | 128-130 |
| E.075 | 3.197 | L | 1.73 | 377 [M + H]+ | oil |
| E.076 | 3.203 | | | | 145-147 |
| E.077 | 3.209 | | | | 156-158 |
| E.078 | 7.001 | | | | 211-213 |
| E.079 | 7.002 | | | | 220-222 |
| E.080 | 7.009 | | | | 172-174 |
| E.081 | 7.014 | | | | 170-172 |
| E.082 | 7.015 | | | | 184-188 |
| E.083 | 7.021 | | | | 135-137 |
| E.084 | 7.026 | | | | 179-181 |
| E.085 | 7.027 | | | | 130-132 |
| E.086 | 7.033 | L | 1.63 | 385 [M + H]+ | oil |
| E.087 | 7.034 | | | | 148-152 |
| E.088 | 7.040 | | | | 194-196 |
| E.089 | 7.046 | | | | 172-176 |
| E.090 | 7.053 | | | | 166-168 (dec) |
| E.091 | 7.058 | | | | 154-156 |
| E.092 | 7.059 | | | | 132-134 |
| E.093 | 7.065 | | | | 142-146 |
| E.094 | 7.070 | | | | 114-116 |
| E.095 | 7.071 | | | | 153-155 |
| E.096 | 7.076 | | | | 245-247 |
| E.097 | 7.082 | | | | 203-205 |

The invention also encompasses the intermediate compounds of general formula II below which are of particular interest.

TABLE 9

Physical data of compounds II

| | | LCMS | |
|---|---|---|---|
| | Method | RT (min) | m/z |
| E.098 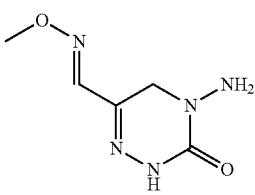 | K | 0.42 | 172 [M + H]+ |

TABLE 9-continued

| | Physical data of compounds II | | | |
|---|---|---|---|---|
| | | \multicolumn{3}{c}{LCMS} |
| | | Method | RT (min) | m/z |
| E.099 | | H | 1.01 | 186 [M + H]⁺ |
| E.100 | | J | 4.98 | 186 [M + H]⁺ |
| E.101 | | J | 2.83 | 158 [M + H]⁺ |
| E.102 | | K | 0.45 | 185 [M + H]⁺ |
| E.103 | | K | 0.47 | 212 [M + H]⁺ |
| E.104 | | K | 0.75 | 320 [M + H]⁺ |
| E.105 | | L | 1.39 | 240 [M + H]⁺ |

TABLE 9-continued

Physical data of compounds II

| | | LCMS | | |
|---|---|---|---|---|
| | | Method | RT (min) | m/z |
| E.106 | (structure) | L | 0.99 | 210 [M + H]$^+$ |
| E.107 | (structure) | L | 1.19 | 224 [M + H]$^+$ |
| E.108 | (structure) | L | 1.32 | 238 [M + H]$^+$ |
| E.109 | (structure) | L | 1.99 | 396 [M + H]$^+$ |
| E.110 | (structure) | L | 1.25 | 266 [M + H]$^+$ |
| E.111 | (structure) | L | 1.29 | 226 [M + H]$^+$ |
| E.112 | (structure) | L | 1.59 | 327 [M + H]$^+$ |

TABLE 9-continued
| | | | LCMS | |
|---|---|---|---|---|
| | | Method | RT (min) | m/z |
| E.113 | 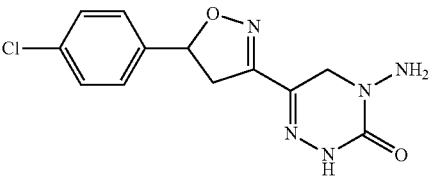 [SMILES: NN1CC(C2=NOC(c3ccc(Cl)cc3)C2)=NNC1=O] | L | 1.58 | 294 [M + H]+ |
| E.114 | 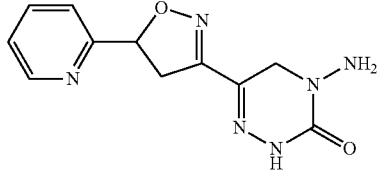 [SMILES: NN1CC(C2=NOC(c3ccccn3)C2)=NNC1=O] | L | 0.47 | 261 [M + H]+ |
| E.115 | 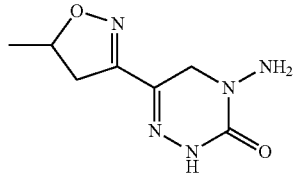 | L | 0.84 | 198 [M + H]+ |
| E.116 | 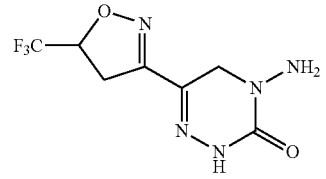 [SMILES: NN1CC(C2=NOC(C(F)(F)F)C2)=NNC1=O] | L | 0.94 | 212 [M + H]+ |
| E.117 | 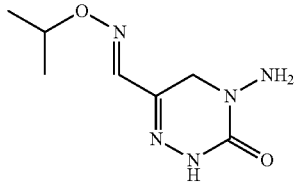 | K | 0.58 | 200 [M + H]+ |
| E.118 | 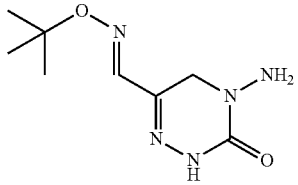 | K | 0.66 | 214 [M + H]+ |
| E.119 | 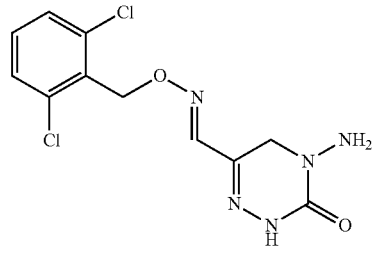 [SMILES: NN1CC(/C=N/OCc2c(Cl)cccc2Cl)=NNC1=O] | K | 0.80 | 316 [M + H]+ |

FORMULATION EXAMPLES

%=Percent by Weight

| Example F1: Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

| Example F3: Granules | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

| Example F4: Dusts | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

| Example F5: Wettable powders | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

Extruder Granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

Coated Granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8a

Suspension Concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

Example F8b

Suspension Concentrate

| Active ingredient | 10% |
|---|---|
| Naphthalenesulfonic acid, sodium salt condensed with formaldehyde | 2% |
| Solution of an acrylic graft copolymer in water and propyleneglycole | 8% |
| Silicone antifoam emulsion | 0.5% |
| DL-propanediol-(1,2) | 3% |
| Heteropolysaccharide | 0.5% |
| 1,2-Benzisothiazol-3-one | 0.2% |
| Water | 75.8% |

The finely ground active ingredient is mixed intimately with the additives. Suspensions of any desired concentration can be prepared from the thus resulting suspension concentrate by dilution with water.

Example F9: Powders for dry seed treatment

| | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

Example F10

Flowable Concentrate for Seed Treatment

| | |
|---|---|
| active ingredient | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Example F11a

Oil-Based Suspension Concentrate (Based on a Vegetable Oil)

| | |
|---|---|
| Active ingredient | 10% |
| Tristyrylphenole with 16 moles EO | 10% |
| Block copolymer of polyhydroxystearic acid and polyalkylene glycols | 2% |
| AEROSIL 200 | 1% |
| Rape seed oil methyl ester | 12% |
| Oleic acid | 65% |

Example F11b

Oil-Based Suspension Concentrate (Based on a Mineral Oil)

| | |
|---|---|
| Active ingredient | 10% |
| Ethoxylated alcohols, C16-18 and C18-unsatd | 5% |
| Dodecyl-benzene sulfonic acid Ca-salt linear | 2.5% |
| 2-Pyrrolidinone, 1-ethenylhexadecyl-, homopolymer | 1% |
| Organophilic clay | 1% |
| Mixture of petroleum | 80.5% |

The finely ground active ingredient is mixed intimately with the additives. Suspensions of any desired concentration can be prepared from the thus resulting suspension concentrate by dilution with water.

Preferably, the term "active ingredient" used above refers to one of the compounds selected from Tables 1 to 7 shown above. It also refers to mixtures of the compound of formula I or I', in particular a compound selected from said Tables 1 to 7, with other insecticides, fungicides, herbicides, safeners, adjuvants and the like, which mixtures are specifically disclosed above.

BIOLOGICAL EXAMPLES

These examples illustrate the pesticidal/insecticidal properties of compounds of formula I or I'.

Example B1

Activity against *Myzus persicae* (Green Peach Aphid) (Mixed Population, Feeding/Residual Contact Activity, Preventive)

Sunflower leaf discs are placed on agar in a 24-well microtiter plate and sprayed with test solutions. After drying, the leaf discs are infested with an aphid population of mixed ages. After an incubation period of 6 days, samples are checked for mortality and special effects (e.g. phytotoxicity).

In this test, compounds listed in the tables above show good activity. In particular compounds E.001, E.002, E.003, E.004, E.005, E.006, E.007, E.008, E.010, E.011, E.012, E.016, E.017, E.018, E.019, E.020, E.021, E.022, E.023, E.024, E.025, E.026, E.027, E.028, E.030, E.031, E.032, E.033, E.034, E.036, E.037, E.039, E.040, E.041, E.044, E.045, E.046, E.050, E.051, E.052, E.053, E.054, E.056, E.057, E.059, E.060, E.061, E.063, E.067, E.068, E.069, E.070, E.071, E.072, E.074, E.075, E.076, E.077, E.078, E.079, E.080, E.081, E.082, E.083, E.084, E.085, E.086, E.087, E.088, E.089, E.090, E.091, E.092, E.093, E.094, E.095, E.096, E.097 show an activity of over 80% at a concentration of 200 ppm.

Example B2

Activity Against *Myzus persicae* (Green Peach Aphid) (Mixed Population, Systemic/Feeding Activity, Curative)

Roots of pea seedlings, infested with an aphid population of mixed ages, are placed directly in the test solutions. 6 days after introduction, samples are checked for mortality and special effects on the plant.

In this test, compounds listed in the tables above show good activity. In particular compounds E.001, E.002, E.003, E.004, E.005, E.006, E.007, E.009, E.010, E.012, E.013, E.018, E.022, E.023, E.024, E.025, E.026, E.027, E.028, E.029, E.032, E.034, E.039, E.040, E.045, E.051, E.052, E.053, E.054, E.057, E.060, E.061, E.072, E.075, E.076, E.077, E.079, E.080, E.081, E.082, E.083, E.085, E.087, E.088, E.089, E.090, E.092, E.093, E.094, E.095, E.096, E.097 show an activity of over 80% at a concentration of 24 ppm.

Example B3

Activity Against *Frankliniella occidentalis* (Western Flower *Thrips*) (Feeding/Residual Contact Activity, Preventive)

Sunflower leaf discs are placed on agar in a 24-well microtiter plate and sprayed with test solutions. After drying, the leaf discs are infested with a *thrips* population of mixed ages.

After an incubation period of 7 days after infestation, samples are checked for mortality and special effects (e.g. phytotoxicity).

In this test, compounds listed in the tables above show good activity. In particular compounds E.001, E.013, E.016, E.017, E.030, E.032, E.035, E.044, E.045, E.046, E.056, E.059, E.061, E.070, E.072, E.076, E.080, E.081, E.082, E.083, E.085, E.087, E.089, E.093, E.094, E.095 show an activity of over 80% at a concentration of 200 ppm.

Example B4

Activity Against *Bemisia tabaci* (Cotton White Fly) (Feeding/Residual Contact Activity, Preventive)

Cotton leaf discs are placed on agar in a 24-well microtiter plate and sprayed with test solutions. After drying, the leaf discs are infested with 12 to 18 adults. After an incubation period of 6 days after infestation, samples are checked for mortality and special effects (e.g. phytotoxicity).

In this test, compounds listed in the tables above show good activity. In particular compounds E.001, E.002, E.003, E.004, E.006, E.007, E.008, E.010, E.013, E.016, E.019, E.024, E.025, E.027, E.028, E.029, E.030, E.032, E.033, E.034, E.035, E.036, E.037, E.038, E.040, E.043, E.044, E.045, E.046, E.053, E.056, E.059, E.060, E.061, E.064, E.077, E.081, E.082, E.084, E.085, E.091, E.092, E.093 show an activity of over 80% at a concentration of 200 ppm.

Example B5

Activity Against *Rhopalosiphum padi* (Bird Chemy Oat Aphid) Mixed Population, (Seed Treatment) Systemic/Feeding Activity on Barley, Preventive A treated barley seed is sown in a 350 ml pot filled with soil. Two weeks after sowing the barley seedling is infested with an aphid population of mixed stages. After an incubation period of seven days the grade of efficacy as well as phytotoxicity (lack of shoot—missing emergence) compared to the control is estimated and expressed in percentage.

In this test, compounds listed in the tables above show good activity. In particular compounds E.002, E.018 show an activity of over 80% at a concentration of 0.3 mg a.i. per seed.

Example B6

*Aphis craccivora* (Cowpea Aphid) Mixed Population, (Seed Treatment) Systemic/Feeding Activity on Sugar Beet, Preventive A treated sugar beet seed is sown in a 350 ml pot filled with soil. Two weeks after sowing the sugar beet seedling is infested with an aphid population of mixed stages. After an incubation period of seven days the grade of efficacy as well as phytotoxicity (lack of shoot—missing emergence) compared to the control is estimated and expressed in percentage.

In this test, compounds listed in the tables above show good activity. In particular compounds E.001, E.002, E.003, E.004, E.017, E.018, E.028 show an activity of over 80% at a concentration of 0.3 mg a.i. per seed.

Example B7

Activity Against *Myzus persicae* (Green Peach Aphid): (Mixed Population, Contact/Feeding)

Pea seedlings, infested with a susceptible aphid population of mixed ages, are treated with diluted test solutions in a spray chamber. 6 days after treatment, samples are checked for mortality.

In this test, compounds listed in the tables above show good activity. In particular compounds E.001, E.002, E.003, E.006, E.007, E.008, E.009, E.017, E.018, E.026, E.027, E.028, E.036 show an activity of over 80% at a concentration of 3 ppm.

Example B8

Activity Against Neonicotinoid Resistant *Myzus persicae* (Green Peach Aphid): (Mixed Population, Contact/Feeding)

Pea seedlings, infested with a Neonicotinoid resistant aphid population of mixed ages, are treated with diluted test solutions in a spray chamber. 6 days after treatment, samples are checked for mortality.

In this test, compounds listed in the tables above show good activity. In particular compounds E.001, E.002, E.003, E.006, E.007, E.008, E.009, E.017, E.018, E.026, E.027, E.028, E.036 show an activity of over 80% at a concentration of 3 ppm.

Example B9

Activity Against *Bemisia tabaci* (Silverleaf Whitefly): (Adults, Contact/Feeding Activity, Curative)

Cotton leaf discs (5 cm diameter) are placed upside down in plastic petri dishes. Dishes are poured out with 5 ml 0.5% Agar. Compounds are applied in the automated track sprayer with 200 L/ha. After drying of the spray deposits, leaf discs are infested with 10 adults. Dishes are covered with a cotton round filter and sealed with a perforated plastic lid. Evaluation is made 4 days after infestation on adult mortality.

In this test, compounds listed in the tables above show good activity. In particular compounds E.013, E.017, E.027, E.032, E.033, E.034, E.036, E.037, E.081, E.095 show an activity of over 80% at a concentration of 50 ppm. In particular compounds E.013, E.017, E.027, E.033, E.034, E.036, E.081, E.095 show an activity of over 80% at a concentration of 12.5 ppm. In particular compound E.013, E.027, E.036 shows an activity of over 80% at a concentration of 3 ppm. In particular compounds E.013, E.036 show an activity of over 80% at a concentration of 0.8 ppm.

Example B10

Activity Against Neonicotinoid Resistant *Bemisia tabaci* (Silverleaf Whitefly): (Adults, Contact/Feeding Activity, Curative)

Cotton leaf discs (5 cm diameter) are placed upside down in plastic petri dishes. Dishes are poured out with 5 ml 0.5% Agar. Compounds are applied in the automated track sprayer with 200 L/ha. After drying of the spray deposits, leaf discs are infested with 10 Neonicotinoid resistant adults. Dishes are covered with a cotton round filter and sealed with a perforated plastic lid. Evaluation is made 4 days after infestation on % adult mortality.

In this test, compounds listed in the tables above show good activity. In particular compounds E.013, E.017, E.027, E.032, E.033, E.034, E.036, E.081, E.095 show an activity of over 80% at a concentration of 200 ppm. In particular compounds E.013, E.017, E.027, E.032, E.033, E.034, E.036, E.081 show an activity of over 80% at a concentration of 50 ppm. In particular compound E.013, E.027, E.032, E.033, E.036, E.081 shows an activity of over 80% at a concentration of 12.5 ppm. In particular compounds E.013, E.027, E.032, E.033, E.036 show an activity of over 80% at a concentration of 3 ppm. In particular compound E.036 shows an activity of over 80% at a concentration of 0.8 ppm.

The invention claimed is:
1. A compound of the formula I or I':

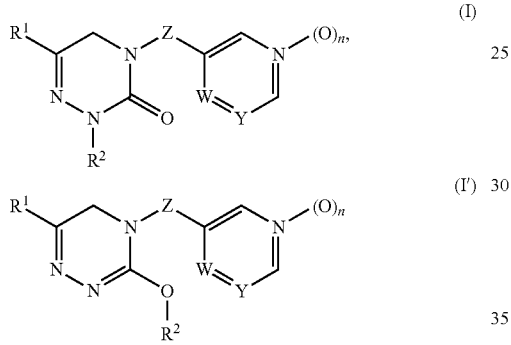

wherein,
$R^2$ is hydrogen, formyl, $C_1$-$C_6$alkyl, $C_1$-$C_3$haloalkyl, $C_1$-$C_3$alkoxy, $C_1$-$C_3$haloalkoxy, $C_1$-$C_6$alkoxy$C_1$-$C_3$alkyl, $C_1$-$C_6$alkoxy$C_1$-$C_3$alkoxy$C_1$-$C_3$alkyl, $C_2$-$C_6$alkynyl, $C_1$-$C_4$cyanoalkyl, $C_2$-$C_6$alkenyl, phenyl$C_1$-$C_4$alkyl, $C_1$-$C_6$alkylcarbonyl, $C_1$-$C_6$haloalkylcarbonyl, $C_1$-$C_6$alkoxycarbonyl, $C_1$-$C_4$alkoxycarbonyl$C_1$-$C_4$alkyl, phenyl$C_1$-$C_5$alkylcarbonyl, phenyl$C_1$-$C_5$alkoxycarbonyl, heteroarylcarbonyl, phenylcarbonyl, $C_1$-$C_6$alkylsulfonyl, phenylsulfonyl, $C_3$-$C_6$cycloalkylcarbonyl, wherein a ring methylene group may optionally be replaced by O or S, $C_3$-$C_6$cycloalkoxycarbonyl, wherein a ring methylene group may optionally be replaced by O or S, $C_3$-$C_6$cycloalkyl$C_1$-$C_4$alkylcarbonyl, wherein a ring or chain methylene group may optionally be replaced by O or S, $C_1$-$C_6$alkoxy$C_1$-$C_6$alkoxycarbonyl, Y is N or C—$R^3$, wherein $R^3$ is hydrogen, hydroxy, $C_1$-$C_4$alkoxy, $C_2$-$C_6$alkenyl, $C_2$-$C_6$alkynyl, $C_3$-$C_6$cycloalkyl, wherein a ring methylene group may optionally be replaced by O or S, $C_3$-$C_6$cycloalkyl$C_1$-$C_4$alkyl, wherein a ring or chain methylene group may optionally be replaced by O or S, halogen, cyano, or nitro, $C_1$-$C_3$haloalkylthio, $C_1$-$C_3$haloalkylsulfenyl, $C_1$-$C_3$haloalkylsulfonyl, or $C_1$-$C_3$haloalkoxy;

W is C—H or N;
n is 0 or 1;
Z is —N=CH— or —$NR^4$—$CH_2$— wherein $R^4$ is hydrogen, formyl, $C_1$-$C_6$alkyl, $C_1$-$C_6$alkylcarbonyl, $C_1$-$C_6$haloalkylcarbonyl, $C_1$-$C_6$alkoxycarbonyl, $C_2$-$C_6$alkenyloxycarbonyl, $C_2$-$C_6$alkynyl, $C_2$-$C_6$alkenyl, or phenyl$C_1$-$C_5$alkyloxycarbonyl;

$R^1$ is either $Q^1$, $Q^2$, or $Q^3$

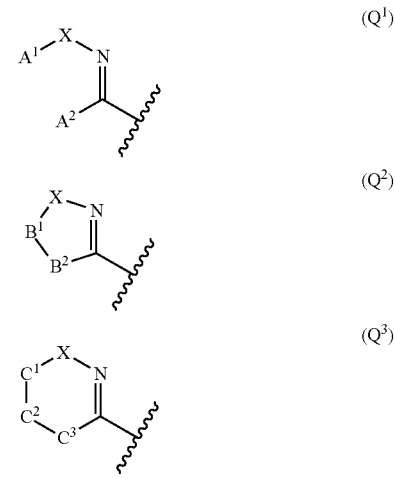

Wherein,
X is O, S, or $NR^5$ wherein $R^5$ is hydrogen, $C_1$-$C_6$alkyl, $C_1$-$C_6$haloalkyl, $A^1$ is hydrogen, $C_1$-$C_6$alkyl, $C_1$-$C_3$haloalkyl, $C_2$-$C_6$alkynyl, $C_1$-$C_4$cyanoalkyl, $C_2$-$C_6$alkenyl, phenyl$C_1$-$C_4$alkyl, heteroaryl$C_1$-$C_4$alkyl, phenyl, heteroaryl, $C_1$-$C_6$alkylcarbonyl, $C_1$-$C_6$haloalkylcarbonyl, $C_1$-$C_6$alkoxycarbonyl, phenyl$C_1$-$C_5$alkylcarbonyl, phenylcarbonyl, $C_1$-$C_6$alkylsulfonyl, phenylsulfonyl, $C_3$-$C_6$cycloalkyl, wherein a ring methylene group may optionally be replaced by O or S, $C_3$-$C_6$cycloalkyl$C_1$-$C_4$alkyl, wherein a ring or chain methylene group may optionally be replaced by O or S, $C_3$-$C_6$cycloalkylcarbonyl, wherein a ring methylene group may optionally be replaced by O or S, or $C_3$-$C_6$cycloalkyl$C_1$-$C_4$alkylcarbonyl, wherein a ring or chain methylene group may optionally be replaced by O or S;

$A^2$ is hydrogen, $C_1$-$C_6$alkyl, $C_1$-$C_3$haloalkyl, $C_2$-$C_6$alkynyl, $C_1$-$C_4$cyanoalkyl, $C_2$-$C_6$alkenyl, phenyl$C_1$-$C_4$alkyl, heteroaryl$C_1$-$C_4$alkyl, phenyl, heteroaryl, $C_3$-$C_6$cycloalkyl, wherein a ring methylene group may optionally be replaced by O or S, $C_3$-$C_6$cycloalkyl$C_1$-$C_4$alkyl, wherein a ring or chain methylene group may optionally be replaced by O or S, $C_1$-$C_6$alkylamino, $C_1$-$C_6$dialkylamino, $C_1$-$C_6$alkyloxy, hydroxy, amino;

$B^1$ is $CR^6R^7$, or C(O), $S(O)_m$, wherein m is 1 or 2
$B^2$ is $CR^8R^9$, O, $NR^{10}$ wherein $R^{10}$ is hydrogen, $C_1$-$C_6$alkyl, or $C_1$-$C_6$haloalkyl;
$C^1$ is $CR^{11}R^{12}$, C(O);
$C^2$ is $CR^{13}R^{14}$;
$C^3$ is $CR^{15}R^{16}$, O, $NR^{17}$; wherein $R^{17}$ is hydrogen, $C_1$-$C_6$alkyl, or $C_1$-$C_6$haloalkyl,
wherein $R^6, R^7, R^8, R^9, R^{11}, R^{12}, R^{13}, R^{14}R^{15}$, and $R^{16}$ are each independently of the other hydrogen, $C_1$-$C_6$alkyl, $C_1$-$C_3$haloalkyl, phenyl, heteroaryl, $C_3$-$C_6$cycloalkyl, wherein a ring methylene group may optionally be replaced by O or S, $C_3$-$C_6$cycloalkyl($C_1$-$C_4$)alkyl, wherein a ring or chain methylene group may optionally be replaced by O or S, or wherein $R^6$, $R^7$, $R^8$, $R^9$, $R^{11}$, $R^{12}$, $R^{13}$, $R^{14}$ $R^{15}$, and $R^{16}$ form a 3-6-membered carbocycle wherein a ring methylene group may optionally be replaced by O or S, wherein the phenyl and the heteroaryl groups above may independently of each other optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro, or a tautomer thereof in each case in a free form or in salt form.

2. A compound according to claim 1 wherein $R^2$ is hydrogen, $C_1$-$C_6$alkylcarbonyl, $C_1$-$C_6$alkoxycarbonyl, formyl, phenyl$C_1$-$C_5$alkylcarbonyl, phenyl$C_1$-$C_5$alkoxycarbonyl, phenylcarbonyl, $C_3$-$C_6$cycloalkylcarbonyl, $C_1$-$C_6$alkoxy$C_1$-$C_6$alkoxycarbonyl, $C_1$-$C_6$alkylcarbonyl, $C_1$-$C_6$alkoxycarbonyl or formyl, wherein the phenyl groups above may independently of each other optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro.

3. A compound according to claim 1 wherein Y is C—H, C—F, N, C—CF$_3$, C—Cl, C—CH$_3$, C-cyclo-Pr or C—CN.

4. A compound according to claim 1 wherein W is C—H.

5. A compound according to claim 1 wherein n is 0.

6. A compound according to claim 1 wherein Z is —N═CH— or —NH—CH$_2$—.

7. A compound according to claim 1 wherein $R^1$ is $Q^1$, X is O, N—CH$_3$ or N—H, $A^1$ is hydrogen, $C_1$-$C_6$alkyl, $C_1$-$C_3$haloalkyl, $C_2$-$C_6$alkynyl, $C_2$-$C_6$alkenyl, phenyl$C_1$-$C_4$alkyl, heteroaryl$C_1$-$C_4$alkyl, $C_3$-$C_6$cycloalkyl, wherein a ring methylene group may optionally be replaced by O or S, or $C_3$-$C_6$cycloalkyl$C_1$-$C_4$alkyl, wherein a ring or chain methylene group may optionally be replaced by O or S, $C_1$-$C_6$alkyl, $C_1$-$C_3$haloalkyl, and $A^2$ is hydrogen, $C_1$-$C_6$alkyl, $C_1$-$C_3$haloalkyl, phenyl, heteroaryl or $C_3$-$C_6$cycloalkyl, or $C_1$-$C_4$alkyl, wherein the phenyl and the heteroaryl groups above may independently of each other optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro.

8. A compound according to claim 1 wherein $R^1$ is $Q^2$,
X is —O, N—CH$_3$ or N—H,
$B^1$ is CH$_2$, CH(CH$_3$), CH(CF$_3$), C(CF$_3$)(CH$_3$), C(CH$_3$)$_2$, C(CF$_3$)$_2$, C(CH$_2$)$_2$, S(O)$_2$, C(Aryl)(H) or C(Aryl)(CH$_3$), and
$B^2$ is O, NH, N(CH$_3$) or CH$_2$.

9. A compound according to claim 1 wherein $R^1$ is $Q^3$,
X is O, N—CH$_3$ or N—H,
$C^1$ is CH$_2$, C(O), CH(CH$_3$), C(CH$_3$)$_2$ or C(CH$_2$)$_2$,
$C^2$ is CH$_2$, CH(CH$_3$), C(CH$_3$)$_2$ or C(CH$_2$)$_2$,
and
$C^3$ is CH$_2$, NH, N(CH$_3$), or O.

10. A compound according to claim 1 wherein:
$R^2$ is H, C(O)CH$_3$, C(O)Ot-Bu, C(O)OCH$_2$Ph, C(O)OEt, C(O)O(CH$_2$)$_2$OCH$_3$, C(O)iso-Butyl, C(O)iso-Propyl, or C(O)cyclo-Pr, Y is C—H, C—F, C—Cl, C—Br, C—CH$_3$, C—CF$_3$, C-cyclo-Pr, C—C≡N, C—CH═CH$_2$, or N,
W is C—H or N,
n is 0 or 1,
Z is N═CH or NH—CH$_2$,
$R^1$ is $Q^1$ with X is O, N-Me or NH, $A^1$ is H, CH$_3$, ethyl, CH$_2$CF$_3$, tert-Butyl, 3,5-Cl$_2$C$_6$H$_3$, CH$_2$-2,6-Cl$_2$C$_6$H$_3$, $A^2$ is H, CH$_3$, Ethyl, CF$_3$, t-C$_4$H$_9$, 3,5-Cl$_2$C$_6$H$_3$.

11. A compound according to claim 1 wherein:
$R^2$ is H, C(O)CH$_3$, C(O)Ot-Bu, C(O)OCH$_2$Ph, C(O)OEt, C(O)O(CH$_2$)$_2$OCH$_3$, C(O)iso-Butyl, C(O)iso-Propyl, or C(O)cyclo-Pr,
Y is C—H, C—F, C—Cl, C—Br, C—CH$_3$, C—CF$_3$, C-cyclo-Pr, C—C≡N, C—CH═CH$_2$, or N,
W is C—H or N,
n is 0 or 1,
Z is N═CH or NH—CH$_2$,
$R^1$ is $Q^2$ with X is O, N-Me or NH, $B^1$ is CMe$_2$, CHMe, C(CF$_3$)Me, C(CF$_3$)$_2$, CH(CF$_3$), CH(3,5-Cl$_2$C$_6$H$_3$), CH(2,6-Cl$_2$C$_6$H$_3$), C(CF$_3$)(3,5-Cl$_2$C$_6$H$_3$), C(CH$_2$)$_2$, $B^2$ is CH$_2$, O or NH.

12. A compound according to claim 1 wherein:
$R^2$ is H, C(O)CH$_3$, C(O)Ot-Bu, C(O)OCH$_2$Ph, C(O)OEt, C(O)O(CH$_2$)$_2$OCH$_3$, C(O)iso-Butyl, C(O)iso-Propyl, or C(O)cyclo-Pr,
Y is C—H, C—F, C—Cl, C—Br, C—CH$_3$, C—CF$_3$, C-cyclo-Pr, C—C≡N, C—CH═CH$_2$, or N,
W is C—H or N,
n is 0 or 1,
Z is N═CH or NH—CH$_2$,
$R^1$ is $Q^3$ with X is O, N-Me or NH, $C^1$ is CH$_2$ or C(O), $C^2$ is CH$_2$, and $C^3$ is O, CH$_2$ or NH.

13. A pesticidal composition comprising a pesticidal effective amount of a compound of formula I or I' according to claim 1.

14. A pesticidal composition according to claim 13, further comprising formulation adjuvants.

15. A pesticidal composition according to claim 13, further comprising at least one additional insecticide, acaricide, nemacitide or molluscicide.

16. A pesticidal composition according to claim 13, further comprising at least one additional fungicide, herbicide, or plant growth regulator.

17. A method of combating and controlling pest which comprises applying to a pest, to a locus of a pest, or to a plant susceptible to attack by a pest a pesticidally effective amount of a compound of formula I or I' according to claim 1.

18. A method of combating and controlling pest which comprises applying to a pest, to a locus of a pest, or to a plant susceptible to attack by a pest a pesticidal composition according to claim 13.

19. A method of combating and controlling pest from the order Hemiptera which are resistant to a neonicotinoid insecticide, which method comprises applying a compound of the formula (I) or (I') according to claim 1 in free form or in agrochemically acceptable salt form to said neonicotinoid resistant insects.

* * * * *